(12) United States Patent
Abudusaimi et al.

(10) Patent No.: US 9,067,887 B2
(45) Date of Patent: Jun. 30, 2015

(54) QUINOLONE COMPOUND

(71) Applicant: Otsuka Pharmaceutical Co., Ltd., Tokyo (JP)

(72) Inventors: Mamuti Abudusaimi, Shanghai (CN); Fangguo Ye, Shanghai (CN); Jiangqin Sun, Shanghai (CN); Hisashi Miyamoto, Osaka (JP); Jay-Fei Cheng, Shanghai (CN); Daisuke Oka, Osaka (JP)

(73) Assignee: OTSUKA PHARMACEUTICAL CO., LTD, Tokyo (JP)

( * ) Notice: Subject to any disclaimer, the term of this patent is extended or adjusted under 35 U.S.C. 154(b) by 0 days.

(21) Appl. No.: 14/193,656

(22) Filed: Feb. 28, 2014

(65) Prior Publication Data
US 2014/0179675 A1 Jun. 26, 2014
US 2015/0005287 A2 Jan. 1, 2015

Related U.S. Application Data

(63) Continuation of application No. PCT/CN2012/080753, filed on Aug. 30, 2012.

(51) Int. Cl.
| | |
|---|---|
| C07D 215/38 | (2006.01) |
| C07D 215/56 | (2006.01) |
| C07D 401/04 | (2006.01) |
| C07D 401/14 | (2006.01) |
| C07D 405/04 | (2006.01) |
| C07D 417/04 | (2006.01) |
| C07D 471/04 | (2006.01) |
| C07D 498/06 | (2006.01) |
| C07D 413/14 | (2006.01) |
| C07D 401/10 | (2006.01) |
| C07D 409/04 | (2006.01) |
| C07D 409/14 | (2006.01) |
| C07D 413/04 | (2006.01) |
| C07D 487/04 | (2006.01) |
| C07D 498/04 | (2006.01) |

(52) U.S. Cl.
CPC .......... *C07D 215/56* (2013.01); *C07D 401/04* (2013.01); *C07D 401/14* (2013.01); *C07D 405/04* (2013.01); *C07D 417/04* (2013.01); *C07D 471/04* (2013.01); *C07D 498/06* (2013.01); *C07D 413/14* (2013.01); *C07D 401/10* (2013.01); *C07D 409/04* (2013.01); *C07D 409/14* (2013.01); *C07D 413/04* (2013.01); *C07D 487/04* (2013.01); *C07D 498/04* (2013.01)

(58) Field of Classification Search
CPC .. C07D 215/12; C07D 227/02; C07D 413/14; C07D 401/14; A61K 31/4709; A61K 31/473
USPC .......................................... 546/159; 514/312
See application file for complete search history.

(56) References Cited

U.S. PATENT DOCUMENTS

| | | | |
|---|---|---|---|
| 4,623,650 A | 11/1986 | Gilligan et al. | |
| 4,797,490 A | 1/1989 | Gilligan et al. | |
| 5,935,952 A | 8/1999 | Todo et al. | |
| 6,335,447 B1 | 1/2002 | Hayashi et al. | |
| 6,337,399 B1 | 1/2002 | Yamada et al. | |
| 7,012,144 B2 | 3/2006 | Park et al. | |
| 2002/0049223 A1* | 4/2002 | Elmore et al. | 514/300 |
| 2007/0224282 A1* | 9/2007 | Kubo et al. | 424/499 |
| 2009/0247578 A1 | 10/2009 | Hubschwerlen et al. | |

FOREIGN PATENT DOCUMENTS

| | | |
|---|---|---|
| CN | 1299356 | 6/2001 |
| EP | 0 107 201 A2 | 10/1983 |
| EP | 0 343 398 | 11/1989 |
| EP | 1 160 241 | 12/2001 |

(Continued)

OTHER PUBLICATIONS

Parenti, CA 141:270985, abstract only of J Med Chem, VOl 47(17), pp. 4258-4267, 2004.*
Gordeez, J Bioorg MEd Chem LEtt, VOl 13, pp. 4213-4216, 2003.*
Hubschwerlen, CA 139:335243, abstract only of Bioort & Med chem, vol. 11(10), pp. 2313-2319, 2003.0.*
Hayashi, CA 139:30223, abstract only of Arzneimittel-Forschung, vol. 52(12), pp. 903-913, 2002.*

(Continued)

*Primary Examiner* — D M Seaman
(74) *Attorney, Agent, or Firm* — Finnegan, Henderson, Farabow, Garrett & Dunner LLP

(57) ABSTRACT

The present invention provides a compound represented by the formula (I)

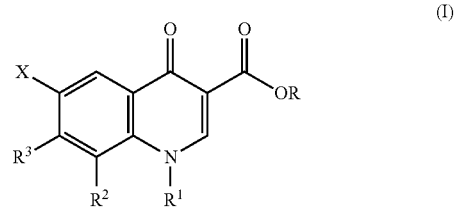

wherein X is a hydrogen atom or a fluorine atom; R is a hydrogen atom or alkyl; $R^1$ is (1) cyclopropyl optionally substituted by 1 to 3 halogen atoms or (2) phenyl optionally substituted by 1 to 3 halogen atoms; $R^2$ is alkyl, alkoxy, haloalkoxy, a halogen atom, cyano, etc.; and $R^3$ is 7-oxo-7,8-dihydro-1,8-naphthyridinyl, 3-pyridyl, etc., or a salt thereof. The compound of the present invention has excellent antimicrobial activity against *Clostridium difficile* and is useful for the prevention or treatment of intestinal infection such as *Clostridium difficile*-associated diarrhea.

22 Claims, 1 Drawing Sheet

(56) References Cited

FOREIGN PATENT DOCUMENTS

| | | |
|---|---|---|
| EP | 2 177 214 | 4/2010 |
| JP | 03-66301 | 10/1991 |
| JP | 2000/229946 * | 8/2000 |
| KR | 10-0196440 | 2/1999 |
| KR | 2001-0031474 | 4/2001 |
| KR | 10-0371723 | 1/2003 |
| KR | 10-0566346 | 3/2006 |
| WO | WO 92/10492 | 6/1992 |
| WO | WO 99/00393 | 1/1999 |
| WO | WO 99/03465 | 1/1999 |
| WO | WO 99/07682 | 2/1999 |
| WO | WO 00/46223 | 8/2000 |
| WO | WO 02/09758 A2 | 2/2002 |

OTHER PUBLICATIONS

English-language International Search Report from Japanese Patent Office for International Application No. PCT/CN2012/080753, mailed Dec. 13, 2012.

Written Opinion of the International Searching Authority from the European Patent Office for International Application PCT/CN2012/080753, mailed Dec. 13, 2012.

Johnson; "New Antibiotics for Selective Treatment of Gastrointestinal Infection Caused by Clostridium Difficile", Expert Opin. Ther. Patents, vol. 20, No. 10, pp. 1389-1399, (2010).

European Search Report, dated Dec. 16, 2014, in European Application No. 12827305.9.

Froelich-Ammon, J. et al., "Novel 1-8-bridged chiral quinolones with activity against topoIsomerase II: stereospecificity of the eukaryotic enzyme," Antimicrobial Agents and Chemotherapy, Apr. 1993, vol. 37(4), pp. 646-651.

Takahata, M. et al., "In Vitro and In Vivo Antimicrobial Activities of T-3811 ME, a Novel Des-F(6)-Quinolone," Antimicrobial Agents and Chemotherapy, 1999, vol. 43(5), pp. 1077-1084.

Wentland, M. P. et al, "Relationship of structure of bridged (2,6-dimethyl-4-pyridinyl)-quinolones marrmalian topoisomerase II inhibition," Bioorganic and Medicinal Chemistry Letters, 1993, vol. 3(8), pp. 1711-1716.

* cited by examiner

QUINOLONE COMPOUND

This application is a continuation application of International Application No. PCT/CN2012/080753, filed Aug. 30, 2012, which claims priority to International Application No. PCT/CN2011/001477, filed Aug. 31, 2011, and International Application No. PCT/CN2012/001044, filed Aug. 6, 2012.

TECHNICAL FIELD

The present invention relates to quinolone compounds and pharmaceutical use thereof.

BACKGROUND ART

*Clostridium difficile* infection is associated with consumption of antibiotics which disrupt the normal microbial flora of the gut, allowing *Clostridium difficile* to establish itself and produce disease. Currently, only vancomycin or metronidazole is recommended for treatment and many patients suffer from relapse on infection (Expert Opin. Ther. Patents (2010) 20(10), pp. 1389-1399).

EP2177214 A1 describes use of ozenoxacin for *Clostridium difficile*.

Some quinolone compounds useful as antibacterial agents are disclosed in JP1-319463 A, WO99/51588, WO99/03465, JP3-66301 B and WO99/07682.

SUMMARY OF INVENTION

The object of the present invention is to provide a novel quinolone compound which has excellent antimicrobial activity, particularly excellent antimicrobial activity against *Clostridium difficile*. Another object of the present invention is to provide a pharmaceutical composition containing said quinolone compound, which is useful for the prevention or treatment of various infectious diseases including antibiotics-associated diarrhea (AAD) such as *Clostridium difficile*-associated diarrhea (CDAD). A further object of the present invention is to provide a method for preventing or treating a bacterial infection including AAD such as CDAD, which comprises administering said quinolone compound to a human or an animal.

The present invention provides a quinolone compound, a pharmaceutical composition comprising said compound, use of said compound, and a method for preventing or treating a bacterial infection, as described in Items 1 to 27 below.

Item 1. A compound represented by the formula (I)

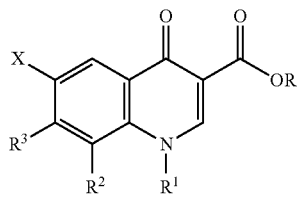

(I)

wherein
X is a hydrogen atom or a fluorine atom;
R is a hydrogen atom or alkyl;
$R^1$ is (1) cyclopropyl optionally substituted by 1 to 3 halogen atoms or (2) phenyl optionally substituted by 1 to 3 halogen atoms;

$R^2$ is a hydrogen atom; alkyl optionally substituted by 1 or 2 substituents selected from the group consisting of a halogen atom and hydroxyl; alkoxy; haloalkoxy; a halogen atom; cyano; cyclopropyl; nitro; amino; formyl; alkenyl or alkynyl; or
$R^1$ and $R^2$ are bonded to form a 5- or 6-membered ring optionally substituted by alkyl;
$R^3$ is
(1) a fused heterocyclic group of the formula

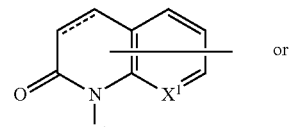

(A)

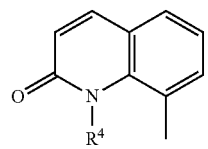

(B)

wherein
┄┄┄ represents a single bond or a double bond,
$X^1$ is $C(R^5)$ or N,
$R^4$ is a hydrogen atom or alkyl, and
$R^5$ is (a) a hydrogen atom,
(b) a halogen atom,
(c) cyano,
(d) nitro,
(e) hydroxy,
(f) alkyl optionally substituted by 1 to 3 halogen atoms,
(g) alkenyl or alkynyl,
(h) aryl, or
(i) alkoxy optionally substituted by 1 to 3 halogen atoms,
when $X^1$ is $C(R^5)$, $R^4$ and $R^5$ are optionally bonded to form a 5- or 6-membered ring optionally substituted by oxo,
said fused heterocyclic group is optionally substituted by 1 or 2 substituents selected from the group consisting of a halogen atom, cyano, nitro, hydroxy and alkyl,
(2) a group of the formula

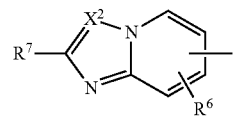

(C)

wherein
$X^2$ is $C(R^8)$ or N, and
$R^6$, $R^7$ and $R^8$ are each independently,
(a) a hydrogen atom,
(b) a halogen atom,
(c) cyano,
(d) nitro,
(e) amino,
(f) alkyl optionally substituted by 1 to 3 substituents selected from the group consisting of a halogen atom, alkoxy and amino,
(g) alkenyl,
(h) alkynyl,
(i) aryl, (j) formyl or CH=N—OH,
(k) carboxy,
(l) carbamoyl,
(m) a 5- to 10-membered aromatic heterocyclic group optionally substituted by alkyl, or
(n) alkenyloxy, (3) a group of the formula

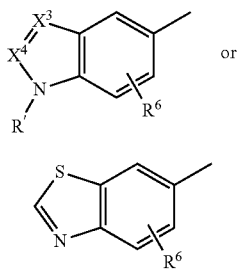

wherein
$X^3$ and $X^4$ are N, or
$X^3$ is N and $X^4$ is CR", wherein R" is hydrogen atom, amino, hydroxy, alkyl optionally substituted by 1 to 3 substituents selected from the group consisting of alkoxy and dimethylamino or mercapto, or
$X^3$ is CH and $X^4$ is N,
R' is a hydrogen atom or alkyl optionally substituted by 1 to 3 substituents selected from the group consisting of substituted hydroxyl and amino, and
$R^6$ is as defined above, (4) a group of the formula

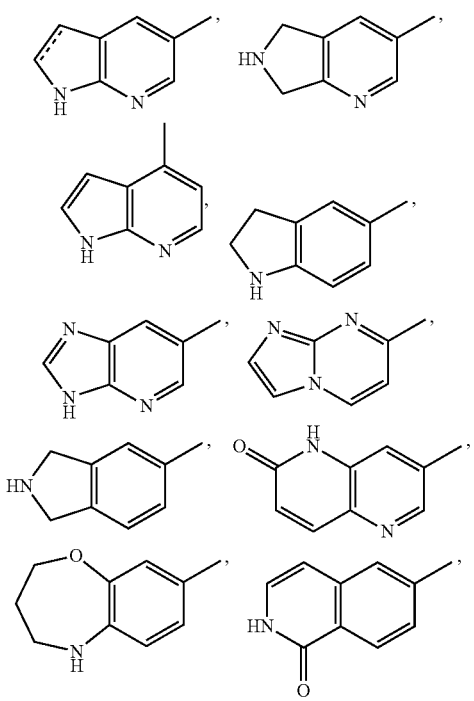

wherein
------ represents a single bond or a double bond and $R^6$ is as defined above, (5) 3-pyridyl optionally substituted by 1 or 2 substituents selected from the group consisting of
   (a) a halogen atom,
   (b) cyano,
   (c) nitro,
   (d) hydroxy,
   (e) amino,
   (f) alkyl optionally substituted by 1 to 3 substituents selected from the group consisting of a halogen atom, alkylamino, dialkylamino and hydroxy,
   (g) alkenyl, alkynyl
   (h) aryl,
   (i) cycloalkyl,
   (j) alkoxy,
   (k) alkylamino,
   (l) dialkylamino,
   (m) phenylamino optionally substituted by 1 to 3 halogen atoms,
   (n) a cyclic amino group optionally substituted by alkoxycarbonyl,
   (o) formyl,
   (p) carbamoyl optionally substituted by alkyl optionally substituted by hydroxy, and
   (q) a 5- to 10-membered aromatic heterocyclic group optionally substituted by alkyl, (6) 4-pyridyl optionally substituted by a halogen atom,
(7) 5-pyrimidinyl optionally substituted by 1 or 2 substituents selected from the group consisting of amino, alkylamino, dialkylamino and carboxy,
(8) 2-indolyl, 3-indolyl, 5-indolyl, 6-indolyl, benzofuranyl, benzothiophenyl, benzoxazolyl or benzothiazolyl, each optionally substituted by 1 or 2 substituents selected from the group consisting of (a) a halogen atom,
(b) cyano,
(c) nitro,
(d) hydroxy,
(e) alkyl optionally substituted by 1 to 3 substituents selected from the group consisting of amino, alkoxycarbonylamino, alkylamino and dialkylamino,
(f) alkoxy,
(g) formyl,
(h) carboxy, and
(j) amino optionally substituted by 1 or 2 substituents selected from the group consisting of
  (i) alkoxycarbonyl,
  (ii) alkylcarbonyl optionally substituted by a substituent selected from the group consisting of
    (A) cycloalkyloxy optionally substituted by 1 to 3 alkyl,
    (B) alkylamino,
    (C) dialkylamino,
    (D) a cyclic amino group optionally substituted by alkoxycarbonyl, and
    (E) a halogen atom,
  (iii) phenylcarbonyl optionally substituted by 1 to 3 substituents selected from the group consisting of alkyl and alkoxy,
  (iv) cycloalkylcarbonyl,
  (v) a 5- to 10-membered aromatic heterocyclylcarbonyl group optionally substituted by alkyl optionally substituted by 1 to 3 halogen atoms,
  (vi) benzylcarbonyl optionally substituted by 1 to 3 substituents selected from the group consisting of a halogen atom and alkoxy,
  (vii) arylsulfonyl optionally substituted by alkoxy,
  (viii) cycloalkylalkylsulfonyl optionally substituted by 1 to 3 substituents selected from the group consisting of alkyl and oxo,
  (ix) a 5- to 10-membered aromatic heterocyclylsulfonyl group optionally substituted by 1 to 3 alkyl, and
  (x) —C(=N—CN)—SR$^9$ wherein R$^9$ is alkyl,
(9) a group of the formula

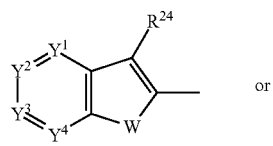

(F)

or

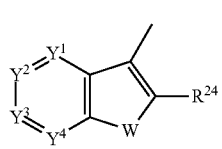

(G)

wherein
one of Y$^1$, Y$^2$, Y$^3$ and Y$^4$ is N or N$^+$(—O$^-$), and the remaining three are each C(R$^{25}$), C(R$^{26}$) and C(R$^{27}$),
W is O, S, NH or N(R$^{23}$)
R$^{23}$ is a hydrogen atom or alkyl, and
R$^{24}$, R$^{25}$, R$^{26}$ and R$^{27}$ are each independently,
  (a) a hydrogen atom,
  (b) cyano, or
  (c) nitro,

(10) a group of the formula

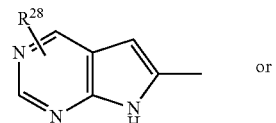

(H)

or

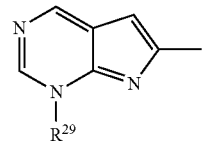

(J)

wherein
R$^{28}$ is a hydrogen atom or hydroxy, and
R$^{29}$ is a hydrogen atom or alkyl,
(11) a group of the formula

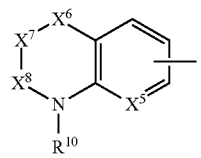

(K)

wherein
X$^5$ is C(R$^{11}$) or N,
X$^6$ is CH$_2$, C(=O), O, S, SO$_2$ or N(R$^{12}$),
X$^7$ is CH(R$^{13}$), C(=O) or N(R$^{14}$),
X$^8$ is CH(R$^{15}$) or C(=O),
R$^{10}$, R$^{12}$ and R$^{14}$ are each independently,
  (a) a hydrogen atom or
  (b) alkyl, and
R$^{11}$, R$^{13}$ and R$^{15}$ are each independently,
  (a) a hydrogen atom,
  (b) a halogen atom,
  (c) cyano,
  (d) nitro,
  (e) amino,
  (f) alkylamino,
  (g) dialkylamino,
  (h) alkyl optionally substituted by hydroxy, or
  (i) alkenyl,
when X$^5$ is C(R$^{11}$), R$^{10}$ and R$^{11}$ are optionally bonded to form a 5- or 6-membered ring optionally substituted by alkyl or oxo, and when X$^6$ is N(R$^{12}$) and X$^7$ is CH(R$^{13}$), R$^{12}$ and R$^{13}$ are optionally bonded to form a 5- or 6-membered ring,
(12) a group of the formula

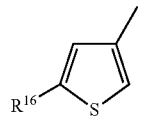

(L)

wherein R$^{16}$ is
  (a) a hydrogen atom,
  (b) alkyl optionally substituted by 1 to 3 substituents selected from the group consisting of cyano, alkylamino and dialkylamino,
  (c) alkenyl optionally substituted by carboxy,
  (d) formyl, (e) carboxy,
(f) carbamoyl,
(g) —C(R$^{17}$)=N—OH wherein R$^{17}$ is a hydrogen atom, cyano or hydroxy,
(h) a 5- to 10-membered aromatic heterocyclic group optionally substituted by alkyl, alkoxycarbonyl, carboxy or phenyl, or
(i) cyano,
(13) a group of the formula

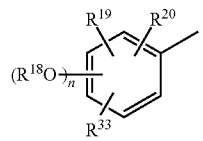

(M)

wherein
R$^{18}$ is a hydrogen atom or alkyl optionally substituted by 1 to 3 substituents selected from the group consisting of a halogen atom and phenyl,
n is 0 or 1,
R$^{19}$, R$^{20}$ and R$^{33}$ are each independently,
  (a) a hydrogen atom,
  (b) a halogen atom,
  (c) cyano,
  (d) alkyl optionally substituted by 1 to 3 substituents selected from the group consisting of
    (i) a halogen atom,
    (ii) cyano,
    (iii) hydroxy,
    (iv) amino,
    (v) alkylamino,
    (vi) dialkylamino, and
    (vii) a cyclic amino group optionally substituted by alkyl,
  (e) alkoxy,
  (f) amino optionally substituted by 1 or 2 substituents selected from the group consisting of
    (i) alkylcarbonyl optionally substituted by a cyclic amino group,
    (ii) alkylsulfonyl,
    (iii) carbamoyl,
    (iv) alkyl, cycloalkyl or cycloalkylalkyl, and
    (v) 5- to 10-membered saturated heterocyclic group,
  (g) carboxy,
  (h) alkoxycarbonyl,
  (i) carbamoyl optionally substituted by alkyl optionally substituted by amino, alkylamino, dialkylamino or alkoxycarbonylamino,
  (j) formyl,
  (k) a 5- to 10-membered aromatic heterocyclic group optionally substituted by alkyl,
  (l) —CH=N—OR$^{21}$ wherein R$^{21}$ is a hydrogen atom or alkyl optionally substituted by alkylamino or dialkylamino,
  (m) nitro,
  (n) a 5- to 10-membered saturated heterocyclic group optionally substituted by amino,
  (o) phenyl, or
  (p) —NHC(SMe)=CHCN,

(14) a group of the formula

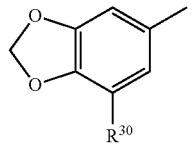

(N)

wherein
R$^{30}$ is (a) a hydrogen atom,
  (b) a halogen atom,
  (c) cyano,
  (d) alkyl optionally substituted by 1 to 3 substituents selected from the group consisting of a halogen atom and hydroxy,
  (e) alkenyl,
  (f) alkynyl,
  (g) alkoxy,
  (h) formyl,
  (i) —CH=N—OH, or
  (j) carbamoyl,
(15) naphthyl or isochromenyl,
(16) quinolyl or isoquinolyl, or their oxide derivatives,
(17) a group of the formula

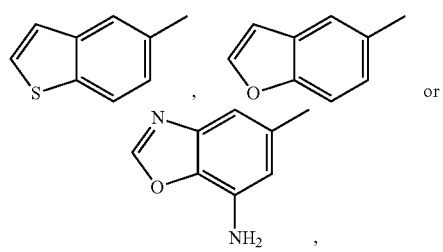

or

(18) a group of the formula

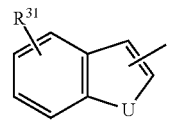

wherein
U is O or S, and
R$^{31}$ is (a) a hydrogen atom,
  (b) a halogen atom,
  (c) alkyl optionally substituted by 1 to 3 halogen atoms,
  (d) carboxy,
  (e) nitro,
  (f) cyano, or
  (g) amino,
(19) a group of the formula

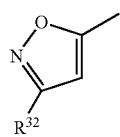

wherein
R³² is (a) a halogen atom,
  (b) phenyl, or
  (c) a group of the formula

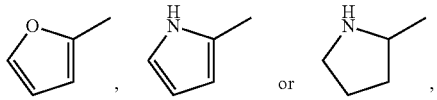

(20) a group of the formula

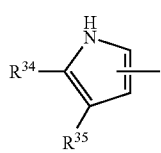

wherein
R³⁴ and R³⁵ are each independently,
  (a) a hydrogen atom, or
  (b) aminoalkyl,
or
R³⁴ and R³⁵ are bonded to form a 6-membered ring optionally substituted by amino or oxo,
(21) a group of the formula

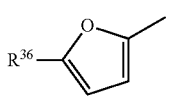

wherein R³⁶ is
  (a) a hydrogen atom,
  (b) a halogen atom,
  (c) nitro, or
  (d) thienyl, or
(22) a group of the formula

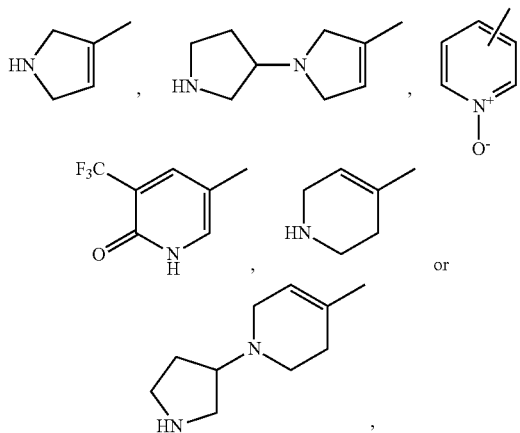

or a salt thereof.

Item 1A. The compound of item 1, wherein
X is a hydrogen atom or a fluorine atom;
R is a hydrogen atom or alkyl;
R¹ is (1) cyclopropyl optionally substituted by 1 to 3 halogen atoms or (2) phenyl optionally substituted by 1 to 3 halogen atoms;
R² is alkyl, alkoxy, haloalkoxy, a chlorine atom or cyano; or
R¹ and R² are bonded to form a 5- or 6-membered ring optionally substituted by alkyl; and
R³ is
(1) a fused heterocyclic group of the formula

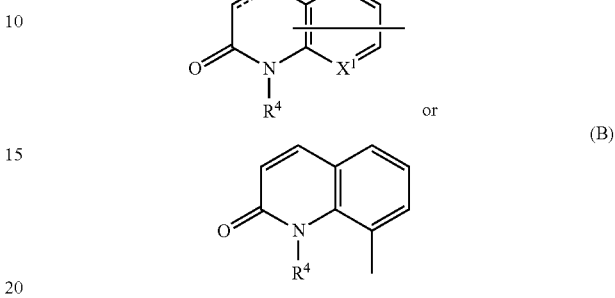

wherein
------ represents a single bond or a double bond,
$X^1$ is $C(R^5)$ or N,
$R^4$ is a hydrogen atom or alkyl, and
$R^5$ is (a) a hydrogen atom,
  (b) a halogen atom,
  (c) cyano,
  (d) nitro,
  (e) hydroxy,
  (f) alkyl optionally substituted by 1 to 3 halogen atoms,
  (g) alkenyl or alkynyl,
  (h) aryl, or
  (i) alkoxy optionally substituted by 1 to 3 halogen atoms,
when $X^1$ is $C(R^5)$, $R^4$ and $R^5$ are optionally bonded to form a 5- or 6-membered ring optionally substituted by oxo,
said fused heterocyclic group is optionally substituted by 1 or 2 substituents selected from the group consisting of a halogen atom, cyano, nitro, hydroxy and alkyl,
(2) a group of the formula (C)

wherein
$X^2$ is $C(R^8)$ or N, and
$R^6$, $R^7$ and $R^8$ are each independently,
  (a) a hydrogen atom,
  (b) a halogen atom,
  (c) cyano,
  (d) nitro,
  (e) amino,
  (f) alkyl optionally substituted by 1 to 3 substituents selected from the group consisting of a halogen atom, alkoxy and amino,
  (g) alkenyl,
  (h) alkynyl,
  (i) aryl,
  (j) formyl or CH=N—OH,
  (k) carboxy,
  (l) carbamoyl, or (m) a 5- to 10-membered aromatic heterocyclic group optionally substituted by alkyl, (3) a group of the formula

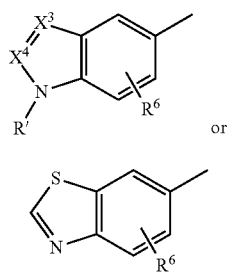

(D)

or (E)

wherein $X^3$ and $X^4$ are N, or $X^3$ is N and $X^4$ is CR", wherein R" is a hydrogen atom, amino, hydroxy, alkyl or mercapto, or $X^3$ is CH and $X^4$ is N, R' is a hydrogen atom or alkyl optionally substituted by 1 to 3 substituents selected from the group consisting of substituted hydroxy and amino, and $R^6$ is as defined above, (4) a group of the formula

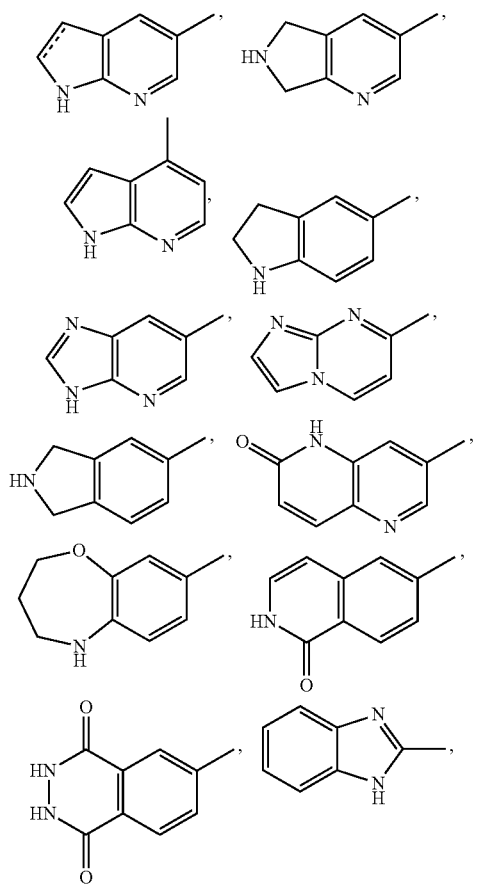

-continued wherein

------ represents a single bond or a double bond and $R^6$ is as defined above, (5) 3-pyridyl optionally substituted by 1 or 2 substituents selected from the group consisting of
  (a) a halogen atom,
  (b) cyano,
  (c) nitro,
  (d) hydroxy,
  (e) amino,
  (f) alkyl optionally substituted by 1 to 3 substituents selected from the group consisting of a halogen atom, alkylamino, dialkylamino and hydroxy,
  (g) alkenyl or alkynyl,
  (h) aryl,
  (i) cycloalkyl,
  (j) alkoxy,
  (k) alkylamino,
  (l) dialkylamino,
  (m) phenylamino optionally substituted by 1 to 3 halogen atoms,
  (n) a cyclic amino group optionally substituted by alkoxycarbonyl,
  (o) formyl,
  (p) carbamoyl optionally substituted by alkyl optionally substituted by hydroxy, and
  (q) a 5- to 10-membered aromatic heterocyclic group optionally substituted by alkyl, (6) 4-pyridyl optionally substituted by a halogen atom, (7) 5-pyrimidinyl optionally substituted by 1 or 2 substituents selected from the group consisting of amino, alkylamino, dialkylamino and carboxy, (8) 2-indolyl, 3-indolyl, 5-indolyl, 6-indolyl, benzofuranyl, benzothiophenyl, benzoxazolyl or benzothiazolyl, each optionally substituted by 1 or 2 substituents selected from the group consisting of
  (a) a halogen atom,
  (b) cyano,
  (c) nitro,
  (d) hydroxy,
  (e) alkyl optionally substituted by 1 to 3 substituents selected from the group consisting of amino, alkoxycarbonylamino, alkylamino and dialkylamino,
  (f) alkoxy,
  (g) formyl,
  (h) carboxy, and
  (j) amino optionally substituted by 1 or 2 substituents selected from the group consisting of (i) alkoxycarbonyl,
(ii) alkylcarbonyl optionally substituted by a substituent selected from the group consisting of
  (A) cycloalkyloxy optionally substituted by 1 to 3 alkyl,
  (B) alkylamino,
  (C) dialkylamino,
  (D) a cyclic amino group optionally substituted by alkoxycarbonyl, and
  (E) a halogen atom,
(iii) phenylcarbonyl optionally substituted by 1 to 3 substituents selected from the group consisting of alkyl and alkoxy,
(iv) cycloalkylcarbonyl,
(v) a 5- to 10-membered aromatic heterocyclylcarbonyl group optionally substituted by alkyl optionally substituted by 1 to 3 halogen atoms,
(vi) benzylcarbonyl optionally substituted by 1 to 3 substituents selected from the group consisting of a halogen atom and alkoxy,
(vii) arylsulfonyl optionally substituted by alkoxy,
(viii) cycloalkylalkylsulfonyl optionally substituted by 1 to 3 substituents selected from the group consisting of alkyl and oxo,
(ix) a 5- to 10-membered aromatic heterocyclylsulfonyl group optionally substituted by 1 to 3 alkyl, and
(x) —C(=N—CN)—SR$^9$ wherein R$^9$ is alkyl,
(9) a group of the formula

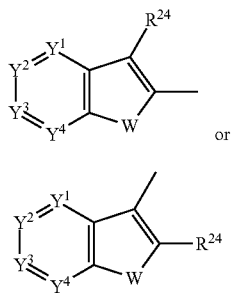

wherein
one of Y$^1$, Y$^2$, Y$^3$ and Y$^4$ is N or N$^+$(—O$^-$), and the remaining three are each C(R$^{25}$), C(R$^{26}$) and C(R$^{27}$),
W is O, S or N(R$^{23}$)
R$^{23}$ is a hydrogen atom or alkyl, and
R$^{24}$, R$^{25}$, R$^{26}$ and R$^{27}$ are each independently,
  (a) a hydrogen atom,
  (b) cyano, or
  (c) nitro,
(10) a group of the formula

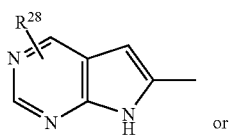

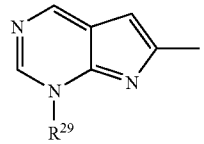

wherein
R$^{28}$ is a hydrogen atom or hydroxy, and
R$^{29}$ is a hydrogen atom or alkyl,
(11) a group of the formula

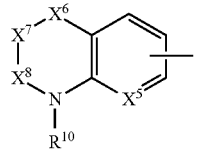

wherein
X$^5$ is C(R$^{11}$) or N,
X$^6$ is CH$_2$, C(=O), O, S, SO$_2$ or N(R$^{12}$),
X$^7$ is CH(R$^{13}$), C(=O) or N(R$^{14}$),
X$^8$ is CH(R$^{15}$) or C(=O),
R$^{10}$, R$^{12}$ and R$^{14}$ are each independently,
  (a) a hydrogen atom or
  (b) alkyl, and
R$^{11}$, R$^{13}$ and R$^{15}$ are each independently,
  (a) a hydrogen atom,
  (b) a halogen atom,
  (c) cyano,
  (d) nitro,
  (e) amino,
  (f) alkylamino,
  (g) dialkylamino,
  (h) alkyl optionally substituted by hydroxy, or
  (i) alkenyl,
when X$^5$ is C(R$^{11}$), R$^{10}$ and R$^{11}$ are optionally bonded to form a 5- or 6-membered ring optionally substituted by alkyl or oxo, and when X$^6$ is N(R$^{12}$) and X$^7$ is CH(R$^{13}$), R$^{12}$ and R$^{13}$ are optionally bonded to form a 5- or 6-membered ring,
(12) a group of the formula

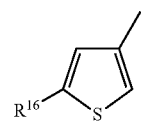

wherein R$^{16}$ is
  (a) a hydrogen atom,
  (b) alkyl optionally substituted by 1 to 3 substituents selected from the group consisting of cyano, alkylamino and dialkylamino,
  (c) alkenyl optionally substituted by carboxy,
  (d) formyl,
  (e) carboxy,
  (f) carbamoyl,
  (g) —C(R$^{17}$)=N—OH wherein R$^{17}$ is a hydrogen atom, cyano or hydroxy, (h) a 5- to 10-membered aromatic heterocyclic group optionally substituted by alkyl, alkoxycarbonyl, carboxy or phenyl, or
(i) cyano,
(13) a group of the formula

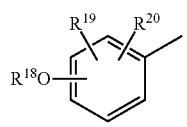

wherein
$R^{18}$ is a hydrogen atom or alkyl optionally substituted by 1 to 3 substituents selected from the group consisting of a halogen atom and phenyl, and
$R^{19}$ and $R^{20}$ are each independently,
(a) a hydrogen atom,
(b) a halogen atom,
(c) cyano,
(d) alkyl optionally substituted by 1 to 3 substituents selected from the group consisting of
  (i) a halogen atom,
  (ii) cyano,
  (iii) hydroxy,
  (iv) amino,
  (v) alkylamino,
  (vi) dialkylamino, and
  (vii) a cyclic amino group optionally substituted by alkyl,
(e) alkoxy,
(f) amino optionally substituted by 1 or 2 substituents selected from the group consisting of
  (i) alkylcarbonyl optionally substituted by a cyclic amino group,
  (ii) alkylsulfonyl,
  (iii) carbamoyl, and
  (iv) alkyl or cycloalkyl,
(g) carboxy,
(h) alkoxycarbonyl,
(i) carbamoyl optionally substituted by alkyl optionally substituted by amino, alkylamino, dialkylamino or alkoxycarbonylamino,
(j) formyl,
(k) a 5- to 10-membered aromatic heterocyclic group optionally substituted by alkyl,
(l) —CH=N—OR$^{21}$ wherein R$^{21}$ is a hydrogen atom or alkyl optionally substituted by alkylamino or dialkylamino, or
(m) nitro,
(14) a group of the formula

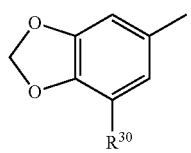

wherein
$R^{30}$ is (a) a hydrogen atom,
(b) a halogen atom,
(c) cyano, (d) alkyl optionally substituted by 1 to 3 substituents selected from the group consisting of a halogen atom and hydroxy,
(e) alkenyl,
(f) alkynyl,
(g) alkoxy,
(h) formyl, or
(i) —CH=N—OH,
(15) naphthyl or isochromenyl, or
(16) quinolyl or isoquinolyl, or oxide derivative thereof, or a salt thereof.

Item 2. The compound of item 1 or 1A, wherein X is a fluorine atom, or a salt thereof.

Item 3. The compound of item 1 or 1A, wherein $R^3$ is a fused heterocyclic group of the formula

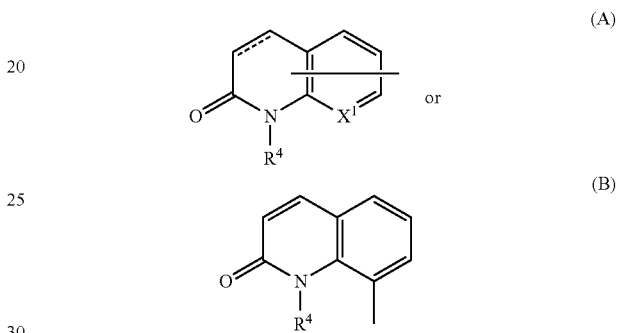

wherein ------, $X^1$ and $R^4$ are as defined in item 1, and said fused heterocyclic group is optionally substituted by 1 or 2 substituents selected from the group consisting of a halogen atom, cyano, nitro, hydroxy and alkyl, or a salt thereof.

Item 4. The compound of item 1 or 1A, wherein $R^3$ is a group of the formula

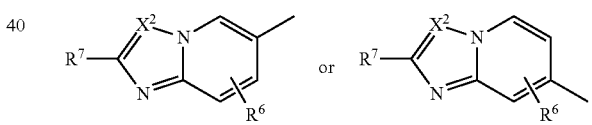

wherein $X^2$, $R^6$ and $R^7$ are as defined in item 1, or a salt thereof.

Item 5. The compound of item 1 or 1A, wherein $R^3$ is a group of the formula

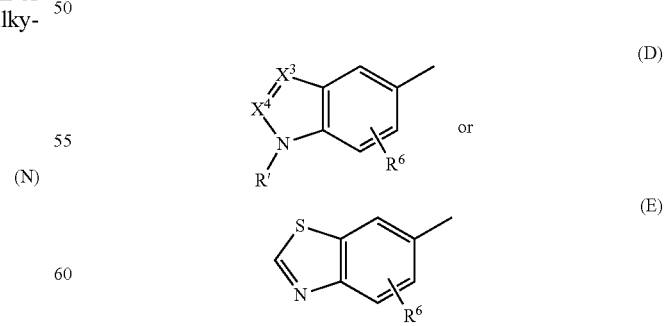

wherein $X^3$, $X^4$, $R^6$ and R' are as defined in item 1, or a salt thereof.

Item 6. The compound of item 1 or 1A, wherein $R^3$ is a group of the formula

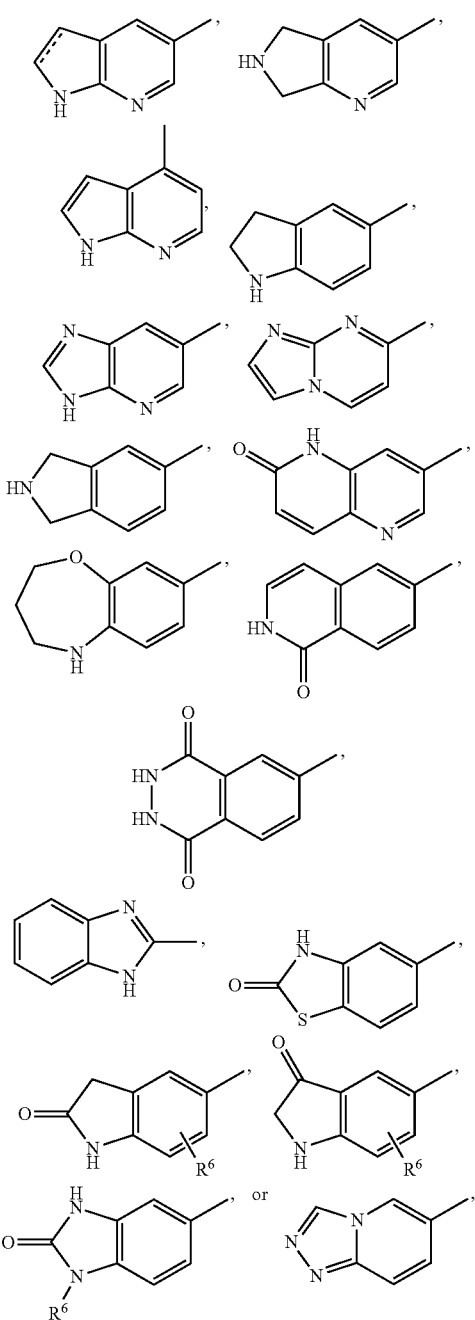

wherein ----- and R⁶ are as defined in item 1, or a salt thereof.

Item 7. The compound of item 1 or 1A, wherein R³ is a group of the formula

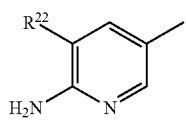

wherein R²² is
(a) a halogen atom,
(b) cyano, (c) nitro,
(d) alkyl optionally substituted by 1 to 3 substituents selected from the group consisting of a halogen atom, alkylamino, dialkylamino and hydroxy,
(e) alkenyl or alkynyl,
(f) aryl,
(g) cycloalkyl,
(h) alkoxy,
(i) formyl, or
(j) carbamoyl optionally substituted by alkyl optionally substituted by hydroxy,
or a salt thereof.

Item 8. The compound of item 1 or 1A, wherein R³ is 5-pyrimidinyl substituted by 1 or 2 substituents selected from the group consisting of amino, alkylamino, dialkylamino and carboxy, or a salt thereof.

Item 9. The compound of item 1 or 1A, wherein R³ is 2-indolyl optionally substituted by 1 or 2 substituents selected from the group consisting of
(a) a halogen atom,
(b) cyano,
(c) nitro,
(d) hydroxy,
(e) alkyl optionally substituted by 1 to 3 substituents selected from the group consisting of amino, alkoxycarbonylamino, alkylamino and dialkylamino,
(f) alkoxy,
(g) formyl,
(h) carboxy, and
(j) amino optionally substituted by 1 or 2 substituents selected from the group consisting of
  (i) alkoxycarbonyl,
  (ii) alkylcarbonyl optionally substituted by a substituent selected from the group consisting of
    (A) cycloalkyloxy optionally substituted by 1 to 3 alkyl,
    (B) alkylamino,
    (C) dialkylamino,
    (D) a cyclic amino group optionally substituted by alkoxycarbonyl, and
    (E) a halogen atom,
  (iii) phenylcarbonyl optionally substituted by 1 to 3 substituents selected from the group consisting of alkyl and alkoxy,
  (iv) cycloalkylcarbonyl,
  (v) a 5- to 10-membered aromatic heterocyclylcarbonyl group optionally substituted by alkyl optionally substituted by 1 to 3 halogen atoms,
  (vi) benzylcarbonyl optionally substituted by 1 to 3 substituents selected from the group consisting of a halogen atom and alkoxy,
  (vii) arylsulfonyl optionally substituted by alkoxy,
  (viii) cycloalkylalkylsulfonyl optionally substituted by 1 to 3 substituents selected from the group consisting of alkyl and oxo,
  (ix) a 5- to 10-membered aromatic heterocyclylsulfonyl group optionally substituted by 1 to 3 alkyl, and
  (x) —C(=N—CN)—SR⁹ wherein R⁹ is alkyl, or a salt thereof.

Item 10. The compound of item 1 or 1A, wherein $R^3$ is a group of the formula

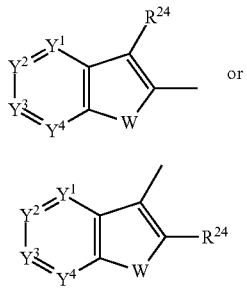

(F)

or (G)

wherein $Y^1, Y^2, Y^3, Y^4$, W and $R^{24}$ are as defined in item 1, or a salt thereof.

Item 11. The compound of item 1 or 1A, wherein $R^3$ is a group of the formula

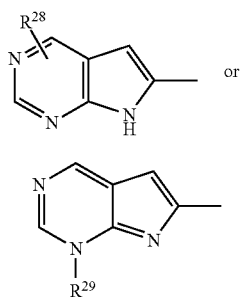

(H)

or (J)

wherein $R^{28}$ and $R^{29}$ are as defined in item 1, or a salt thereof.

Item 12. The compound of item 1 or 1A, wherein $R^3$ is a group of the formula

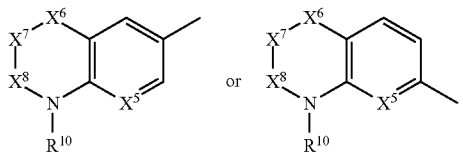

or wherein $X^5, X^6, X^7, X^8$ and $R^{10}$ are as defined in item 1, or a salt thereof.

Item 13. The compound of item 1 or 1A, wherein $R^3$ is a group of the formula

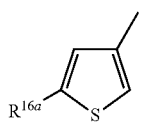

wherein $R^{16a}$ is
(a) alkyl optionally substituted by 1 to 3 substituents selected from the group consisting of cyano, alkylamino and dialkylamino,
(b) alkenyl optionally substituted by carboxy,
(c) formyl,
(d) carboxy,
(e) carbamoyl,
(f) —C($R^{17}$)=N—OH wherein $R^{17}$ is a hydrogen atom, cyano or hydroxy,
(g) a 5- to 10-membered aromatic heterocyclic group optionally substituted by alkyl, alkoxycarbonyl, carboxy or phenyl, or
(h) cyano,
or a salt thereof.

Item 14. The compound of item 1 or 1A, wherein $R^3$ is a group of the formula

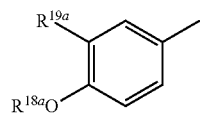

wherein
$R^{18a}$ is alkyl, and
$R^{19a}$ is (a) a halogen atom,
(b) cyano,
(c) alkyl optionally substituted by 1 to 3 substituents selected from the group consisting of
(i) a halogen atom,
(ii) cyano,
(iii) hydroxy,
(iv) amino,
(v) alkylamino,
(vi) dialkylamino, and
(vii) a cyclic amino group optionally substituted by alkyl,
(d) alkoxy,
(e) amino optionally substituted by 1 or 2 substituents selected from the group consisting of
(i) alkylcarbonyl optionally substituted by a cyclic amino group,
(ii) alkylsulfonyl,
(iii) carbamoyl, and
(iv) alkyl or cycloalkyl,
(f) carboxy,
(g) alkoxycarbonyl,
(h) carbamoyl optionally substituted by alkyl optionally substituted by amino, alkylamino, dialkylamino or alkoxycarbonylamino,
(i) formyl,
(j) a 5- to 10-membered aromatic heterocyclic group optionally substituted by alkyl,
(k) —CH=N—O$R^{21}$ wherein $R^{21}$ is a hydrogen atom or alkyl optionally substituted by alkylamino or dialkylamino, or
(l) nitro,
or a salt thereof.

Item 15. The compound of item 1 or 1A, wherein $R^3$ is a group of the formula

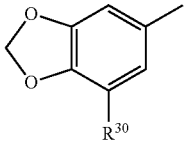

(N)

wherein $R^{30}$ is as defined in item 1, or a salt thereof.

Item 16. The compound of item 1 or 1A, wherein $R^3$ is naphthyl or isochromenyl, or a salt thereof.

Item 17. The compound of item 1 or 1A, wherein $R^3$ is quinolyl or isoquinolyl, or oxide derivative thereof, or a salt thereof.

Item 18. The compound of item 1 or 1A, wherein R is a hydrogen atom, or a salt thereof.

Item 19. The compound of item 1 or 1A, wherein $R^1$ is cyclopropyl, 2-fluorocyclopropyl or 2,4-difluorophenyl, or a salt thereof.

Item 20. The compound of item 1 or 1A, wherein $R^2$ is methyl, methoxy or a chlorine atom, or a salt thereof.

Item 21. A pharmaceutical composition comprising a compound of item 1 or 1A or a salt thereof and a pharmaceutically acceptable carrier.

Item 22. An antimicrobial agent comprising a compound of item 1 or 1A or a salt thereof.

Item 23. A compound of item 1 or 1A or a salt thereof for use as a medicament.

Item 24. A compound of item 1 or 1A or a salt thereof for use as an antimicrobial agent.

Item 25. A compound of item 1 or 1A or a salt thereof for use in the prevention or treatment of a bacterial infection.

Item 26. Use of a compound of item 1 or 1A or a salt thereof for the manufacture of a medicament for preventing or treating a bacterial infection.

Item 27. A method for preventing or treating a bacterial infection which comprises administering an effective amount of a compound of item 1 or 1A or a salt thereof to a human or an animal.

The compound of the formula (I) or a salt thereof (hereinafter sometimes to be abbreviated as compound (I)) has excellent antibacterial activity against various gram positive and gram negative bacteria, and is useful for the prevention or treatment of various infectious diseases induced by various bacteria in human, other animals and fish and is also useful as an external antimicrobial or disinfectant agent for medical instruments or the like.

DETAILED DESCRIPTION OF THE INVENTION

Figure 1:
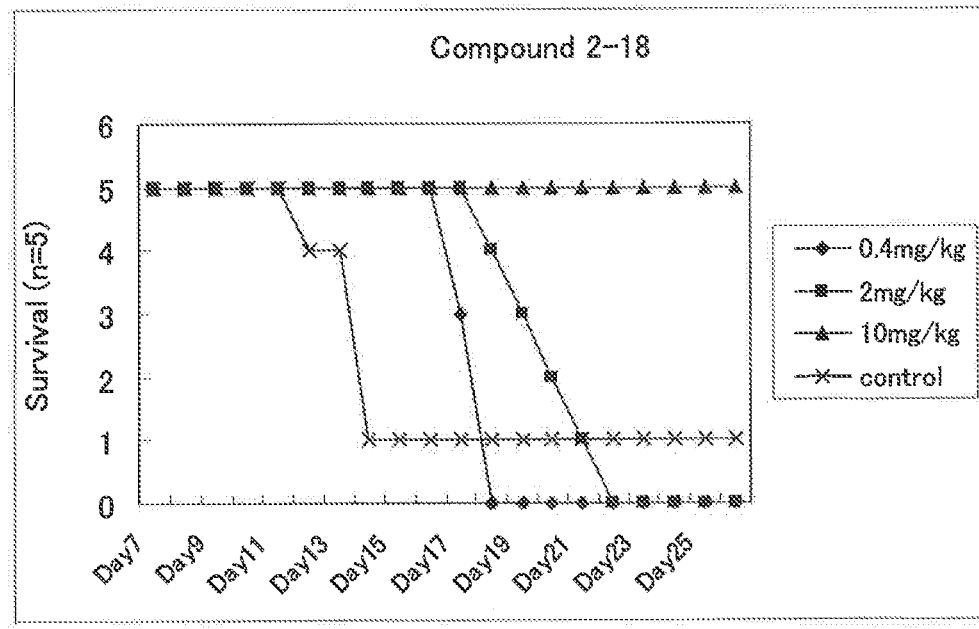
FIG. 1 is a graph showing the results of the animals administered with compound 2-18 in Experimental Example 2.

Specific examples of groups in the formula (I) are as follows.

Examples of "halogen atom" include fluorine atom, chlorine atom, bromine atom, and iodine atom.

Examples of "alkyl" and "alkyl" moiety in "alkylamino", "dialkylamino", "alkylcarbonyl", "cycloalkylalkylsulfonyl", "cycloalkylalkyl", "aminoalkyl" and "alkylsulfonyl" include straight or branched $C_{1-6}$ alkyl such as methyl, ethyl, propyl, isopropyl, butyl, isobutyl, sec-butyl, tert-butyl, pentyl, 1-ethylpropyl, isopentyl, neopentyl, tert-pentyl, hexyl, 1,2,2-trimethylpropyl, 3,3-dimethylbutyl, 2-ethylbutyl, isohexyl, 3-methylpentyl, etc.

Examples of "alkenyl" include straight or branched $C_{2-6}$ alkenyl such as vinyl, 1-propenyl, 2-propenyl, 1-butenyl, 2-butenyl, 3-butenyl, 1-methyl-2-propenyl, 2-pentenyl, 2-hexenyl, etc.

Examples of "alkynyl" include straight or branched $C_{2-6}$ alkynyl such as ethynyl, 2-propynyl, 2-butynyl, 3-butynyl, 1-methyl-2-propynyl, 2-pentynyl, 2-hexynyl, etc.

Examples of "alkoxy" and "alkoxy" moiety in "haloalkoxy", "alkoxycarbonyl" and "alkoxycarbonylamino" include straight or branched $C_{1-6}$ alkoxy such as methoxy, ethoxy, propoxy, isopropoxy, butoxy, isobutoxy, sec-butoxy, tert-butoxy, pentyloxy, isopentyloxy, neopentyloxy, tert-pentyloxy, hexyloxy, isohexyloxy, 3-methylpentyloxy, etc.

Examples of "haloalkoxy" include straight or branched $C_{1-6}$ alkoxy substituted by 1 to 3 halogen atoms. Examples thereof include fluoromethoxy, difluoromethoxy, trifluoromethoxy, chloromethoxy, dichloromethoxy, trichloromethoxy, bromomethoxy, dibromomethoxy, dichlorofluoromethoxy, 2,2,2-trifluoroethoxy, 2-chloroethoxy, 3,3,3-trifluoropropoxy, 2-chloropropoxy, 3-chloropropoxy, 3-bromopropoxy, 4,4,4-trifluorobutoxy, 2-chlorobutoxy, 4-chlorobutoxy, 4-bromobutoxy, 5,5,5-trifluoropentyloxy, 5-chloropentyloxy, 6,6,6-trifluorohexyloxy, 6-chlorohexyloxy, etc. Preferable examples thereof include difluoromethoxy.

Examples of "alkenyloxy" include straight or branched $C_{2-6}$ alkenyloxy such as vinyloxy, 1-propenyloxy, 2-propenyloxy, 1-butenyloxy, 2-butenyloxy, 3-butenyloxy, 1-methyl-2-propenyloxy, 2-pentenyloxy, 2-hexenyloxy, etc.

Examples of "aryl" and "aryl" moiety in "arylsulfonyl" include $C_{6-14}$ (preferably $C_{6-10}$) aryl such as phenyl, naphthyl (e.g., 1-naphthyl, 2-naphthyl), etc. Preferable examples thereof include phenyl.

Examples of "5- to 10-membered aromatic heterocyclic group" and "5- to 10-membered aromatic heterocyclyl" moiety in "5- to 10-membered aromatic heterocyclylcarbonyl group" and "5- to 10-membered aromatic heterocyclylsulfonyl group" include 5- to 10-membered (preferably 5- or 6-membered) aromatic heterocyclic group containing 1 to 4 (preferably 1 to 3, more preferably 1 or 2) heteroatoms selected from a nitrogen atom, an oxygen atom and a sulfur atom. Examples thereof include furyl, thienyl, pyrrolyl, pyrazolyl, imidazolyl, triazolyl (e.g., 1,2,3-triazolyl, 1,2,4-triazolyl), tetrazolyl, isoxazolyl, oxazolyl, furazanyl, isothiazolyl, thiazolyl, pyridyl (e.g., 2-pyridyl, 3-pyridyl, 4-pyridyl), pyridazinyl, pyrimidinyl, pyrazinyl, benzofuranyl, isobenzofuranyl, benzo[b]thiophenyl, benzo[c]thiophenyl, indolyl, isoindolyl, indolizinyl, indazolyl, benzimidazolyl, benzotriazolyl, benzoxazolyl, 1,2-benzisoxazolyl, benzothiazolyl, 1,2-benzisothiazolyl, purinyl, quinolyl, isoquinolyl, quinolizinyl, cinnolinyl, quinazolinyl, quinoxalinyl, phthalazinyl, naphthyridinyl, pteridinyl, etc. Preferable examples thereof include pyrrolyl, imidazolyl, oxazolyl, triazolyl (e.g., 1,2,3-triazolyl, 1,2,4-triazolyl), tetrazolyl, pyridyl (e.g., 2-pyridyl, 3-pyridyl, 4-pyridyl), benzimidazolyl, etc.

Examples of "alkylamino" include $C_{1-6}$ alkylamino such as methylamino, ethylamino, propylamino, isopropylamino, butylamino, isobutylamino, sec-butylamino, tert-butylamino, pentylamino, isopentylamino, neopentylamino, tert-pentylamino, hexylamino, etc.

Examples of "dialkylamino" include di($C_{1-6}$ alkyl)amino such as dimethylamino, diethylamino, dipropylamino, diisopropylamino, dibutylamino, diisobutylamino, di(sec-butyl)amino, di(tert-butyl)amino, dipentylamino, di(tert-pentyl)amino, dihexylamino, ethylmethylamino, etc.

Examples of "aminoalkyl" include amino-$C_{1-6}$ alkyl such as aminomethyl, 2-aminoethyl, 3-aminopropyl, 4-aminobutyl, 5-aminopentyl, 6-aminohexyl, etc.

Examples of "cycloalkyl" and "cycloalkyl" moiety in "cycloalkyloxy", "cycloalkylcarbonyl", "cycloalkylalkyl" and "cycloalkylalkylsulfonyl" include $C_{3-8}$ cycloalkyl such as cyclopropyl, cyclobutyl, cyclopentyl, cyclohexyl, cycloheptyl, cyclooctyl, norbornanyl (e.g., 2-norbornanyl), etc.

Examples of "cycloalkylalkyl" include $C_{3-8}$ cycloalkyl-$C_{1-6}$ alkyl such as cyclopropylmethyl, cyclobutylmethyl, cyclopentylmethyl, cyclohexylmethyl, cycloheptylmethyl, cyclooctylmethyl, norbornanylmethyl (e.g., norbornan-2-ylmethyl), etc.

Examples of "cyclic amino group" includes a 4- to 7-membered (preferably 5- or 6-membered) cyclic amino group containing one nitrogen atom and optionally further containing one heteroatom selected from a nitrogen atom, an oxygen atom and a sulfur atom. Examples thereof include 1-azetidinyl, 1-pyrrolidinyl, 1-imidazolidinyl, 1-pyrazolidinyl, piperidino, 1-piperazinyl, morpholino, thiomorpholino, 1-azepanyl, 1,4-oxazepane-4-yl, etc. Preferable examples thereof include 1-pyrrolidinyl, piperidino, 1-piperazinyl, morpholino, thiomorpholino, etc.

Examples of "alkoxycarbonyl" include $C_{1-6}$ alkoxy-carbonyl wherein the alkoxy moiety is $C_{1-6}$ alkoxy. Examples thereof include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, hexyloxycarbonyl, etc.

Examples of "alkoxycarbonylamino" include $C_{1-6}$ alkoxycarbonylamino wherein the alkoxy moiety is $C_{1-6}$ alkoxy. Examples thereof include methoxycarbonylamino, ethoxycarbonylamino, propoxycarbonylamino, isopropoxycarbonylamino, butoxycarbonylamino, isobutoxycarbonylamino, sec-butoxycarbonylamino, tert-butoxycarbonylamino, pentyloxycarbonylamino, hexyloxycarbonylamino, etc.

Examples of "alkylcarbonyl" include $C_{1-6}$ alkyl-carbonyl wherein the alkyl moiety is $C_{1-6}$ alkyl. Examples thereof include acetyl, ethylcarbonyl, propylcarbonyl, isopropylcarbonyl, butylcarbonyl, isobutylcarbonyl, sec-butylcarbonyl, tert-butylcarbonyl, pentylcarbonyl, hexylcarbonyl, etc.

Examples of "cycloalkyloxy" include $C_{3-8}$ cycloalkyloxy such as cyclopropyloxy, cyclobutyloxy, cyclopentyloxy, cyclohexyloxy, cycloheptyloxy, cyclooctyloxy, etc.

Examples of "cycloalkylcarbonyl" include $C_{3-8}$ cycloalkylcarbonyl such as cyclopropylcarbonyl, cyclobutylcarbonyl, cyclopentylcarbonyl, cyclohexylcarbonyl, cycloheptylcarbonyl, cyclooctylcarbonyl, etc.

Examples of "5- to 10-membered aromatic heterocyclylcarbonyl group" include a 5- to 10-membered (preferably 5- or 6-membered) aromatic heterocyclylcarbonyl group wherein the heterocyclyl moiety contains 1 to 4 (preferably 1 to 3, more preferably 1 or 2) heteroatoms selected from a nitrogen atom, an oxygen atom and a sulfur atom. Examples of the heterocyclyl moiety are same as the examples of the 5- to 10-membered aromatic heterocyclic group mentioned above. Preferable examples of "5- to 10-membered aromatic heterocyclylcarbonyl group" include pyridylcarbonyl (e.g., 2-pyridylcarbonyl, 3-pyridylcarbonyl, 4-pyridylcarbonyl).

Examples of "arylsulfonyl" include $C_{6-14}$ (preferably $C_{6-10}$) arylsulfonyl such as phenylsulfonyl, naphthylsulfonyl (e.g., 1-naphthylsulfonyl, 2-naphthylsulfonyl), etc. Preferable examples thereof include phenylsulfonyl.

Examples of "cycloalkylalkylsulfonyl" include $C_{3-8}$ cycloalkyl-$C_{1-6}$ alkylsulfonyl such as cyclopropylmethylsulfonyl, cyclobutylmethylsulfonyl, cyclopentylmethylsulfonyl, cyclohexylmethylsulfonyl, cycloheptylmethylsulfonyl, cyclooctylmethylsulfonyl, norbornanylmethylsulfonyl (e.g., norbornan-2-ylmethylsulfonyl), etc.

Examples of "5- to 10-membered aromatic heterocyclylsulfonyl group" include a 5- to 10-membered (preferably 5- or 6-membered) aromatic heterocyclylsulfonyl group wherein the heterocyclyl moiety contains 1 to 4 (preferably 1 to 3, more preferably 1 or 2) heteroatoms selected from a nitrogen atom, an oxygen atom and a sulfur atom. Examples of the heterocyclyl moiety are same as the examples of the 5- to 10-membered aromatic heterocyclic group mentioned above. Preferable examples of "5- to 10-membered aromatic heterocyclylsulfonyl group" include imidazolylsulfonyl.

Examples of "alkylsulfonyl" include $C_{1-6}$ alkylsulfonyl wherein the alkyl moiety is $C_{1-6}$ alkyl. Examples thereof include methylsulfonyl, ethylsulfonyl, propylsulfonyl, isopropylsulfonyl, butylsulfonyl, isobutylsulfonyl, sec-butylsulfonyl, tert-butylsulfonyl, pentylsulfonyl, hexylsulfonyl, etc.

Examples of "cyclopropyl optionally substituted by 1 to 3 halogen atoms" include cyclopropyl optionally substituted by 1 fluorine atom such as cyclopropyl, 2-fluorocyclopropyl, etc.

Examples of "phenyl optionally substituted by 1 to 3 halogen atoms" include phenyl substituted by two fluorine atoms such as 2,4-difluorophenyl, etc.

Examples of "5- to 10-membered saturated heterocyclic group" include a 5- to 10-membered (preferably 5- or 6-membered) saturated heterocyclic group containing 1 to 4 (preferably 1 to 3, more preferably 1 or 2) heteroatoms selected from a nitrogen atom, an oxygen atom and a sulfur atom. Examples thereof include pyrrolidinyl, piperidyl, piperazinyl, morpholinyl, thiomorpholinyl, etc.

Examples of "6-membered ring optionally substituted by amino or oxo" formed by $R^{34}$ and $R^{35}$ include a 6-membered ring optionally containing one nitrogen atom, and said ring is optionally substituted by amino or oxo. Examples thereof include cyclohexene and dihydropyridine, each optionally substituted by amino or oxo.

Examples of "5- or 6-membered ring optionally substituted by alkyl" formed by $R^1$ and $R^2$ include a 5- or 6-membered (preferably 6-membered) ring containing one nitrogen atom and optionally further containing one oxygen atom, and said ring is optionally substituted by alkyl. Preferably, $R^1$ and $R^2$ are optionally bonded to form —O—CH$_2$—CH(CH$_3$)— wherein the oxygen atom is bonded to the phenyl ring of the quinolone ring as shown below.

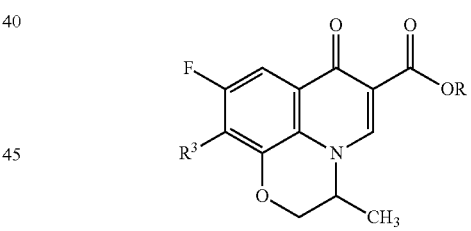

Examples of "5- or 6-membered ring optionally substituted by oxo" formed by $R^4$ and $R^5$ include a 5- or 6-membered (preferably 6-membered) ring containing one nitrogen atom and optionally further containing one oxygen atom, and said ring is optionally substituted by oxo. Preferably, $R^4$ and $R^5$ are optionally bonded to form —CH$_2$—O—(C=O)— wherein the carbonyl is bonded to the phenyl ring of the quinolone ring as shown below.

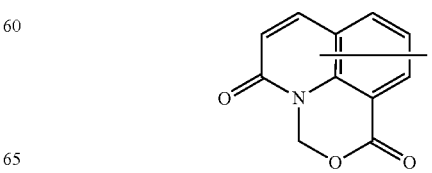

Examples of "5- or 6-membered ring optionally substituted by alkyl or oxo" formed by $R^{10}$ and $R^{11}$ include a 5- or 6-membered (preferably 5-membered) ring containing 2 or 3 nitrogen atoms, and said ring is optionally substituted by alkyl or oxo. Preferably, $R^{10}$ and $R^{11}$ are optionally bonded to form —(C=O)—NH—, —C($R^{31}$)=N— or —N=N— wherein $R^{31}$ is a hydrogen atom or alkyl, and the nitrogen atom is bonded to the phenyl ring of the fused ring, as shown below.

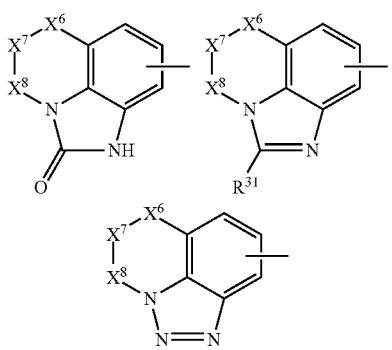

Examples of "5- or 6-membered ring" formed by $R^{12}$ and $R^{13}$ include a 5- or 6-membered (preferably 6-membered) ring containing one nitrogen atom. Preferably, $R^{12}$ and $R^{13}$ are optionally bonded to form —(CH$_2$)$_4$— as shown below.

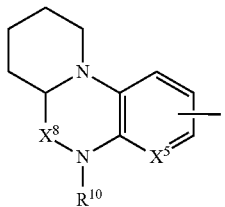

X is a hydrogen atom or a fluorine atom, preferably, a fluorine atom.

R is a hydrogen atom or alkyl, preferably, a hydrogen atom.

$R^1$ is (1) cyclopropyl optionally substituted by 1 to 3 halogen atoms or (2) phenyl optionally substituted by 1 to 3 halogen atoms, preferably, cyclopropyl, 2-fluorocyclopropyl or 2,4-difluorophenyl.

$R^2$ is a hydrogen atom; alkyl optionally substituted by 1 or 2 substituents selected from the group consisting of a halogen atom and hydroxyl; alkoxy; haloalkoxy; a halogen atom; cyano; cyclopropyl; nitro; amino; formyl; alkenyl or alkynyl, preferably, alkyl, alkoxy, haloalkoxy, a chlorine atom or cyano, more preferably, $C_{1-6}$ alkyl, $C_{1-6}$ alkoxy, $C_{1-6}$ alkoxy substituted by 1 to 3 halogen atoms, a chlorine atom or cyano, still more preferably, methyl, methoxy or a chlorine atom.

Examples of a fused heterocyclic group of the formula (A) or (B) include a fused heterocyclic group of the formula

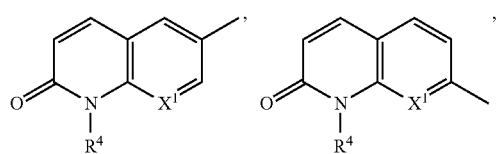

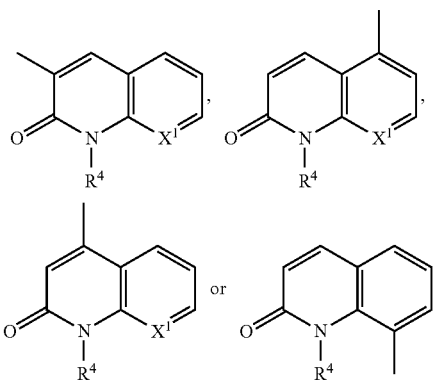

wherein $X^1$ and $R^4$ are as defined above, and said fused heterocyclic group is optionally substituted by 1 or 2 substituents selected from the group consisting of a halogen atom, cyano, nitro, hydroxy and alkyl.

Preferable examples of a fused heterocyclic group of the formula (A) or (B) include a fused heterocyclic group of the formula

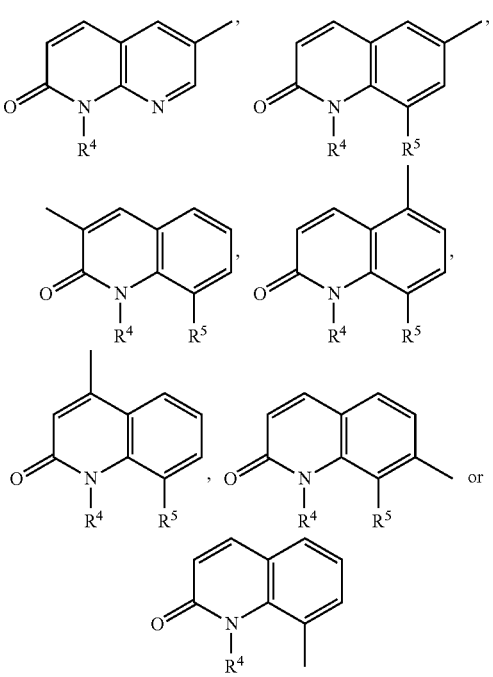

wherein $R^4$ and $R^5$ are as defined above, and said fused heterocyclic group is optionally substituted by 1 or 2 substituents selected from the group consisting of a halogen atom, cyano, nitro, hydroxy and alkyl.

Other preferable examples of a fused heterocyclic group of the formula (A) or (B) include a fused heterocyclic group of the formula

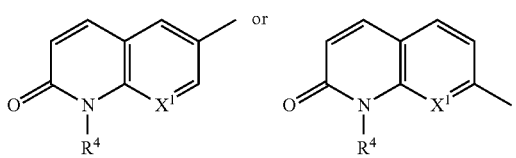

wherein $X^1$ and $R^4$ are as defined above, and said fused heterocyclic group is optionally substituted by 1 or 2 substituents selected from the group consisting of a halogen atom, cyano, nitro, hydroxy and alkyl.

Examples of a group of the formula (C) include a group of the formula

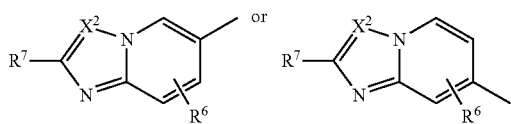

wherein $X^2$, $R^6$ and $R^7$ are as defined above.

Preferable examples of a group of the formula (C) include a group of the formula

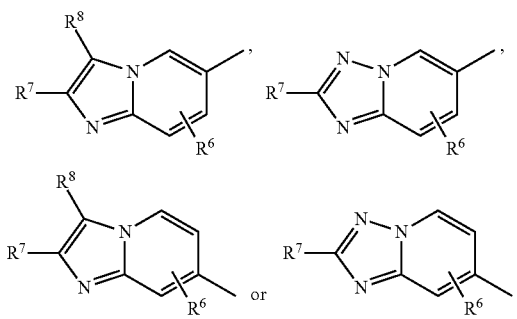

wherein $R^6$, $R^7$ and $R^8$ are as defined above.

In the above formulas, $R^6$, $R^7$ and $R^8$ are each independently,
   (a) a hydrogen atom,
   (b) a halogen atom,
   (c) cyano,
   (d) nitro,
   (e) amino,
   (f) alkyl optionally substituted by 1 to 3 substituents selected from the group consisting of a halogen atom and amino,
   (g) alkenyl,
   (h) alkynyl,
   (i) aryl,
   (j) formyl,
   (k) carboxy,
   (l) carbamoyl, or
   (m) a 5- to 10-membered aromatic heterocyclic group (e.g., pyridyl, triazolyl) optionally substituted by alkyl.

Examples of a group of the formula (D) or (E) include a group of the formula

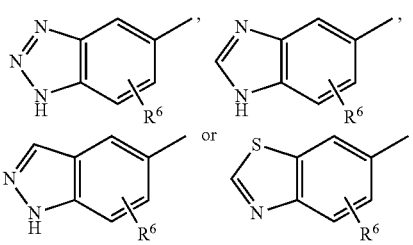

wherein $R^6$ is as defined above. $R^6$ is preferably a hydrogen atom, a halogen atom, nitro or amino.

Preferably, $R^3$ is 3-pyridyl optionally substituted by 1 or 2 substituents selected from the group consisting of
   (a) a halogen atom,
   (b) cyano,
   (c) nitro,
   (d) hydroxy,
   (e) amino,
   (f) alkyl optionally substituted by 1 to 3 substituents selected from the group consisting of a halogen atom, alkylamino, dialkylamino and hydroxy,
   (g) alkenyl,
   (h) aryl,
   (i) cycloalkyl,
   (j) alkoxy,
   (k) alkylamino,
   (l) dialkylamino,
   (m) phenylamino optionally substituted by 1 to 3 halogen atoms,
   (n) a cyclic amino group (e.g., 1-piperazinyl, morpholino) optionally substituted by alkoxycarbonyl,
   (o) formyl,
   (p) carbamoyl, and
   (q) a 5- to 10-membered aromatic heterocyclic group (e.g., triazolyl) optionally substituted by alkyl.

More preferably, $R^3$ is a group of the formula

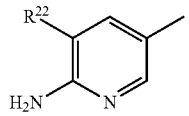

wherein $R^{22}$ is
   (a) a halogen atom,
   (b) cyano,
   (c) nitro,
   (d) alkyl optionally substituted by 1 to 3 substituents selected from the group consisting of a halogen atom, alkylamino, dialkylamino and hydroxy,
   (e) alkenyl,
   (f) aryl,
   (g) cycloalkyl,
   (h) alkoxy,
   (i) formyl, or
   (j) carbamoyl.
Preferably, $R^{22}$ is
   (a) cyano,
   (b) nitro,
   (c) aryl,
   (d) formyl, or
   (e) carbamoyl.

Preferably, $R^3$ is 5-pyrimidinyl substituted by 1 or 2 substituents selected from the group consisting of amino, alkylamino and dialkylamino.

Preferably, $R^3$ is 2-indolyl, 3-indolyl, 5-indolyl or 6-indolyl, each optionally substituted by 1 or 2 substituents selected from the group consisting of
(a) a halogen atom,
(b) cyano,
(c) nitro,
(d) hydroxy,
(e) alkyl optionally substituted by 1 to 3 substituents selected from the group consisting of amino, alkoxycarbonylamino, alkylamino and dialkylamino,
(f) alkoxy,
(g) formyl,
(h) carboxy, and
(j) amino optionally substituted by 1 or 2 substituents selected from the group consisting of
  (i) alkoxycarbonyl,
  (ii) alkylcarbonyl optionally substituted by a substituent selected from the group consisting of
    (A) cycloalkyloxy optionally substituted by 1 to 3 alkyl,
    (B) alkylamino,
    (C) dialkylamino,
    (D) a cyclic amino group (e.g., morpholino, 1-piperazinyl) optionally substituted by alkoxycarbonyl, and
    (E) a halogen atom,
  (iii) phenylcarbonyl optionally substituted by 1 to 3 substituents selected from the group consisting of alkyl and alkoxy,
  (iv) cycloalkylcarbonyl,
  (v) a 5- to 10-membered aromatic heterocyclylcarbonyl group (e.g, pyridylcarbonyl) optionally substituted by alkyl optionally substituted by 1 to 3 halogen atoms,
  (vi) benzylcarbonyl optionally substituted by 1 to 3 substituents selected from the group consisting of a halogen atom and alkoxy,
  (vii) arylsulfonyl optionally substituted by alkoxy,
  (viii) cycloalkylalkylsulfonyl optionally substituted by 1 to 3 substituents selected from the group consisting of alkyl and oxo (e.g., camphorsulfonyl),
  (ix) a 5- to 10-membered aromatic heterocyclylsulfonyl group (e.g., imidazolylsulfonyl) optionally substituted by 1 to 3 alkyl, and
  (x) —C(=N—CN)—SR$^9$ wherein R$^9$ is alkyl.

More preferably, $R^3$ is 2-indolyl optionally substituted by 1 or 2 substituents selected from the group consisting of
(a) a halogen atom,
(b) cyano,
(c) nitro,
(d) hydroxy,
(e) alkyl optionally substituted by 1 to 3 substituents selected from the group consisting of amino, alkoxycarbonylamino, alkylamino and dialkylamino,
(f) alkoxy,
(g) formyl,
(h) carboxy, and
(j) amino optionally substituted by 1 or 2 substituents selected from the group consisting of
  (i) alkoxycarbonyl,
  (ii) alkylcarbonyl optionally substituted by a substituent selected from the group consisting of
    (A) cycloalkyloxy optionally substituted by 1 to 3 alkyl,
    (B) alkylamino,
    (C) dialkylamino,
    (D) a cyclic amino group (e.g., morpholino, 1-piperazinyl) optionally substituted by alkoxycarbonyl, and
    (E) a halogen atom,
  (iii) phenylcarbonyl optionally substituted by 1 to 3 substituents selected from the group consisting of alkyl and alkoxy,
  (iv) cycloalkylcarbonyl,
  (v) a 5- to 10-membered aromatic heterocyclylcarbonyl group (e.g, pyridylcarbonyl) optionally substituted by alkyl optionally substituted by 1 to 3 halogen atoms,
  (vi) benzylcarbonyl optionally substituted by 1 to 3 substituents selected from the group consisting of a halogen atom and alkoxy,
  (vii) arylsulfonyl optionally substituted by alkoxy,
  (viii) cycloalkylalkylsulfonyl optionally substituted by 1 to 3 substituents selected from the group consisting of alkyl and oxo (e.g., camphorsulfonyl),
  (ix) a 5- to 10-membered aromatic heterocyclylsulfonyl group (e.g., imidazolylsulfonyl) optionally substituted by 1 to 3 alkyl, and
  (x) —C(=N—CN)—SR$^9$ wherein R$^9$ is alkyl.

Examples of a group of the formula (F) or (G) include a group of the formula

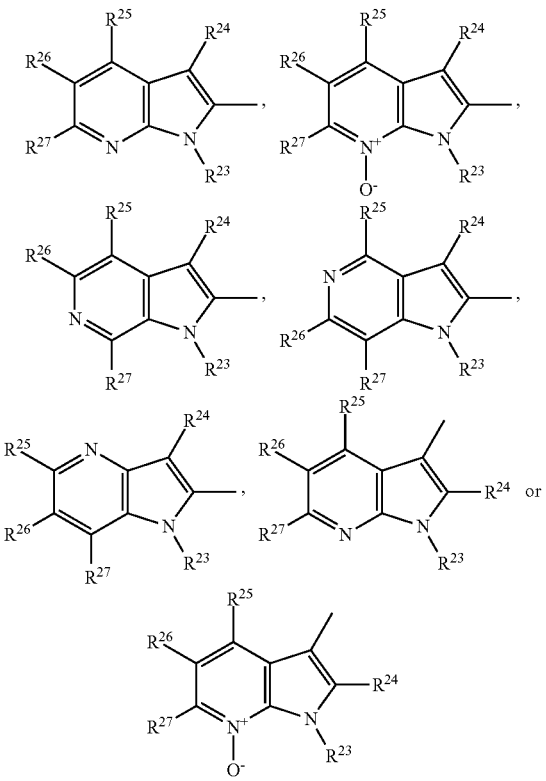

wherein
$R^{23}$ is a hydrogen atom or alkyl, and
$R^{24}$, $R^{25}$, $R^{26}$ and $R^{27}$ are each independently,
(a) a hydrogen atom,
(b) cyano, or
(c) nitro.

Examples of a group of the formula (K) include a group of the formula

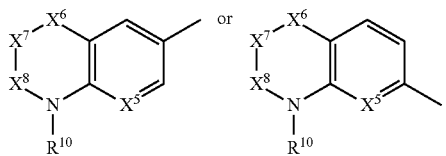

wherein $X^5$, $X^6$, $X^7$, $X^8$ and $R^{10}$ are as defined above.

Preferable examples of a group of the formula (K) include a group of the formula

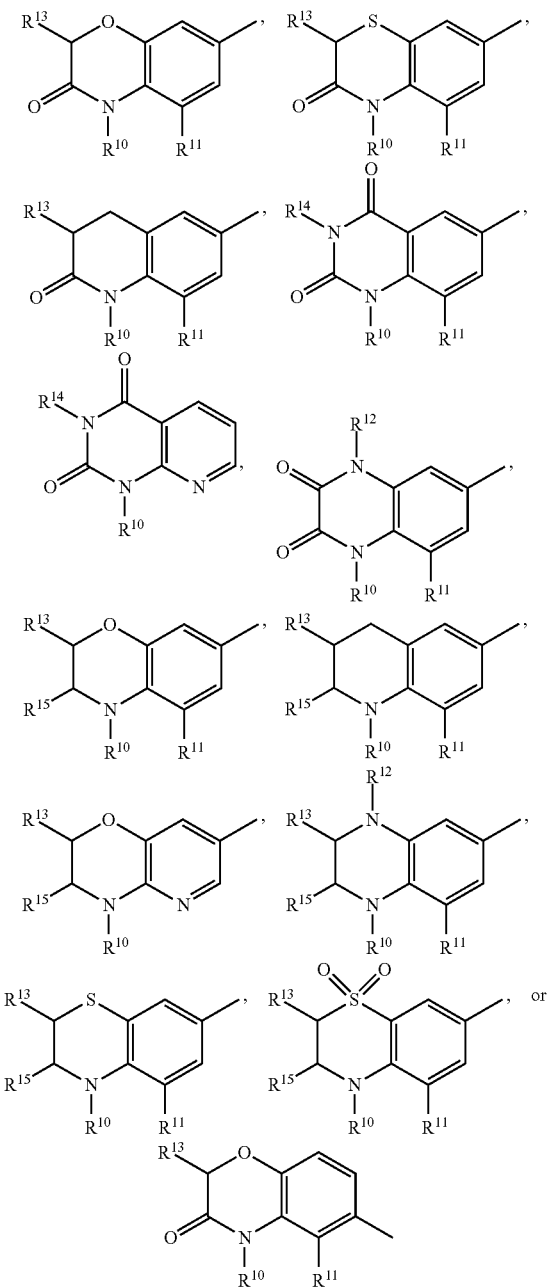

wherein $R^{10}$, $R^{11}$, $R^{12}$, $R^{13}$, $R^{14}$ and $R^{15}$ are as defined above.

When $R^{10}$ and $R^{11}$ are bonded to form a 5- or 6-membered ring optionally substituted by alkyl or oxo, preferable examples of a group of the formula (K) include a group of the formula

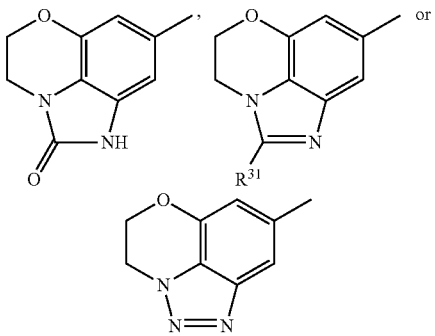

wherein $R^{31}$ is a hydrogen atom or alkyl.

When $R^{12}$ and $R^{13}$ are bonded to form a 5- or 6-membered ring, preferable examples of a group of the formula (K) include a group of the formula

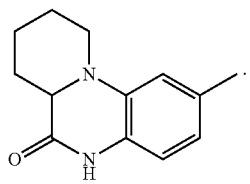 [SMILES: Cc1ccc2c(c1)N1CCCCC1C(=O)N2 ; "."]

More preferable examples of a group of the formula (K) include a group of the formula

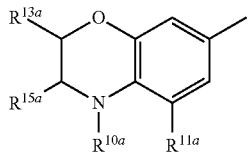

wherein $R^{10a}$ is
 (a) a hydrogen atom or
 (b) alkyl, and
$R^{11a}$, $R^{13a}$ and $R^{15a}$ are each independently,
 (a) a hydrogen atom,
 (b) a halogen atom,
 (c) cyano,
 (d) nitro,
 (e) amino,
 (f) alkylamino,
 (g) dialkylamino,
 (h) alkyl optionally substituted by hydroxy, or
 (i) alkenyl,
$R^{10a}$ and $R^{11a}$ are optionally bonded to form a 5- or 6-membered ring optionally substituted by alkyl or oxo,
provided that $R^{10a}$, $R^{11a}$, $R^{13a}$ and $R^{15a}$ are not simultaneously hydrogen atom.

Preferably, $R^3$ is a group of the formula

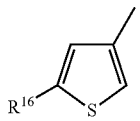

wherein $R^{16}$ is
(a) a hydrogen atom,
(b) alkyl optionally substituted by 1 to 3 substituents selected from the group consisting of cyano, alkylamino and dialkylamino,
(c) alkenyl optionally substituted by carboxy,
(d) formyl,
(e) carboxy,
(f) carbamoyl,
(g) —C($R^{17}$)=N—OH wherein $R^{17}$ is a hydrogen atom, cyano or hydroxy, or
(h) a 5- to 10-membered aromatic heterocyclic group (e.g., tetrazolyl, pyrrolyl, oxazolyl, benzimidazolyl, triazolyl) optionally substituted by alkyl, alkoxycarbonyl, carboxy or phenyl.

More preferably, $R^3$ is a group of the formula

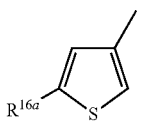

wherein $R^{16a}$ is
(a) alkyl optionally substituted by 1 to 3 substituents selected from the group consisting of cyano, alkylamino and dialkylamino,
(b) alkenyl optionally substituted by carboxy,
(c) formyl,
(d) carboxy,
(e) carbamoyl,
(f) —C($R^{17}$)=N—OH wherein $R^{17}$ is a hydrogen atom, cyano or hydroxy, or
(g) a 5- to 10-membered aromatic heterocyclic group (e.g., tetrazolyl, pyrrolyl, oxazolyl, benzimidazolyl, triazolyl) optionally substituted by alkyl, alkoxycarbonyl, carboxy or phenyl.

Preferably, $R^3$ is a group of the formula

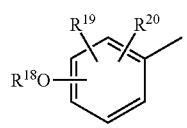

wherein
$R^{18}$ is alkyl optionally substituted by 1 to 3 substituents selected from the group consisting of a halogen atom and phenyl, and
$R^{19}$ and $R^{20}$ are each independently,
(a) a hydrogen atom,
(b) a halogen atom,
(c) cyano,
(d) alkyl optionally substituted by 1 to 3 substituents selected from the group consisting of
(i) a halogen atom,
(ii) cyano,
(iii) hydroxy,
(iv) amino,
(v) alkylamino,
(vi) dialkylamino, and
(vii) a cyclic amino group (e.g., 1-piperazinyl) optionally substituted by alkyl,
(e) alkoxy,
(f) amino optionally substituted by 1 or 2 substituents selected from the group consisting of
(i) alkylcarbonyl optionally substituted by a cyclic amino group (e.g., morpholino),
(ii) alkylsulfonyl, and
(iii) carbamoyl,
(g) carboxy,
(h) alkoxycarbonyl,
(i) carbamoyl optionally substituted by alkyl optionally substituted by amino, alkylamino, dialkylamino or alkoxycarbonylamino,
(j) formyl,
(k) a 5- to 10-membered aromatic heterocyclic group (e.g., oxazolyl, benzimidazolyl), or
(l) —CH=N—O$R^{21}$ wherein $R^{21}$ is a hydrogen atom or alkyl optionally substituted by alkylamino or dialkylamino.

More preferably, $R^3$ is a group of the formula

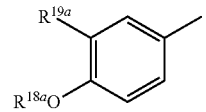

wherein
$R^{18a}$ is alkyl, and
$R^{19a}$ is (a) a halogen atom,
(b) cyano,
(c) alkyl optionally substituted by 1 to 3 substituents selected from the group consisting of
(i) a halogen atom,
(ii) cyano,
(iii) hydroxy,
(iv) amino,
(v) alkylamino,
(vi) dialkylamino, and
(vii) a cyclic amino group (e.g., 1-piperazinyl) optionally substituted by alkyl,
(d) alkoxy,
(e) amino optionally substituted by 1 or 2 substituents selected from the group consisting of
(i) alkylcarbonyl optionally substituted by a cyclic amino group (e.g., morpholino),
(ii) alkylsulfonyl, and
(iii) carbamoyl,
(f) carboxy,
(g) alkoxycarbonyl,
(h) carbamoyl optionally substituted by alkyl optionally substituted by amino, alkylamino, dialkylamino or alkoxycarbonylamino,
(i) formyl,
(j) a 5- to 10-membered aromatic heterocyclic group (e.g., oxazolyl, benzimidazolyl), or
(k) —CH=N—O$R^{21}$ wherein $R^{21}$ is a hydrogen atom or alkyl optionally substituted by alkylamino or dialkylamino.

Preferable examples of compound (I) are as described below.

[Compound I-1]

A compound of the formula (I) wherein

R is a hydrogen atom;

$R^1$ is cyclopropyl, 2-fluorocyclopropyl or 2,4-difluorophenyl;

$R^2$ is $C_{1-6}$ alkyl (e.g., methyl), $C_{1-6}$ alkoxy (e.g., methoxy) or a chlorine atom; or $R^1$ and $R^2$ are optionally bonded to form —O—CH$_2$—CH(CH$_3$)— wherein the oxygen atom is bonded to the phenyl ring of the quinolone ring; and $R^3$ is a fused heterocyclic group of the formula

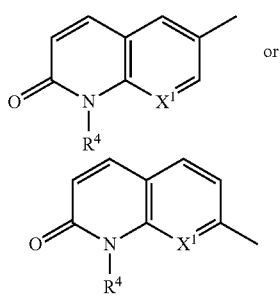

or wherein $X^1$ is $C(R^5)$ or N, $R^4$ is a hydrogen atom or $C_{1-6}$ alkyl, and $R^5$ is (a) a hydrogen atom,
(b) a halogen atom,
(c) cyano,
(d) nitro,
(e) hydroxy,
(f) $C_{1-6}$ alkyl optionally substituted by 1 to 3 halogen atoms,
(g) $C_{2-6}$ alkynyl,
(h) $C_{6-14}$ aryl, or
(i) $C_{1-6}$ alkoxy optionally substituted by 1 to 3 halogen atoms, when $X^1$ is $C(R^5)$, $R^4$ and $R^5$ are optionally bonded to form —CH$_2$—O—(C=O)— wherein the carbonyl is bonded to the phenyl ring of the quinolone ring, said fused heterocyclic group is optionally substituted by 1 or 2 substituents selected from the group consisting of a halogen atom, cyano, nitro, hydroxy and $C_{1-6}$ alkyl, or a salt thereof.

[Compound I-2]

A compound of the formula (I) wherein

R is a hydrogen atom;

$R^1$ is cyclopropyl, 2-fluorocyclopropyl or 2,4-difluorophenyl;

$R^2$ is $C_{1-6}$ alkyl (e.g., methyl), $C_{1-6}$ alkoxy (e.g., methoxy) or a chlorine atom; or $R^1$ and $R^2$ are optionally bonded to form —O—CH$_2$—CH(CH$_3$)— wherein the oxygen atom is bonded to the phenyl ring of the quinolone ring; and $R^3$ is a group of the formula

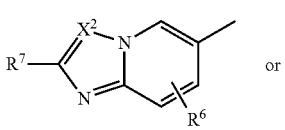

or

-continued

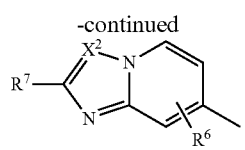

$X^2$ is $C(R^8)$ or N, and $R^6$, $R^7$ and $R^8$ are each independently,
(a) a hydrogen atom,
(b) a halogen atom,
(c) cyano,
(d) nitro,
(e) amino,
(f) $C_{1-6}$ alkyl optionally substituted by 1 to 3 substituents selected from the group consisting of a halogen atom and amino,
(g) $C_{2-6}$ alkenyl,
(h) $C_{2-6}$ alkynyl,
(i) $C_{6-14}$ aryl,
(j) formyl,
(k) carboxy,
(l) carbamoyl, or
(m) a 5- to 10-membered aromatic heterocyclic group (e.g., pyridyl, triazolyl) optionally substituted by $C_{1-6}$ alkyl, or a salt thereof.

[Compound I-3]

A compound of the formula (I) wherein

R is a hydrogen atom;

$R^1$ is cyclopropyl, 2-fluorocyclopropyl or 2,4-difluorophenyl;

$R^2$ is $C_{1-6}$ alkyl (e.g., methyl), $C_{1-6}$ alkoxy (e.g., methoxy) or a chlorine atom; and $R^3$ is a group of the formula

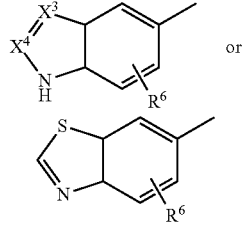

wherein $X^3$ and $X^4$ are N, or $X^3$ is N and $X^4$ is CH, or $X^3$ is CH and $X^4$ is N, and $R^6$ is a hydrogen atom, a halogen atom, nitro or amino, or a salt thereof.

[Compound I-4]

A compound of the formula (I) wherein

R is a hydrogen atom;

$R^1$ is cyclopropyl, 2-fluorocyclopropyl or 2,4-difluorophenyl;

$R^2$ is $C_{1-6}$ alkyl (e.g., methyl), $C_{1-6}$ alkoxy (e.g., methoxy) or a chlorine atom; and $R^3$ is a group of the formula

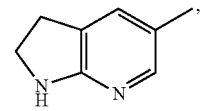

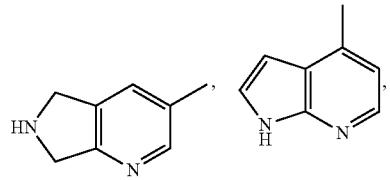

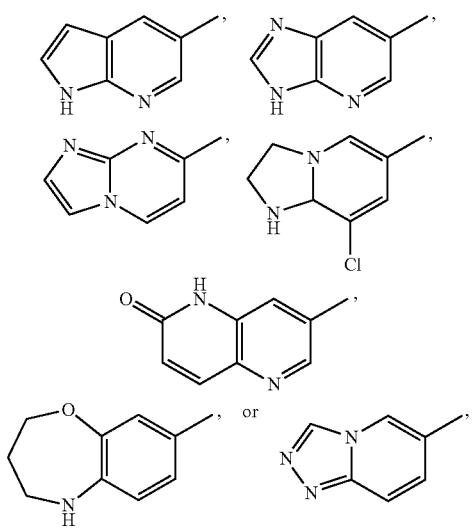

or a salt thereof.

[Compound I-5]

A compound of the formula (I) wherein

R is a hydrogen atom;

R$^1$ is cyclopropyl, 2-fluorocyclopropyl or 2,4-difluorophenyl;

R$^2$ is C$_{1-6}$ alkyl (e.g., methyl), C$_{1-6}$ alkoxy (e.g., methoxy) or a chlorine atom; or R$^1$ and R$^2$ are optionally bonded to form —O—CH$_2$—CH(CH$_3$)— wherein the oxygen atom is bonded to the phenyl ring of the quinolone ring; and R$^3$ is a group of the formula

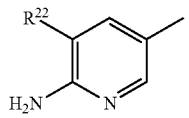

wherein R$^{22}$ is
  (a) a halogen atom,
  (b) cyano,
  (c) nitro,
  (d) C$_{1-6}$ alkyl optionally substituted by 1 to 3 substituents selected from the group consisting of a halogen atom, C$_{1-6}$ alkylamino, di(C$_{1-6}$ alkyl)amino and hydroxy,
  (e) C$_{2-6}$ alkenyl,
  (f) C$_{6-14}$ aryl,
  (g) C$_{3-8}$ cycloalkyl,
  (h) C$_{1-6}$ alkoxy,
  (i) formyl, or
  (j) carbamoyl,
or a salt thereof.

[Compound I-6]

A compound of the formula (I) wherein

R is a hydrogen atom;

R$^1$ is cyclopropyl, 2-fluorocyclopropyl or 2,4-difluorophenyl;

R$^2$ is C$_{1-6}$ alkyl (e.g., methyl), C$_{1-6}$ alkoxy (e.g., methoxy) or a chlorine atom; or R$^1$ and R$^2$ are optionally bonded to form —O—CH$_2$—CH(CH$_3$)— wherein the oxygen atom is bonded to the phenyl ring of the quinolone ring; and R$^3$ is a group of the formula

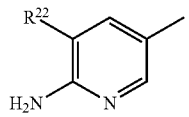

wherein R$^{22}$ is
  (a) cyano,
  (b) nitro,
  (c) C$_{6-14}$ aryl,
  (d) formyl, or
  (e) carbamoyl,
or a salt thereof.

[Compound I-7]

A compound of the formula (I) wherein

R is a hydrogen atom;

R$^1$ is cyclopropyl, 2-fluorocyclopropyl or 2,4-difluorophenyl;

R$^2$ is C$_{1-6}$ alkyl (e.g., methyl), C$_{1-6}$ alkoxy (e.g., methoxy) or a chlorine atom; and R$^3$ is 5-pyrimidinyl substituted by 1 or 2 substituents selected from the group consisting of amino, C$_{1-6}$ alkylamino and di(C$_{1-6}$ alkyl)amino, or a salt thereof.

[Compound I-8]

A compound of the formula (I) wherein

R is a hydrogen atom;

R$^1$ is cyclopropyl, 2-fluorocyclopropyl or 2,4-difluorophenyl;

R$^2$ is C$_{1-6}$ alkyl (e.g., methyl), C$_{1-6}$ alkoxy (e.g., methoxy) or a chlorine atom; and R$^3$ is 2-indolyl optionally substituted by 1 or 2 substituents selected from the group consisting of
  (a) a halogen atom,
  (b) cyano,
  (c) nitro,
  (d) hydroxy,
  (e) C$_{1-6}$ alkyl optionally substituted by 1 to 3 substituents selected from the group consisting of amino, C$_{1-6}$ alkoxy-carbonylamino, C$_{1-6}$ alkylamino and di(C$_{1-6}$ alkyl)amino,
  (f) C$_{1-6}$ alkoxy,
  (g) formyl,
  (h) carboxy, and
  (j) amino optionally substituted by 1 or 2 substituents selected from the group consisting of
    (i) C$_{1-6}$ alkoxy-carbonyl,
    (ii) C$_{1-6}$ alkyl-carbonyl optionally substituted by a substituent selected from the group consisting of
      (A) C$_{3-8}$ cycloalkyloxy optionally substituted by 1 to 3 C$_{1-6}$ alkyl,
      (B) C$_{1-6}$ alkylamino,
      (C) di(C$_{1-6}$ alkyl)amino,
      (D) a cyclic amino group (e.g., morpholino, 1-piperazinyl) optionally substituted by C$_{1-6}$ alkoxy-carbonyl, and
      (E) a halogen atom,
    (iii) phenylcarbonyl optionally substituted by 1 to 3 substituents selected from the group consisting of C$_{1-6}$ alkyl and C$_{1-6}$ alkoxy,
    (iv) C$_{3-8}$ cycloalkyl-carbonyl,
    (v) a 5- to 10-membered aromatic heterocyclylcarbonyl group (e.g., pyridylcarbonyl) optionally substituted by C$_{1-6}$ alkyl optionally substituted by 1 to 3 halogen atoms,
    (vi) benzylcarbonyl optionally substituted by 1 to 3 substituents selected from the group consisting of a halogen atom and C$_{1-6}$ alkoxy, (vii) C$_{6-14}$ arylsulfonyl optionally substituted by C$_{1-6}$ alkoxy,
(viii) C$_{3-8}$ cycloalkyl-C$_{1-6}$ alkylsulfonyl optionally substituted by 1 to 3 substituents selected from the group consisting of C$_{1-6}$ alkyl and oxo (e.g., camphorsulfonyl),
(ix) a 5- to 10-membered aromatic heterocyclylsulfonyl group (e.g., imidazolylsulfonyl) optionally substituted by 1 to 3 C$_{1-6}$ alkyl, and
(x) —C(=N—CN)—SR$^9$ wherein R$^9$ is C$_{1-6}$ alkyl, or a salt thereof.

[Compound I-9]
A compound of the formula (I) wherein
R is a hydrogen atom;
R$^1$ is cyclopropyl, 2-fluorocyclopropyl or 2,4-difluorophenyl;
R$^2$ is C$_{1-6}$ alkyl (e.g., methyl), C$_{1-6}$ alkoxy (e.g., methoxy) or a chlorine atom; and
R$^3$ is a group of the formula

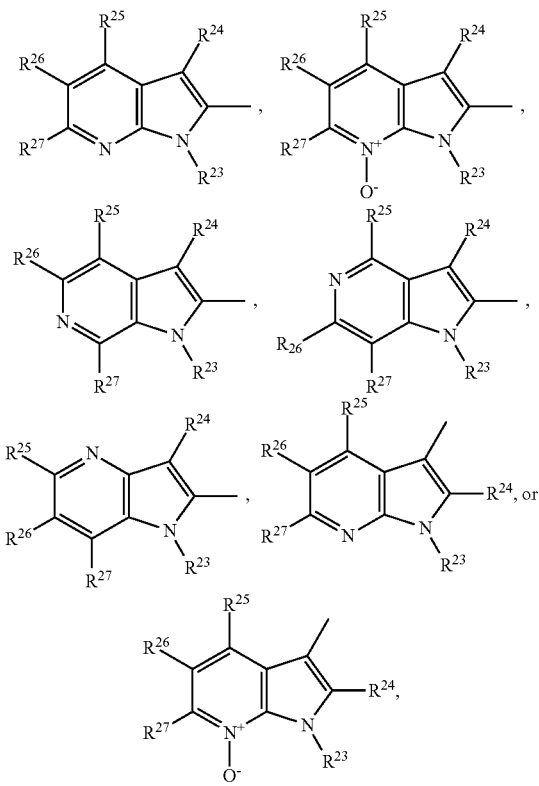

wherein
R$^{23}$ is a hydrogen atom or C$_{1-6}$ alkyl, and
R$^{24}$, R$^{25}$, R$^{26}$ and R$^{27}$ are each independently,
 (a) a hydrogen atom,
 (b) cyano, or
 (c) nitro,
or a salt thereof.

[Compound I-10]
A compound of the formula (I) wherein
R is a hydrogen atom;
R$^1$ is cyclopropyl, 2-fluorocyclopropyl or 2,4-difluorophenyl;
R$^2$ is C$_{1-6}$ alkyl (e.g., methyl), C$_{1-6}$ alkoxy (e.g., methoxy) or a chlorine atom; and
R$^3$ is a group of the formula

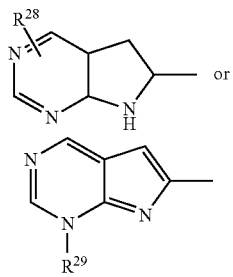

wherein
R$^{28}$ is a hydrogen atom or hydroxy, and
R$^{29}$ is a hydrogen atom or C$_{1-6}$ alkyl,
or a salt thereof.

[Compound I-11]
A compound of the formula (I) wherein
R is a hydrogen atom;
R$^1$ is cyclopropyl, 2-fluorocyclopropyl or 2,4-difluorophenyl;
R$^2$ is C$_{1-6}$ alkyl (e.g., methyl), C$_{1-6}$ alkoxy (e.g., methoxy) or a chlorine atom; and
R$^3$ is a group of the formula

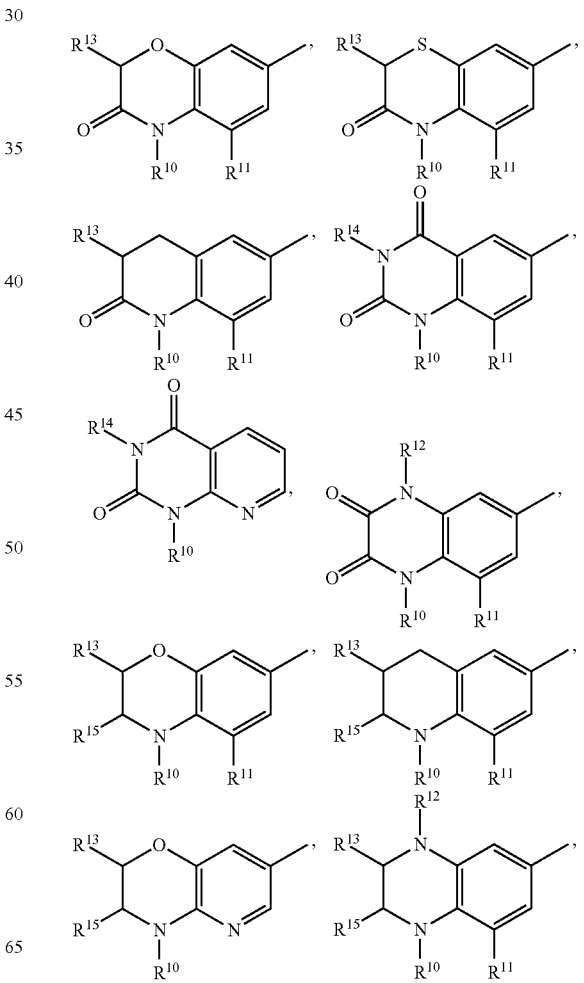

41

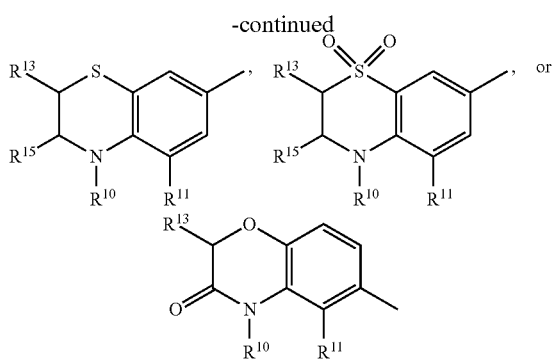

wherein
$R^{10}$, $R^{12}$ and $R^{14}$ are each independently,
(a) a hydrogen atom or
(b) $C_{1-6}$ alkyl, and
$R^{11}$, $R^{13}$ and $R^{15}$ are each independently,
(a) a hydrogen atom,
(b) a halogen atom,
(c) cyano,
(d) nitro,
(e) amino,
(f) $C_{1-6}$ alkylamino,
(g) di($C_{1-6}$ alkyl)amino,
(h) $C_{1-6}$ alkyl optionally substituted by hydroxy, or
(i) $C_{2-6}$ alkenyl, or
$R^{10}$ and $R^{11}$ are optionally bonded to form —(C=O)—NH—, —C($R^{31}$)=N— or —N=N— wherein $R^{31}$ is a hydrogen atom or $C_{1-6}$ alkyl, and the nitrogen atom is bonded to the phenyl ring of the fused ring,
or
$R^{12}$ and $R^{13}$ are optionally bonded to form —(CH$_2$)$_4$—,
or a salt thereof.

[Compound I-12]
A compound of the formula (I) wherein
R is a hydrogen atom;
$R^1$ is cyclopropyl, 2-fluorocyclopropyl or 2,4-difluorophenyl;
$R^2$ is $C_{1-6}$ alkyl (e.g., methyl), $C_{1-6}$ alkoxy (e.g., methoxy) or a chlorine atom; and
$R^3$ is a group of the formula

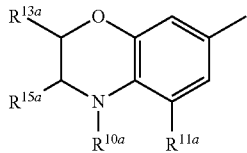

wherein $R^{10a}$ is
(a) a hydrogen atom or
(b) $C_{1-6}$ alkyl, and
$R^{11a}$, $R^{13a}$ and $R^{15a}$ are each independently,
(a) a hydrogen atom,
(b) a halogen atom,
(c) cyano,
(d) nitro,
(e) amino,
(f) $C_{1-6}$ alkylamino,
(g) di($C_{1-6}$ alkyl)amino,
(h) $C_{1-6}$ alkyl optionally substituted by hydroxy, or
(i) $C_{2-6}$ alkenyl, and

42 provided that $R^{10a}$, $R^{11a}$, $R^{13a}$ and $R^{15a}$ are not simultaneously hydrogen atom,
or a salt thereof.

[Compound I-13]
A compound of the formula (I) wherein
R is a hydrogen atom;
$R^1$ is cyclopropyl, 2-fluorocyclopropyl or 2,4-difluorophenyl;
$R^2$ is $C_{1-6}$ alkyl (e.g., methyl), $C_{1-6}$ alkoxy (e.g., methoxy) or a chlorine atom; and
$R^3$ is a group of the formula

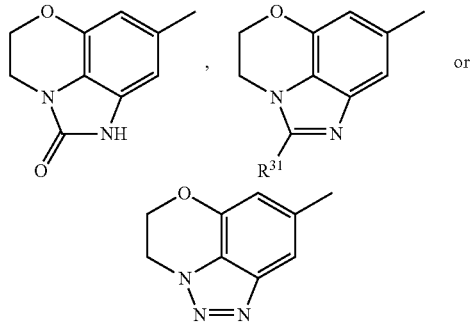

wherein $R^{31}$ is a hydrogen atom or $C_{1-6}$ alkyl,
or a salt thereof.

[Compound I-14]
A compound of the formula (I) wherein
R is a hydrogen atom;
$R^1$ is cyclopropyl, 2-fluorocyclopropyl or 2,4-difluorophenyl;
$R^2$ is $C_{1-6}$ alkyl (e.g., methyl), $C_{1-6}$ alkoxy (e.g., methoxy) or a chlorine atom; and
$R^3$ is a group of the formula

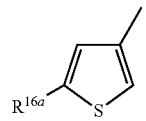

wherein $R^{16a}$ is
(a) $C_{1-6}$ alkyl optionally substituted by 1 to 3 substituents selected from the group consisting of cyano, $C_{1-6}$ alkylamino and di($C_{1-6}$ alkyl)amino,
(b) $C_{2-6}$ alkenyl optionally substituted by carboxy,
(c) formyl,
(d) carboxy,
(e) carbamoyl,
(f) —C($R^{17}$)=N—OH wherein $R^{17}$ is a hydrogen atom, cyano or hydroxy, or
(g) a 5- to 10-membered aromatic heterocyclic group (e.g., tetrazolyl, pyrrolyl, oxazolyl, benzimidazolyl, triazolyl) optionally substituted by $C_{1-6}$ alkyl, $C_{1-6}$ alkoxy-carbonyl, carboxy or phenyl,
or a salt thereof.

[Compound I-15]
A compound of the formula (I) wherein
R is a hydrogen atom;
$R^1$ is cyclopropyl, 2-fluorocyclopropyl or 2,4-difluorophenyl;
$R^2$ is $C_{1-6}$ alkyl (e.g., methyl), $C_{1-6}$ alkoxy (e.g., methoxy) or a chlorine atom; and $R^3$ is a group of the formula

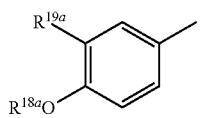

wherein
$R^{18a}$ is $C_{1-6}$ alkyl, and
$R^{19a}$ is (a) a halogen atom,
(b) cyano,
(c) $C_{1-6}$ alkyl optionally substituted by 1 to 3 substituents selected from the group consisting of
  (i) a halogen atom,
  (ii) cyano,
  (iii) hydroxy,
  (iv) amino,
  (v) $C_{1-6}$ alkylamino,
  (vi) di($C_{1-6}$ alkyl)amino, and
  (vii) a cyclic amino group (e.g., 1-piperazinyl) optionally substituted by $C_{1-6}$ alkyl,
(d) $C_{1-6}$ alkoxy,
(e) amino optionally substituted by 1 or 2 substituents selected from the group consisting of
  (i) $C_{1-6}$ alkyl-carbonyl optionally substituted by a cyclic amino group (e.g., morpholino),
  (ii) $C_{1-6}$ alkylsulfonyl, and
  (iii) carbamoyl,
(f) carboxy,
(g) $C_{1-6}$ alkoxy-carbonyl,
(h) carbamoyl optionally substituted by $C_{1-6}$ alkyl optionally substituted by amino, $C_{1-6}$ alkylamino, di($C_{1-6}$ alkyl)amino or $C_{1-6}$ alkoxy-carbonylamino,
(i) formyl,
(j) a 5- to 10-membered aromatic heterocyclic group (e.g., oxazolyl, benzimidazolyl), or
(k) —CH=N—OR$^{21}$ wherein $R^{21}$ is a hydrogen atom or $C_{1-6}$ alkyl optionally substituted by $C_{1-6}$ alkylamino or di($C_{1-6}$ alkyl)amino,
or a salt thereof.

[Compound I-16]
A compound of the formula (I) wherein
R is a hydrogen atom;
$R^1$ is cyclopropyl, 2-fluorocyclopropyl or 2,4-difluorophenyl;
$R^2$ is $C_{1-6}$ alkyl (e.g., methyl), $C_{1-6}$ alkoxy (e.g., methoxy) or a chlorine atom; and
$R^3$ is a group of the formula

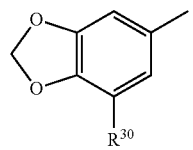

wherein
$R^{30}$ is (a) a hydrogen atom,
(b) a halogen atom,
(c) cyano,
(d) $C_{1-6}$ alkyl optionally substituted by 1 to 3 substituents selected from the group consisting of a halogen atom and hydroxy,
(e) $C_{2-6}$ alkenyl,
(f) $C_{2-6}$ alkynyl,
(g) $C_{1-6}$ alkoxy,
(h) formyl, or
(i) —CH=N—OH,
or a salt thereof.

Examples of salts of the compound of the formula (I) include pharmaceutically acceptable salts. Suitable pharmaceutically acceptable salts of the compound of the formula (I) are conventional non-toxic salts and include, for example, a salt with a base or an acid addition salt such as a salt with an inorganic base, for example, an alkali metal salt (e.g., sodium salt, potassium salt, etc.), an alkaline earth metal salt (e.g., calcium salt, magnesium salt, etc.), an ammonium salt; a salt with an organic base, for example, an organic amine salt (e.g., trimethylamine salt, triethylamine salt, pyridine salt, picoline salt, ethanolamine salt, triethanolamine salt, dicyclohexylamine salt, N,N'-dibenzylethylenediamine salt, etc.); an inorganic acid addition salt (e.g., hydrochloride, hydrobromide, sulfate, hydrogensulfate, phosphate, etc.); an organic carboxylic or sulfonic acid addition salt (e.g., formate, acetate, trifluoroacetate, maleate, tartrate, citrate, fumarate, methanesulfonate, benzenesulfonate, toluenesulfonate, etc.); and a salt with a basic or acidic amino acid (e.g., arginine, aspartic acid, glutamic acid, etc.).

Compound (I) can be produced, for example, by a method according to the following reaction schemes.

Reaction Scheme I

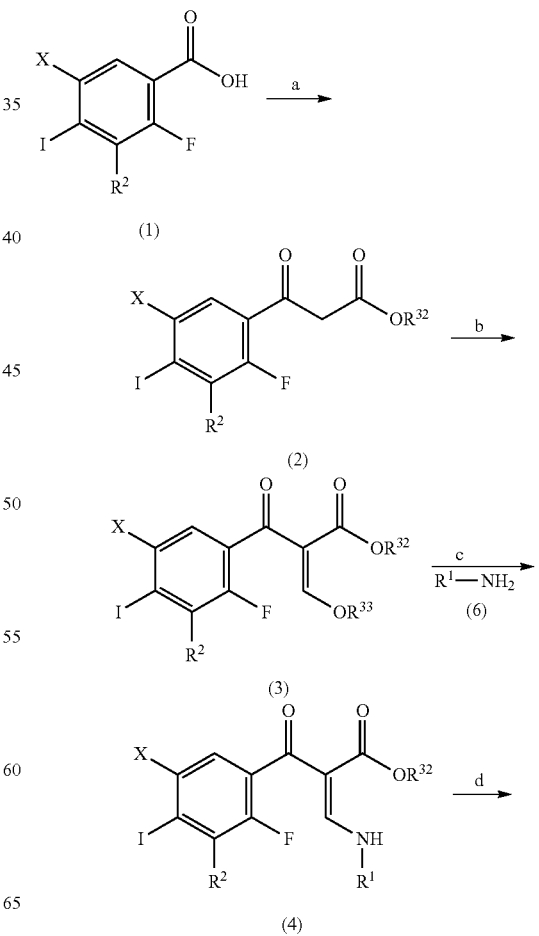

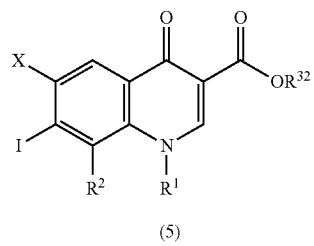

(5)

wherein X, $R^1$ and $R^2$ are as defined above, $R^{32}$ is alkyl and $R^{33}$ is alkyl.

Step a

Compound (1) can be converted to acid halide by reacting compound (1) with a halogenating agent in the presence or absence of a solvent. The solvent includes aromatic hydrocarbons such as benzene, toluene and xylene; halogenated hydrocarbons such as dichloromethane, chloroform and carbon tetrachloride; ethers such as dioxane, tetrahydrofuran and diethyl ether; N,N-dimethylformamide (DMF); dimethyl sulfoxide (DMSO); and the like. The halogenating agent may be any conventional halogenating agents which can convert hydroxy in carboxy group into a halogen atom, and includes, for example, thionyl chloride, phosphorus oxychloride, phosphorus oxybromide, phosphorus pentachloride, phosphorus pentabromide, and the like. The amounts of compound (1) and the halogenating agent are not particularly limited, but, in case of using no solvent, the halogenating agent is usually used in a large excess amount, and in case of using a solvent, the halogenating agent is usually used in an amount of at least 1 mole, preferably 2 to 4 moles, per 1 mole of compound (1). The reaction temperature and the reaction period of time are not particularly limited, but the reaction is usually carried out at a temperature of from room temperature to about 100° C. for about 30 minutes to about 6 hours.

The obtained acid halide is reacted with magnesium salt of malonic acid monoalkyl ester to give compound (2). Magnesium salt of malonic acid monoalkyl ester can be prepared in situ from potassium salt of malonic acid monoalkyl ester such as potassium ethyl malonate in the presence of magnesium chloride and a basic compound such as triethylamine. The reaction can be carried out in a suitable solvent. The solvent used in the reaction may be any conventional solvents unless they give any undesirable effect on the reaction, and includes, for example, esters such as ethyl acetate; ethers such as diethyl ether, dioxane, tetrahydrofuran, monoglyme and diglyme; alcohols such as methanol, ethanol and isopropanol; aromatic hydrocarbons such as benzene, toluene and xylene; aliphatic hydrocarbons such as n-hexane, heptane, cyclohexane and ligroin; amines such as pyridine and N,N-dimethylaniline; halogenated hydrocarbons such as chloroform, dichloromethane and carbon tetrachloride; aprotic polar solvents such as DMF, DMSO and hexamethylphosphoric triamide (HMPA); and a mixture of these solvents. The reaction is usually carried out at a temperature of from about 0° C. to about 150° C., preferably from about 0° C. to about 120° C., for about 0.5 to about 20 hours. Potassium salt of malonic acid monoalkyl ester is usually used in an amount of at least 1 mole, preferably 1 to 2 moles, per 1 mole of compound (1). Magnesium chloride and the basic compound are usually used in an amount of at least 1 mole, preferably 1 to 2 moles, per 1 mole of compound (1).

Step b

Compound (3) can be prepared by reacting compound (2) with trialkyl orthoformate such as trimethyl orthoformate and triethyl orthoformate in acetic anhydride. The reaction is usually carried out at a temperature of from about 0° C. to about 200° C., preferably from about 0° C. to about 150° C., for about 0.5 to about 20 hours. Trialkyl orthoformate is usually used in an amount of at least 1 mole, preferably 1 to 10 moles, per 1 mole of compound (2).

Step c

Compound (4) can be prepared by reacting compound (3) with compound (6).

The reaction between compound (3) and compound (6) can be carried out in a suitable solvent. The solvent employed in the reaction may be any conventional solvents unless they give any undesirable effect on the reaction, and includes, for example, alcohols such as methanol, ethanol and propanol; ethers such as diethyl ether, dioxane, tetrahydrofuran, monoglyme and diglyme; aromatic hydrocarbons such as benzene, toluene and xylene; aliphatic hydrocarbons such as n-hexane, heptane, cyclohexane and ligroin; halogenated hydrocarbons such as chloroform, methylene chloride and carbon tetrachloride; aprotic polar solvents such as DMF, DMSO and HMPA; and the like. The reaction is usually carried out at a temperature of from about 0° C. to about 150° C., preferably from room temperature to about 100° C., for about 0.1 to about 15 hours. Compound (6) is usually used in an amount of at least 1 mole, preferably 1 to 2 moles, per 1 mole of compound (3).

Step d

Compound (5) can be prepared by cyclization of compound (4).

The cyclization of compound (4) can be carried out in a suitable solvent in the presence of a basic compound. The solvent employed in the reaction may be any conventional solvents unless they give any undesirable effect on the reaction, and includes, for example, ethers such as diethyl ether, dioxane, tetrahydrofuran, monoglyme and diglyme; aliphatic hydrocarbons such as n-hexane, heptane and ligroin; halogenated hydrocarbons such as chloroform, methylene chloride and carbon tetrachloride; aprotic polar solvents such as DMF, DMSO and HMPA; and the like. The basic compound employed in the reaction includes inorganic bases such as metallic sodium, metallic potassium, sodium hydride, sodium amide, sodium hydroxide, potassium hydroxide, sodium carbonate and potassium carbonate, metal alcoholates such as sodium methylate and sodium ethylate, organic bases such as 1,8-diazabicyclo[5.4.0]undec-7-ene (DBU), N-benzyltrimethylammonium hydroxide and tetrabutylammonium hydroxide, and the like. The reaction is usually carried out at a temperature of from about 0° C. to about 200° C., preferably from room temperature to about 150° C., for about 0.5 to about 15 hours. The basic compound is usually used in an amount of at least 1 mole, preferably 1 to 2 moles, per 1 mole of the compound (4).

Reaction Scheme II

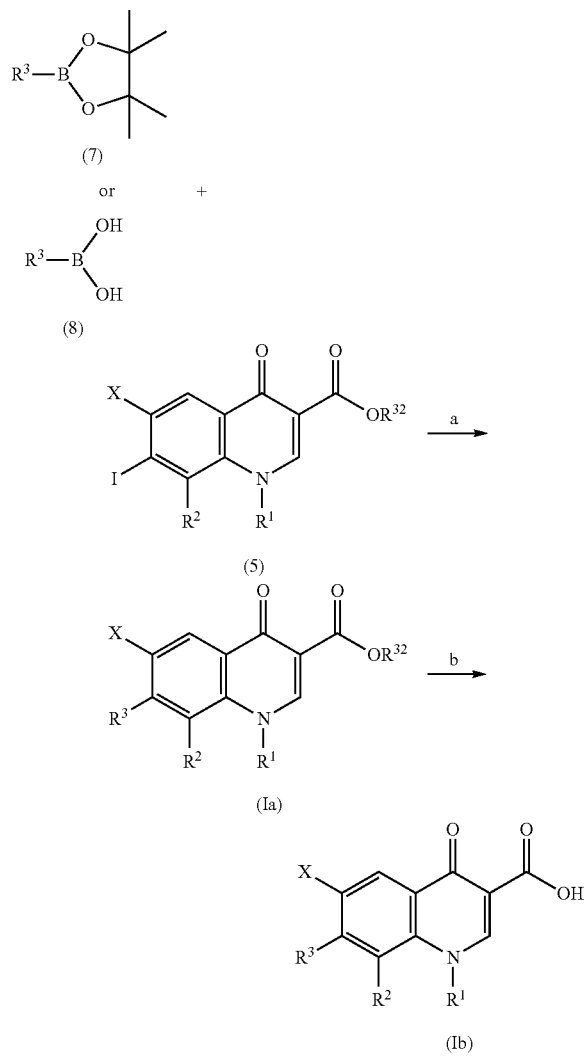

wherein X, $R^1$, $R^2$, $R^3$ and $R^{32}$ are as defined above.

Step a

Compound (Ia) can be prepared by reacting compound (5) and compound (7) or compound (8) in an inert solvent or without using any solvents, in the presence or absence of a basic compound, in the presence of a palladium catalyst.

Examples of inert solvents include water; ethers such as dioxane, tetrahydrofuran, diethyl ether, 1,2-dimethoxyethane, diethylene glycol dimethyl ether and ethylene glycol dimethyl ether; aromatic hydrocarbons such as benzene, toluene and xylene; alcohols such as methanol, ethanol and isopropanol; ketones such as acetone and methyl ethyl ketone; and aprotic polar solvents such as DMF, DMSO, HMPA and acetonitrile. These inert solvents can be used singly or in combinations of two or more.

The palladium catalyst used in the reaction is not particularly limited, but include, for example, tetravalent palladium catalysts such as sodium hexachloropalladate(IV) tetrahydrate and potassium hexachloropalladate(IV); divalent palladium catalysts such as palladium(II) chloride, palladium(II) bromide, palladium(II) acetate, palladium(II) acetylacetonate, dichlorobis(benzonitrile)palladium(II), dichlorobis(acetonitrile)palladium(II), dichlorobis(triphenylphosphine) palladium(II), dichlorotetramine palladium(II), dichloro(cycloocta-1,5-diene)palladium(II), palladium(II) trifluoroacetate, and 1,1'-bis(diphenylphosphino)ferrocene dichloropalladium(II) dichloromethane complex (Pd(dppf) $Cl_2 \cdot CH_2Cl_2$); zerovalent palladium catalysts such as tris (dibenzylideneacetone)dipalladium(0), tris(dibenzylideneacetone)dipalladium(0) chloroform complex and tetrakis (triphenylphosphine)palladium(0), etc. These palladium catalysts are used singly or in combinations of two or more.

In the reaction, the amount of the palladium catalyst is not particularly limited, but is typically in the range from 0.000001 to 20 moles in terms of palladium relative to 1 mole of compound (5). The amount of the palladium catalyst is preferably in the range from 0.0001 to 5 moles in terms of palladium relative to 1 mole of compound (5).

This reaction advantageously proceeds in the presence of a suitable ligand. Examples of ligands of the palladium catalyst include, for example, 2,2'-bis(diphenylphosphino)-1,1'-binaphthyl (BINAP), tri-o-tolylphosphine, bis(diphenylphosphino)ferrocene, triphenylphosphine, tri-t-butylphosphine and 4,5-bis(diphenylphosphino)-9,9-dimethyxanthene (Xantphos). These ligands are used singly or in combinations of two or more.

The proportion of the palladium catalyst and ligand is not particularly limited. The amount of the ligand is about 0.1 to about 100 moles per 1 mole of the palladium catalyst, and preferably about 0.5 to about 15 moles per 1 mole of the palladium catalyst.

Various known inorganic and organic bases can be used as basic compounds.

Inorganic bases include, for example, alkali metal hydroxides such as sodium hydroxide, potassium hydroxide, cesium hydroxide and lithium hydroxide; alkali metal carbonates such as sodium carbonate, potassium carbonate, cesium carbonate and lithium carbonate; alkali metal hydrogen carbonates such as lithium hydrogen carbonate, sodium hydrogen carbonate and potassium hydrogen carbonate; alkali metals such as sodium and potassium; phosphates such as sodium phosphate and potassium phosphate; amides such as sodium amide; and alkali metal hydrides such as sodium hydride and potassium hydride.

Organic bases include, for example, alkali metal lower alkoxides such as sodium methoxide, sodium ethoxide, sodium t-butoxide, potassium methoxide, potassium ethoxide and potassium t-butoxide, and amines such as triethylamine, tripropylamine, pyridine, quinoline, piperidine, imidazole, N-ethyldiisopropylamine, dimethylaminopyridine, trimethylamine, dimethylaniline, N-methylmorpholine, 1,5-diazabicyclo[4.3.0]non-5-ene (DBN), 1,8-diazabicyclo [5.4.0]undec-7-ene (DBU), 1,4-diazabicyclo[2.2.2]octane (DABCO), etc.

Such basic compounds can be used singly or in combinations of two or more. More preferable basic compounds used in the reaction include alkali metal carbonates such as sodium carbonate, potassium carbonate, cesium carbonate and lithium carbonate.

The basic compound is usually used in an amount of 0.5 to 10 moles per 1 mole of compound (5), and preferably 0.5 to 6 moles per 1 mole of compound (5).

Compound (7) or compound (8) is usually used in an amount of at least 1 mole per 1 mole of compound (5), and preferably about 1 to about 5 moles per 1 mole of compound (5).

The reaction can be conducted under normal pressure, under inert gas atmosphere including nitrogen, argon, etc., or under increased pressure.

The reaction proceeds usually from room temperature to about 200° C., and preferably from room temperature to about 150° C., and is usually completed in about 1 to about 30 hours. The reaction is also achieved by heating at about 100° C. to about 200° C. for about 5 minutes to about 1 hour using a microwave reactor.

Step b

Compound (Ib) can be prepared by hydrolysis of compound (Ia).

The hydrolysis of compound (Ia) can be carried out under the conditions of conventional hydrolysis, for example, in the presence of a basic compound such as sodium hydroxide, potassium hydroxide, barium hydroxide or potassium carbonate; a mineral acid such as sulfuric acid, hydrochloric acid or nitric acid; or an organic acid such as acetic acid or an aromatic sulfonic acid, in a solvent including water, alcohols such as methanol, ethanol and isopropanol; ketones such as acetone and methyl ethyl ketone; ethers such as dioxane and ethylene glycol diethyl ether; acetic acid; or a mixture thereof. The reaction is usually carried out at a temperature of from room temperature to about 200° C., preferably from room temperature to about 150° C., for about 0.1 to about 30 hours.

Reaction Scheme III

Preparation of boronate and boronic acid

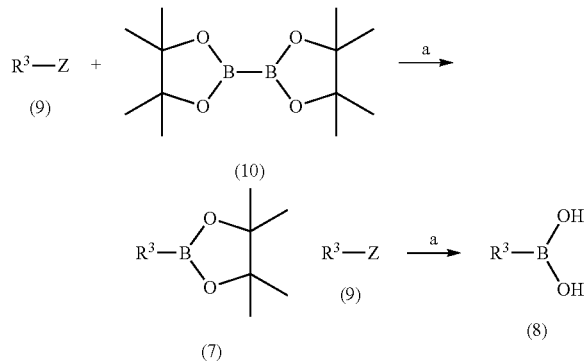

wherein $R^3$ is as defined above, and Z is a bromine atom or an iodine atom.

Step a

Compound (7) can be prepared by reacting compound (9) with bis(pinacolato)diboron (10) in an inert solvent in the presence of a palladium catalyst and a basic compound.

Examples of inert solvents and palladium catalyst are same as those described in Step a in Reaction Scheme II.

The basic compound employed in the reaction includes potassium acetate, triethylamine, N-methylmorpholin, sodium carbonate, potassium carbonate, cesium carbonate, lithium carbonate, potassium phosphate and sodium hydrogen carbonate.

In the reaction, the amount of the palladium catalyst is not particularly limited, but is typically in the range from 0.000001 to 20 moles in terms of palladium relative to 1 mole of compound (9). The amount of the palladium catalyst is preferably in the range from 0.0001 to 5 moles in terms of palladium relative to 1 mole of compound (9).

The basic compound is usually used in an amount of 0.5 to 10 moles per 1 mole of compound (9), and preferably 0.5 to 6 moles per 1 mole of compound (9).

Bis(pinacolato)diboron (10) is usually used in an amount of at least 1 mole per 1 mole of compound (9), and preferably about 1 to about 5 moles per 1 mole of compound (9).

The reaction can be conducted under normal pressure, under inert gas atmosphere including nitrogen, argon, etc., or under increased pressure.

The reaction proceeds usually from room temperature to about 200° C., and preferably from room temperature to about 150° C., and is usually completed in about 1 to about 30 hours.

Step b

Compound (8) can be prepared by reacting compound (9) with trialkyl borate such as trimethyl borate, triethyl borate, tri(isopropyl) borate and tri(n-butyl) borate in an inert solvent in the presence of n-butyllithium or lithium diisopropylamide.

Examples of inert solvents are same as those described in Step a in Reaction Scheme II.

The trialkyl borate is usually used in an amount of at least 1 mole per 1 mole of compound (9), and preferably about 1 to about 5 moles per 1 mole of compound (9).

n-Butyllithium or lithium diisopropylamide is usually used in an amount of at least 1 mole per 1 mole of compound (9), and preferably about 1 to about 5 moles per 1 mole of compound (9).

The reaction is usually carried out at a temperature of from about −70° C. to about 0° C. for about 0.1 to about 15 hours.

Compound (I) of the present invention can easily be converted into a salt thereof by treating with a pharmaceutically acceptable acid or base. The acid includes inorganic acids such as hydrochloric acid, sulfuric acid, phosphoric acid and hydrobromic acid and organic acids such as oxalic acid, maleic acid, fumaric acid, malic acid, tartaric acid, citric acid, benzoic acid, lactic acid, methanesulfonic acid and propionic acid. The base includes sodium hydroxide, potassium hydroxide, calcium hydroxide, sodium carbonate, potassium hydrogen carbonate, and the like.

The compound thus obtained can easily be isolated and purified by conventional methods, such as, for example, extraction with solvents, dilution method, recrystallization, column chromatography and preparative thin layer chromatography.

Compound (I) shows an excellent antimicrobial activity against mycoplasma, *Pseudomonas aeruginosa*, anaerobic bacteria, resistant cells against various antimicrobials, clinically isolated bacteria, and gram negative and gram positive bacteria such as *Clostridium difficile, Enterococcus faecalis* and *Staphylococcus pyogenes* and hence is useful as an antimicrobial agent for the treatment of diseases induced by these microorganisms. Compound (I) also shows low toxicity and less side effects and is characteristic in good absorbability and in sustained activity.

Since compound (I) shows an excellent antimicrobial activity against *Clostridium difficile*, it is useful for the prevention or treatment of intestinal infections including antibiotics-associated diarrhea (AAD) such as *Clostridium difficile*-associated diarrhea (CDAD).

The compounds of the present invention are usually used in the form of a usual pharmaceutical preparation. The pharmaceutical preparation can be prepared in admixture with conventional pharmaceutically acceptable diluents or carriers, such as fillers, bulking agents, binding agents, wetting agents, disintegrators, surfactants and lubricating agents. The pharmaceutical preparation includes various preparations suitable for treatment of the diseases, for example, tablets, pills, powders, solutions, suspensions, emulsions, granules, capsules, suppositories, injections such as solutions and suspensions, and the like. In the preparation of tablets, there may be used any conventional carriers, for example, excipients such as lactose, white sugar, sodium chloride, glucose, urea, starches, calcium carbonate, kaolin, crystalline cellulose and silicate, binding agents such as water, ethanol, propanol, simple syrup, glucose solution, starch solution, gelatin solution, carboxymethyl cellulose, shellac, methyl cellulose, potassium phosphate and polyvinylpyrrolidone, disintegrators such as dry starch, sodium alginate, agar powder, laminaran powder, sodium hydrogen carbonate, calcium carbonate, polyoxyethylene sorbitan fatty acid esters, sodium lauryl sulfate, stearic monoglyceride, starches and lactose, disintegration inhibitors such as white sugar, stearin, cacao butter and hydrogenated oils, absorption promoters such as quaternary ammonium salts and sodium lauryl sulfate, wetting agents such as glycerin and starches, adsorbents such as starches, lactose, kaolin, bentonite and colloidal silicates, lubricants such as purified talc, stearates, boric acid powder and polyethylene glycol, and the like. The tablets may also be coated with conventional coating agents, for example, may be in the form of a sugar coated tablet, a gelatin-coated tablets, an enteric coating tablet, a film coating tablet, or a double or multiple layers tablet. In the preparation of pills, there may be used conventional carriers, including excipients such as glucose, lactose, starches, cacao butter, hydrogenated vegetable oils, kaolin and talc, binding agents such as gum arabic powder, tragacanth powder, gelatin and ethanol, disintegrators such as laminaran and agar, and the like. In the preparation of suppositories, there may be used conventional carriers, such as, for example, polyethylene glycol, cacao butter, higher alcohols, higher alcohol esters, gelatin and semi-synthesized glycerides. In the preparation of injections, the solutions, emulsions or suspensions of the compounds are sterilized and are preferably made isotonic with the body liquid. These solutions, emulsions and suspensions are prepared by admixing the active compound with a conventional diluent, such as water, aqueous lactic acid solution, ethyl alcohol, propylene glycol, ethoxylated isostearyl alcohol, polyoxylated isostearyl alcohol or polyoxyethylene sorbitan fatty acid esters. The preparations may also be incorporated with sodium chloride, glucose or glycerin in an amount sufficient to make them isotonic with the body liquid. The preparations may also be incorporated with conventional solubilizers, buffering agents, anesthetizing agents, and further, with coloring agents, preservatives, perfumes, flavors, sweetening agents, and other medicaments. The preparations in the form of a paste, cream or gel may be prepared by using as a diluent such as white petrolatum, paraffin, glycerin, cellulose derivatives, polyethylene glycol, silicone, bentonite, or the like. When the compound of the active ingredient precipitates in the injection, an acid such as, for example, methanesulfonic acid, propionic acid, hydrochloric acid, succinic acid or lactic acid may be added to the injection as required to preserve the injection in a stable solution.

Compound (I) may be contained in any amount in the preparations, and are usually contained in an amount of from 1 to 70% by weight based on the whole weight of the preparations.

The pharmaceutical preparations of the present invention can be administered in any methods. Suitable method for administration may be selected in accordance with the preparation form, age and sex of patients, severity of the diseases, and the like. For instance, tablets, pills, solutions, suspensions, emulsions, granules and capsules are administered in oral route. In case of injection, it is administered intravenously in a single form or together with an auxiliary liquid such as glucose or amino solution. The injections may also be administered in intramuscular, intracutaneous, subcutaneous, or intraperitoneal route. Suppositories are administered in intrarectal route.

The dosage of the pharmaceutical preparations of the present invention may vary according to administration methods, age and sex of patients, severity of the diseases, and the like, usually in the range of about 0.1 to about 100 mg, more preferably in the range of about 0.1 to about 50 mg, of compound (I) per 1 kg body weight of the patient per day. The preparation is usually administered by dividing into 2 to 4 times per day.

The present invention is illustrated by the following Examples, Experimental Examples and Preparation Examples. It is to be understood that the present invention is not limited to these Examples, Experimental Examples or Preparation Examples and various changes and modifications can be made without departing from the scope and spirit of the present invention.

EXAMPLES

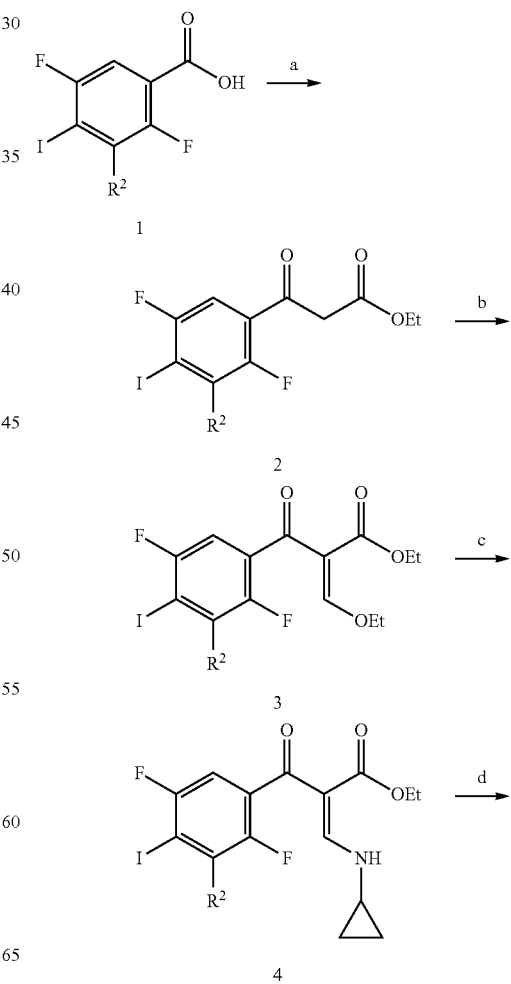

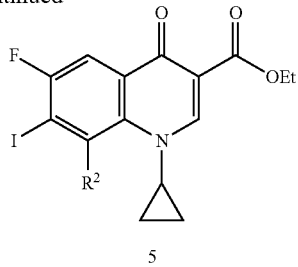

5

Reaction reagents and conditions: a. KO$_2$CCH$_2$CO$_2$Et, MgCl$_2$, Et$_3$N, 80° C.; b. HC(EtO)$_3$, 150 C; c. Cyclopropylamine; d. K$_2$CO$_3$, DMSO, 100° C.

In our work, Suzuki coupling was employed as key reaction to construct our final products. For the coupling, the corresponding iodo-intermediates could be prepared through well-known methods that were wildly used to synthesis of quinolones before (General Scheme I).

Example 1

Synthesis of Intermediate 5a (R$^2$=Me)

1.1. Compound 2: A mixture of compound 1 (2 g, 6.71 mmol) and thionyl chloride (9.8 mL) was refluxed for 3 hr, and then concentrated to give acid chloride. To the residue was added dry EtOAc (10 mL) and then the mixture was concentrated. A mixture of potassium ethyl malonate (1.6 g, 9.40 mmol) and MgCl$_2$ (1.91 g, 20.13 mmol) in dry EtOAc was stirred for 30 min below 50° C. To the mixture was added Et$_3$N (2.83 mL, 20.13 mmol) below 50° C. Then, the mixture was refluxed for 1 hr. To the mixture was added dropwise a solution of the acid chloride in dry EtOAc (10 mL) at 50-70° C. and then the mixture was refluxed for 1.5 hr. Water (30 mL) and 5 N HCl (30 mL) were added to the reaction mixture under ice-cooling. The EtOAc solution was washed with water, dried and concentrated to give compound 2 as a yellow oil, which was used in the next step without purification.

1.2. Compound 3: A mixture of compound 2 (11 g, 29.88 mmol), triethyl orthoformate (7.47 mL, 44.82 mmol) and acetic anhydride (6.77 mL, 71.72 mmol) was heated at 150° C. for 1 hr, and then concentrated to give compound 3, which was used in the next step without purification.

1.3. Compound 4: To compound 3 (obtained above) were added EtOH (50 mL) and cyclopropylamine (2.48 mL, 35.86 mmol). The mixture was stirred for 30 min and concentrated to give compound 4, which was used in the next step without purification.

1.4. Intermediate 5a: Compound 4 (obtained above) was dissolved in dry DMSO (100 mL). K$_2$CO$_3$ (16.52 g, 119.53 mmol) was added to the solution. The reaction mixture was stirred at 100° C. for 1 hr. When TLC (EtOAc/dipropyl ether=1/1) indicated the reaction was completed, the mixture was cooled to room temperature, poured into water, and extracted with EtOAc. The organic layer was washed with brine, dried and concentrated to give a yellow solid which was recrystallized from EtOAc. Intermediate 5a was obtained as a white solid in 75% overall yield. $^1$H NMR (400 MHz, DMSO) δ 8.60 (s, 1H), 7.70 (d, J=7.8 Hz, 1H), 4.29-4.14 (m, 3H), 2.96 (s, 3H), 1.28 (t, J=7.1 Hz, 3H), 1.14 (q, J=7.0 Hz, 2H), 0.87-0.76 (m, 2H).

The following compounds were synthesized according to General Scheme I.

Example 2

Intermediate 5b (R$^2$=OMe): $^1$H NMR (400 MHz, DMSO) δ 8.51 (s, 1H), 7.69 (d, J=7.7 Hz, 1H), 4.23 (dd, J=14.0, 6.9 Hz, 2H), 4.03 (s, 1H), 3.80 (s, 3H), 1.28 (t, J=7.0 Hz, 3H), 1.09 (d, J=6.2 Hz, 2H), 0.97 (m, 2H).

Example 3

Intermediate 5c (R$^2$=Cl): $^1$H NMR (400 MHz, DMSO) δ 8.61 (s, 1H), 7.81 (d, J=7.6 Hz, 1H), 4.23 (m, 3H), 1.28 (t, J=7.1 Hz, 3H), 1.21-1.08 (dd, J=7.1, 2.2 Hz, 2H), 0.99-0.92 (m, 2H).

Example 4

Intermediate 5d: $^1$H NMR (400 MHz, CDCl$_3$) δ 8.59-8.51 (d, J=3.1 Hz, 1H), 8.03-7.92 (d, J=7.5 Hz, 1H), 4.98-4.73 (dddd, J=62.9, 6.3, 4.9, 3.4 Hz, 1H), 4.44-4.34 (q, J=7.1 Hz, 2H), 3.91-3.83 (dt, J=8.6, 5.4 Hz, 1H), 2.95-2.88 (s, 3H), 1.59-1.48 (m, 1H), 1.45-1.38 (t, J=7.1 Hz, 3H), 1.35-1.18 (m, 1H).

Example 5

Intermediate 5e: $^1$H NMR (400 MHz, CDCl$_3$) δ 8.51-8.43 (d, J=2.0 Hz, 1H), 7.94-7.86 (d, J=7.6 Hz, 1H), 4.90-4.65 (dddd, J=62.7, 6.0, 5.1, 3.3 Hz, 1H), 4.37-4.28 (q, J=7.1 Hz, 2H), 3.80-3.76 (s, 3H), 3.75-3.69 (dt, J=8.7, 5.5 Hz, 1H), 1.61-1.47 (m, 2H), 1.46-1.30 (m, 4H).

Example 6

Intermediate 5f: $^1$H NMR (400 MHz, DMSO) δ 8.65 (s, 1H), 7.48 (d, J=8.16 Hz, 1H), 4.79 (q, J=6.65 Hz, 1H), 4.62 (dd, J=1.82, 11.36 Hz, 1H), 4.44 (dd, J=2.20, 11.36 Hz, 1H), 4.23 (qd, J=2.95, 7.09 Hz, 2H), 1.40 (d, J=6.65 Hz, 3H), 1.28 (t, J=7.09 Hz, 3H).

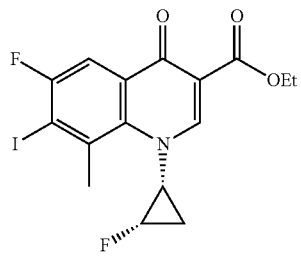

5d

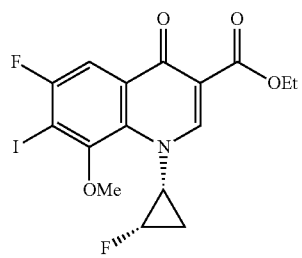

5e

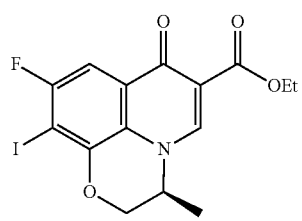

5f

General Scheme II. Preparation of boronote and boroni acid

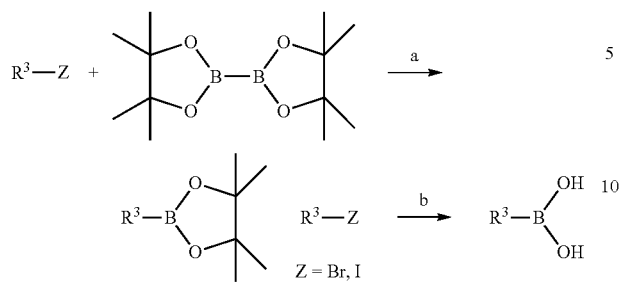

Reaction reagents and conditions: a. Pd(dppf)Cl$_2$·CH$_2$Cl$_2$ (5% mol), KOAc, dioxane, 80° C.; b. nBuLi (or LDA), B(OIPr)$_3$, THF General Scheme II outlined the preparation of required boronic acids and boronates. They are readily prepared through general methods.

Example 7

Synthesis of Boronic Acid 7

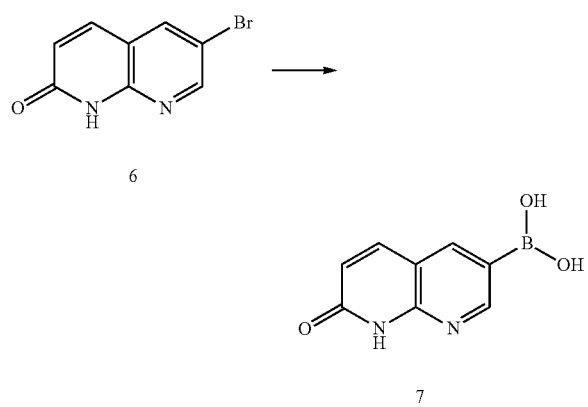

Reaction reagents and conditions: a. 1) NaH, THF, r.t.; 2) nBuLi, B(OiPr)$_3$, −70° C. to 0° C.

7.1 Boronic acid 7: To a solution of compound 6 (10 g, 44.44 mmol) in dry tetrahydrofuran (350 mL) was added sodium hydride (2 g, 66.66 mmol, 80% dispersion) at 0° C. After the mixture was stirred at room temperature for 30 min, the mixture was cooled below −60° C. in a dry ice/acetone bath, and n-butyllithium (70 mL, 112 mmol, 1.6 M in hexane) was added over 30 min. The mixture was kept stirring for another 30 min, then triisopropyl borate (40 mL, 177 mmol) was added dropwise. The reaction mixture was stirred for 10 min, and then warmed to 0° C. slowly in an ice bath. HCl (5 N) was added to the mixture to adjust pH=3-4, and the mixture was stirred for 20 min. Aq. NaOH was added to the mixture to adjust pH=10. After filtration, the organic layer was separated. The aqueous layer was extracted with a mixture of ethyl acetate/THF (4/1; 2×120 mL) and EtOAc (100 mL). The aqueous layer was adjusted to pH=5-6 with HCl. The precipitate thus formed was collected by filtration and dried to give boronic acid 7 (3.5 g, 41%) as a white solid.

Example 8

Synthesis of Boronate 10

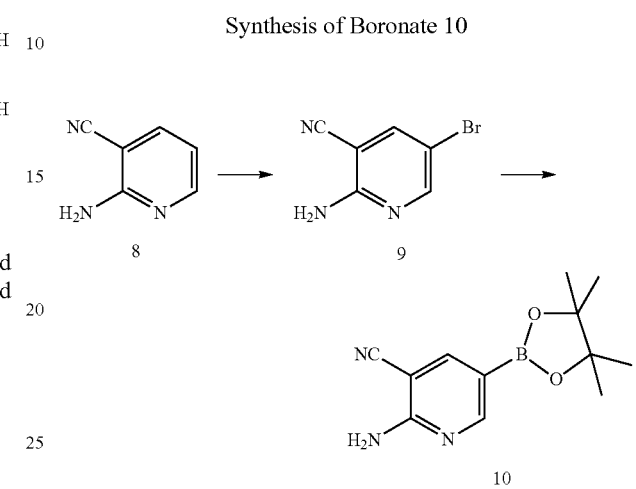

8.1 Compound 9: 2-Aminonicotinonitrile 8 (100 g, 0.839 mol) was dissolved in HOAc (800 mL). To the solution was added Na$_2$CO$_3$ (88.97 g, 0.839 mol). Then, Br$_2$ (46.4 mL, 0.923 mol) was added dropwise. The reaction mixture was stirred at room temperature for 50 min. To the mixture was added water (600 mL). The mixture was cooled to about 5° C. The precipitate thus formed was collected by filtration and dried to give compound 9 (207 g, 96%).

8.2 Boronate 10: Compound 9 (50 g, 0.224 mol), bis(pinacolato)diboron (85.6 g, 0.337 mol), KOAc (44.1 g, 0.449 mol) and Pd(dppf)Cl$_2$.CH$_2$Cl$_2$ (2.77 g, 3.4 mmol) were charged into a flask. Dioxane (400 mL) was added. The reaction mixture was stirred at 100° C. for 2 hr under Ar. When LC-MS indicated that the reaction was completed, the mixture was cooled to room temperature. The mixture was filtered through diatomite, concentrated, diluted with a mixture of ethyl acetate and hexane in 3/1 ratio (1000 mL), filtered through silica gel (300-400 mesh), concentrated, crystallized and dried to give boronate 10 (32 g, 66%) as a white solid.

Example 9

Synthesis of Boronate 13

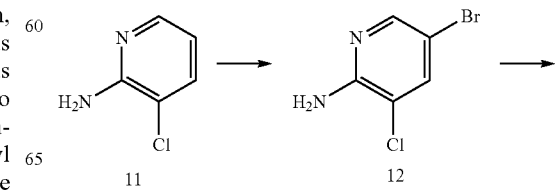

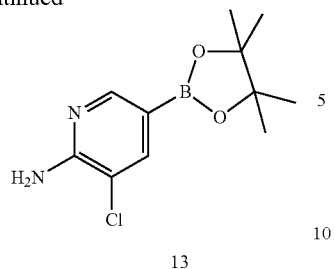

13

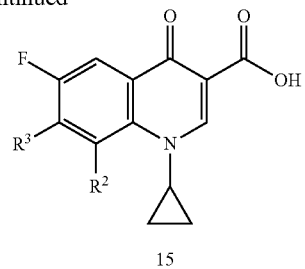

15

Reaction reagents and conditions: a. Pd(dppf)Cl$_2$·CH$_2$Cl$_2$ (5% mol), K$_2$CO$_3$, dioxane, 80° C; b. NaOH, EtOH 9.1 Compound 12: 3-Chloropyridin-2-amine (100 g, 0.778 mol) was dissolved in acetic acid (1200 mL). To the solution was added Na$_2$CO$_3$ (82.4 g, 0.778 mol). Then, Br$_2$ (39.1 mL, 0.856 mmol) was added dropwise. After addition, the reaction mixture was stirred at room temperature for 30 min. To the mixture was added water (800 mL). The mixture was cooled to about 5° C. The resulting solid was collected by filtration and dried to give compound 12 (147 g, 91%) as a white solid.

9.2 Boronate 13: Compound 12 (4 g, 17.2 mmol), bis(pinacolato)diboron (4.79 g, 18.8 mmol), KOAc (3.37 g, 34.2 mmol) and Pd(dppf)Cl$_2$·CH$_2$Cl$_2$ (0.210 g, 0.25 mmol) were charged into a flask. Dioxane (80 mL) was added. The mixture was stirred at 85° C. for 2 hr under Ar. When LC-MS indicated that the reaction was completed, the mixture was cooled to room temperature. The mixture was filtered through diatomite and concentrated. The residue was diluted with ethyl acetate and hexane (3/1, 100 mL), filtered through silica gel (300-400 mesh), concentrated and crystallized by n-hexane to give boronate 13 (3.4 g, 78%) as a white solid.

General Scheme III

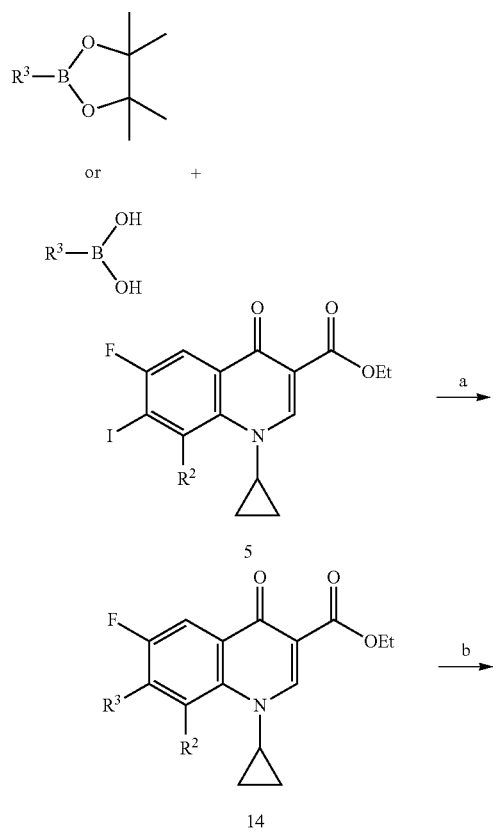

Example 10

Synthesis of Compound 1-2

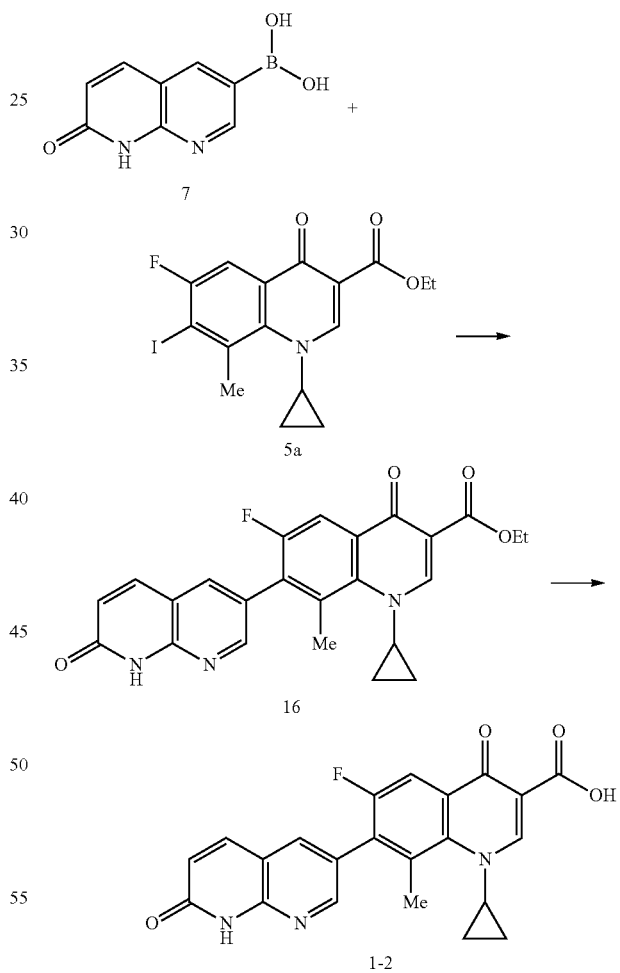

10.1 Compound 16: Intermediate 5a (30 g, 65 mmol), boronic acid 7 (17 g, 71.6 mmol) and K$_2$CO$_3$ (27, 195 mmol) were charged into a flask. Dioxane (600 mL) and water (60 mL) were added. The solution was deoxygenated with N$_2$ for 15 min. Pd(dppf)Cl$_2$·CH$_2$Cl$_2$ (2.8 g, 3.24 mmol) was added to the mixture. The reaction mixture was stirred at 85° C. overnight. When the reaction was completed, the reaction mixture was cooled to room temperature. The precipitate was filtered, dissolved in water, filtered, triturated with EtOH, filtered and dried to give compound 16 (16 g, 57%) as an off-white solid. The obtained compound was pure enough for use.

The organic filtrate was concentrated. To the residue were added water, dichloromethane and EtOAc. The precipitate thus formed was collected by filtration and dissolved in HCl (5 N). After filtration to remove Pd residue, the filtrate was basified with aq. NaOH (pH=7-8). The precipitate was collected by filtration and dried to give compound 16 (3 g, 11%) as an off-white solid.

10.2 Compound 1-2: Compound 16 (33 g, 76.1 mmol) was suspended in EtOH (300 mL). Aq. NaOH (4 N, 100 mL) was added to the suspension, and the mixture was stirred at 60° C. for 2 hr. 200 mL of EtOH was evaporated under reduced pressure. To the residue was added HCl (5 N) to adjust pH=4. The resulting precipitate was filtered, triturated with EtOH, filtered and dried to give compound 1-2 (30 g, 97%) as an off-white solid. m.p. >300° C. $^1$H NMR (400 MHz, DMSO) δ 14.64 (s, 1H), 12.39 (s, 1H), 8.92 (s, 1H), 8.58 (s, 1H), 8.28 (s, 1H), 8.01 (m, 2H), 6.67 (d, J=9.4 Hz, 1H), 4.42 (s, 1H), 2.68 (s, 3H), 1.27 (d, J=6.4 Hz, 2H), 1.12-1.03 (m, 2H). $^{13}$C NMR (101 MHz, DMSO) δ 176.92, 165.25, 162.85, 158.16, 155.72, 152.71, 150.92, 149.62, 139.29, 138.79, 137.62, 133.70, 133.52, 131.80, 127.47, 127.38, 123.75, 123.42, 113.89, 108.05, 107.81, 107.29, 41.29, 20.64, 20.62, 10.62. HPLC-MS m/z 406 (MH$^+$). Anal. Calcd for $C_{22}H_{16}FN_3O_4$: C, 65.18; H, 3.98; N, 10.37. Found: C, 63.50; H, 4.00; N, 9.91.

Example 11

Synthesis of compound 2-18

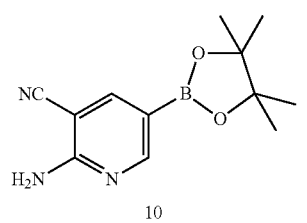

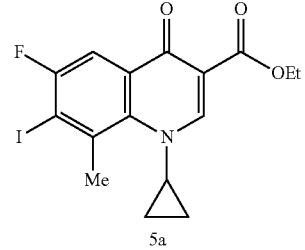

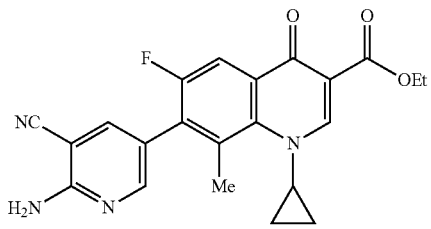

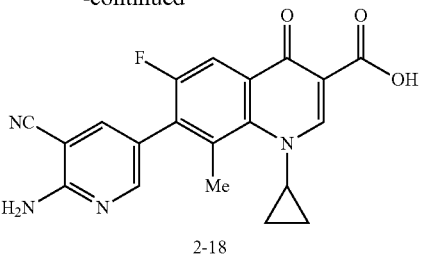

2-18

11.1 Compound 17: Boronate 10 (14 g, 56.1 mmol), intermediate 5a (20 g, 46.7 mmol), Cs$_2$CO$_3$ (15.22 g, 46.7 mmol) and Pd(dppf)Cl$_2$.CH$_2$Cl$_2$ (0.98 g, 1.2 mmol) were charged into a flask. Dioxane (500 mL) and water (5 mL) were added. The mixture was stirred at 110° C. overnight under Ar. The mixture was cooled to room temperature. The mixture was filtered, and the solid was washed with dioxane and ethyl acetate. The solid was dissolved in hot CH$_2$Cl$_2$ (1200 mL), and the solution was filtered through diatomite. The operation was repeated twice. The organic layers were combined and concentrated. To the residue was added ethyl acetate (200 mL). The solid was collected by filtration, washed with ethyl acetate (60 mL) and dried to give compound 17 (17.6 g, 90%) as a white solid.

11.2 Compound 2-18: Compound 17 (43 g, 0.101 mol) was dissolved in THF and EtOH (1/1, 500 mL). To the solution was added NaOH (60 mL, 4 N). The mixture was stirred at room temperature for 2 hr. HCl (63 mL, 4 N) was added to acidify the mixture (pH=3-4). The solid was collected by filtration, washed with EtOH (100 mL) and dried to give compound 2-18 (35.7 g, 99%) as a white solid. m.p. >300° C. $^1$H NMR (400 MHz, DMSO) δ 14.65 (s, 1H), 8.89 (s, 1H), 8.32-8.23 (m, 1H), 8.08 (d, J=2.09 Hz, 1H), 7.94 (d, J=8.87 Hz, 1H), 7.28 (s, 2H), 4.40 (tt, J=3.74, 7.17 Hz, 1H), 2.67 (s, 3H), 1.31-1.19 (m, 2H), 1.10-0.99 (m, 2H). $^{13}$C NMR (101 MHz, DMSO) δ 176.95, 176.92, 165.32, 159.60, 158.29, 155.86, 154.07, 152.67, 143.59, 139.32, 133.39, 133.22, 131.73, 127.13, 127.05, 116.93, 116.52, 107.96, 107.71, 107.27, 89.15, 41.32, 20.64, 20.62, 10.65. HPLC-MS m/z 379 (MH$^+$). Anal. Calcd for $C_{20}H_{15}FN_4O_3$: C, 63.49; H, 4.00; N, 14.81. Found: C, 62.04; H, 4.20; N, 13.97.

Example 12

Synthesis of Compound 3-11

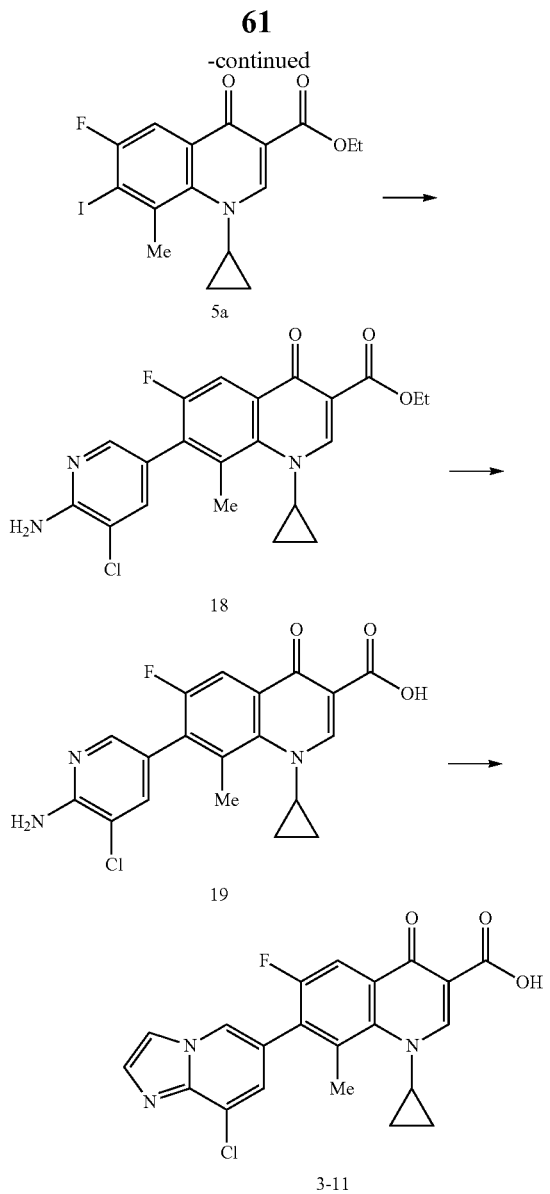

12.1 Compound 18: Boronate 13 (20 g, 75.4 mmol), intermediate 5a (24.1 g, 58.03 mmol), Cs$_2$CO$_3$ (26.5 g, 81.2 mmol) and Pd(dppf)Cl$_2$.CH$_2$Cl$_2$ (1.42 g, 1.7 mmol) were charged into a flask. Dioxane (400 mL) and water (4 mL) were added. The mixture was stirred at 100° C. overnight under Ar. The mixture was cooled to room temperature. The mixture was filtered, and the solid was washed with dioxane and ethyl acetate. The solid was dissolved in hot CH$_2$Cl$_2$ (1200 mL), and the solution was filtered through diatomite. The operation was repeated twice. The organic layers were combined and concentrated. To the residue was added ethyl acetate (200 mL). The solid was collected by filtration, washed with ethyl acetate (60 mL) and dried to give compound 18 (21 g, 85%) as a white solid.

12.2 Compound 19: Compound 18 (39 g, 91.91 mmol) was dissolved in THF and EtOH (1/1, 600 mL). To the mixture was added NaOH (4 N, 60 mL). The mixture was stirred at room temperature for 2 hr. HCl (4 N, 62 mL) was added to acidify the solution (pH=3-4). The solid was collected by filtration, washed with EtOH (100 mL) and dried to give compound 19 (34 g, 98%) as a white solid.

12.3 Compound 3-11: Chloroacetaldehyde (40% in water, 80 mL) was added to a solution of compound 19 (34 g, 91.9 mmol) in EtOH (600 mL). The mixture was refluxed for 3 hr. When LC-MS indicated that the reaction was completed, the mixture was cooled to 5° C. and filtered. The solid was dried to give compound 3-11 (21 g). The mother liquid was basified (pH=7-8) with aq. NaOH. The precipitate was collected by filtration, washed with EtOH and dried to give compound 3-11 (11.5 g) as a white solid. In total, 32.5 g of compound 3-11 was obtained in 93% yield. m.p.: 307-311° C. $^1$H NMR (400 MHz, DMSO) δ 14.53 (s, 1H), 8.98-8.84 (m, 2H), 8.28 (d, J=1.16 Hz, 1H), 7.98 (d, J=8.83 Hz, 1H), 7.90 (d, J=0.89 Hz, 1H), 7.77 (s, 1H), 4.43 (tt, J=3.70, 7.10 Hz, 1H), 3.50-3.36 (m, 1H), 2.72 (s, 3H), 1.26 (d, J=6.80 Hz, 2H), 1.07 (d, J=18.24 Hz, 2H). $^{13}$C NMR (101 MHz, DMSO) δ 176.91, 176.88, 165.23, 158.22, 155.77, 152.84, 139.98, 139.17, 139.16, 132.44, 132.15, 131.98, 131.54, 127.86, 127.78, 127.38, 120.72, 118.97, 116.37, 108.15, 107.91, 107.37, 41.38, 20.54, 20.52, 10.72. HPLC-MS: m/z 412 (MH$^+$). Anal. Calcd for C$_{21}$H$_{15}$ClFN$_3$O$_3$: C, 61.25; H, 3.67; N, 10.20. Found: C, 58.59; H, 3.86; N, 9.76.

Compounds listed in the following Tables were synthesized according to General Scheme III.

TABLE 1

| Compound No. | R$^3$ = | R$^2$ = | R$^1$ = | NMR | MS (MH$^+$) | HPLC |
|---|---|---|---|---|---|---|
| 1-1 | 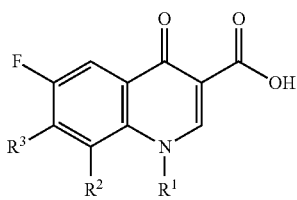 | OMe | Cyclopropyl | $^1$H NMR (400 MHz, DMSO) δ 14.63 (s, 1H), 12.41 (s, 1H), 8.82 (s, 1H), 8.69 (s, 1H), 8.38 (s, 1H), 8.05 (d, J = 9.6 Hz, 1H), 7.99 (d, J = 9.1 Hz, 1H), 6.66 (dd, J = 9.5, 1.6 Hz, 1H), 4.24 (s, 1H), 3.42 (s, 3H), 1.19 (d, J = 7.2 Hz, 4H). | 422 | 98% |

TABLE 1-continued

| Compound No. | R³ = | R² = | R¹ = | NMR | MS (MH⁺) | HPLC |
|---|---|---|---|---|---|---|
| 1-2 | (1,8-naphthyridin-2(1H)-one-6-yl) | Me | Cyclopropyl | ¹H NMR (400 MHz, DMSO) δ 14.64 (s, 1H), 12.39 (s, 1H), 8.92 (s, 1H), 8.58 (s, 1H), 8.28 (s, 1H), 8.01 (m, 2H), 6.67 (d, J = 9.4 Hz, 1H), 4.42 (s, 1H), 2.68 (s, 3H), 1.27 (d, J = 6.4 Hz, 2H), 1.12-1.03 (m, 2H). | 406 | 98% |
| 1-3 | (1,8-naphthyridin-2(1H)-one-6-yl) | OMe | (2-fluorocyclopropyl) | ¹H NMR (400 MHz, DMSO) δ 14.49 (s, 1H), 12.41 (s, 1H), 8.85 (d, J = 1.3 Hz, 1H), 8.67 (s, 1H), 8.36 (s, 1H), 8.05 (d, J = 9.6 Hz, 1H), 8.00 (d, J = 9.1 Hz, 1H), 6.77-6.54 (m, 1H), 5.24-4.97 (m, 1H), 4.29-4.10 (m, 1H), 3.44 (s, 3H), 1.89-1.59 (m, 2H). | 440 | 98% |
| 1-4 | (1,8-naphthyridin-2(1H)-one-6-yl) | Me | (2-fluorocyclopropyl) | ¹H NMR (400 MHz. DMSO) δ 14.50 (s, 1H), 12.39 (s, 1H), 8.90 (d, J = 3.0 Hz, 1H), 8.58 (s, 1H), 8.27 (s, 1H), 8.02 (m, 2H), 6.74-6.61 (m, 1H), 5.17 (dd, J = 64.3, 3.1 Hz, 1H), 4.39 (m, 1H), 2.60 (s, 3H), 1.84-1.50 (m, 2H). | 424 | 98% |
| 1-5 | (1,8-naphthyridin-2(1H)-one-6-yl) | Cl | Cyclopropyl | ¹H NMR (400 MHz, DMSO) δ 14.22 (s, 1H), 12.42 (s, 1H), 8.94 (s, 1H), 8.61 (d, J = 2.0 Hz, 1H), 8.31 (d, J = 2.0 Hz, 1H), 8.20 (d, J = 8.5 Hz, 1H), 8.03 (d, J = 9.6 Hz, 1H), 6.67 (d, J = 9.5 Hz, 1H), 4.51-4.34 (m, 1H), 1.29-1.19 (m, 2H), 1.17-1.05 (m, 2H). | 426 | 98% |
| 1-7 | (8-chloroquinolin-2(1H)-one-6-yl) | Me | Cyclopropyl | ¹H NMR (400 MHz, DMSO) δ 14.65 (s, 1H), 11.27 (s, 1H), 8.91 (s, 1H), 8.04 (d, J = 9.5 Hz, 1H), 7.98 (d, J = 8.8 Hz, 1H), 7.78 (s, 2H), 6.69 (d, J = 9.5 Hz, 1H), 4.49-4.30 (m, 1H), 2.65 (s, 3H), 1.25 (d, J = 6.7 Hz, 2H), 1.08 (s, 2H). | 439 | 98% |
| 1-8 | (8-fluoroquinolin-2(1H)-one-6-yl) | Me | Cyclopropyl | ¹H NMR (400 MHz, DMSO) δ 14.66 (s, 1H), 11.99 (s, 1H), 8.91 (s, 1H), 8.03 (d, J = 9.1 Hz, 1H), 7.98 (d, J = 8.8 Hz, 1H), 7.60 (s, 1H), 7.57 (d, J = 11.5 Hz, 1H), 6.66 (d, J = 9.6 Hz, 1H), 4.51-4.29 (m, 1H), 1.25 (d, J = 6.3 Hz, 2H), 1.15-0.94 (m, 2H). | 423 | 98% |
| 1-9 | (8-chloroquinolin-2(1H)-one-6-yl) | OMe | Cyclopropyl | ¹H NMR (400 MHz, DMSO) δ 14.64 (s, 1H), 11.30 (s, 1H), 8.82 (s, 1H), 8.15-8.03 (m, 1H), 8.00-7.93 (d, J = 9.1 Hz, 1H), 7.93-7.80 (d, J = 12.9 Hz, 2H), 6.79-6.51 (d, J = 9.4 Hz, 1H), 4.28-4.15 (m, 1H), 3.51-3.38 (s, 3H), 1.31-1.09 (m, 4H). | 455 | 93% |

TABLE 1-continued

[Structure: 6-fluoro-4-oxo-1,4-dihydroquinoline-3-carboxylic acid core with R³ at position 7, R² at position 8, R¹ on N]

| Compound No. | R³ = | R² = | R¹ = | NMR | MS (MH⁺) | HPLC |
|---|---|---|---|---|---|---|
| 1-10 | [8-fluoro-2-oxo-1,2-dihydroquinolin-6-yl] | OMe | Cyclopropyl | ¹H NMR (400 MHz, DMSO) δ 14.69-14.59 (s, 1H), 12.08-11.94 (s, 1H), 8.90-8.74 (s, 1H), 8.13-8.01 (d, J = 1.8 Hz, 1H), 7.99-7.91 (d, J = 9.1 Hz, 1H), 7.77-7.71 (s, 1H), 7.68-7.59 (d, J = 11.6 Hz, 1H), 6.71-6.62 (d, J = 9.6 Hz, 1H), 4.30-4.17 (ddd, J = 11.2, 7.5, 4.7 Hz, 1H), 3.47-3.39 (s, 3H), 1.22-1.11 (m, 4H). | 439 | 95% |
| 1-11 | [8-phenyl-2-oxo-1,2-dihydroquinolin-6-yl] | Me | Cyclopropyl | ¹H NMR (400 MHz, DMSO) δ 14.68 (s, 1H), 9.92 (s, 1H), 8.91 (s, 1H), 8.09 (d, J = 9.6 Hz, 1H), 7.99 (d, J = 8.8 Hz, 1H), 7.81 (s, 1H), 7.62-7.53 (m, 4H), 7.52-7.47 (m, 1H), 7.46 (s, 1H), 6.65 (d, J = 9.5 Hz, 1H), 4.65-4.23 (m, 1H), 2.70 (s, 3H), 1.24 (d, J = 7.0 Hz, 2H), 1.07 (s, 2H). | 481 | 98% |
| 1-12 | [8-trifluoromethoxy-2-oxo-1,2-dihydroquinolin-6-yl] | Me | Cyclopropyl | ¹H NMR (400 MHz, DMSO) δ 14.68 (s, 1H), 12.23 (s, 1H), 8.92 (s, 1H), 8.10 (d, J = 9.5 Hz, 1H), 8.00 (d, J = 8.7 Hz, 1H), 7.87 (s, 1H), 7.70 (s, 1H), 6.70 (d, J = 9.3 Hz, 1H), 4.43 (s, 1H), 2.64 (s, 3H), 1.23 (s, 2H), 1.07 (d, J = 12.5 Hz, 2H). | 489 | 98% |
| 1-13 | [8-ethynyl-2-oxo-1,2-dihydroquinolin-6-yl] | Me | Cyclopropyl | ¹H NMR (400 MHz, DMSO) δ 14.66 (s, 1H), 10.55 (s, 1H), 8.91 (s, 1H), 8.04 (d, J = 9.5 Hz, 1H), 7.99 (d, J = 8.7 Hz, 1H), 7.84 (s, 1H), 7.74 (s, 1H), 6.68 (d, J = 9.4 Hz, 1H), 4.75 (s, 1H), 4.40 (m, 1H), 2.64 (s, 3H), 1.25 (d, J = 6.9 Hz, 2H), 1.08 (s, 2H). | 429 | 90% |
| 1-14 | [8-methoxy-2-oxo-1,2-dihydroquinolin-6-yl] | Me | Cyclopropyl | ¹H NMR (400 MHz, DMSO) δ 14.70 (s, 1H), 11.06 (s, 1H), 8.91 (s, 1H), 8.05-7.87 (m, 2H), 7.31 (s, 1H), 7.16 (s, 1H), 6.60 (d, J = 9.5 Hz, 1H), 4.40 (dd, J = 7.0, 3.4 Hz, 1H), 3.94 (s, 3H), 2.65 (s, 3H), 1.25 (d, J = 7.1 Hz, 2H), 1.08 (s, 2H). | 435 | 90% |
| 1-15 | [8-trifluoromethyl-2-oxo-1,2-dihydroquinolin-6-yl] | Me | Cyclopropyl | ¹H NMR (400 MHz, DMSO) δ 14.65 (s, 1H), 10.97 (s, 1H), 8.92 (s, 1H), 8.28-8.06 (m, 2H), 8.01 (d, J = 8.8 Hz, 1H), 7.95 (s, 1H), 6.74 (d, J = 8.5 Hz, 1H), 4.49-4.33 (m, 1H), 2.64 (s, 3H), 1.25 (d, J = 6.8 Hz, 2H), 1.10 (s, 2H). | 473 | 90% |

TABLE 1-continued

| Compound No. | R³ = | R² = | R¹ = | NMR | MS (MH⁺) | HPLC |
|---|---|---|---|---|---|---|
| 1-16 | 6-yl-2-oxo-1,2-dihydroquinoline | Me | Cyclopropyl | ¹H NMR (400 MHz, DMSO) δ 14.72 (s, 1H), 11.95 (s, 1H), 8.91 (s, 1H), 7.99 (d, J = 7.9 Hz, 2H), 7.76 (s, 1H), 7.54 (d, J = 8.4 Hz, 1H), 7.47 (d, J = 8.4 Hz, 1H), 6.59 (d, J = 9.5 Hz, 1H), 4.40 (s, 1H), 2.63 (s, 3H), 1.25 (d, J = 6.1 Hz, 2H), 1.07 (s, 2H). | 405 | 98% |
| 1-17 | 8-bromo-2-oxo-1,2-dihydroquinolin-6-yl | Me | Cyclopropyl | ¹H NMR (400 MHz, DMSO) δ 14.66 (s, 1H), 10.76 (s, 1H), 8.92 (s, 1H), 8.03 (d, J = 9.7 Hz, 1H), 7.99 (d, J = 8.8 Hz, 1H), 7.93 (s, 1H), 7.83 (s, 1H), 6.68 (d, J = 9.4 Hz, 1H), 2.65 (s, 3H), 1.25 (m, 2H), 1.07 (m, 2H). | 482; 484 | 96% |
| 1-18 | 8-cyano-2-oxo-1,2-dihydroquinolin-6-yl | Me | Cyclopropyl | ¹H NMR (400 MHz, DMSO) δ 14,63 (s, 1H), 11.86 (s, 1H), 8.92 (s, 1H), 8.16 (m, 3H), 8.00 (d, J = 8.7 Hz, 1H), 6.80 (s, 1H), 4.42 (s, 1H), 2.65 (s, 3H), 1.26 (m, 2H), 1.09 (m, 2H). | 430 | 96% |
| 1-19 | 8-methyl-2-oxo-1,2-dihydroquinolin-6-yl | Me | Cyclopropyl | ¹H NMR (400 MHz, DMSO) δ 14.69 (s, 1H), 11.10 (s, 1H), 8.90 (s, 1H), 7.97 (t, J = 9.04 Hz, 2H), 7.58 (s, 1H), 7.39 (s, 1H), 6.59 (d, J = 9.48 Hz, 1H), 4.39 (dt, J = 3.29, 6.75 Hz, 1H), 3.36 (s, 3H), 2.63 (s, 3H), 1.25 (d, J = 6.45 Hz, 2H), 1.06 (s, 2H). | 419 | 96% |
| 1-20 | tricyclic lactone-quinolinone | Me | Cyclopropyl | ¹H NMR (400 MHz, DMSO) δ 14.64 (s, 1H), 8.93 (s, 1H), 8.21 (s, 1H), 8.18 (s, 1H), 8.15 (d, J = 9.7 Hz, 1H), 8.02 (d, J = 8.9 Hz, 1H), 6.81 (d, J = 9.7 Hz, 1H), 6.24 (s, 2H), 4.41 (m, 2H), 2.65 (s, 4H), 1.25 (m, 2H), 1.10 (m, 2H). | 461 | 90% |
| 1-21 | 2-oxo-1,2-dihydroquinolin-3-yl | Me | Cyclopropyl | ¹H NMR (400 MHz, DMSO) δ 14.75 (s, 1H), 12.18 (s, 1H), 8.91 (s, 1H), 8.14 (s, 1H), 7.96 (d, J = 8.8 Hz, 1H), 7.78 (d, J = 7.7 Hz, 1H), 7.60 (d, J = 7.8 Hz, 1H), 7.41 (d, J = 7.9 Hz, 1H), 7.28 (d, J = 7.4 Hz, 1H), 4.43 (s, 1H), 2.71 (s, 3H), 1.24 (s, 2H), 1.05 (s, 2H). | 405 | 98% |
| 1-22 | 1-methyl-2-oxo-1,2-dihydroquinolin-3-yl | Me | Cyclopropyl | ¹H NMR (400 MHz, DMSO) δ 14.75 (s, 1H), 8.91 (s, 1H), 8.16 (s, 1H), 7.95 (d, J = 8.2 Hz, 1H), 7.90 (s, 1H), 7.85 (d, J = 7.3 Hz, 1H), 7.66 (d, J = 8.5 Hz, 1H), 7.38 (d, J = 6.7 Hz, 1H), 4.42 (s, 1H), 3.74 (s, 3H), 2.69 (s, 3H), 1.23 (s, 2H), 1.05 (s, 2H). | 419 | 95% |

TABLE 1-continued

| Compound No. | R³ = | R² = | R¹ = | NMR | MS (MH⁺) | HPLC |
|---|---|---|---|---|---|---|
| 1-23 | 5-(2-oxo-1,2-dihydroquinolinyl) with methyl | Me | Cyclopropyl | ¹H NMR (400 MHz, DMSO) δ 14.72 (s, 1H), 12.04 (s, 1H), 8.93 (s, 1H), 8.04 (d, J = 8.2 Hz, 1H), 7.68 (t, J = 7.5 Hz, 1H), 7.48 (d, J = 8.1 Hz, 1H), 7.35 (d, J = 9.7 Hz, 1H), 7.17 (d, J = 7.1 Hz, 1H), 6.49 (d, J = 9.7 Hz, 1H), 4.39 (s, 1H), 2.50 (s, 3H), 1.16 (m, 4H). | 405 | 96% |
| 1-24 | 8-(2-oxo-1,2-dihydroquinolinyl) with methyl | Me | Cyclopropyl | ¹H NMR (400 MHz, DMSO) δ 14.82 (s, 1H), 10.88 (s, 1H), 8.95 (s, 1H), 8.20-7.94 (m, 2H), 7.86 (d, J = 30.6 Hz, 1H), 7.44 (d, J = 7.5 Hz, 1H), 7.36 (s, 1H), 6.57 (s, 1H), 4.41 (s, 1H), 2.67 (s, 3H), 1.47-0.92 (m, 4H). | 405 | 90% |
| 1-25 | 4-(2-oxo-1,2-dihydroquinolinyl) with methyl | Me | Cyclopropyl | ¹H NMR (400 MHz, DMSO) δ 14.66 (s, 1H), 12.12 (s, 1H), 8.94 (s, 1H), 8.06 (d, J = 8.5 Hz, 1H), 7.58 (s, 1H), 7.45 (d, J = 7.0 Hz, 1H), 7.13 (s, 1H), 7.02 (d, J = 8.0 Hz, 1H), 6.65 (s, 1H), 4.40 (m, 1H), 2.62 (s, 3H), 1.28-1.04 (m, 4H). | 405 | 90% |
| 1-26 | 7-(2-oxo-1,2-dihydroquinolinyl) with methyl | Me | Cyclopropyl | ¹H NMR (400 MHz, DMSO) δ 14.70 (s, 1H), 11.88 (s, 1H), 8.92 (s, 1H), 8.01 (d, J = 8.8 Hz, 2H), 7.86 (d, J = 7.8 Hz, 1H), 7.29 (s, 1H), 7.22 (d, J = 7.6 Hz, 1H), 6.60 (d, J = 9.6 Hz, 1H), 4.40 (s, 1H), 2.62 (s, 3H), 1.24 (d, J = 5.6 Hz, 2H), 1.07 (s, 2H). | 405 | 94% |
| 1-27 | OH, 6-(4-hydroxy-2-oxo-1,2-dihydroquinolinyl) with methyl | Me | Cyclopropyl | ¹H NMR (400 MHz, DMSO) δ 14.80 (s, 1H), 11.57 (s, 1H), 11.48 (s, 1H), 8.97 (s, 1H), 8.04 (d, J = 8.5 Hz, 1H), 7.82 (s, 1H), 7.60 (d, J = 8.1 Hz, 1H), 7.49 (d, J = 8.2 Hz, 1H), 5.86 (s, 1H), 4.45 (s, 1H), 2.68 (s, 3H), 1.30 (d, J = 5.7 Hz, 2H), 1.13 (s, 2H). | 421 | 98% |
| 1-28 | OH, NO₂, 6-(4-hydroxy-3-nitro-2-oxo-1,2-dihydroquinolinyl) with methyl | Me | Cyclopropyl | ¹H NMR (400 MHz, DMSO) δ 14.75 (s, 1H), 10.73 (s, 1H), 8.90 (s, 1H), 7.97 (d, J = 8.4 Hz, 1H), 7.89 (s, 1H), 7.43 (s, 1H), 7.28 (d, J = 7.6 Hz, 1H), 4.40 (s, 1H), 2.62 (s, 3H), 1.24 (s, 2H), 1.06 (s, 2H). | 466 | 96% |
| 1-29 | 6-(2-oxo-1,2-dihydroquinolinyl) | OMe | Cyclopropyl | ¹H NMR (400 MHz, DMSO) δ 14.69 (s, 1H), 11.96 (s, 1H), 8.81 (s, 1H), 8.01 (d, J = 9.6 Hz, 1H), 7.95 (d, J = 9.1 Hz, 1H), 7.87 (s, 1H), 7.68 (d, J = 8.6 Hz, 1H), 7.49 (d, J = 8.6 Hz, 1H), 6.57 (dd, J = 9.5, 1.7 Hz, 1H), 4.32-4.10 (m, 1H), 3.38 (s, 3H), 1.18 (m, 4H). | 421 | 98% |

TABLE 1-continued

| Compound No. | R³ = | R² = | R¹ = | NMR | MS (MH⁺) | HPLC |
|---|---|---|---|---|---|---|
| 1-30 | 6-substituted-2-oxo-1,2-dihydroquinolin-6-yl | Cl | Cyclopropyl | ¹H NMR (400 MHz, DMSO) δ 14.41 (s, 1H), 11.96 (s, 1H), 8.91 (s, 1H), 8.20 (d, J = 8.8 Hz, 1H), 7.95 (d, J = 9.1 Hz, 1H), 7.80 (s, 1H), 7.68 (d, J = 8.6 Hz, 1H), 7.49 (d, J = 8.6 Hz, 1H), 6.62 (dd, J = 9.5, 1.7 Hz, 1H), 4.32-4.10 (m, 1H), 1.30 (m, 2H), 1.18 (m, 2H). | 425 | 96% |
| 1-31 | 7-substituted-2-oxo-1,2-dihydroquinolin-7-yl | OMe | Cyclopropyl | ¹H NMR (400 MHz, DMSO) δ 14.67 (s, 1H), 11.89 (s, 1H), 8.82 (s, 1H), 8.17-7.90 (m, 2H), 7.85 (d, J = 8.0 Hz, 1H), 7.48 (s, 1H), 7.35 (d, J = 7.9 Hz, 1H), 6.60 (d, J = 11.2 Hz, 1H), 4.28-4.14 (m, 1H), 3.41 (s, 4H), 1.18 (m, 4H). | 421 | 90% |
| 1-32 | 4-methyl-2-oxo-1,2-dihydroquinolin-6-yl | Me | Cyclopropyl | ¹H NMR (400 MHz, DMSO) δ 14.69 (s, 1H), 11.78 (s, 1H), 8.91 (s, 1H), 7.98 (d, J = 8.77 Hz, 1H), 7.72 (s, 1H), 7.54 (s, 1H), 7.50-7.44 (m, 1H), 6.48 (s, 1H), 2.63 (s, 3H), 2.44 (s, 3H), 1.28-1.21 (m, 2H), 1.12-1.02 (m, 2H). | 419 | 96% |
| 1-33 | 3-cyano-2-oxo-1,2-dihydroquinolin-6-yl | Me | Cyclopropyl | ¹H NMR (400 MHz, DMSO) δ 14.62 (s, 1H), 13.15 (s, 1H), 8.92 (s, 1H), 8.87 (s, 1H), 8.77 (d, J = 1.74 Hz, 1H), 8.38 (d, J = 1.97 Hz, 1H), 8.02 (d, J = 8.86 Hz, 1H), 4.42 (tt, J = 3.74, 7.15 Hz, 1H), 2.66 (s, 3H), 1.25 (q, J = 6.85 Hz, 2H), 1.08 (s, 2H). | 431 | 96% |
| 1-34 | 4-methyl-2-oxo-1,2-dihydro-1,8-naphthyridin-6-yl | Me | Cyclopropyl | ¹H NMR (400 MHz, DMSO) δ 9.11 (s, 1H), 8.92 (s, 1H), 8.31 (d, J = 8.86 Hz, 1H), 8.16 (d, J = 8.54 Hz, 1H), 8.03 (d, J = 8.91 Hz, 1H), 6.51 (s, 1H), 4.44 (tt, J = 3.64, 7.02 Hz, 2H), 2.69 (s, 3H), 2.51 (s, 3H), 1.24 (d, J = 6.83 Hz, 2H), 1.10 (s, 2H). | 420 | 95% |
| 1-35 | 8-chloro-2-oxo-1,2,3,4-tetrahydroquinolin-6-yl | OMe | Cyclopropyl | ¹H NMR (400 MHz, DMSO) δ 14.75-14.55 (m, 1H), 9.83-9.67 (d, J = 3.2 Hz, 1H), 8.89-8.73 (s, 1H), 7.96-7.86 (d, J = 9.1 Hz, 1H), 7.58-7.47 (s, 1H), 7.42-7.34 (s, 1H), 4.30-4.14 (tt, J = 7.3, 4.5 Hz, 1H), 3.52-3.39 (s, 3H), 3.11-2.95 (t, J = 7.5 Hz, 2H), 2.62-2.56 (dd, J = 8.5, 6.3 Hz, 2H), 1.21-1.12 (m, 4H). | 457 | 99% |
| 1-36 | 8-vinyl-2-oxo-1,2,3,4-tetrahydroquinolin-6-yl | OMe | Cyclopropyl | ¹H NMR (400 MHz, CDCl₃) δ 14.52-14.39 (s, 1H), 8.87-8.82 (s, 1H), 8.01-7.92 (m, 1H), 7.75-7.69 (s, 1H), 7.39-7.34 (t, J = 1.7 Hz, 1H), 7.21-7.18 (s, 1H), 6.79-6.69 (dd, J = 17.3, 11.0 Hz, 1H), 5.70-5.62 (d, J = 17.3 Hz, 1H), 5.54-5.44 (d, J = 11.0 Hz, 1H), 4.09-3.99 (d, J = 3.7 Hz, 1H), 3.45-3.36 (s, 3H), 3.03-2.95 (dd, J = 8.5, 6.5 Hz, 2H), 2.68-2.59 (dd, J = 8.7, 6.5 Hz, 2H), 1.26-1.21 (dd, J = 5.2, 1.8 Hz, 2H), 1.11-1.03 (dt, J = 4.0, 1.9 Hz, 2H). | 449 | 85% |

TABLE 1-continued

| Compound No. | R³ = | R² = | R¹ = | NMR | MS (MH⁺) | HPLC |
|---|---|---|---|---|---|---|
| 1-37 | 3,4-dihydro-8-fluoro-2(1H)-quinolinon-6-yl | OMe | Cyclopropyl | ¹H NMR (400 MHz, DMSO) δ 14.73-14.60 (s, 1H), 10.38-10.26 (s, 1H), 8.84-8.76 (s, 1H), 7.96-7.88 (d, J = 0.1 Hz, 1H), 7.36-7.28 (d, J = 11.2 Hz, 1H), 7.25-7.19 (s, 1H), 4.29-4.18 (ddd, J = 11.3, 7.3, 4.4 Hz, 1H), 3.47-3.43 (s, 3H), 3.07-2.99 (t, J = 7.4 Hz, 2H), 2.60-2.53 (dd, J = 8.5, 6.5 Hz, 2H), 1.21-1.08 (d, J = 5.3 Hz, 4H). | 441 | 85% |
| 1-38 | 3,4-dihydro-8-methyl-2(1H)-quinolinon-6-yl | OMe | Cyclopropyl | ¹H NMR (400 MHz, DMSO) δ 14.70 (s, 1H), 9.62 (s, 1H), 8.79 (s, 1H), 7.89 (d, J = 9.2 Hz, 1H), 7.20 (d, J = 8.5 Hz, 2H), 4.39-4.16 (m, 1H), 3.42 (s, 3H), 3.03-2.88 (m, 2H), 2.54 (m, 5H), 1.16 (m, 4H). | 436 | 99% |
| 1-39 | 3,4-dihydro-2(1H)-[1,8]naphthyridinon-6-yl | OMe | Cyclopropyl | ¹H NMR (400 MHz, DMSO) δ 15.13-14.27 (m, 1H), 10.76-10.64 (s, 5H), 8.98-8.88 (s, 1H), 8.19-8.14 (d, J = 2.2 Hz, 1H), 8.00-7.94 (d, J = 8.7 Hz, 1H), 7.75-7.70 (d, J = 2.1 Hz, 1H), 4.49-4.32 (tt, J = 7.3, 3.8 Hz, 1H), 3.03-2.95 (m, 2H), 2.69-2.64 (s, 3H), 2.62-2.56 (t, J = 7.5 Hz, 2H), 1.28-1.22 (m, 2H), 1.09-1.03 (m, 2H). | 408 | 90% |
| 1-40 | 2(1H)-[1,5]naphthyridinon-7-yl | Me | Cyclopropyl | ¹H NMR (400 MHz, DMSO) δ 14.60 (s, 1H), 12.01 (s, 1H), 8.92 (s, 1H), 8.53 (s, 1H), 8.08-7.98 (m, 2H), 7.72 (s, 1H), 6.85 (d, J = 9.75 Hz, 1H), 4.41 (s, 1H), 3.34 (s, 1H), 2.65 (s, 3H), 2.54 (s, 3H), 1.24 (d, J = 6.54 Hz, 2H), 1.09 (s, 2H). | 406 | 96% |
| 1-41 | quinolin-3-yl | Me | Cyclopropyl | ¹H NMR (400 MHz, DMSO) δ 14.85-14.51 (s, 1H), 9.00-8.91 (m, 2H), 8.60-8.53 (s, 1H), 8.18-8.09 (t, J = 8.4 Hz, 2H), 8.09-8.02 (m, 1H), 7.95-7.84 (s, 1H), 7.79-7.68 (s, 1H), 4.51-4.31 (s, 1H), 2.79-2.61 (s, 3H), 1.36-1.20 (d, J = 6.9 Hz, 2H), 1.16-1.04 (s, 2H). | 389 | 100% |
| 1-42 | 1H-isochromen-3-yl | Me | Cyclopropyl | ¹H NMR (400 MHz, DMSO) δ 15.01-14.88 (d, J = 2.6 Hz, 1H), 8.95-8.82 (d, J = 2.5 Hz, 1H), 8.05-7.94 (d, J = 6.7 Hz, 1H), 7.89-7.77 (d, J = 9.4 Hz, 1H), 7.62-7.40 (m, 3H), 6.33-6.21 (s, 1H), 5.59-5.49 (s, 2H), 4.48-4.35 (s, 1H), 2.86-2.76 (s, 3H), 1.30-1.15 (d, J = 7.0 Hz, 2H), 1.00-0.88 (s, 2H). | 392 | 100% |
| 1-43 | quinolin-6-yl | Me | Cyclopropyl | ¹H NMR (400 MHz, MeOD) δ 9.05-8.91 (s, 1H), 8.87-8.77 (s, 1H), 8.43-8.36 (s, 1H), 8.14-8.06 (d, J = 7.3 Hz, 1H), 8.02-7.88 (d, J = 21.7 Hz, 2H), 7.74-7.62 (d, J = 8.7 Hz, 1H), 7.59-7.51 (s, 1H), 4.35-4.15 (s, 1H), 2.73-2.53 (m, 3H), 1.05-0.93 (s, 2H), 0.85-0.71 (d, J = 8.0 Hz, 2H). | 389 | 97% |

TABLE 1-continued

| Compound No. | R³ = | R² = | R¹ = | NMR | MS (MH⁺) | HPLC |
|---|---|---|---|---|---|---|
| 1-44 | quinoline N-oxide (3-yl) | Me | Cyclopropyl | ¹H NMR (400 MHz, DMSO) δ 14.72-14.59 (s, 1H), 9.01-8.91 (s, 1H), 8.88-8.80 (s, 1H), 8.66-8.56 (d, J = 8.6 Hz, 1H), 8.25-8.16 (d, J = 8.0 Hz, 1H), 8.14-8.09 (s, 1H), 8.08-8.01 (d, J = 8.6 Hz, 1H), 7.95-7.89 (d, J = 8.7 Hz, 1H), 7.88-7.79 (d, J = 7.7 Hz, 1H), 4.51-4.35 (s, 1H), 2.75-2.67 (s, 3H), 1.30-1.19 (d, J = 6.8 Hz, 2H), 1.16-1.07 (s, 2H). | 405 | 97.5% |
| 1-45 | naphthalen-2-yl | Me | Cyclopropyl | ¹H NMR (400 MHz, DMSO) δ 14.85-14.58 (s, 1H), 9.00-8.88 (s, 1H), 8.19-8.07 (d, J = 8.3 Hz, 1H), 8.07-7.94 (m, 4H), 7.68-7.58 (d, J = 6.0 Hz, 2H), 7.57-7.48 (d, J = 8.2 Hz, 1H), 4.49-4.33 (s, 1H), 2.72-2.59 (s, 3H), 1.33-1.19 (d, J = 7.4 Hz, 2H), 1.16-1.00 (s, 2H). | 388 | 98% |
| 1-46 | isoquinolin-4-yl | Me | Cyclopropyl | ¹H NMR (400 MHz, DMSO) δ 9.89-9.59 (s, 1H), 9.01-8.32 (d, J = 2.5 Hz, 1H), 8.69-8.58 (d, J = 2.4 Hz, 1H), 8.47-8.34 (d, J = 7.6 Hz, 1H), 8.14-8.04 (d, J = 8.1 Hz, 1H), 7.95-7.80 (t, J = 8.7 Hz, 2H), 7.57-7.46 (d, J = 7.9 Hz, 1H), 4.48-4.34 (s, 1H), 2.52-2.50 (s, 3H), 1.29-1.01 (m, 4H). | 389 | 98% |
| 1-47 | phthalazine-1,4-dione-6-yl | Me | Cyclopropyl | ¹H NMR (400 MHz, DMSO) δ 14.96-14.46 (s, 1H), 12.04-11.50 (s, 1H), 8.98-8.89 (s, 1H), 8.34-8.17 (d, J = 12.3 Hz, 1H), 8.17-8.01 (m, 2H), 7.97-7.90 (d, J = 8.1 Hz, 1H), 4.48-4.36 (dd, J = 7.3, 4.1 Hz, 1H), 2.66-2.56 (s, 3H), 1.31-1.17 (d, J = 7.1 Hz, 2H), 1.15-1.03 (s, 2H). | 422 | 99% |
| 1-48 | isoquinoline N-oxide (4-yl) | Me | Cyclopropyl | ¹H NMR (400 MHz, DMSO) δ 9.19-9.11 (s, 1H), 8.98-8.92 (s, 1H), 8.45-8.39 (s, 1H), 8.13-8.00 (dd, J = 16.7, 8.4 Hz, 2H), 7.80-7.69 (t, J = 7.7 Hz, 1H), 7.66-7.55 (t, J = 7.7 Hz, 1H), 7.38-7.29 (d, J = 8.3 Hz, 1H), 4.47-4.34 (s, 1H), 2.65-2.54 (s, 3H), 1.28-1.07 (m, 4H). | 405 | 98% |
| 1-49 | N-methylisoquinolinium (4-yl) | Me | Cyclopropyl | ¹H NMR (400 MHz, DMSO) δ 14.69-14.45 (s, 1H), 10.31-10.19 (s, 1H), 9.06-8.94 (d, J = 3.6 Hz, 2H), 8.73-8.62 (d, J = 8.2 Hz, 1H), 8.61-8.43 (m, 2H), 8.32-8.21 (t, J = 7.5 Hz, 1H), 8.21-8.11 (m, 2H), 7.83-7.71 (d, J = 8.3 Hz, 1H), 4.67-4.52 (s, 3H), 4.50-4.39 (d, J = 7.6 Hz, 1H), 2.52-2.50 (m, 3H), 1.32-1.03 (m, 4H). | 404 | 100% |

TABLE 1-continued

| Compound No. | R³ = | R² = | R¹ = | NMR | MS (MH⁺) | HPLC |
|---|---|---|---|---|---|---|
| 1-50 | (1-methylquinolinium-3-yl) | Me | Cyclopropyl | ¹H NMR (400 MHz, DMSO) δ 14.72-14.45 (s, 1H), 8.86-9.78 (s, 1H), 9.58-9.48 (s, 1H), 9.02-8.92 (s, 1H), 8.70-8.60 (d, J = 9.0 Hz, 1H), 8.59-8.51 (d, J = 8.2 Hz, 1H), 8.46-8.36 (t, J = 7.9 Hz, 1H), 8.24-8.06 (t, J = 9.7 Hz, 2H), 4.78-4.67 (s, 2H), 4.53-4.40 (s, 1H), 2.82-2.71 (s, 3H), 1.37-1.18 (d, J = 6.4 Hz, 2H), 1.16-1.07 (m, 2H). | 404 | 98% |
| 1-51 | quinolin-5-yl | Me | Cyclopropyl | ¹H NMR (400 MHz, DMSO) δ 9.10-9.01 (d, J = 4.0 Hz, 1H), 8.98-8.91 (d, J = 2.6 Hz, 1H), 8.30-8.19 (d, J = 8.4 Hz, 1H), 8.14-8.07 (s, 1H), 8.05-7.97 (t, J = 7.7 Hz, 1H), 7.96-7.89 (d, J = 8.4 Hz, 1H), 7.78-7.68 (d, J = 6.8 Hz, 1H), 7.65-7.57 (m, 1H), 4.45-4.33 (s, 1H), 2.48-2.40 (d, J = 2.8 Hz, 3H), 1.28-1.03 (m, 4H). | 389 | 93.6% |
| 1-52 | quinolin-7-yl | Me | Cyclopropyl | ¹H NMR (400 MHz, DMSO) δ 14.78-14.66 (s, 1H), 9.06-8.97 (s, 1H), 8.96-8.88 (d, J = 8.1 Hz, 1H), 8.54-8.46 (d, J = 8.1 Hz, 1H), 8.26-8.14 (d, J = 8.3 Hz, 1H), 8.14-8.06 (s, 1H), 8.06-7.98 (d, J = 8.6 Hz, 1H), 7.74-7.58 (d, J = 8.3 Hz, 2H), 4.51-4.29 (s, 1H), 2.73-2.60 (s, 3H), 1.29-1.18 (d, J = 7.0 Hz, 2H), 1.15-1.07 (s, 2H). | 389 | 100% |
| 1-53 | quinolin-8-yl | Me | Cyclopropyl | ¹H NMR (400 MHz, DMSO) δ 8.96-8.88 (d, J = 2.4 Hz, 1H), 8.85-8.78 (s, 1H), 8.57-8.47 (d, J = 8.2 Hz, 1H), 8.25-8.13 (d, J = 8.3 Hz, 1H), 8.03-7.95 (d, J = 8.3 Hz, 1H), 7.88-7.77 (m, 2H), 7.69-7.54 (d, J = 8.7 Hz, 1H), 4.44-4.31 (s, 1H), 2.48-2.42 (s, 3H), 1.29-1.16 (d, J = 7.6 Hz, 2H), 1.15-1.02 (s, 2H). | 389 | 98% |
| 1-54 | quinolin-4-yl | Me | Cyclopropyl | ¹H NMR (400 MHz, DMSO) δ 9.17-9.09 (s, 1H), 9.01-8.91 (d, J = 2.7 Hz, 1H), 8.26-8.17 (d, J = 8.5 Hz, 1H), 8.15-8.06 (d, J = 8.5 Hz, 1H), 7.94-7.84 (s, 1H), 2.48-2.42 (m, 2H), 7.72-7.59 (d, J = 9.2 Hz, 2H), 7.56-7.45 (d, J = 8.3 Hz, 1H), 4.45-4.35 (s, 1H), 2.52-2.45 (s, 3H), 1.29-1.03 (dd, J = 16.6, 7.5 Hz, 4H). | 389 | 98% |
| 1-55 | quinolin-8-yl N-oxide | Me | Cyclopropyl | ¹H NMR (400 MHz, DMSO) δ 15.08-14.78 (s, 1H), 8.95-8.83 (s, 2H), 8.48-8.37 (d, J = 6.0 Hz, 1H), 8.33-8.19 (d, J = 8.2 Hz, 1H), 8.14-8.02 (d, J = 8.5 Hz, 1H), 7.94-7.76 (m, 2H), 7.68-7.59 (d, J = 7.1 Hz, 1H), 7.58-7.49 (t, J = 7.2 Hz, 1H), 4.47-4.34 (s, 1H), 2.73-2.56 (s, 3H), 1.31-0.99 (m, 4H). | 405 | 95% |

TABLE 1-continued

[Structure: fluoroquinolone core with R¹ on N, R² at position 8, R³ at position 7, F at position 6, with 4-oxo and 3-carboxylic acid]

| Compound No. | R³ = | R² = | R¹ = | NMR | MS (MH⁺) | HPLC |
|---|---|---|---|---|---|---|
| 1-56 | 4-quinolinyl N-oxide | Me | Cyclopropyl | ¹H NMR (400 MHz, DMSO) δ 9.00-8.91 (s, 1H), 8.85-8.75 (d, J = 6.1 Hz, 1H), 8.73-8.64 (d, J = 8.6 Hz, 1H), 8.13-8.05 (d, J = 8.4 Hz, 1H), 7.97-7.86 (d, J = 8.1 Hz, 1H), 7.80-7.71 (s, 1H), 7.65-7.58 (d, J = 5.8 Hz, 1H), 7.57-7.48 (d, J = 8.4 Hz, 1H), 4.46-4.35 (s, 1H), 2.57-2.52 (s, 3H), 1.28-1.04 (m, 4H). | 405 | 96% |
| 1-57 | 5-quinolinyl N-oxide | Me | Cyclopropyl | ¹H NMR (400 MHz, DMSO) δ 14.95-14.35 (m, 1H), 9.01-8.90 (t, J = 2.0 Hz, 1H), 8.80-8.63 (m, 2H), 8.13-8.06 (m, 1H), 8.04-7.95 (t, J = 7.8 Hz, 1H), 7.84-7.75 (d, J = 6.5 Hz, 1H), 7.52-7.41 (ddd, J = 10.0, 5.1, 2.5 Hz, 1H), 7.38-7.29 (d, J = 8.4 Hz, 1H), 4.46-4.32 (d, J = 6.9 Hz, 1H), 2.49-2.44 (s, 3H), 1.29-0.99 (m, 4H). | 405 | 93.3% |
| 1-58 | 7-quinolinyl N-oxide | Me | Cyclopropyl | ¹H NMR (400 MHz, DMSO) δ 8.98-8.89 (s, 1H), 8.73-8.64 (d, J = 6.6 Hz, 1H), 8.58-8.52 (s, 1H), 8.35-8.26 (d, J = 8.2 Hz, 1H), 8.12-7.99 (t, J = 10.7 Hz, 2H), 7.83-7.75 (d, J = 8.3 Hz, 1H), 7.65-7.53 (s, 1H), 4.46-4.36 (s, 1H), 2.65-2.59 (s, 3H), 1.29-1.19 (d, J = 7.8 Hz, 2H), 1.14-1.07 (s, 2H). | 405 | 96.2% |
| 1-59 | 6-quinolinyl N-oxide | Me | Cyclopropyl | ¹H NMR (400 MHz, DMSO) δ 8.96-8.87 (s, 1H), 8.75-8.64 (d, J = 7.2 Hz, 2H), 8.28-8.19 (s, 1H), 8.10-7.99 (d, J = 8.5 Hz, 2H), 7.90-7.80 (d, J = 9.0 Hz, 1H), 7.63-7.52 (s, 1H), 4.48-4.34 (s, 1H), 2.65-2.57 (s, 3H), 1.30-1.18 (d, J = 7.1 Hz, 2H), 1.14-1.02 (s, 2H). | 405 | 99% |
| 1-60 | 6-isoquinolinyl | Me | Cyclopropyl | ¹H NMR (400 MHz, DMSO) δ 9.77-9.61 (s, 1H), 9.00-8.90 (d, J = 3.1 Hz, 1H), 8.75-8.62 (d, J = 5.8 Hz, 1H), 8.57-8.42 (d, J = 8.2 Hz, 1H), 8.31-8.21 (s, 1H), 8.22-8.13 (d, J = 5.3 Hz, 1H), 8.11-8.01 (d, J = 8.7 Hz, 1H), 7.94-7.81 (d, J = 8.4 Hz, 1H), 4.49-4.34 (s, 1H), 2.68-2.59 (s, 3H), 1.34-1.18 (d, J = 7.6 Hz, 2H), 1.15-1.00 (s, 2H). | 389 | 93.6% |
| 1-61 | 6-isoquinolinyl N-oxide | Me | Cyclopropyl | ¹H NMR (400 MHz, DMSO) δ 9.19-9.10 (s, 1H), 9.03-8.95 (s, 1H), 8.37-8.27 (d, J = 6.9 Hz, 1H), 8.18-8.05 (m, 4H), 7.81-7.73 (d, J = 8.4 Hz, 1H), 4.52-4.42 (t, J = 5.2 Hz, 1H), 2.74-2.65 (s, 3H), 1.36-1.27 (d, J = 7.1 Hz, 2H), 1.19-1.10 (s, 2H). | 405 | 1005 |

TABLE 1-continued

| Compound No. | R³ = | R² = | R¹ = | NMR | MS (MH⁺) | HPLC |
|---|---|---|---|---|---|---|
| 1-62 | (1-oxo-1,2-dihydroisoquinolin-6-yl, 3-methyl) | Me | Cyclopropyl | $^1$H NMR (400 MHz, DMSO) δ 14.82-14.70 (s, 1H), 11.54-11.41 (s, 1H), 9.03-8.93 (s, 1H), 8.44-8.33 (d, J = 8.2 Hz, 1H), 8.14-8.01 (d, J = 8.0 Hz, 1H), 7.84-7.75 (s, 1H), 7.58-7.51 (d, J = 7.6 Hz, 1H), 7.39-7.26 (s, 1H), 6.76-6.64 (d, J = 6.6 Hz, 1H), 4.52-4.40 (s, 1H), 2.70-2.61 (s, 3H), 1.37-1.22 (d, J = 6.8 Hz, 2H), 1.19-1.04 (s, 2H). | 405 | 100% |
| 1-63 | (fused tricyclic structure with 7-oxo-1,8-naphthyridinyl substituent) | | | $^1$H NMR (400 MHz, DMSO) δ 15.18 (s, 1H), 12.31 (s, 1H), 9.09 (s, 1H), 8.82 (d, J = 2.0 Hz, 1H), 8.45 (d, J = 1.7 Hz, 1H), 8.03 (t, J = 9.3 Hz, 2H), 7.76 (d, J = 8.4 Hz, 1H), 6.63 (d, J = 9.4 Hz, 1H), 5.00 (d, J = 6.7 Hz, 1H), 4.58 (d, J = 10.8 Hz, 1H), 4.45 (d, J = 10.0 Hz, 1H), 2.54 (s, 1H), 1.52 (d, J = 6.7 Hz, 3H). | 390 | 98% |
| 1-64 | (fused tricyclic structure with 7-oxo-1,8-naphthyridinyl substituent, F) | | | $^1$H NMR (400 MHz, DMSO) δ 14.96 (s, 1H), 12.35 (s, 1H), 9.10 (s, 1H), 8.68 (s, 1H), 8.34 (s, 1H), 8.01 (d, J = 9.53 Hz, 1H), 7.79 (d, J = 9.70 Hz, 1H), 6.64 (d, J = 9.45 Hz, 1H), 5.01 (d, J = 6.68 Hz, 1H), 4.60-4.54 (m, 1H), 4.46 (d, J = 9.78 Hz, 1H), 1.49 (d, J = 6.71 Hz, 3H). | 408 | 96% |
| 1-65 | (quinolin-3-yl) | Me | Cyclopropyl | $^1$H NMR (400 MHz, DMSO) δ 9.27 (s, 1H), 8.95 (s, 1H), 8.87 (d, J = 15.4 Hz, 1H), 8.41-8.22 (m, 3H), 8.01 (t, J = 7.3 Hz, 1H), 7.85 (t, J = 7.3 Hz, 1H), 7.73 (d, J = 8.2 Hz, 1H), 4.45 (m, 1H), 2.77 (s, 3H), 1.31 (d, J = 6.2 Hz, 2H), 1.11 (s, 2H). | 371 | 97% |

TABLE 2

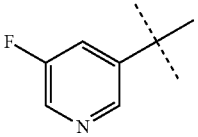

| Compound No. | R³ = | R² = | R¹ = | NMR | MS (MH⁺) | HPLC |
|---|---|---|---|---|---|---|
| 2-1 | 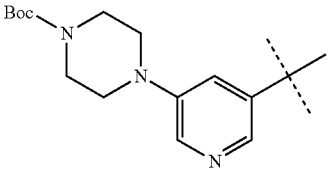 | Me | Cyclopropyl | ¹H NMR (400 MHz, DMSO) δ 8.28 (s, 1H), 7.98 (s, 1H), 7.80 (s, 1H), 7.33 (d, J = 8.90 Hz, 1H), 7.16 (d, J = 9.30 Hz, 1H), 3.66 (d, J = 3.58 Hz, 1H), 1.96 (s, 3H), 0.58 (d, J = 5.78 Hz, 2H), 0.37 (d, J = 1.61 Hz, 2H). | 357 | 94% |
| 2-2 | 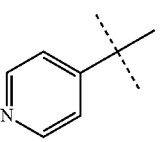 | Me | Cyclopropyl | ¹H NMR (400 MHz, DMSO) δ 8.93 (s, 1H), 8.48 (d, J = 2.77 Hz, 1H), 8.13 (s, 1H), 8.01 (d, J = 8.72 Hz, 1H), 7.61 (s, 1H), 4.50-4.30 (m, 1H), 3.49 (d, J = 5.30 Hz, 5H), 3.36-3.29 (m, 5H), 2.66 (d, J = 15.95 Hz, 3H), 1.43 (s, 9H), 1.28-1.21 (m, 2H), 1.08 (s, 2H). | 523 | 98% |
| 2-3 | 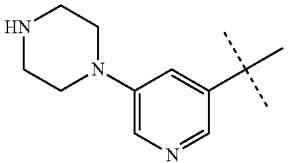 | Me | Cyclopropyl | ¹H NMR (400 MHz, DMSO) δ 8.92 (s, 1H), 8.79 (d, J = 5.61 Hz, 2H), 8.01 (d, J = 8.93 Hz, 1H), 7.50 (d, J = 5.50 Hz, 2H), 4.40 (s, 1H), 2.61 (s, 3H), 1.24 (d, J = 5.97 Hz, 2H), 1.07 (s, 2H). | 339 | 98% |
| 2-4 | 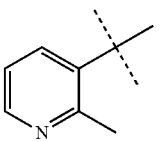 | Me | Cyclopropyl | ¹H NMR (400 MHz, DMSO) δ 9.00 (s, 2H), 8.92 (s, 1H), 8.49 (d, J = 2.73 Hz, 1H), 8.12 (s, 1H), 7.98 (t, J = 11.57 Hz, 1H), 7.56 (s, 1H), 4.44-4.34 (m, 1H), 3.64 (s, 5H), 3.26 (s, 4H), 2.62 (s, 3H), 1.23 (d, J = 6.27 Hz, 2H), 1.07 (s, 2H). | 423 | 95% |
| 2-5 | 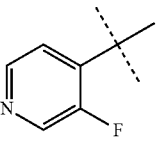 | Me | Cyclopropyl | ¹H NMR (400 MHz, DMSO) δ 8.93 (s, 1H), 8.71 (t, J = 26.47 Hz, 1H), 8.04 (d, J = 8.68 Hz, 2H), 7.61 (d, J = 45.28 Hz, 1H), 4.44-4.38 (m, 1H), 2.55 (s, 2H), 2.34 (d, J = 9.33 Hz, 3H), 1.23 (s, 2H), 1.06 (dd, J = 4.45, 8.57 Hz, 2H). | 353 | 95% |
| 2-6 | 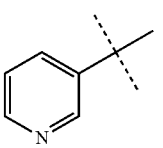 | Me | Cyclopropyl | ¹H NMR (400 MHz, DMSO) δ 14.55 (s, 1H), 8.92 (s, 1H), 8.83 (t, J = 8.69 Hz, 1H), 8.65 (dt, J = 8.70, 17.42 Hz, 1H), 8.05 (d, J = 8.87 Hz, 1H), 7.73-7.52 (m, 1H), 4.41 (tt, J = 3.77, 7.16 Hz, 1H), 2.64 (s, 3H), 1.31-1.16 (m, 2H), 1.10-0.97 (m, 2H). | 357 | 98% |
| 2-7 | 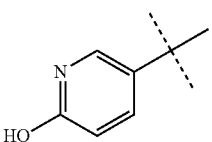 | Me | Cyclopropyl | ¹H NMR (400 MHz, DMSO) δ 8.93 (s, 1H), 8.85-8.61 (m, 2H), 8.03 (d, J = 6.60 Hz, 1H), 7.96 (s, 2H), 7.69 (dd, J = 5.19, 7.64 Hz, 1H), 4.41 (ddd, J = 3.87, 7.26, 10.97 Hz, 1H), 2.75-2.72 (m, 5H), 1.33-1.20 (m, 3H), 1.13-1.03 (m, 2H). | 339 | 98% |
| 2-8 |  | Me | Cyclopropyl | ¹H NMR (400 MHz, MeOD) δ 8.79 (s, 1H), 7.92-7.71 (m, 2H), 7.55 (t, J = 17.62 Hz, 1H), 6.84 (t, J = 36.31 Hz, 1H), 4.16-4.04 (m, 1H), 3.02 (s, 5H), 1.09-1.01 (m, 2H), 0.81 (q, J = 7.23 Hz, 2H). | 355 | 98% |

TABLE 2-continued

| Compound No. | R³ = | R² = | R¹ = | NMR | MS (MH⁺) | HPLC |
|---|---|---|---|---|---|---|
| 2-9 | 6-methoxypyridin-3-yl | Me | Cyclopropyl | $^1$H NMR (400 MHz, MeOD) δ 8.06 (t, J = 38.62 Hz, 2H), 7.68 (dd, J = 8.35, 33.76 Hz, 2H), 7.47 (d, J = 8.87 Hz, 1H), 7.13-6.77 (m, 2H), 4.33 (s, 1H), 3.97 (d, J = 7.85 Hz, 3H), 2.20-1.90 (m, 2H), 1.35-1.22 (m, 1H), 1.05 (s, 1H). | 369 | 98% |
| 2-10 | 2-methoxypyridin-3-yl | Me | Cyclopropyl | $^1$H NMR (400 MHz, MeOD) δ 9.06 (s, 1H), 8.33 (s, 1H), 8.01 (d, J = 9.18 Hz, 1H), 7.67 (t, J = 24.14 Hz, 2H), 7.17 (s, 1H), 4.37 (s, 1H), 3.94 (s, 3H), 2.66 (s, 3H), 1.32 (d, J = 6.60 Hz, 2H), 1.07 (s, 2H). | 369 | 98% |
| 2-11 | 5-(3,4-difluorophenylamino)pyridin-3-yl | Me | Cyclopropyl | $^1$H NMR (400 MHz, MeOD) δ 9.05 (s, 1H), 8.29 (s, 2H), 8.09 (d, J = 7.83 Hz, 1H), 7.94 (d, J = 23.80 Hz, 2H), 7.39-7.20 (m, 2H), 7.09 (s, 1H), 4.36 (s, 1H), 2.77 (s, 3H), 1.30 (s, 2H), 1.09 (s, 2H). | 466 | 98% |
| 2-12 | 5-morpholinopyridin-3-yl | Me | Cyclopropyl | $^1$H NMR (400 MHz, MeOD) δ 9.02 (s, 1H), 8.40 (d, J = 92.33 Hz, 2H), 8.16-8.03 (m, 2H), 7.98-7.80 (m, 1H), 7.75-7.50 (m, 2H), 4.34 (s, 1H), 3.82 (d, J = 24.28 Hz, 4H), 3.45 (s, 4H), 2.70 (d, J = 23.16 Hz, 3H), 1.27 (dd, J = 11.61, 24.61 Hz, 3H), 1.09 (s, 2H). | 424 | 98% |
| 2-13 | 2,3-dihydro-1H-pyrrolo[2,3-b]pyridin-5-yl | Me | Cyclopropyl | $^1$H NMR (400 MHz, DMSO) δ 14.68 (s, 1H), 8.91 (s, 1H), 8.69 (s, 1H), 7.97 (d, J = 8.46 Hz, 1H), 7.79 (s, 1H), 7.63 (s, 1H), 4.40 (s, 1H), 3.82 (d, J = 6.95 Hz, 2H), 3.21 (s, 2H), 2.63 (d, J = 43.98 Hz, 3H), 1.22 (d, J = 5.36 Hz, 2H), 1.05 (s, 2H). | 380 | 97% |
| 2-14 | 6-amino-5-nitropyridin-3-yl | Me | Cyclopropyl | $^1$H NMR (400 MHz, DMSO) δ 14.69 (s, 2H), 8.91 (s, 1H), 8.49 (s, 2H), 8.24 (s, 2H), 7.98 (d, J = 8.62 Hz, 1H), 4.41 (s, 1H), 2.65 (d, J = 31.48 Hz, 3H), 1.24 (d, J = 6.48 Hz, 2H), 1.07 (s, 2H). | 399 | 99% |
| 2-15 | 6-aminopyridin-3-yl | Me | Cyclopropyl | $^1$H NMR (400 MHz, DMSO) δ 14.67 (s, 1H), 8.91 (s, 1H), 8.13 (d, J = 25.11 Hz, 1H), 8.07 (s, 1H), 7.95 (dd, J = 8.95, 25.35 Hz, 2H), 7.06 (d, J = 8.71 Hz, 1H), 4.41 (s, 1H), 2.65 (d, J = 25.72 Hz, 3H), 1.22 (d, J = 5.45 Hz, 2H), 1.05 (s, 2H). | 354 | 99% |
| 2-16 | 6-(methylamino)-5-nitropyridin-3-yl | Me | Cyclopropyl | $^1$H NMR (400 MHz, DMSO) δ 8.91 (s, 1H), 8.74 (s, 1H), 8.54 (t, J = 24.30 Hz, 2H), 7.99 (d, J = 8.68 Hz, 1H), 4.41 (s, 1H), 3.10 (d, J = 17.91 Hz, 3H), 2.70 (s, 3H), 1.25 (d, J = 5.66 Hz, 2H), 1.07 (s, 2H). | 413 | 99% |

TABLE 2-continued

| Compound No. | R³ = | R² = | R¹ = | NMR | MS (MH⁺) | HPLC |
|---|---|---|---|---|---|---|
| 2-17 | 6,7-dihydro-5H-pyrrolo[3,4-b]pyridin-3-yl | Me | Cyclopropyl | ¹H NMR (400 MHz, DMSO) δ 14.63 (s, 1H), 9.79 (s, 2H), 8.92 (s, 1H), 8.61 (s, 1H), 8.01 (d, J = 13.11 Hz, 2H), 4.67 (d, J = 32.94 Hz, 4H), 4.40 (s, 1H), 2.62 (s, 3H), 1.23 (s, 3H), 1.07 (s, 2H). | 380 | 97% |
| 2-18 | 2-amino-3-cyanopyridin-5-yl | Me | Cyclopropyl | ¹H NMR (400 MHz, DMSO) δ 14.65 (s, 1H), 8.89 (s, 1H), 8.27 (s, 1H), 8.07 (t, J = 6.62 Hz, 1H), 7.94 (d, J = 8.87 Hz, 1H), 7.28 (s, 2H), 4.40 (tt, J = 3.75, 7.16 Hz, 1H), 3.31 (s, 1H), 2.67 (s, 3H), 1.31-1.19 (m, 2H), 1.10-1.00 (m, 2H). | 379 | 99% |
| 2-19 | 5-(5-methyl-1H-1,2,4-triazol-3-yl)pyridin-3-yl | Me | Cyclopropyl | ¹H NMR (400 MHz, DMSO) δ 9.28 (s, 1H), 8.93 (s, 1H), 8.70 (s, 1H), 8.36 (s, 1H), 8.03 (d, J = 8.65 Hz, 1H), 4.41 (s, 2H), 2.65 (s, 3H), 2.44 (s, 3H), 1.25 (d, J = 6.79 Hz, 2H), 1.10 (s, 2H). | 420 | 97% |
| 2-20 | 2-amino-3-carbamoylpyridin-5-yl | Me | Cyclopropyl | ¹H NMR (400 MHz, DMSO) δ 8.91 (s, 1H), 8.19 (d, J = 11.25 Hz, 3H), 7.99 (d, J = 8.83 Hz, 1H), 7.62 (s, 1H), 4.41 (s, 2H), 2.69 (s, 3H), 1.25 (d, J = 5.80 Hz, 2H), 1.05 (s, 2H). | 397 | 99% |
| 2-21 | 2-amino-3-chloropyridin-5-yl | Me | Cyclopropyl | ¹H NMR (400 MHz, DMSO) δ 14.72 (s, 1H), 8.89 (s, 1H), 8.11-7.87 (m, 2H), 7.74 (s, 1H), 6.71 (s, 2H), 4.39 (s, 1H), 2.63 (d, J = 29.40 Hz, 3H), 1.20 (t, J = 25.86 Hz, 2H), 0.99 (d, J = 41.43 Hz, 2H). | 388 | 98% |
| 2-22 | 2-amino-3-(trifluoromethyl)pyridin-5-yl | Me | Cyclopropyl | ¹H NMR (400 MHz, DMSO) δ 14.71 (s, 1H), 8.90 (s, 1H), 8.26 (s, 1H), 7.95 (d, J = 8.81 Hz, 1H), 7.86 (s, 1H), 6.89 (s, 2H), 4.39 (s, 1H), 2.66 (s, 3H), 1.24 (d, J = 5.61 Hz, 2H), 1.06 (s, 2H). | 422 | 98% |
| 2-23 | 2-amino-3-methylpyridin-5-yl | Me | Cyclopropyl | ¹H NMR (400 MHz, DMSO) δ 14.71 (s, 1H), 8.98 (s, 1H), 8.13-8.02 (m, 2H), 7.92 (d, J = 14.79 Hz, 3H), 4.47 (s, 1H), 2.71 (d, J = 23.60 Hz, 3H), 2.31 (s, 3H), 1.29 (d, J = 5.54 Hz, 2H), 1.15 (d, J = 22.69 Hz, 2H). | 368 | 99% |
| 2-24 | 2-amino-3-chloropyridin-5-yl | OMe | Cyclopropyl | ¹H NMR (400 MHz, DMSO) δ 14.67 (s, 1H), 8.79 (s, 1H), 8.11 (s, 1H), 7.90 (s, 1H), 7.82 (s, 1H), 6.73 (s, 2H), 4.22 (s, 1H), 3.46 (s, 3H), 3.31 (s, 2H), 1.16 (s, 4H). | 404 | 98% |

TABLE 2-continued

[Structure: 6-fluoro-4-oxo-quinoline-3-carboxylic acid core with R3 at position 7, R2 at position 8, and R1 on N1]

| Compound No. | R³ = | R² = | R¹ = | NMR | MS (MH⁺) | HPLC |
|---|---|---|---|---|---|---|
| 2-25 | 3-(trifluoromethyl)-2-aminopyridin-5-yl | OMe | Cyclopropyl | ¹H NMR (400 MHz, DMSO) δ 14.66 (s, 1H), 8.80 (s, 1H), 8.39 (s, 1H), 8.13-7.81 (m, 2H), 6.91 (s, 2H), 4.23 (s, 1H), 3.31 (s, 3H), 1.17 (d, J = 6.99 Hz, 3H). | 438 | 99% |
| 2-26 | 3-cyano-2-aminopyridin-5-yl | OMe | Cyclopropyl | ¹H NMR (400 MHz, DMSO) δ 14.74 (d, J = 61.68 Hz, 1H), 8.76 (d, J = 28.90 Hz, 1H), 8.39 (s, 1H), 7.97 (s, 1H), 7.92 (d, J = 9.13 Hz, 1H), 4.23 (s, 1H), 3.46 (s, 3H), 1.17 (d, J = 7.13 Hz, 4H). | 395 | 98% |
| 2-27 | 3-fluoro-2-aminopyridin-5-yl | Me | Cyclopropyl | ¹H NMR (400 MHz, DMSO), 8.89 (s, 1H), 7.95-7.93 (m, 2H), 7.83 (s, 1H), 7.60-6.57 (d, 1H), 4.39 (s, 1H), 2.63 (d, J = 29.40 Hz, 3H), 1.20 (t, J = 25.86 Hz, 2H), 0.99 (d, J = 41.43 Hz, 2H). | 372 | 98% |
| 2-28 | 3-formyl-2-aminopyridin-5-yl | OMe | Cyclopropyl | ¹H NMR (400 MHz, DMSO) δ 9.95 (s, 1H), 8.94-8.66 (m, 1H), 8.49-8.39 (m, 1H), 8.26 (d, J = 1.30 Hz, 1H), 7.91 (dd, J = 19.79, 31.75 Hz, 2H), 4.27-4.17 (m, 1H), 3.50-3.42 (m, 3H), 1.17 (dt, J = 7.59, 17.66 Hz, 3H). | 398 | 98% |
| 2-29 | 3-formyl-2-aminopyridin-5-yl | Me | Cyclopropyl | ¹H NMR (400 MHz, DMSO) δ 9.95 (s, 1H), 8.92 (d, J = 13.25 Hz, 1H), 8.32 (d, J = 1.05 Hz, 1H), 8.17 (d, J = 1.69 Hz, 1H), 8.00 (t, J = 18.18 Hz, 1H), 7.83 (d, J = 33.09 Hz, 1H), 4.40 (dt, J = 3.59, 10.71 Hz, 1H), 2.68 (d, J = 12.78 Hz, 3H), 1.25 (q, J = 6.89 Hz, 2H), 1.14-0.93 (m, 2H). | 382 | 98% |
| 2-30 | 3-methoxy-2-aminopyridin-5-yl | Me | Cyclopropyl | ¹H NMR (400 MHz, DMSO) δ 14.64 (s, 2H), 8.90 (s, 1H), 7.97 (d, J = 8.81 Hz, 1H), 7.64 (d, J = 1.21 Hz, 1H), 7.34 (s, 1H), 4.40 (td, J = 3.75, 7.19 Hz, 1H), 3.90 (s, 3H), 2.78-2.61 (m, 3H), 1.23 (q, J = 7.19 Hz, 2H), 1.16-0.97 (m, 2H). | 384 | 95% |
| 2-31 | 3-chloro-2-aminopyridin-5-yl | Me | (1R,2S)-2-fluorocyclopropyl | ¹H NMR (400 MHz, DMSO) δ 14.64 (s, 2H), 8.90 (s, 1H), 7.97 (d, J = 8.81 Hz, 1H), 7.64 (d, J = 1.21 Hz, 1H), 7.34 (s, 1H), 4.40 (td, J = 3.75, 7.19 Hz, 1H), 3.90 (s, 3H), 2.78-2.61 (m, 3H), 1.23 (q, J = 7.19 Hz, 2H), 1.16-0.97 (m, 2H). | 406 | 99% |
| 2-32 | 3-cyclopropyl-2-aminopyridin-5-yl | Me | Cyclopropyl | ¹H NMR (400 MHz, DMSO) δ 14.62 (s, 1H), 8.90 (s, 1H), 7.99 (d, J = 1.60 Hz, 1H), 7.95 (t, J = 10.20 Hz, 1H), 7.70-7.53 (m, 1H), 4.39 (td, J = 3.61, 7.03 Hz, 1H), 2.62 (d, J = 19.25 Hz, 3H), 1.84 (ddd, J = 5.42, 8.33, 13.56 Hz, 1H), 1.21 (t, J = 6.56 Hz, 1H), 1.05 (d, J = 8.64 Hz, 1H), 1.03-0.96 (m, 2H), 0.78-0.65 (m, 2H). | 394 | 98% |

TABLE 2-continued

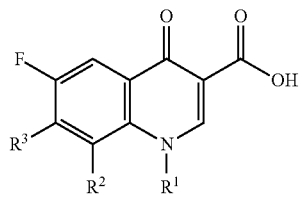

| Compound No. | R³ = | R² = | R¹ = | NMR | MS (MH⁺) | HPLC |
|---|---|---|---|---|---|---|
| 2-33 | H₂NOC— / H₂N—pyridine | Me | fluorocyclopropyl | ¹H NMR (400 MHz, DMSO) δ 8.88 (d, J = 3.01 Hz, 1H), 8.18 (s, 1H), 8.13 (s, 1H), 8.09 (s, 1H), 7.99 (d, J = 8.77 Hz, 1H), 7.54 (s, 1H), 5.29-5.01 (m, 1H), 4.50-4.31 (m, 1H), 2.71-2.57 (m, 2H), 1.76 (ddd, J = 9.04, 15.14, 17.62 Hz, 1H), 1.53 (d, J = 26.94 Hz, 1H). | 415 | 98% |
| 2-34 | Cl— / H₂N—pyridine | Cl | Cyclopropyl | ¹H NMR (400 MHz, DMSO) δ 8.92 (s, 1H), 8.11 (d, J = 8.56 Hz, 1H), 8.02 (d, J = 0.96 Hz, 1H), 7.81 (d, J = 1.67 Hz, 1H), 4.44-4.39 (m, 2H), 1.32-1.17 (m, 2H), 1.17-1.04 (m, 2H). | 408 | 94% |
| 2-35 | F— / H₂N—pyridine | OMe | Cyclopropyl | ¹H NMR (400 MHz, DMSO) δ 8.80 (s, 1H), 7.99 (s, 1H), 7.92 (d, J = 9.3 Hz, 1H), 7.69 (d, J = 12.0 Hz, 1H), 4.29-4.14 (m, 1H), 3.47 (s, 3H), 1.24-1.04 (m, 4H). | 387 | 99% |
| 2-36 | HO-ethyl-NHC(O)— / H₂N—pyridine | Me | Cyclopropyl | ¹H NMR (400 MHz, DMSO) δ 14.67 (s, 1H), 8.92 (s, 1H), 8.37 (s, 1H), 8.30 (d, J = 2.3 Hz, 1H), 8.11-7.88 (m, 3H), 7.51 (s, 1H), 4.55-4.30 (m, 3H), 3.20 (m, 2H), 2.68 (s, 3H), 1.25 (d, J = 6.4 Hz, 2H), 1.08 (d, J = 7.0 Hz, 2H). | 441 | 98% |
| 2-37 | NC— / H₂N—pyridine | OMe | fluorocyclopropyl | ¹H NMR (400 MHz, DMSO) δ 14.52 (s, 1H), 8.82 (d, J = 1.51 Hz, 1H), 8.38 (s, 1H), 8.11 (s, 1H), 7.94 (d, J = 9.20 Hz, 1H), 7.36 (s, 2H), 5.10 (ddd, J = 5.42, 8.45, 64.07 Hz, 1H), 4.24-4.12 (m, 1H), 1.86-1.55 (m, 2H). | 413 | 98% |
| 2-38 | Cl— / H₂N—pyridine | OMe | fluorocyclopropyl | ¹H NMR (400 MHz, DMSO) δ 14.55 (s, 1H), 8.82 (d, J = 1.46 Hz, 1H), 8.15 (d, J = 36.97 Hz, 1H), 7.92 (d, J = 9.24 Hz, 1H), 7.80 (s, 1H), 6.75 (s, 2H), 5.10 (ddd, J = 5.43, 8.45, 64.08 Hz, 1H), 4.29-4.12 (m, 1H), 1.93-1.53 (m, 2H). | 422 | 98% |
| 2-39 | NC— / H₂N—pyridine | Me | 2,4-difluorophenyl | ¹H NMR (400 MHz, DMSO) δ 14.39 (s, 1H), 8.80 (s, 1H), 8.16-8.08 (m, 2H), 7.98-7.86 (m, 2H), 7.69-7.59 (m, 1H), 7.37 (dd, J = 5.20, 11.82 Hz, 1H), 7.26 (s, 2H), 1.67 (s, 3H). | 451 | 99% |

TABLE 2-continued

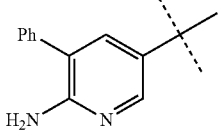

| Compound No. | R³ = | R² = | R¹ = | NMR | MS (MH⁺) | HPLC |
|---|---|---|---|---|---|---|
| 2-40 | 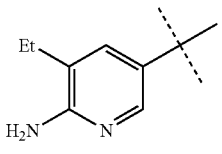 | Me | Cyclopropyl | ¹H NMR (400 MHz, CDCl₃) δ 14.60-14.29 (s, 1H), 8.96-8.89 (s, 1H), 8.05-7.96 (m, 2H), 7.48-7.40 (m, 4H), 7.40-7.33 (dt, J = 8.5, 2.8 Hz, 1H), 7.33-7.29 (s, 1H), 4.88-4.75 (s, 2H), 4.17-3.98 (s, 1H), 2.73-2.62 (s, 3H), 1.28-1.20 (m, 2H), 1.02-0.93 (s, 2H). | 430 | 99% |
| 2-41 | 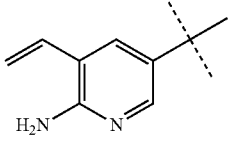 | Me | Cyclopropyl | ¹H NMR (400 MHz, DMSO) δ 14.83-14.68 (s, 1H), 8.99-8.81 (s, 1H), 7.96-7.89 (d, J = 8.9 Hz, 1H), 7.88-7.81 (s, 1H), 7.36-7.20 (s, 1H), 6.19-6.08 (s, 2H), 4.47-4.31 (s, 1H), 2.75-2.60 (s, 3H), 1.36-1.10 (m, 6H), 1.10-0.94 (t, J = 3.1 Hz, 2H). | 382 | 93% |
| 2-42 | 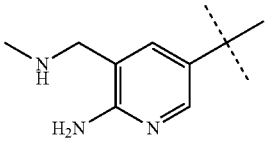 | Me | Cyclopropyl | ¹H NMR (400 MHz, DMSO) δ 14.83-14.67 (s, 3H), 8.97-8.85 (s, 3H), 8.00-7.85 (m, 6H), 7.72-7.60 (t, J = 1.7 Hz, 3H), 6.97-6.81 (dd, J = 17.3, 11.0 Hz, 3H), 6.45-6.27 (s, 6H), 5.85-5.70 (m, 4H), 5.44-5.26 (dd, J = 11.0, 1.2 Hz, 3H), 4.47-4.33 (s, 1H), 2.76-2.60 (s, 9H), 1.30-1.18 (m, 6H), 1.12-0.98 (m, 5H), 1.32-1.20 (m, 7H). | 380 | 99% |
| 2-43 | 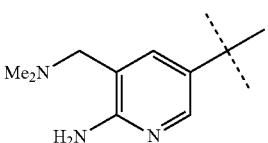 | Me | Cyclopropyl | ¹H NMR (400 MHz, DMSO) δ 8.95-8.90 (s, 1H), 8.36-8.31 (m, 1H), 8.13-8.07 (d, J = 2.0 Hz, 1H), 8.02-7.97 (d, J = 8.8 Hz, 1H), 4.49-4.36 (m, 3H), 2.90-2.79 (s, 5H), 2.76-2.67 (s, 3H), 1.33-1.20 (q, J = 6.9 Hz, 2H), 1.10-0.98 (m, 2H). | 397 | 98% |
| 2-44 | 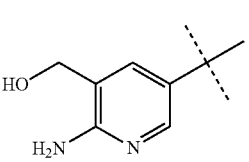 | Me | Cyclopropyl | ¹H NMR (400 MHz, DMSO) δ 8.93-8.91 (s, 1H), 8.24-8.20 (m, 1H), 8.01-7.96 (d, J = 8.8 Hz, 1H), 7.93-7.87 (t, J = 2.8 Hz, 1H), 4.49-4.38 (tt, J = 7.2, 3.9 Hz, 1H), 4.24-4.14 (t, J = 5.5 Hz, 2H), 2.85-2.77 (s, 6H), 1.29-1.20 (m, 2H), 1.09-0.98 (m, 2H). | 411 | 97% |
| 2-45 | 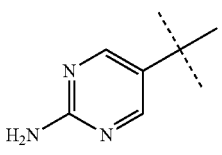 | Me | Cyclopropyl | ¹H NMR (400 MHz, DMSO) δ 8.94-8.89 (s, 1H), 8.15-8.09 (d, J = 2.1 Hz, 1H), 8.02-7.96 (d, J = 8.9 Hz, 1H), 7.92-7.88 (s, 1H), 4.46-4.37 (m, 1H), 4.57-4.46 (s, 2H), 2.71-2.65 (s, 3H), 1.25-1.18 (d, J = 6.7 Hz, 2H), 1.10-0.98 (m, 2H). | 384 | 90% |
| 2-46 | 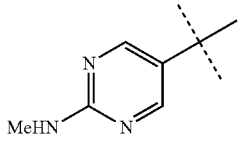 | Me | Cyclopropyl | ¹H NMR (400 MHz, DMSO) δ 14.71 (s, 1H), 8.89 (s, 1H), 8.35 (s, 2H), 7.94 (d, J = 8.67 Hz, 1H), 7.09 (s, 2H), 4.39 (s, 1H), 2.70 (s, 3H), 1.24 (d, J = 5.31 Hz, 2H), 1.03 (s, 2H). | 354 | 99% |
| 2-47 |  | Me | Cyclopropyl | ¹H NMR (400 MHz, DMSO) δ 14.72 (s, 1H), 8.89 (s, 1H), 8.41 (s, 2H), 7.95 (d, J = 8.41 Hz, 1H), 7.60 (d, J = 28.12 Hz, 1H), 4.40 (s, 1H), 2.88 (s, 3H), 2.70 (s, 3H), 1.25 (d, J = 5.56 Hz, 2H), 1.03 (s, 2H). | 369 | 99% |

TABLE 2-continued

| Compound No. | R³ = | R² = | R¹ = | NMR | MS (MH⁺) | HPLC |
|---|---|---|---|---|---|---|
| 2-48 | 2-(EtHN)pyrimidin-5-yl | Me | Cyclopropyl | $^1$H NMR (400 MHz, DMSO) δ 14.73 (s, 1H), 8.89 (s, 1H), 8.39 (s, 2H), 7.95 (d, J = 8.73 Hz, 1H), 7.64 (s, 1H), 4.39 (s, 1H), 2.70 (s, 3H), 2.53 (d, J = 9.32 Hz, 3H), 1.24 (d, J = 6.11 Hz, 2H), 1.17 (t, J = 6.98 Hz, 2H), 1.03 (s, 2H). | 383 | 97% |
| 2-49 | 2-(Me₂N)pyrimidin-5-yl | Me | Cyclopropyl | $^1$H NMR (400 MHz, DMSO) δ 14.72 (s, 2H), 8.90 (s, 1H), 8.48 (s, 2H), 7.96 (d, J = 8.59 Hz, 1H), 4.39 (s, 1H), 3.24 (d, J = 22.01 Hz, 6H), 2.70 (s, 3H), 1.25 (d, J = 6.03 Hz, 2H), 1.04 (d, J = 7.73 Hz, 2H). | 383 | 98% |
| 2-50 | 2-aminopyrimidin-5-yl | Cl | Cyclopropyl | $^1$H NMR (400 MHz, DMSO) δ 8.92 (s, 1H), 8.35 (s, 2H), 8.13 (d, J = 8.6 Hz, 1H), 7.15 (s, 2H), 4.41 (m, 3.8 Hz, 1H), 1.37-1.17 (m, 2H), 1.18-1.02 (m, 2H). | 375 | 99% |
| 2-51 | 2-aminopyrimidin-5-yl | Me | 2-fluorocyclopropyl | $^1$H NMR (400 MHz, DMSO) δ 8.87 (d, J = 3.2 Hz, 1H), 8.35 (d, J = 1.0 Hz, 2H), 7.97 (d, J = 8.9 Hz, 1H), 7.08 (s, 2H), 5.33-4.97 (m, 2H), 4.37 (m, 1H), 2.65 (s, 3H), 1.89-1.41 (m, 2H). | 373 | 99% |
| 2-52 | 2-aminopyrimidin-5-yl | MeO | 2-fluorocyclopropyl | $^1$H NMR (400 MHz, DMSO) δ 14.54 (s, 1H), 8.82 (d, J = 1.2 Hz, 1H), 8.44 (s, 2H), 7.93 (d, J = 9.2 Hz, 1H), 7.10 (s, 2H), 5.09 (m, 1H), 4.37-3.96 (m, 1H), 3.50 (s, 3H), 1.98-1.52 (m, 2H). | 389 | 98% |
| 2-53 | 2-(HO₂C)pyrimidin-5-yl | Me | Cyclopropyl | $^1$H NMR (400 MHz, DMSO) δ 14.65 (s, 1H), 8.91 (d, J = 4.9 Hz, 1H), 8.76 (s, 2H), 8.15-7.85 (m, 1H), 4.63-4.29 (m, 1H), 2.50 (s, 3H), 1.29-1.15 (m, 2H), 1.06 (d, J = 7.0 Hz, 2H). | 384 | 99% |
| 2-54 | 2-aminopyrimidin-5-yl | MeO | Cyclopropyl | $^1$H NMR (400 MHz, DMSO) δ 8.86 (s, 1H), 8.52 (s, 2H), 8.00 (d, J = 9.2 Hz, 1H), 7.18 (s, 2H), 4.29 (m, 1H), 3.55 (s, 3H), 1.27-1.11 (m, 4H). | 371 | 99% |
| 2-55 | 2-(EtHN)-3-chloropyridin-5-yl | Me | Cyclopropyl | $^1$H NMR (400 MHz, DMSO) δ 14.67 (s, 1H), 8.79 (s, 1H), 8.19 (s, 1H), 7.90 (d, J = 9.3 Hz, 1H), 7.81 (s, 1H), 6.91 (t, J = 5.6 Hz, 1H), 4.29-4.11 (m, 1H), 3.53-3.41 (m, 5H), 1.26-1.06 (m, 7H). | 432 | 98% |

TABLE 2-continued

| Compound No. | R³ = | R² = | R¹ = | NMR | MS (MH⁺) | HPLC |
|---|---|---|---|---|---|---|
| 2-56 | | | | ¹H NMR (400 MHz, DMSO) δ 9.06 (s, 1H), 8.38 (s, 1H), 8.13 (d, J = 1.75 Hz, 1H), 7.72 (d, J = 9.80 Hz, 1H), 7.29 (s, 2H), 5.06-4.90 (m, 1H), 4.58 (d, J = 10.62 Hz, 1H), 4.44 (d, J = 9.71 Hz, 1H), 1.48 (d, J = 6.75 Hz, 3H). | 381 | 95% |
| 2-57 | | | | ¹H NMR (400 MHz, DMSO) δ 14.95 (s, 1H), 8.91 (s, 1H), 8.37-8.33 (d, J = 2.5 Hz, 1H), 8.24-8.19 (d, J = 8.3 Hz, 1H), 8.14-8.10 (d, J = 2.5 Hz, 1H), 7.58-7.51 (d, J = 8.3 Hz, 1H), 7.22 (s, 2H), 4.42-4.36 (tt, J = 7.1, 3.7 Hz, 1H), 2.71 (s, 3H), 1.30-1.25 (m, 2H), 1.05-0.94 (m, 2H). | 361 | 95% |
| 2-58 | | | | ¹H NMR (400 MHz, DMSO) δ 14.95 (s, 1H), 8.89 (s, 1H), 8.32 (d, J = 3.5 Hz, 1H), 8.21 (d, J = 8.2 Hz, 1H), 8.06 (s, 1H), 7.79 (s, 1H), 7.53 (d, J = 8.2 Hz, 1H), 6.61 (s, 2H), 4.39 (s, 1H), 2.72 (s, 3H), 1.27 (d, J = 6.1 Hz, 2H), 1.03 (s, 2H). | 370 | 99% |
| 2-59 | | | | ¹H NMR (400 MHz, DMSO) δ 15.00 (s, 1H), 9.06 (s, 1H), 8.17 (s, 1H), 7.50 (s, 1H), 7.72 (d, J = 9.8 Hz, 1H), 6.86 (t, J = 5.7 Hz, 1H), 4.98 (d, J = 6.7 Hz, 1H), 4.57 (d, J = 10.2 Hz, 1H), 4.48-4.32 (m, 1H), 3.55-3.37 (m, 2H), 1.48 (d, J = 6.8 Hz, 2H), 1.17 (t, J = 7.1 Hz, 2H). | 418 | 98% |
| 2-60 | | | | ¹H NMR (400 MHz, DMSO) δ 14.55 (s, 1H), 8.82 (d, J = 1.6 Hz, 1H), 8.18 (s, 1H), 7.92 (d, J = 9.3 Hz, 1H), 7.80 (s, 1H), 6.92 (t, J = 5.7 Hz, 1H), 5.10 (ddd, J = 64.1, 8.4, 5.4 Hz, 1H), 4.32-4.06 (m, 1H), 3.58-3.37 (m, 5H), 1.93-1.51 (m, 2H), 1.19 (t, J = 7.1 Hz, 3H). | 450 | 98% |

TABLE 3

| Compound No. | R³ = | R² = | R¹ = | NMR | MS (MH⁺) | HPLC |
|---|---|---|---|---|---|---|
| 3-1 | (6-substituted imidazo[1,2-a]pyridin-6-yl) | Me | Cyclopropyl | ¹H NMR (400 MHz, DMSO) δ 14.59 (s, 1H), 9.08 (s, 1H), 8.94 (s, 1H), 8.33 (d, J = 1.3 Hz, 1H), 8.16 (d, J = 1.7 Hz, 1H), 8.06 (t, J = 8.5 Hz, 2H), 7.85 (d, J = 9.4 Hz, 1H), 4.49-4.38 (m, 1H), 2.70 (s, 3H), 1.25 (d, J = 6.6 Hz, 2H), 1.09 (s, 2H). | 378 | 98% |
| 3-2 | (imidazo[1,2-a]pyrimidin-6-yl) | Me | Cyclopropyl | ¹H NMR (400 MHz, DMSO) δ 14.63 (s, 1H), 9.38 (s, 1H), 8.91 (d, J = 25.3 Hz, 1H), 8.79 (s, 1H), 8.13 (s, 1H), 8.06 (d, J = 8.8 Hz, 1H), 8.01 (s, 1H), 4.44 (s, 1H), 2.75 (s, 3H), 1.25 (s, 2H), 1.09 (s, 2H). | 379 | 95% |
| 3-3 | (5-tert-butyl-[1,2,4]triazolo-2-(pyridin-2-yl)) | Me | Cyclopropyl | ¹H NMR (400 MHz, DMSO) δ 14.70 (s, 1H), 9.41 (s, 1H), 9.00 (s, 1H), 8.80 (s, 1H), 8.36 (s, 1H), 8.17 (s, 1H), 8.07 (s, 2H), 7.86 (s, 1H), 7.61 (s, 1H), 4.49 (s, 1H), 2.79 (s, 3H), 1.31 (s, 3H), 1.17 (s, 2H). | 456 | 98% |
| 3-4 | (imidazo[1,2-a]pyridin-6-yl) | Me | Cyclopropyl | ¹H NMR (400 MHz, DMSO) δ 14.57 (d, J = 5.1 Hz, 1H), 9.05 (d, J = 6.5 Hz, 1H), 8.94 (s, 1H), 8.44 (s, 1H), 8.23 (s, 1H), 8.11 (s, 1H), 8.05 (d, J = 8.8 Hz, 1H), 7.54 (d, J = 6.4 Hz, 1H), 4.43 (s, 1H), 2.68 (s, 3H), 1.24 (d, J = 5.0 Hz, 2H), 1.11 (s, 2H). | 378 | 97% |
| 3-5 | (imidazo[1,2-a]pyridin-6-yl) | OMe | Cyclopropyl | ¹H NMR (400 MHz, DMSO) δ 14.64 (s, 1H), 9.13 (d, J = 6.3 Hz, 1H), 8.90 (s, 1H), 8.53 (s, 1H), 8.31 (d, J = 11.7 Hz, 2H), 8.09 (d, J = 9.1 Hz, 1H), 7.72 (d, J = 5.8 Hz, 1H), 4.30 (s, 1H), 3.57 (s, 3H), 1.25 (s, 4H). | 394 | 95% |

TABLE 3-continued

| Compound No. | R³ = | R² = | R¹ = | NMR | MS (MH⁺) | HPLC |
|---|---|---|---|---|---|---|
| 3-6 | imidazo[1,2-a]pyridin-6-yl | Me | Cyclopropyl | ¹H NMR (400 MHz, DMSO) δ 9.30 (s, 1H), 8.93 (s, 1H), 8.64 (s, 1H), 8.04 (t, J = 9.2 Hz, 2H), 7.75 (d, J = 9.2 Hz, 1H), 4.42 (s, 1H), 2.69 (s, 3H), 1.24 (s, 2H), 1.09 (s, 2H). | 379 | 97% |
| 3-7 | imidazo[1,2-a]pyridin-6-yl | OMe | Cyclopropyl | ¹H NMR (400 MHz, DMSO) δ 14.61 (s, 1H), 9.33 (s, 1H), 8.83 (s, 1H), 8.64 (s, 1H), 8.06 (d, J = 9.2 Hz, 1H), 8.01 (d, J = 9.1 Hz, 1H), 7.86 (d, J = 9.3 Hz, 1H), 4.24 (s, 1H), 3.48 (s, 3H), 1.19 (d, J = 5.2 Hz, 4H). | 395 | 98% |
| 3-8 | 8-CN-imidazo[1,2-a]pyridin-6-yl | Me | Cyclopropyl | ¹H NMR (400 MHz, DMSO) δ 14.60 (s, 1H), 9.11 (s, 1H), 8.93 (s, 1H), 8.22 (d, J = 1.2 Hz, 1H), 8.17 (s, 1H), 8.03 (d, J = 8.9 Hz, 1H), 7.84 (d, J = 1.1 Hz, 1H), 4.43 (tt, J = 7.1, 3.7 Hz, 1H), 2.70 (s, 3H), 1.26 (d, J = 6.8 Hz, 2H), 1.09 (s, 2H). | 379 | 98% |
| 3-9 | 8-CF₃-imidazo[1,2-a]pyridin-6-yl | Me | Cyclopropyl | ¹H NMR (400 MHz, DMSO) δ 14.60 (s, 1H), 9.07 (s, 1H), 8.93 (s, 1H), 8.22 (s, 1H), 8.02 (d, J = 8.9 Hz, 1H), 7.81 (s, 1H), 7.80 (s, 1H), 4.49-4.37 (m, 1H), 1.27 (t, J = 9.8 Hz, 2H), 1.14-1.05 (m, 2H). | 446 | 97% |

TABLE 3-continued

[Structure: quinolone with COOH, F, R², R³, and N-R¹ substituents]

| Compound No. | R³ = | R² = | R¹ = | NMR | MS (MH⁺) | HPLC |
|---|---|---|---|---|---|---|
| 3-10 | [6-substituted-8-methyl-imidazo[1,2-a]pyridine] | Me | Cyclopropyl | ¹H NMR (400 MHz, DMSO) δ 14.62 (s, 1H), 8.94 (s, 2H), 8.35 (s, 1H), 8.23 (s, 1H), 8.05 (d, J = 8.7 Hz, 1H), 7.75 (s, 1H), 4.43 (s, 1H), 2.69 (s, 3H), 2.66 (s, 3H), 1.24 (s, 2H), 1.08 (s, 2H). | 392 | 98% |
| 3-11 | [6-substituted-8-chloro-imidazo[1,2-a]pyridine] | Me | Cyclopropyl | ¹H NMR (400 MHz, DMSO) δ 14.61 (s, 1H), 8.92 (s, 1H), 8.79 (d, J = 1.2 Hz, 1H), 8.16 (d, J = 1.1 Hz, 1H), 8.01 (d, J = 8.8 Hz, 1H), 7.76 (d, J = 1.1 Hz, 1H), 7.58 (s, 1H), 4.42 (tt, J = 7.2, 3.8 Hz, 1H), 2.70 (d, J = 202 Hz, 3H), 1.26 (d, J = 6.9 Hz, 2H), 1.15-1.03 (m, 2H). | 412 | 99% |
| 3-12 | [6-substituted-3-nitro-imidazo[1,2-a]pyridine] | Me | Cyclopropyl | ¹H NMR (400 MHz, DMSO) δ 9.40 (s, 1H), 8.94 (s, 1H), 8.88 (s, 1H), 8.18 (d, J = 9.3 Hz, 1H), 8.05 (d, J = 8.8 Hz, 1H), 7.89 (d, J = 9.3 Hz, 1H), 4.43 (s, 1H), 2.69 (s, 3H), 1.24 (d, J = 6.1 Hz, 2H), 1.12 (s, 2H). | 423 | 96% |
| 3-13 | [6-substituted-7-chloro-imidazo[1,2-a]pyridine] | OMe | Cyclopropyl | ¹H NMR (400 MHz, DMSO) δ 14.60 (s, 1H), 8.90 (s, 1H), 8.83 (s, 1H), 8.22 (d, J = 1.0 Hz, 1H), 7.98 (d, J = 9.2 Hz, 1H), 7.75 (d, J = 1.0 Hz, 1H), 7.66 (s, 1H), 4.29-4.18 (m, 1H), 3.51 (d, J = 13.2 Hz, 3H), 1.25-1.14 (m, 4H). | 428 | 100% |

TABLE 3-continued
| Compound No. | R³ = | R² = | R¹ = | NMR | MS (MH⁺) | HPLC |
|---|---|---|---|---|---|---|
| 3-14 | 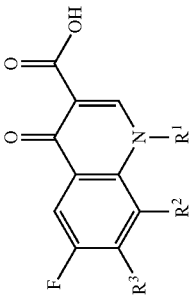 | OMe | Cyclopropyl | ¹H NMR (400 MHz, DMSO) δ 14.59 (s, 1H), 9.19 (s, 1H), 8.83 (s, 1H), 8.28 (s, 1H), 8.01 (d, J = 9.2 Hz, 1H), 7.92 (s, 1H), 7.81 (s, 1H), 4.25 (dt, J = 11.0, 5.7 Hz, 1H), 3.50 (d, J = 12.8 Hz, 3H), 1.19 (m, 4H). | 462 | 98% |
| 3-15 | 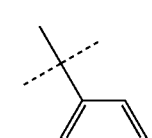 | Me | Cyclopropyl | ¹H NMR (400 MHz, DMSO) δ 9.61 (s, 1H), 8.93 (s, 1H), 8.51 (s, 1H), 8.13 (s, 1H), 8.04 (d, J = 8.8 Hz, 1H), 7.97 (d, J = 9.2 Hz, 1H), 7.62 (d, J = 9.2 Hz, 1H), 7.55 (s, 1H), 4.42 (s, 1H), 2.69 (s, 3H), 1.24 (s, 2H), 1.10 (s, 2H). | 421 | 98% |
| 3-16 | 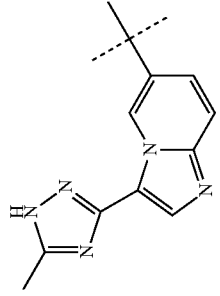 | Me | Cyclopropyl | ¹H NMR (400 MHz, DMSO) δ 14.87-13.95 (m, 2H), 9.60 (s, 1H), 8.94 (s, 1H), 8.44 (s, 1H), 8.05 (t, J = 9.5 Hz, 2H), 7.71 (d, J = 9.4 Hz, 1H), 4.46-4.39 (m, 1H), 2.71 (m, 3H), 2.46 (s, 3H), 1.25 (d, J = 6.3 Hz, 2H), 1.11 (s, 2H). | 459 | 98% |
| 3-17 | | Cl | Cyclopropyl | ¹H NMR (400 MHz, DMSO) δ 14.44-13.91 (m, 1H), 9.16 (s, 1H), 8.95 (s, 1H), 8.37 (s, 1H), 8.23 (d, J = 8.6 Hz, 1H), 8.08 (s, 1H), 7.81 (s, 1H), 4.43 (m, 1H), 1.23 (m, 2H), 1.16 (s, 2H). | 398 | 98% |

TABLE 3-continued

| Compound No. | R³ = | R² = | R¹ = | NMR | MS (MH⁺) | HPLC |
|---|---|---|---|---|---|---|
| 3-18 | 6-(8-fluoroimidazo[1,2-a]pyridinyl) | Me | Cyclopropyl | ¹H NMR (400 MHz, DMSO) δ 14.62 (s, 1H), 8.92 (s, 1H), 8.68 (s, 1H), 8.19 (d, J = 2.9 Hz, 1H), 8.01 (d, J = 8.8 Hz, 1H), 7.73 (d, J = 1.0 Hz, 1H), 7.32 (d, J = 11.7 Hz, 1H), 4.42 (m, 1H), 2.72 (s, 3H), 1.25 (d, 2H), 1.12-1.04 (m, 2H). | 396 | 98% |
| 3-19 | 6-(8-nitroimidazo[1,2-a]pyridinyl) | Me | Cyclopropyl | ¹H NMR (400 MHz, DMSO) δ 9.29 (s, 1H), 8.94 (s, 1H), 8.54 (s, 1H), 8.36 (s, 1H), 8.05 (d, J = 8.9 Hz, 1H), 8.00 (s, 1H), 4.49-4.38 (m, 1H), 2.74 (s, 3H), 1.25 (d, J = 6.9 Hz, 2H), 1.11 (s, 2H). | 423 | 98% |
| 3-20 | 6-(8-chloroimidazo[1,2-a]pyridinyl) | Cl | Cyclopropyl | ¹H NMR (400 MHz, DMSO) δ 8.95 (s, 1H), 8.88 (t, J = 4.2 Hz, 1H), 8.22 (t, J = 2.4 Hz, 1H), 8.20 (d, J = 8.5 Hz, 1H), 7.82 (s, 1H), 7.68 (s, 1H), 4.48-4.36 (m, 1H), 1.26-1.19 (m, 2H), 1.14 (m, 2H). | 432 | 98% |
| 3-21 | 6-(4-chloroimidazo[1,2-a]pyridinyl) | Me | Cyclopropyl | ¹H NMR (400 MHz, DMSO) δ 14.60 (s, 1H), 8.93 (s, 1H), 8.71 (s, 1H), 8.06 (s, 1H), 8.02 (d, J = 8.8 Hz, 1H), 4.43 (tt, J = 7.0, 3.6 Hz, 1H), 2.70 (d, J = 17.8 Hz, 3H), 1.30-1.20 (m, 2H), 1.15-1.05 (m, 2H). | 413 | 98% |

TABLE 3-continued

| Compound No. | R³ = | R² = | R¹ = | NMR | MS (MH⁺) | HPLC |
|---|---|---|---|---|---|---|
| 3-22 | 6-(tert-butyl)-8-fluoroimidazo[1,2-a]pyridinyl | Me | Cyclopropyl | ¹H NMR (400 MHz, DMSO) δ 14.57 (s, 1H), 9.22 (s, 1H), 8.93 (s, 1H), 8.71 (s, 1H), 8.02 (d, J = 8.8 Hz, 1H), 7.85 (d, J = 10.8 Hz, 1H), 4.47-4.37 (m, 1H), 2.72 (s, 3H), 1.29-1.22 (m, 2H), 1.10 (s, 2H). | 397 | 99% |
| 3-23 | 6-(tert-butyl)-8-fluoroimidazo[1,2-a]pyridinyl | OMe | Cyclopropyl | ¹H NMR (400 MHz, DMSO) δ 14.57 (s, 1H), 9.26 (s, 1H), 8.84 (s, 1H), 8.72 (s, 1H), 8.01 (d, J = 9.1 Hz, 1H), 7.92 (d, J = 10.9 Hz, 1H), 4.28-4.18 (m, 1H), 3.51 (s, 3H), 1.20 (d, J = 5.5 Hz, 4H). | 413 | 95% |
| 3-24 | 6-(tert-butyl)-8-chloroimidazo[1,2-a]pyridinyl | OMe | (1R,2S)-2-fluorocyclopropyl | ¹H NMR (400 MHz, DMSO) δ 14.47 (s, 1H), 8.89 (t, J = 1.3 Hz, 1H), 8.86 (d, J = 1.8 Hz, 1H), 8.23 (d, J = 1.3 Hz, 1H), 8.00 (d, J = 9.1 Hz, 1H), 7.75 (d, J = 1.2 Hz, 1H), 7.63 (t, J = 1.3 Hz, 1H), 5.31-4.93 (dtd, J = 64.0, 5.5, 3.3 Hz, 1H), 4.26-4.12 (dt, J = 8.9, 5.4 Hz, 1H), 3.54 (s, 3H), 1.93-1.49 (m, 2H). | 446 | 98% |
| 3-25 | 6-(tert-butyl)-8-chloroimidazo[1,2-a]pyridinyl | Me | 2,4-difluorophenyl | ¹H NMR (400 MHz, CDCl₃) δ 14.07 (s, 1H), 8.55 (s, 1H), 8.14 (d, J = 8.4 Hz, 1H), 8.00 (d, J = 17.0 Hz, 1H), 7.66 (dd, J = 11.6, 4.8 Hz, 2H), 7.49 (d, J = 4.4 Hz, 1H), 7.13-7.03 (m, 2H), 7.01 (d, J = 0.8 Hz, 1H), 5.22 (s, 1H), 1.72 (s, 3H). | 484 | 98% |

TABLE 3-continued

| Compound No. | R³ = | R² = | R¹ = | NMR | MS (MH⁺) | HPLC |
|---|---|---|---|---|---|---|
| 3-26 | (6-tBu-imidazo[1,2-a]pyridin-8-Me) | Me | Cyclopropyl | ¹H NMR (400 MHz, DMSO) δ 14.64 (s, 1H), 9.09 (s, 1H), 8.93 (s, 1H), 8.58 (s, 1H), 8.02 (d, J = 8.8 Hz, 1H), 7.54 (s, 1H), 4.46-4.36 (m, 1H), 2.70 (s, 3H), 2.64 (s, 3H), 1.25 (d, J = 6.2 Hz, 2H), 1.09 (s, 2H). | 393 | 98% |
| 3-27 | (6-tBu-imidazo[1,2-a]pyridin-8-Cl) | Me | (1-F-cyclopropyl) | ¹H NMR (400 MHz, DMSO) δ 14.48 (s, 1H), 8.90 (d, J = 3.0 Hz, 1H), 8.78 (s, 1H), 8.16 (s, 1H), 8.03 (d, J = 8.8 Hz, 1H), 7.75 (s, 1H), 7.57 (s, 1H), 5.16 (d, J = 64.5 Hz, 1H), 4.44-4.33 (m, 1H), 2.65 (s, 3H), 1.83-1.68 (m, 1H), 1.62 (m, 1H). | 430 | 98% |
| 3-28 | (6-tBu-imidazo[1,2-a]pyridin-8-CF₃) | Me | Cyclopropyl | ¹H NMR (400 MHz, DMSO) δ 14.59 (s, 1H), 9.63 (s, 1H), 8.94 (s, 1H), 8.81 (s, 1H), 8.30 (s, 1H), 8.04 (d, J = 8.9 Hz, 1H), 4.50-4.37 (m, 1H), 2.73 (s, 3H), 1.24 (t, J = 9.6 Hz, 2H), 1.12 (s, 2H). | 447 | 98% |
| 3-29 | (6-tBu-imidazo[1,2-a]pyridin-8-CH₂NH₂) | Me | Cyclopropyl | ¹H NMR (400 MHz, DMSO) δ 9.33 (s, 1H), 8.94 (s, 1H), 8.74 (s, 1H), 8.63 (s, 2H), 8.05 (d, J = 8.8 Hz, 1H), 7.84 (s, 1H), 4.51 (s, 2H), 4.46-4.36 (m, 1H), 2.31 (s, 3H), 1.26 (d, J = 6.8 Hz, 2H), 1.09 (s, 2H). | 408 | 95% |

TABLE 3-continued

| Compound No. | R³ = | R² = | R¹ = | NMR | MS (MH⁺) | HPLC |
|---|---|---|---|---|---|---|
| 3-30 | imidazo[1,2-a]pyridine with Cl | OMe | Cyclopropyl | ¹H NMR (400 MHz, DMSO) δ 14.58 (s, 1H), 9.37 (s, 1H), 8.84 (s, 1H), 8.72 (s, 1H), J = 8.13 (s, 1H), 8.00 (d, J = 9.0 Hz, 1H), 4.29-4.18 (m, 1H), 3.51 (s, 3H), 1.20 (d, J = 5.4 Hz, 4H). | 429 | 96% |
| 3-31 | [1,2,4]triazolo[1,5-a]pyridine | Me | Cyclopropyl | ¹H NMR (400 MHz, DMSO) δ 9.43 (s, 1H), 8.99 (s, 1H), 8.14-8.01 (m, 2H), 7.54 (d, J = 9.8 Hz, 1H), 4.49 (s, 2H), 2.77 (s, 3H), 1.30 (s, 2H), 1.14 (s, 2H). | 379 | 88% |
| 3-32 | imidazo[1,2-a]pyridine | OMe | Cyclopropyl | ¹H NMR (400 MHz, DMSO) δ 9.42 (s, 1H), 8.92 (s, 1H), 8.83 (s, 1H), 8.00 (s, 2H), 7.57 (d, J = 9.3 Hz, 1H), 4.23 (s, 1H), 3.51 (s, 3H), 1.18 (s, 4H). | 395 | 95% |
| 3-33 | imidazo[4,5-b]pyridine | Me | Cyclopropyl | ¹H NMR (400 MHz, DMSO) δ 8.98 (s, 1H), 8.74 (s, 1H), 8.48 (s, 1H), 8.23 (s, 1H), 8.04 (d, J = 8.9 Hz, 1H), 4.39 (s, 2H), 2.64 (s, 3H), 1.29 (s, 2H), 1.07 (s, 2H). | 379 | 99% |
| 3-34 | benzotriazole | Me | Cyclopropyl | ¹H NMR (400 MHz, DMSO) δ 15.02-14.73 (m, 1H), 9.01 (s, 1H), 8.10 (s, 3H), 7.54 (s, 1H), 4.51 (s, 1H), 1.33 (s, 2H), 1.18 (s, 2H). | 379 | 95% |

TABLE 3-continued

| Compound No. | R³ = | R² = | R¹ = | NMR | MS (MH⁺) | HPLC |
|---|---|---|---|---|---|---|
| 3-35 | 5-indazolyl-7-NO₂ | Me | Cyclopropyl | ¹H NMR (400 MHz, DMSO) δ 14.68 (s, 1H), 14.19 (s, 1H), 8.93 (s, 1H), 8.53 (s, 1H), 8.44 (s, 1H), 8.40 (s, 1H), 8.01 (d, J = 8.5 Hz, 1H), 4.42 (s, 1H), 2.64 (s, 3H), 1.22 (m, 2H), 1.12 (m, 2H). | 423 | 98% |
| 3-36 | 5-indazolyl-7-NH₂ | Me | Cyclopropyl | ¹H NMR (400 MHz, DMSO) δ 12.87 (s, 1H), 8.97 (s, 1H), 8.10 (s, 1H), 8.01 (d, J = 8.7 Hz, 1H), 7.02 (s, 1H), 6.48 (s, 1H), 4.46 (s, 1H), 2.70 (s, 2H), 1.30 (s, 2H), 1.12 (s, 2H). | 393 | 98% |
| 3-37 | 5-indazolyl | Me | Cyclopropyl | ¹H NMR (400 MHz, DMSO) δ 14.83 (s, 1H), 13.45 (b, 1H), 8.98 (s, 1H), 8.26 (s, 1H), 8.04 (d, J = 8.6 Hz, 1H), 7.90 (s, 1H), 7.78 (d, J = 8.5 Hz, 1H), 7.42 (d, J = 8.4 Hz, 1H), 4.46 (s, 1H), 2.68 (s, 3H), 1.31 (d, J = 5.7 Hz, 2H), 1.14 (s, 2H). | 378 | 92% |
| 3-38 | 5-indazolyl-7-Cl | Me | Cyclopropyl | ¹H NMR (400 MHz, DMSO) δ 14.69 (s, 1H), 13.83 (s, 1H), 8.91 (s, 1H), 8.31 (s, 1H), 7.98 (d, J = 8.8 Hz, 1H), 7.83 (s, 1H), 7.53 (s, 1H), 4.46-4.34 (m, 1H), 2.63 (s, 3H), 1.25 (d, J = 6.9 Hz, 2H), 1.09 (s, 2H). | 412 | 98% |

TABLE 3-continued

| Compound No. | R³ = | R² = | R¹ = | NMR | MS (MH⁺) | HPLC |
|---|---|---|---|---|---|---|
| 3-39 | 5-nitro-1H-indazol-3-yl | OMe | Cyclopropyl | ¹H NMR (400 MHz, DMSO) δ 14.74 (s, 1H), 14.27 (s, 1H), 8.90 (s, 1H), 8.62 (d, J = 10.6 Hz, 3H), 8.07 (d, J = 9.1 Hz, 1H), 4.31 (s, 1H), 3.44 (s, 3H), 1.26 (s, 4H). | 439 | 95% |
| 3-40 | 1H-benzimidazol-5-yl | Me | Cyclopropyl | ¹H NMR (400 MHz, DMSO) δ 14.77 (s, 1H), 13.23 (s, 1H), 8.91 (s, 1H), 8.49 (s, 1H), 7.98 (d, J = 8.3 Hz, 1H), 8.01 (d, J = 8.0 Hz, 1H), 7.67 (s, 1H), 7.25 (d, J = 7.9 Hz, 1H), 4.40 (s, 1H), 2.61 (s, 2H), 1.25 (s, 2H), 1.09 (s, 2H). | 378 | 98% |
| 3-41 | benzothiazol-5-yl | Me | Cyclopropyl | ¹H NMR (400 MHz, DMSO) δ 14.72 (s, 1H), 9.52 (s, 1H), 8.92 (s, 1H), 8.30 (s, 1H), 8.27 (d, J = 8.4 Hz, 1H), 8.01 (d, J = 8.8 Hz, 1H), 7.58 (d, J = 8.1 Hz, 1H), 4.40 (s, 1H), 2.62 (s, 3H), 1.25 (d, J = 5.9 Hz, 2H), 1.08 (s, 2H). | 395 | 95% |
| 3-42 | 1H-pyrrolo[2,3-b]pyridin-5-yl | Me | Cyclopropyl | ¹H NMR (400 MHz, DMSO) δ 14.77 (s, 1H), 11.96 (s, 1H), 8.92 (s, 1H), 8.24 (s, 1H), 8.06 (s, 1H), 7.99 (d, J = 8.7 Hz, 1H), 7.61 (s, 1H), 6.57 (s, 1H), 4.41 (s, 1H), 2.64 (s, 3H), 1.26 (d, J = 6.1 Hz, 2H), 1.09 (s, 2H). | 378 | 98% |
| 3-43 | 3-cyanoimidazo[1,2-a]pyridin-6-yl | Me | Cyclopropyl | ¹H NMR (400 MHz, DMSO) δ 14.76-14.48 (s, 1H), 8.97-8.90 (d, J = 2.7 Hz, 2H), 8.63-8.55 (s, 1H), 8.07-7.97 (t, J = 9.2 Hz, 2H), 7.69-7.58 (m, 1H), 4.48-4.39 (s, 2H), 2.73-2.65 (s, 3H), 1.27-1.20 (m, 2H), 1.14-1.06 (s, 2H). | 403 | 95% |

TABLE 3-continued

| Compound No. | R³ = | R² = | R¹ = | NMR | MS (MH⁺) | HPLC |
|---|---|---|---|---|---|---|
| 3-44 | OHC- (imidazo[1,2-a]pyridin-6-yl) | Me | Cyclopropyl | ¹H NMR (400 MHz, DMSO) δ 10.02-9.98 (s, 1H), 9.48-9.43 (s, 1H), 8.95-8.90 (s, 1H), 8.67-8.62 (s, 1H), 8.12-8.07 (d, J = 9.2 Hz, 1H), 8.07-8.01 (d, J = 8.9 Hz, 1H), 7.82-7.75 (dd, J = 9.4, 1.7 Hz, 1H), 4.48-4.36 (s, 1H), 2.72-2.67 (s, 3H), 1.25-1.21 (t, J = 3.8 Hz, 2H), 1.14-1.06 (m, 2H). | 406 | 90% |
| 3-45 | ethynyl-(imidazo[1,2-a]pyridin-6-yl) | Me | Cyclopropyl | ¹H NMR (400 MHz, DMSO) δ 9.93 (s, 1H), 8.83 (s, 1H), 8.40 (s, 1H), 8.09-8.05 (dd, J = 9.2, 1.0 Hz, 1H), 8.05-8.00 (d, J = 8.7 Hz, 1H), 7.81-7.72 (dd, J = 9.3, 1.7 Hz, 1H), 5.35-5.16 (s, 1H), 4.53-4.33 (m, 1H), 2.75-2.64 (s, 3H), 1.28-1.20 (d, J = 6.2 Hz, 2H), 1.15-1.03 (d, J = 3.8 Hz, 2H). | 402 | 98% |
| 3-46 | vinyl-pyrazolo[1,5-a]pyridine | Me | Cyclopropyl | ¹H NMR (400 MHz, DMSO) δ 14.70-14.56 (s, 1H), 9.23-9.15 (m, 1H), 8.99-8.89 (s, 1H), 8.72-8.65 (s, 1H), 8.08-7.99 (d, J = 8.8 Hz 1H), 7.84-7.77 (s, 1H), 7.16-7.04 (m, 1H), 6.93-6.82 (m, 1H), 5.82-5.69 (dd, J = 11.2, 1.6 Hz, 1H), 4.49-4.36 (t, J = 3.5 Hz, 1H), 2.75-2.68 (s, 3H), 1.33-1.19 (t, J = 6.5 Hz, 2H), 1.16-1.03 (s, 2H). | 405 | 97% |
| 3-47 | HO₂C-(imidazo[1,2-a]pyridin-6-yl) | Me | Cyclopropyl | ¹H NMR (400 MHz, DMSO) δ 14.76-14.48 (s, 1H), 8.96-8.91 (s, 4H), 8.86-8.79 (s, 4H), 8.64-8.56 (d, J = 2.3 Hz, 4H), 8.06-7.99 (d, J = 8.8 Hz, 4H), 7.86-7.79 (d, J = 9.4 Hz, 4H), 7.52-7.43 (s, 3H), 4.48-4.37 (s, 1H), 2.74-2.67 (s, 12H), 1.29-1.20 (d, J = 6.8 Hz, 9H), 1.11-1.01 (t, J = 3.0 Hz, 6H). | 422 | 96% |
| 3-48 | F₃C-(imidazo[1,2-a]pyridin-6-yl) | Me | Cyclopropyl | ¹H NMR (400 MHz, DMSO) δ 14.76-14.48 (s, 1H), 8.95-8.89 (s, 1H), 8.84-8.78 (s, 1H), 8.63-8.58 (s, 1H), 8.05-8.00 (d, J = 8.8 Hz, 1H), 7.90-7.84 (d, J = 9.4 Hz, 1H), 7.53-7.45 (d, J = 9.3 Hz, 1H), 4.47-4.40 (s, 1H), 2.73-2.68 (s, 3H), 1.27-1.21 (d, J = 6.6 Hz, 2H), 1.12-1.02 (s, 2H). | 446 | 90% |

TABLE 3-continued

| Compound No. | R³ = | R² = | R¹ = | NMR | MS (MH⁺) | HPLC |
|---|---|---|---|---|---|---|
| 3-49 | (3-chloroimidazo[1,2-a]pyridin-6-yl) | Me | Cyclopropyl | ¹H NMR (400 MHz, DMSO) δ 8.93 (s, 1H), 8.66 (s, 1H), 8.06-7.99 (d, J = 8.7 Hz, 1H), 7.99-7.95 (s, 1H), 7.94-7.88 (d, J = 9.3 Hz, 1H), 7.55-7.47 (dd, J = 9.3, 1.6 Hz, 1H), 4.52-4.32 (m, 1H), 2.77-2.61 (s, 3H), 1.33-1.17 (d, J = 6.6 Hz, 2H), 1.19-1.05 (t, J = 3.3 Hz, 2H). | 412 | 98% |
| 3-50 | (3-bromoimidazo[1,2-a]pyridin-6-yl) | Me | Cyclopropyl | ¹H NMR (400 MHz, DMSO) δ 8.93 (s, 1H), 8.60 (s, 1H), 8.06-8.00 (d, J = 8.7 Hz, 1H), 8.00-7.96 (s, 1H), 7.92-7.86 (d, J = 9.3 Hz, 1H), 7.56-7.48 (d, J = 9.4 Hz, 1H), 4.55-4.26 (m, 1H), 2.81-2.60 (s, 3H), 1.37-1.21 (d, J = 6.5 Hz, 2H), 1.15-1.05 (m, 2H). | 456, 458 | 97% |
| 3-51 | (8-phenylimidazo[1,2-a]pyridin-6-yl) | Me | Cyclopropyl | ¹H NMR (400 MHz, DMSO) δ 14.71-14.62 (s, 1H), 8.96-8.88 (s, 1H), 8.83-8.75 (s, 1H), 8.25-8.16 (d, J = 7.5 Hz, 2H), 8.15-8.07 (s, 1H), 8.07-7.97 (d, J = 8.8 Hz, 1H), 7.77-7.71 (s, 1H), 7.57-7.42 (m, 4H), 4.50-4.33 (s, 1H), 2.82-2.71 (s, 3H), 1.31-1.22 (d, J = 6.7 Hz, 2H), 1.15-1.04 (s, 2H). | 454 | 99% |
| 3-52 | (8-ethylpyrrolo[2,3-b]pyridin-6-yl) | Me | Cyclopropyl | ¹H NMR (400 MHz, DMSO) δ 14.71-14.60 (s, 1H), 8.95-8.88 (s, 1H), 8.73-8.65 (s, 1H), 8.10-7.96 (m, 2H), 7.74-7.88 (s, 1H), 7.40-7.32 (s, 1H), 7.11-7.02 (m, 1H), 6.96-6.83 (m, 1H), 5.70-5.60 (dd, J = 11.2, 2.0 Hz, 1H), 4.47-4.38 (t, J = 3.5 Hz, 1H), 2.78-2.69 (s, 3H), 1.31-1.20 (d, J = 6.9 Hz, 2H), 1.14-1.01 (s, 2H). | 405 | 93% |

TABLE 3-continued

[Structure: quinolone core with F, R³, R², N-R¹, and COOH groups]

| Compound No. | R³ = | R² = | R¹ = | NMR | MS (MH⁺) | HPLC |
|---|---|---|---|---|---|---|
| 3-53 | [imidazo[1,2-a]pyridin-6-yl with 8-vinyl substituent] | Me | Cyclopropyl | ¹H NMR (400 MHz, DMSO) δ 14.71-14.60 (s, 1H), 8.95-8.88 (s, 1H), 8.73-8.65 (s, 1H), 8.10-7.96 (m, 2H), 7.74-7.68 (s, 1H), 7.40-7.32 (s, 1H), 7.11-7.02 (m, 1H), 6.96-6.83 (m, 1H), 5.70-5.60 (dd, J = 11.2, 2.0 Hz, 1H), 4.47-4.38 (t, J = 3.5 Hz, 1H), 2.78-2.69 (s, 3H), 1.31-1.20 (d, J = 6.9 Hz, 2H), 1.14-1.01 (s, 2H). | 403 | 95% |
| 3-54 | [imidazo[1,2-b]pyridazin-6-yl] | Me | Cyclopropyl | ¹H NMR (400 MHz, DMSO) δ 14.76-14.39 (s, 1H), 9.20-9.07 (d, J = 7.0 Hz, 1H), 8.95-8.90 (s, 1H), 8.67-8.60 (s, 1H), 8.08-8.00 (m, 2H), 7.32-7.24 (m, 1H), 4.47-4.36 (s, 1H), 2.75-2.61 (s, 3H), 1.30-1.19 (m, 2H), 1.15-1.03 (q, J = 3.8, 3.1 Hz, 2H). | 379 | 98% |
| 3-55 | [pyrazolo[1,5-a]pyridin-6-yl with 4-CN] | Me | Cyclopropyl | ¹H NMR (400 MHz, DMSO) δ 14.76-14.36 (s, 1H), 9.68-9.65 (d, J = 1.5 Hz, 1H), 8.95-8.92 (s, 1H), 8.84-8.81 (s, 1H), 8.63-8.59 (d, J = 1.5 Hz, 1H), 8.06-8.01 (d, J = 8.8 Hz, 1H), 4.46-4.39 (s, 1H), 2.76-2.69 (s, 3H), 1.30-1.20 (m, 2H), 1.14-1.05 (s, 2H). | 404 | 98% |
| 3-56 | [imidazo[1,2-a]pyridin-6-yl with 8-CN] | OMe | [trans-2-fluorocyclopropyl with methyl] | ¹H NMR (400 MHz, DMSO) δ 14.73-14.06 (s, 1H), 9.21-9.18 (m, 1H), 8.87-8.83 (d, J = 1.86 Hz, 1H), 8.32-8.27 (d, J = 1.33 Hz, 1H), 8.20-8.16 (s, 1H), 8.04-7.97 (d, J = 9.06 Hz, 1H), 7.87-7.80 (d, J = 1.20 Hz, 1H), 5.31-4.87 (m, 1H), 4.32-4.12 (m, 1H), 3.67-3.47 (s, 3H), 1.95-1.56 (m, 2H). | 437 | 98% |

TABLE 3-continued

| Compound No. | R³ = | R² = | R¹ = | NMR | MS (MH⁺) | HPLC |
|---|---|---|---|---|---|---|
| 3-57 | imidazo[1,2-a]pyridine with F (structure) | OMe | Cyclopropyl | ¹H NMR (400 MHz, DMSO) δ 14.61 (s, 1H), 8.83 (s, 1H), 8.77 (s, 1H), 8.23 (d, J = 2.1 Hz, 1H), 7.99 (d, J = 9.2 Hz, 1H), 7.73 (d, J = 1.0 Hz, 1H), 7.40 (d, J = 11.8 Hz, 1H), 4.46-4.08 (m, 1H), 3.51 (d, J = 10.5 Hz, 3H), 1.19 (d, J = 6.9 Hz, 4H). | 412 | 90% |
| 3-58 | isoindoline (structure) | Me | Cyclopropyl | ¹H NMR (400 MHz, DMSO) δ 14.83-14.57 (s, 1H), 9.82-9.48 (s, 2H), 9.01-8.84 (d, J = 2.6 Hz, 1H), 8.05-7.90 (dd, J = 8.5, 2.7 Hz, 1H), 7.65-7.57 (d, J = 7.5 Hz, 1H), 7.51-7.46 (s, 1H), 7.45-7.36 (d, J = 7.7 Hz, 1H), 4.72-4.50 (s, 4H), 4.47-4.28 (d, J = 6.8 Hz, 1H), 2.64-2.53 (d, J = 2.7 Hz, 3H), 1.31-1.14 (d, J = 6.1 Hz, 2H), 1.14-0.96 (s, 2H). | 379 | 95% |
| 3-59 | indoline (structure) | Me | Cyclopropyl | ¹H NMR (400 MHz, DMSO) δ 8.95-8.83 (d, J = 2.4 Hz, 1H), 7.98-7.86 (d, J = 8.8 Hz, 1H), 7.25-7.15 (s, 1H), 7.14-7.01 (d, J = 7.9 Hz, 1H), 6.97-6.81 (d, J = 7.9 Hz, 1H), 3.65-3.50 (m, 2H), 4.45-4.29 (dp, J = 9.2, 4.7, 3.9 Hz, 1H), 3.16-2.99 (t, J = 8.4 Hz, 2H), 2.65-2.56 (s, 3H), 1.28-1.16 (d, J = 6.6 Hz, 3H), 1.12-0.97 (m, 2H). | 379 | 99% |
| 3-60 | 2-aminobenzimidazole (structure) | Me | Cyclopropyl | ¹H NMR (400 MHz, DMSO) δ 15.01-14.39 (m, 1H), 12.95-12.53 (s, 2H), 9.03-8.82 (t, J = 1.9 Hz, 1H), 8.73-8.47 (s, 2H), 8.10-7.90 (d, J = 8.4 Hz, 1H), 7.62-7.44 (m, 1H), 4.51-4.23 (m, 1H), 7.44-7.31 (s, 1H), 7.31-7.11 (d, J = 8.6 Hz, 1H), 2.65-2.55 (s, 3H), 1.30-1.16 (m, 2H), 1.16-0.96 (s, 2H). | 393 | 90% |
| 3-61 | benzimidazole (structure) | Me | Cyclopropyl | ¹H NMR (400 MHz, MeOD) δ 9.17-9.06, J = 2.8 Hz, 1H), 8.30-8.15 (m, 1H), 7.94-7.80 (m, 2H), 7.65-7.49 (dt, J = 7.5, 5.3 Hz, 2H), 4.47-4.32 (dd, J = 6.9 Hz, 1H), 2.96-2.81 (d, J = 2.8 Hz, 3H), 1.43-1.27 (dd, J = 10.8, 4.5 Hz, 2H), 1.21-1.05 (s, 2H). | 378 | 100% |

TABLE 3-continued

| Compound No. | R³ = | R² = | R¹ = | NMR | MS (MH⁺) | HPLC |
|---|---|---|---|---|---|---|
| 3-62 | benzothiazol-2-yl (via CMe) | Me | Cyclopropyl | ¹H NMR (400 MHz, DMSO) δ 14.63-14.42 (s, 1H), 8.99-8.89 (s, 1H), 8.33-8.25 (d, J = 7.8 Hz, 1H), 8.25-8.18 (d, J = 8.0 Hz, 1H), 8.14-8.05 (d, J = 8.7 Hz, 1H), 7.71-7.56 (dt, J = 22.8, 7.4 Hz, 2H), 4.51-4.31 (s, 1H), 2.85-2.70 (s, 3H), 1.30-1.20 (d, J = 7.0 Hz, 2H), 1.13-0.97 (s, 2H). | 395 | 100% |
| 3-63 | 2-Me-benzimidazol-5-yl | Me | Cyclopropyl | ¹H NMR (400 MHz, DMSO) δ 15.01-14.28 (s, 2H), 9.04-8.82 (t, J = 2.3 Hz, 1H), 8.05-7.98 (d, J = 8.3 Hz, 1H), 7.98-7.92 (dd, J = 10.5, 2.5 Hz, 1H), 7.90-7.83 (s, 1H), 7.56-7.47 (d, J = 8.2 Hz, 1H), 4.46-4.34 (t, J = 6.3 Hz, 1H), 2.87-2.78 (t, J = 2.1 Hz, 3H), 2.64-2.55 (s, 3H), 1.29-1.16 (m, 2H), 1.16-1.03 (s, 2H). | 392 | 100% |
| 3-64 | 1-(2-aminoethyl)benzimidazol-5-yl | Me | Cyclopropyl | ¹H NMR (400 MHz, DMSO) δ 15.01-14.28 (s, 2H), 9.04-8.82 (t, J = 2.3 Hz, 1H), 8.05-7.98 (d, J = 8.3 Hz, 1H), 7.98-7.92 (dd, J = 10.5, 2.5 Hz, 1H), 7.90-7.83 (s, 1H), 7.56-7.47 (d, J = 8.2 Hz, 1H), 4.46-4.34 (t, J = 6.3 Hz, 1H), 2.87-2.78 (t, J = 2.1 Hz, 3H), 2.64-2.55 (m, 6H), 1.29-1.16 (m, 2H), 1.16-1.03 (s, 2H). | 421 | 100% |
| 3-65 | 1-(2-dimethylaminoethyl)benzimidazol-5-yl | Me | Cyclopropyl | ¹H NMR (400 MHz, DMSO) δ 15.05-14.35 (m, 1H), 10.46-9.91 (m, 1H), 9.02-8.80 (s, 1H), 8.80-8.47 (d, J = 15.2 Hz, 1H), 8.12-7.64 (m, 3H), 7.44-7.25 (dd, J = 23.7, 8.0 Hz, 1H), 4.84-4.63 (d, J = 8.8 Hz, 2H), 4.49-4.32 (s, 1H), 3.01-2.77 (d, J = 17.9 Hz, 6H), 1.37-1.13 (d, J = 6.9 Hz, 2H), 1.17-0.86 (s, 2H). | 449 | 96% |

TABLE 3-continued
| Compound No. | R³ = | R² = | R¹ = | NMR | MS (MH⁺) | HPLC |
|---|---|---|---|---|---|---|
| 3-66 |  | Me | Cyclopropyl | ¹H NMR (400 MHz, DMSO) δ 14.97-14.24 (s, 2H), 9.14-8.97 (m, 2H), 8.98-8.88 (s, 2H), 8.07-7.89 (dd, J = 24.1, 8.9 Hz, 6H), 7.86-7.79 (s, 1H), 7.52-7.37 (t, J = 9.6 Hz, 3H), 4.57-4.31 (t, J = 6.8 Hz, 5H), 2.66-2.55 (s, 7H), 1.60-1.40 (m, 7H), 1.30-1.16 (m, 2H), 1.16-0.98 (s, 2H). | 406 | 97% |
| 3-67 |  | Me | Cyclopropyl | ¹H NMR (400 MHz, DMSO) δ 14.97-14.24 (s, 2H), 9.14-8.97 (m, 2H), 8.98-8.88 (s, 2H), 8.07-7.89 (dd, J = 24.1, 8.9 Hz, 6H), 7.86-7.79 (s, 1H), 7.52-7.37 (t, J = 9.6 Hz, 3H), 4.57-4.31 (t, J = 6.8 Hz, 5H), 2.66-2.55 (s, 3H), 1.60-1.40 (m, 7H), 1.30-1.16 (m, 2H), 1.16-0.98 (s, 2H). | 392 | 100% |
| 3-68 |  | Me | Cyclopropyl | ¹H NMR (400 MHz, DMSO) δ 8.95-8.91 (s, 1H), 8.65-8.59 (s, 1H), 8.31-8.25 (s, 1H), 8.23-8.17 (s, 1H), 8.05-7.98 (m, 1H), 4.48-4.35 (s, 3H), 1.30-1.22 (s, 2H), 1.16-1.06 (s, 2H). | 423 | 97% |
| 3-69 |  | Me | Cyclopropyl | ¹H NMR (400 MHz, DMSO) δ 14.96-14.48 (m, 1H), 10.94-10.65 (d, J = 25.6 Hz, 2H), 9.01-8.77 (m, 1H), 8.05-7.81 (d, J = 8.6 Hz, 1H), 7.18-7.00 (d, J = 7.8 Hz, 1H), 7.00-6.78 (m, 2H), 4.47-4.25 (td, J = 6.9, 3.6 Hz, 1H), 2.67-2.54 (s, 3H), 1.27-1.10 (d, J = 6.3 Hz, 2H), 1.14-0.88 (s, 2H). | 394 | 94% |

TABLE 3-continued
| Compound No. | R³ = | R² = | R¹ = | NMR | MS (MH⁺) | HPLC |
|---|---|---|---|---|---|---|
| 3-70 | 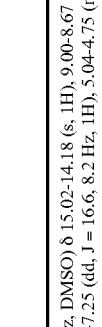 (EtO₂)HC | Me | Cyclopropyl | ¹H NMR (400 MHz, DMSO) δ 15.02-14.18 (s, 1H), 9.00-8.67 (m, 2H), 8.12-7.68 (m, 3H), 7.49-7.25 (dd, J = 16.6, 8.2 Hz, 1H), 5.04-4.75 (m, 1H), 4.62-4.23 (m, 9H), 3.77-3.55 (m, 2H), 3.57-3.23 (d, J = 7.0 Hz, 1H), 2.70-2.53 (s, 3H), 1.37-1.15 (t, J = 8.0 Hz, 2H), 1.15-0.84 (td, J = 16.0, 7.8 Hz, 9H). | 494 | 90% |
| 3-71 | 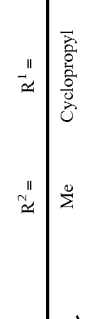 | Me | Cyclopropyl | ¹H NMR (400 MHz, DMSO) δ 14.45-14.13 (s, 1H), 11.09-10.85 (s, 1H), 8.73-8.58 (d, J = 2.7 Hz, 1H), 7.85-7.61 (m, 2H), 7.31-7.15 (m, 1H), 7.07-6.83 (m, 2H), 4.27-4.07 (s, 1H), 3.82-3.71 (d, J = 2.5 Hz, 3H), 1.27-1.08 (m, 2H), 1.08-0.86 (s, 2H). | 408 | 93% |
| 3-72 |  | OMe | Cyclopropyl | ¹H NMR (400 MHz, DMSO) δ 15.07-14.72 (s, 1H), 9.21-8.97 (s, 1H), 8.95-8.73 (m, 1H) 8.41-8.14 (m, 1H), 8.12-7.95 (s, 1H), 3.40-3.18 (m, 4H), 7.95-7.79 (d, J = 8.6 Hz, 1H), 7.79-7.60 (dd, J = 8.5, 3.9 Hz, 2H), 4.34-4.10 (d, J = 6.3 Hz, 1H), 1.30-1.02 (s, 4H). | 376 | 95% |
| 3-73 | 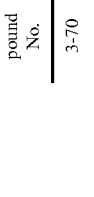 | Me | Cyclopropyl | ¹H NMR (400 MHz, DMSO) δ 14.85-14.61 (s, 1H), 10.68-10.51 (s, 1H), 9.04-8.78 (m, 1H), 8.01-7.81 (m, 1H), 7.36-7.11 (m, 2H), 7.11-6.87 (dd, J = 7.8, 2.7 Hz, 1H), 4.47-4.29 (s, 1H), 3.72-3.47 (s, 2H), 1.27-1.08 (m, 2H), 1.08-0.86 (s, 2H). | 393 | 97% |

TABLE 3-continued

| Compound No. | R³ = | R² = | R¹ = | NMR | MS (MH⁺) | HPLC |
|---|---|---|---|---|---|---|
| 3-74 | (5-substituted 2-oxoindoline with 7-NO₂) | Me | Cyclopropyl | ¹H NMR (400 MHz, DMSO) δ 14.85-14.61 (s, 1H), 10.68-10.51 (s, 1H), 9.04-8.78 (m, 1H), 8.01-7.81 (m, 1H), 7.36-7.11 (m, 2H), 7.11-6.87 (dd, J = 7.8, 2.7 Hz, 1H), 4.47-4.29 (s, 1H), 3.72-3.47 (s, 2H), 2.66-2.57 (d, J = 2.7 Hz, 3H), 2.55-2.45 (d, J = 3.4 Hz, 4H). | 424 | 97% |
| 3-75 | (benzimidazol-5-yl) | OMe | Cyclopropyl | ¹H NMR (400 MHz, DMSO) δ 14.80-14.62 (m, 1H), 8.38-8.18 (m, 1H), 8.03-7.83 (m, 1H), 8.96-8.82 (m, 1H), 7.77-7.59 (m, 1H), 7.37-7.22 (m, 1H), 4.48-4.29 (m, 1H), 3.24-3.08 (m, 2H), 3.94-3.70 (m, 2H), 1.32-1.12 (m, 2H), 0.86 (m, 2H). | 394 | 100% |
| 3-76 | (benzimidazol-5-yl with CH₂N(Me)₂) | Me | Cyclopropyl | ¹H NMR (400 MHz, DMSO) δ 15.11-14.26 (d, J = 53.0 Hz, 1H), 10.22-9.45 (m, 1H), 9.01-8.84 (m, 1H), 8.77-8.58 (s, 1H), 8.09-7.92 (d, J = 8.5 Hz, 1H), 7.88-7.68 (s, 1H), 7.51-7.33 (s, 1H), 4.84-4.58 (s, 2H), 4.53-4.25 (s, 1H), 2.96-2.72 (s, 6H), 2.72-2.56 (s, 3H), 1.34-1.17 (d, J = 6.5 Hz, 2H), 1.17-0.93 (d, J = 10.1 Hz, 2H). | 435 | 94% |
| 3-77 | (benzothiazol-2(3H)-one-6-yl) | Me | Cyclopropyl | ¹H NMR (400 MHz, DMSO) δ 14.87-14.59 (s, 1H), 12.20-12.00 (s, 1H), 9.01-8.79 (s, 1H), 8.09-7.83 (d, J = 8.6 Hz, 1H), 7.74-7.59 (s, 1H), 7.39-7.20 (m, 2H), 4.48-4.31 (s, 1H), 2.72-2.56 (s, 3H), 1.36-1.12 (d, J = 6.9 Hz, 2H), 1.12-0.79 (s, 2H). | 411 | 98% |

TABLE 3-continued

| Compound No. | R³ = | R² = | R¹ = | NMR | MS (MH⁺) | HPLC |
|---|---|---|---|---|---|---|
| 3-78 | (5-oxo-indolin-6-yl) | Me | Cyclopropyl | ¹H NMR (400 MHz, DMSO) δ 14.85-14.61 (s, 1H), 10.68-10.51 (s, 1H), 9.04-8.78 (m, 1H), 8.01-7.81 (m, 1H), 7.36-7.11 (m, 2H), 7.11-6.87 (dd, J = 7.8, 2.7 Hz, 1H), 4.47-4.29 (s, 1H), 3.72-3.47 (s, 2H), 1.27-1.08 (m, 2H), 1.08-0.86 (s, 2H). | 393 | 95% |
| 3-79 | (7-vinyloxy-benzotriazol-5-yl) | Me | Cyclopropyl | ¹H NMR (400 MHz, DMSO) δ 14.82-14.60 (s, 1H), 11.50-11.28 (s, 1H), 8.99-8.81 (s, 1H), 8.09-7.90 (m, 2H), 7.66-7.53 (d, J = 1.1 Hz, 1H), 6.91-6.78 (s, 1H), 6.17-5.99 (d, J = 15.7 Hz, 1H), 5.38-5.23 (d, J = 9.0 Hz, 1H), 4.48-4.31 (dd, J = 8.4, 4.4 Hz, 1H), 3.61-3.41 (s, 1H), 2.71-2.56 (s, 3H), 1.32-1.16 (s, 2H), 1.14-0.97 (s, 2H). | 421 | 97% |
| 3-80 | (7-vinyloxy-benzotriazol-5-yl) | MeO | Cyclopropyl | ¹H NMR (400 MHz, DMSO) δ 14.82-14.60 (s, 1H), 11.50-11.28 (s, 1H), 8.99-8.81 (s, 1H), 8.09-7.90 (m, 2H), 7.66-7.53 (d, J = 1.1 Hz, 1H), 6.91-6.78 (s, 1H), 6.17-5.99 (d, J = 15.7 Hz, 1H), 5.38-5.23 (d, J = 9.0 Hz, 1H), 4.48-4.31 (dd, J = 8.4, 4.4 Hz, 1H), 3.61-3.41 (s, 1H), 2.71-2.56 (s, 3H), 1.14-0.97 (s, 4H). | 437 | 90% |

TABLE 3-continued

| Compound No. | R³ = | R² = | R¹ = | NMR | MS (MH⁺) | HPLC |
|---|---|---|---|---|---|---|
| 3-81 | 5-amino-benzoxazol-6-yl | Me | Cyclopropyl | ¹H NMR (400 MHz, DMSO) δ 14.85-14.61 (s, 1H), 10.95-10.69 (s, 1H), 9.06-8.79 (s, 2H), 8.05-7.90 (d, J = 8.7 Hz, 1H), 7.28-7.09 (s, 1H), 6.85-6.63 (s, 1H), 4.46-4.29 (tt, J = 7.4, 4.0 Hz, 1H), 2.72-2.54 (s, 3H), 1.32-1.14 (d, J = 5.8 Hz, 2H), 1.14-0.97 (d, J = 3.8 Hz, 2H). | 394 | 94% |
| 3-82 | 5-amino-benzoxazol-6-yl | OMe | Cyclopropyl | ¹H NMR (400 MHz, DMSO) δ 14.89-14.50 (s, 2H), 11.09-10.63 (s, 1H), 9.21-8.97 (s, 1H), 8.97-8.73 (s, 1H), 8.07-7.85 (m, 1H), 3.48-3.31 (m, 5H), 7.42-7.26 (m, 1H), 7.04-6.87 (m, 1H), 4.31-4.13 (p, J = 5.6 Hz, 1H), 2.72-2.54 (s, 3H), 1.27-1.01 (d, J = 5.6 Hz, 4H). | 410 | 98% |
| 3-83 | 4-chloro-benzimidazol-5-yl | OMe | Cyclopropyl | ¹H NMR (400 MHz, DMSO) δ 15.05-14.39 (s, 1H), 13.02-12.32 (s, 1H), 8.97-8.77 (s, 1H), 8.47-8.20 (s, 1H), 7.85-7.39 (m, 2H), 7.33-6.98 (d, J = 8.0 Hz, 1H), 4.47-4.23 (s, 1H), 2.74-2.52 (s, 3H), 1.34-1.13 (m, 2H), 1.13-0.71 (s, 2H). | 428 | 100% |
| 3-84 | benzofuran-5-yl | Me | Cyclopropyl | ¹H NMR (400 MHz, DMSO) δ 14.75 (d, J = 8.7 Hz, 1H), 8.91 (s, 1H), 8.13 (s, 1H), 7.99 (t, J = 11.1 Hz, 1H), 7.78 (t, J = 13.2 Hz, 1H), 7.72 (s, 1H), 7.33 (d, J = 8.5 Hz, 1H), 7.07 (s, 1H), 4.40 (m, 1H), 2.61 (s, 3H), 1.24 (d, J = 5.7 Hz, 2H), 1.08 (s, 2H). | 378 | 98% |

TABLE 3-continued

| Compound No. | R³ = | R² = | R¹ = | NMR | MS (MH⁺) | HPLC |
|---|---|---|---|---|---|---|
| 3-85 | (5-benzothienyl) | Me | Cyclopropyl | ¹H NMR (400 MHz, DMSO) δ 14.70 (s, 1H), 8.90 (s, 1H), 8.21 (d, J = 8.0 Hz, 1H), 7.98 (d, J = 8.1 Hz, 1H), 7.94 (s, 1H), 7.90 (s, 1H), 7.56 (s, 1H), 7.38 (d, J = 7.9 Hz, 1H), 4.38 (s, 1H), 2.65 (s, 3H), 1.17 (m, 2H), 1.06 (m, 2H). | 394 | 98% |
| 3-86 | (full structure shown) | | | ¹H NMR (400 MHz, DMSO) δ 15.38-14.22 (s, 1H), 9.14-9.08 (s, 1H), 9.00-8.94 (s, 1H), 8.32-8.24 (s, 1H), 7.93-7.90 (s, 1H), 7.90-7.86 (d, J = 9.72 Hz, 1H), 5.07-4.96 (d, J = 6.74 Hz, 1H), 4.65-4.56 (d, J = 11.26 Hz, 1H), 4.53-4.43 (d, J = 9.86 Hz, 1H), 1.54-1.46 (d, J = 6.76 Hz, 3H). | 414 | 99% |
| 3-87 | (full structure shown) | | | ¹H NMR (400 MHz, DMSO) δ 14.87 (s, 1H), 8.93 (s, 1H), 8.77 (s, 1H), 8.27 (d, J = 8.2 Hz, 1H), 8.15 (s, 1H), 7.73 (d, J = 0.9 Hz, 1H), 7.63 (m, 2H), 4.46-4.36 (m, 1H), 2.76 (s, 3H), 1.29 (d, J = 6.5 Hz, 2H), 1.08 (t, J = 7.4 Hz, 2H). | 394 | 99% |

TABLE 4

| Compound No. | R³ = | NMR | MS (MH⁺) | HPLC |
|---|---|---|---|---|
| 4-1 | 3-indolyl | ¹H NMR (400 MHz, DMSO) δ 14.49 (s, 1H), 11.38 (s, 1H), 8.70 (s, 1H), 7.78 (d, J = 9.1 Hz, 1H), 7.42 (d, J = 7.9 Hz, 1H), 7.26 (d, J = 8.1 Hz, 1H), 7.00-6.92 (m, 1H), 6.86 (t, J = 7.5 Hz, 1H), 6.51 (s, 1H), 4.24-4.16 (m, 1H), 2.56 (s, 3H), 1.03 (dd, J = 12.0, 4.6 Hz, 2H), 0.86 (d, J = 7.4 Hz, 2H). | 377 | 95% |
| 4-2 | 2-indolyl | ¹H NMR (400 MHz, DMSO) δ 14.70 (s, 1H), 11.59 (s, 1H), 8.92 (s, 1H), 8.00 (d, J = 9.1 Hz, 1H), 7.64 (d, J = 7.5 Hz, 1H), 7.48 (d, J = 8.0 Hz, 1H), 7.19 (t, J = 7.5 Hz, 1H), 7.08 (t, J = 7.3 Hz, 1H), 6.73 (s, 1H), 4.42 (s, 1H), 2.78 (s, 3H), 1.27 (d, J = 6.1 Hz, 2H), 1.07 (s, 2H). | 377 | 100% |
| 4-3 | N-methyl-3-indolyl | ¹H NMR (400 MHz, DMSO) δ 14.66 (s, 1H), 8.93 (s, 1H), 8.05 (d, J = 8.6 Hz, 1H), 7.65 (d, J = 7.7 Hz, 1H), 7.57 (d, J = 8.0 Hz, 1H), 7.30-7.24 (m, 1H), 7.14 (t, J = 7.3 Hz, 1H), 6.68 (s, 1H), 4.41 (s, 1H), 3.58 (s, 3H), 2.65 (s, 3H), 1.24 (s, 4H). | 391 | 98% |
| 4-4 | 5-indolyl | ¹H NMR (400 MHz, DMSO) δ 14.82 (s, 1H), 11.36 (s, 1H), 8.90 (s, 1H), 7.95 (d, J = 7.8 Hz, 1H), 7.57 (s, 3H), 7.46 (s, 1H), 7.07 (d, J = 8.5 Hz, 1H), 6.53 (s, 1H), 4.39 (s, 1H), 2.62 (s, 3H), 1.24 (s, 2H), 1.09 (d, J = 18.8 Hz, 2H). | 377 | 87% |

TABLE 4-continued

[Structure: 1-cyclopropyl-6-fluoro-8-methyl-4-oxo-1,4-dihydroquinoline-3-carboxylic acid with R³ substituent at 7-position]

| Compound No. | R³ = | NMR | MS (MH⁺) | HPLC |
|---|---|---|---|---|
| 4-5 | 4-Me-indol-2-yl | ¹H NMR (400 MHz, DMSO) δ 14.71 (s, 1H), 11.55 (s, 1H), 8.92 (s, 1H), 8.00 (d, J = 9.0 Hz, 1H), 7.30 (d, J = 8.4 Hz, 1H), 7.09 (t, J = 7.4 Hz, 1H), 6.87 (d, J = 6.9 Hz, 1H), 6.75 (s, 1H), 4.42 (s, 1H), 2.79 (s, 3H), 2.09 (s, 3H), 1.28 (d, J = 6.0 Hz, 2H), 1.07 (s, 2H). | 391 | 90% |
| 4-6 | 6-MeO-indol-2-yl | ¹H NMR (400 MHz, DMSO) δ 14.71 (s, 1H), 11.43 (s, 1H), 8.91 (s, 1H), 7.99 (d, J = 8.7 Hz, 1H), 7.37 (d, J = 8.6 Hz, 1H), 6.84 (d, J = 8.7 Hz, 1H), 6.63 (s, 1H), 4.41 (s, 1H), 3.78 (s, 4H), 2.77 (s, 3H), 1.26 (d, J = 5.7 Hz, 2H), 1.07 (s, 2H). | 407 | 92.3% |
| 4-9 | 5-NC-indol-2-yl | ¹H NMR (400 MHz, DMSO) δ 14.65 (s, 1H), 12.23 (d, J = 30.1 Hz, 1H), 8.93 (s, 1H), 8.20 (d, J = 11.8 Hz, 1H), 7.65 (s, 1H), 7.53 (s, 2H), 6.87 (d, J = 26.1 Hz, 1H), 4.38 (d, J = 31.7 Hz, 1H), 2.74 (d, J = 19.6 Hz, 3H), 1.24 (d, J = 8.9 Hz, 2H), 1.07 (s, 2H). | 402 | 92.8% |
| 4-10 | 5-F-indol-2-yl | ¹H NMR (400 MHz, DMSO) δ 14.67 (s, 1H), 11.70 (s, 1H), 8.92 (s, 1H), 8.00 (d, J = 8.9 Hz, 1H), 7.52-7.44 (m, 1H), 7.41 (d, J = 9.8 Hz, 1H), 7.04 (t, d = 9.3 Hz, 1H), 6.72 (s, 1H), 4.42 (s, 1H), 2.77 (s, 3H), 1.26 (d, J = 6.4 Hz, 2H), 1.07 (s, 2H). | 395 | 89.7% |
| 4-11 | 4-Cl-indol-2-yl | ¹H NMR (400 MHz, DMSO) δ 14.68 (s, 1H), 11.98 (s, 1H), 8.93 (s, 1H), 8.02 (d, J = 9.1 Hz, 1H), 7.47 (d, J = 7.3 Hz, 1H), 7.19 (q, J = 7.8 Hz, 2H), 6.76 (s, 1H), 4.42 (s, 1H), 2.78 (s, 3H), 1.27 (d, J = 6.2 Hz, 2H), 1.08 (s, 2H). | 411 | 97% |

TABLE 4-continued

[Structure: quinolone core with COOH, =O, N-cyclopropyl, 8-Me, 6-F, 7-R³]

| Compound No. | R³ = | NMR | MS (MH⁺) | HPLC |
|---|---|---|---|---|
| 4-12 | [2-indolyl with 4-CN] | ¹H NMR (400 MHz, DMSO) δ 14.64 (s, 1H), 12.30 (s, 1H), 8.93 (s, 1H), 8.04 (d, J = 8.3 Hz, 1H), 7.86 (d, J = 6.8 Hz, 1H), 7.64 (s, 1H), 7.36 (s, 1H), 6.91 (s, 1H), 4.43 (s, 1H), 2.78 (s, 3H), 1.28 (s, 2H), 1.09 (s, 2H). | 402 | 99% |
| 4-13 | [2-indolyl with 4-F] | ¹H NMR (400 MHz, DMSO) δ 14.66 (s, 1H), 11.93 (s, 1H), 8.92 (s, 1H), 8.01 (d, J = 9.1 Hz, 1H), 7.33 (d, J = 8.3 Hz, 1H), 7.17 (d, J = 6.5 Hz, 1H), 6.87 (t, J = 8.9 Hz, 1H), 6.80 (s, 1H), 4.42 (s, 1H), 2.78 (s, 3H), 1.27 (d, J = 6.4 Hz, 2H), 1.07 (s, 2H). | 395 | 87% |
| 4-14 | [2-indolyl with 7-Me] | ¹H NMR (400 MHz, DMSO) δ 14.70 (s, 1H), 11.43 (s, 1H), 8.92 (s, 1H), 8.00 (d, J = 8.8 Hz, 1H), 7.46 (s, 1H), 6.98 (s, 2H), 6.67 (s, 1H), 4.42 (s, 1H), 2.77 (s, 3H), 1.26 (d, J = 6.3 Hz, 2H), 1.09 (s, 2H). | 391 | 92.7% |
| 4-15 | [2-indolyl with 6-Me] | ¹H NMR (400 MHz, DMSO) δ 11.07 (s, 1H), 9.02 (s, 1H), 8.04 (s, 1H), 7.55 (s, 2H), 7.29 (s, 1H), 6.96 (s, 1H), 6.67 (s, 1H), 2.85 (s, 3H), 2.47 (s, 3H), 1.34 (s, 2H), 1.09 (s, 2H). | 391 | 99% |
| 4-16 | [2-indolyl with 5-NO₂] | ¹H NMR (400 MHz, DMSO) δ 14.64 (s, 1H), 12.41 (s, 1H), 8.93 (s, 1H), 8.69 (s, 1H), 8.07 (d, J = 13.8 Hz, 2H), 7.67 (s, 1H), 7.05 (s, 1H), 4.42 (s, 1H), 2.78 (s, 3H), 1.26 (s, 2H), 1.08 (s, 2H). | 422 | 100% |

TABLE 4-continued

[Structure: quinolone core with COOH, =O, N-cyclopropyl, 8-Me, 7-R³, 6-F]

| Compound No. | R³ = | NMR | MS (MH⁺) | HPLC |
|---|---|---|---|---|
| 4-17 | 6-fluoroindol-2-yl | ¹H NMR (400 MHz, DMSO) δ 14.70 (s, 1H), 11.70 (s, 1H), 8.92 (s, 1H), 8.00 (d, J = 9.0 Hz, 1H), 7.65 (s, 1H), 7.24 (d, J = 10.1 Hz, 1H), 6.96 (t, J = 9.1 Hz, 1H), 6.76 (s, 1H), 4.42 (s, 1H), 2.77 (s, 3H), 1.26 (d, J = 5.7 Hz, 2H), 1.07 (s, 2H). | 395 | 88% |
| 4-18 | 7-fluoroindol-2-yl | ¹H NMR (400 MHz, DMSO) δ 14.68 (s, 1H), 12.08 (s, 1H), 8.92 (s, 1H), 8.01 (d, J = 8.9 Hz, 1H), 7.47 (d, J = 6.4 Hz, 1H), 7.04 (d, J = 9.3 Hz, 2H), 6.79 (s, 1H), 4.42 (s, 1H), 2.76 (s, 3H), 1.26 (d, J = 6.2 Hz, 2H), 1.08 (s, 2H). | 395 | 89.1% |
| 4-19 | 6-carboxyindol-2-yl (HO₂C) | ¹H NMR (400 MHz, DMSO) δ 14.65 (s, 1H), 12.66 (s, 1H), 11.98 (s, 1H), 8.93 (s, 1H), 8.12 (s, 1H), 8.03 (d, J = 8.8 Hz, 1H), 7.70 (q, J = 8.2 Hz, 2H), 6.83 (s, 1H), 4.43 (s, 1H), 2.78 (s, 3H), 1.27 (d, J = 6.2 Hz, 2H), 1.08 (s, 2H). | 421 | 100% |
| 4-20 | 6-chloroindol-2-yl | ¹H NMR (400 MHz, DMSO) δ 14.68 (s, 1H), 11.78 (s, 1H), 8.92 (s, 1H), 8.01 (d, J = 9.0 Hz, 1H), 7.66 (d, J = 8.6 Hz, 1H), 7.51 (s, 1H), 7.10 (d, J = 8.4 Hz, 1H), 6.77 (s, 1H), 4.42 (s, 1H), 2.77 (s, 3H), 1.26 (d, J = 6.1 Hz, 2H), 1.07 (s, 2H). | 411 | 90% |
| 4-21 | 4-nitroindol-2-yl | ¹H NMR (400 MHz, DMSO) δ 14.49 (s, 1H), 12.71 (s, 1H), 8.92 (s, 1H), 8.15 (s, 1H), 8.04 (d, J = 9.4 Hz, 2H), 7.43 (s, 1H), 7.29 (s, 1H), 4.42 (s, 1H), 2.79 (s, 3H), 1.27 (s, 2H), 1.08 (s, 2H). | 422 | 97% |

TABLE 4-continued
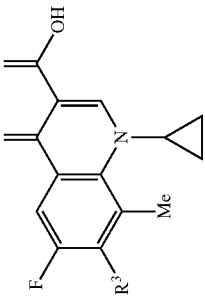
| Compound No. | R³ = | NMR | MS (MH⁺) | HPLC |
|---|---|---|---|---|
| 4-22 | 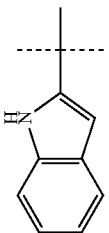 | ¹H NMR (400 MHz, MeOD) δ 8.96 (s, 1H), 7.93 (d, J = 9.1 Hz, 1H), 7.55 (d, J = 12.6 Hz, 2H), 7.47 (s, 1H), 7.34 (d, J = 8.1 Hz, 1H), 6.77 (s, 1H), 6.57 (d, J = 7.9 Hz, 1H), 6.51 (s, 1H), 4.29 (s, 1H), 2.78 (s, 3H), 1.38-1.24 (m, 2H), 1.20 (s, 2H). | 393 | 90% |
| 4-23 | 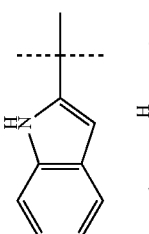 | ¹H NMR (400 MHz, DMSO) δ 14.68 (s, 1H), 11.82 (s, 1H), 8.92 (s, 1H), 8.01 (d, J = 8.5 Hz, 1H), 7.70 (s, 1H), 7.50 (d, J = 8.3 Hz, 1H), 7.19 (d, J = 9.4 Hz, 1H), 6.73 (s, 1H), 4.42 (s, 1H), 2.76 (s, 3H), 1.26 (d, J = 6.1 Hz, 2H), 1.07 (s, 2H). | 411 | 90% |
| 4-24 | 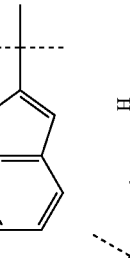 | ¹H NMR (400 MHz, DMSO) δ 14.63 (s, 1H), 11.61 (s, 1H), 8.95 (d, J = 9.5 Hz, 1H), 8.41 (s, 1H), 7.99 (s, 1H), 7.67 (d, J = 9.1 Hz, 1H), 6.52 (s, 1H), 4.43 (s, 1H), 2.78 (s, 3H), 1.25 (s, 2H), 1.08 (s, 2H). | 422 | 90% |
| 4-25 | 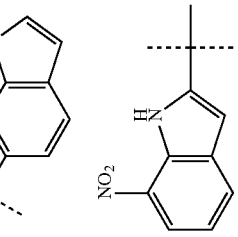 | ¹H NMR (400 MHz, DMSO) δ 14.82 (s, 1H), 11.31 (s, 1H), 8.91 (s, 1H), 7.97 (d, J = 8.4 Hz, 1H), 7.71 (d, J = 7.8 Hz, 1H), 7.48 (s, 1H), 7.41 (s, 1H), 6.99 (d, J = 7.9 Hz, 1H), 6.53 (s, 1H), 4.40 (s, 1H), 2.63 (s, 3H), 1.24 (s, 2H), 1.08 (s, 2H). | 377 | 100% |
| 4-26 |  | ¹H NMR (400 MHz, DMSO) δ 14.70 (s, 1H), 12.37 (s, 1H), 8.93 (s, 1H), 8.19 (t, J = 9.0 Hz, 2H), 8.01 (d, J = 8.0 Hz, 1H), 7.34 (s, 1H), 7.00 (s, 1H), 4.43 (s, 1H), 2.75 (s, 3H), 1.24 (s, 2H), 1.11 (s, 2H). | 422 | 99% |

TABLE 4-continued

[Structure: quinolone core with COOH, C=O, F, Me, cyclopropyl N, and R³ substituent]

| Compound No. | R³ = | NMR | MS (MH⁺) | HPLC |
|---|---|---|---|---|
| 4-27 | 5-(BocHN)-indol-2-yl | ¹H NMR (400 MHz, DMSO) δ 14.73 (s, 1H), 11.45 (s, 1H), 9.17 (s, 1H), 8.92 (s, 1H), 7.99 (d, J = 8.6 Hz, 1H), 7.77 (s, 1H), 7.35 (d, J = 8.5 Hz, 1H), 7.24 (s, 1H), 6.64 (s, 1H), 4.42 (s, 2H), 1.46 (d, J = 29.9 Hz, 9H), 1.25 (s, 2H), 1.06 (s, 2H). | 492 | 100% |
| 4-28 | 5-(H₂N)-indol-2-yl | ¹H NMR (400 MHz, DMSO) δ 14.67 (s, 1H), 11.94 (s, 1H), 9.97 (s, 2H), 8.93 (s, 1H), 8.02 (d, J = 8.7 Hz, 1H), 7.65 (s, 1H), 7.60 (d, J = 8.6 Hz, 1H), 7.19-7.13 (m, 1H), 6.84 (s, 1H), 4.42 (s, 2H), 2.76 (s, 3H), 1.14-1.00 (m, 4H). | 392 | 94% |
| 4-29 | 5-(H₂N)-indol-2-yl | ¹H NMR (400 MHz, DMSO) δ 14.67 (s, 1H), 11.94 (s, 1H), 9.97 (s, 2H), 8.93 (s, 1H), 8.02 (d, J = 8.7 Hz, 1H), 7.65 (s, 1H), 7.60 (d, J = 8.6 Hz, 1H), 7.19-7.13 (m, 1H), 6.84 (s, 1H), 4.42 (s, 2H), 2.76 (s, 3H), 1.14-1.00 (m, 4H). | 391 | 100% |
| 4-30 | 6-(BocHN)-indol-2-yl | ¹H NMR (400 MHz, DMSO) δ 14.73 (s, 1H), 11.38 (s, 1H), 9.33 (s, 1H), 8.91 (s, 1H), 7.98 (d, J = 9.1 Hz, 1H), 7.81 (s, 1H), 7.48 (d, J = 8.3 Hz, 1H), 7.09 (d, J = 8.7 Hz, 1H), 6.64 (s, 1H), 4.42 (s, 1H), 2.78 (s, 3H), 1.51 (s, 10H), 1.25 (d, J = 8.9 Hz, 2H), 1.08 (dd, J = 14.0, 6.3 Hz, 2H). | 492 | 97% |
| 4-31 | indol-2-yl | ¹H NMR (400 MHz, DMSO) δ 14.31 (s, 1H), 11.68 (s, 1H), 8.94 (s, 1H), 8.17 (d, J = 8.7 Hz, 1H), 7.66 (d, J = 7.8 Hz, 1H), 7.49 (d, J = 8.1 Hz, 1H), 7.21 (t, J = 7.5 Hz, 1H), 7.06 (t, J = 7.4 Hz, 1H), 6.80 (s, 1H), 4.44 (s, 1H), 1.25 (d, J = 6.4 Hz, 2H), 1.12 (s, 2H). | 397 | 100% |
| 4-32 | 6-(H₂N)-indol-2-yl | ¹H NMR (400 MHz, DMSO) δ 14.72 (s, 1H), 11.74 (s, 1H), 9.35 (s, 2H), 8.92 (s, 1H), 8.00 (d, J = 9.0 Hz, 1H), 7.66 (d, J 8.5 Hz, 1H), 7.34 (s, 1H), 6.94 (d, J = 8.3 Hz, 1H), 6.76 (s, 1H), 4.42 (s, 1H), 2.78 (s, 3H), 1.27 (d, J = 5.6 Hz, 3H), 1.06 (s, 2H). | 392 | 97% |

TABLE 4-continued

| Compound No. | R³ = | NMR | MS (MH⁺) | HPLC |
|---|---|---|---|---|
| 4-33 | 4-NHBoc-indol-2-yl | ¹H NMR (400 MHz, DMSO) δ 14.73 (s, 1H), 11.56 (s, 1H), 9.17 (s, 1H), 8.93 (s, 1H), 8.00 (d, J = 7.7 Hz, 1H), 7.46 (s, 2H), 7.12 (d, J = 20.9 Hz, 2H), 5.18-4.56 (m, 1H), 4.44 (s, 1H), 2.80 (s, 3H), 1.24 (s, 2H), 1.07 (s, 2H). | 492 | 91% |
| 4-34 | 4-NH₂-indol-2-yl | ¹H NMR (400 MHz, DMSO) δ 14.70 (s, 1H), 11.77 (s, 1H), 8.93 (s, 1H), 8.01 (d, J = 8.4 Hz, 1H), 7.23-7.03 (m, 2H), 6.88(s, 1H), 6.76 (d, J = 6.4 Hz, 1H), 4.43 (m, 1H), 2.77(s, 3H), 1.24 (d, J = 6.6 Hz, 2H), 1.12 (s, 2H). | 392 | 99% |
| 4-35 | 5-F-indol-2-yl | ¹H NMR (400 MHz, DMSO) δ 14.28 (s, 1H), 11.79 (s, 1H), 8.94 (s, 1H), 8.17 (d, J = 8.8 Hz, 1H), 7.56-7.38 (m, 2H), 7.06 (t, J = 8.8 Hz, 1H), 6.79 (s, 1H), 4.44 (s, 1H), 1.24 (d, J = 6.6 Hz, 2H), 1.12 (s, 2H). | 415 | 91% |
| 4-36 | 7-F-indol-2-yl | ¹H NMR (400 MHz, DMSO) δ 14.28 (s, 1H), 12.16 (s, 1H), 8.95 (s, 1H), 8.18 (d, J = 8.0 Hz, 1H), 7.49 (d, J = 4.2 Hz, 1H), 7.05 (d, J = 8.5 Hz, 2H), 6.85 (s, 1H), 4.43 (s, 1H), 1.24 (s, 2H), 1.13 (s, 2H). | 415 | 95% |
| 4-37 | 4-Cl-indol-2-yl | ¹H NMR (400 MHz, DMSO) δ 14.26 (s, 1H), 12.07 (s, 1H), 8.95 (s, 1H), 8.19 (d, J = 8.5 Hz, 1H), 7.49 (d, J = 7.6 Hz, 1H), 7.29-7.07 (m, 2H), 6.81 (s, 1H), 4.44 (s, 1H), 1.25 (s, 2H), 1.13 (s, 2H). | 431 | 95% |

TABLE 4-continued

[Core structure: 1-cyclopropyl-6-fluoro-8-methyl-4-oxo-7-R³-quinoline-3-carboxylic acid]

| Compound No. | R³ = | NMR | MS (MH⁺) | HPLC |
|---|---|---|---|---|
| 4-38 | 2-(4-fluoro-1H-indol-2-yl), attached via 2-position | ¹H NMR (400 MHz, DMSO) δ 14.28 (s, 1H), 12.04 (s, 1H), 8.95 (s, 1H), 8.19 (d, J = 8.7 Hz, 1H), 7.34 (d, J = 8.0 Hz, 1H), 7.20 (s, 1H), 6.93-6.81 (m, 2H), 4.44 (s, 1H), 1.24 (s, 2H), 1.13 (s, 2H). | 415 | 87% |
| 4-39 | 2-[4-(4-methoxybenzamido)-1H-indol-2-yl] | ¹H NMR (400 MHz, DMSO) δ 14.71 (s, 1H), 11.66 (s, 1H), 10.06 (s, 1H), 8.92 (s, 1H), 8.02 (s, 3H), 7.46 (s, 1H), 7.31 (s, 1H), 7.19 (s, 1H), 7.06 (s, 1H), 6.90 (s, 1H), 4.42 (s, 1H), 3.85 (s, 3H), 2.79 (s, 3H), 1.26 (s, 2H), 1.07 (s, 2H). | 526 | 95.6% |
| 4-40 | 2-[4-(4-methoxyphenylsulfonamido)-1H-indol-2-yl] | ¹H NMR (400 MHz, DMSO) δ 14.71 (s, 1H), 11.62 (s, 1H), 10.05 (s, 1H), 8.93 (s, 1H), 7.99 (d, J = 9.2 Hz, 1H), 7.70 (d, J = 7.5 Hz, 2H), 7.28-6.87 (m, 6H), 4.42 (s, 1H), 3.75 (s, 3H), 2.68 (s, 3H), 1.25 (d, J = 9.3 Hz, 2H), 1.05 (d, J = 18.8 Hz, 2H). | 562 | 96% |

TABLE 4-continued

| Compound No. | R³ = | NMR | MS (MH⁺) | HPLC |
|---|---|---|---|---|
| 4-41 | (indole with HN-C(O)-iPr at 4-position, 2-Me) | ¹H NMR (400 MHz, DMSO) δ 14.73 (s, 1H), 11.66 (s, 1H), 9.62 (s, 1H), 8.93 (s, 1H), 8.02 (d, J = 8.7 Hz, 1H), 7.72 (s, 1H), 7.21 (s, 1H), 7.12 (s, 1H), 7.04 (s, 1H), 4.44 (s, 1H), 3.05 (s, 1H), 2.82 (d, J = 25.3 Hz, 3H), 1.12 (d, J = 24.4 Hz, 10H). | 462 | 87% |
| 4-42 | (indole with CH₂NH₂ at 4-position, 2-Me) | ¹H NMR (400 MHz, DMSO) δ 11.87 (s, 1H), 9.18 (s, 1H), 8.08-7.63 (m, 2H), 7.48 (s, 2H) 7.20 (s, 2H), 6.95 (s, 2H), 4.54 (s, 1H), 4.24 (s, 2H), 2.81 (s, 3H), 1.29 (s, 2H), 1.06 (s, 2H). | 406 | 97% |
| 4-43 | (indole with CH₂NHBoc at 4-position, 2-Me) | ¹H NMR (400 MHz, DMSO) δ 14.78 (s, 1H), 11.70 (s, 1H), 8.98 (s, 1H), 8.06 (d, J = 9.0 Hz, 1H), 7.49 (s, 1H), 7.43 (d, J = 7.4 Hz, 1H), 7.20 (s, 1H), 7.00 (d, J = 6.8 Hz, 1H), 6.91 (s, 1H), 4.49 (s, 3H), 2.84 (s, 3H), 1.46 (s, 9H), 1.30 (s, 2H), 1.13 (s, 2H). | 506 | 98% |
| 4-44 | (5-substituted 3-nitroindole, gem-dimethyl) | ¹H NMR (400 MHz, DMSO) δ 14.76 (s, 1H), 12.92 (s, 1H), 8.92 (s, 1H), 8.79 (s, 1H), 8.07 (s, 1H), 7.99 (d, J = 8.6 Hz, 1H), 7.77 (d, J = 8.3 Hz, 1H), 7.37 (d, J = 8.0 Hz, 1H), 4.40 (s, 1H), 2.62 (s, 3H), 1.25 (d, J = 5.7 Hz, 2H), 1.10 (s, 2H). | 422 | 100% |

TABLE 4-continued

| Compound No. | R³ = | NMR | MS (MH⁺) | HPLC |
|---|---|---|---|---|
| 4-45 | (2-cyclohexanecarboxamido-1H-indol-4-yl) | ¹H NMR (400 MHz, DMSO) δ 11.65 (s, 1H), 9.57 (s, 1H), 8.82 (s, 1H), 7.93 (d, J = 8.3 Hz, 1H), 7.71 (d, J = 5.5 Hz, 1H), 7.19 (s, 1H), 7.09 (s, 1H), 7.00 (s, 1H), 4.32 (s, 1H), 2.72 (d, J = 18.9 Hz, 3H), 1.89-1.77 (m, 5H), 1.65 (s, 1H), 1.45 (d, J = 10.5 Hz, 2H), 1.35-1.16 (m, 6H), 0.97 (s, 2H). | 502 | 89% |
| 4-46 | (2-{[((1S,3R,5S)-3-isopropyl-5-methylcyclohexyl)oxy]acetamido}-1H-indol-4-yl) | ¹H NMR (400 MHz, DMSO) δ 14.69 (s, 1H), 11.94 (s, 1H), 9.39 (s, 1H), 8.92 (s, 1H), 8.00 (d, J = 7.8 Hz, 1H), 7.72 (s, 1H), 7.28 (s, 1H), 7.15 (s, 1H), 6.81 (s, 1H), 4.43 (s, 1H), 4.27-4.13 (m, 2H), 2.79 (s, 3H), 2.33 (s, 1H), 2.17 (s, 1H), 1.59 (d, J = 14.2 Hz, 2H), 1.26 (s, 5H), 1.07 (s, 2H), 0.85 (dd, J = 54.3, 14.6 Hz, 14H). | 588 | 86.3% |

TABLE 4-continued

| Compound No. | R³ = | NMR | MS (MH⁺) | HPLC |
|---|---|---|---|---|
| 4-47 | [indole linked to 6-(trifluoromethyl)pyridine-3-carboxamide] | ¹H NMR (400 MHz, DMSO) δ 14.73 (s, 1H), 11.74 (s, 1H), 10.60 (s, 1H), 9.30 (s, 1H), 8.92 (s, 1H), 8.61 (d, J = 7.6 Hz, 1H), 8.11 (d, J = 7.9 Hz, 1H), 8.01 (d, J = 8.8 Hz, 1H), 7.59 (d, J = 6.7 Hz, 1H), 7.37 (d, J = 7.8 Hz, 1H), 7.24 (d, J = 8.0 Hz, 1H), 6.97 (s, 1H), 4.43 (s, 1H), 2.79 (s, 3H), 1.25 (s, 2H), 1.07 (s, 2H). | 565 | 96% |
| 4-48 | [indole linked to camphorsulfonamide] | ¹H NMR (400 MHz, DMSO) δ 14.70 (s, 1H), 11.74 (s, 1H), 9.76 (s, 1H), 8.93 (s, 1H), 8.01 (d, J = 8.7 Hz, 1H), 7.29 (d, J = 6.6 Hz, 1H), 7.23-7.01 (m, 3H), 4.43 (s, 1H), 3.49 (d, J = 14.6 Hz, 1H), 3.06 (d, J = 14.8 Hz, 1H), 2.37 (dd, J = 27.4, 15.5 Hz, 2H), 2.04 (s, 1H), 1.91 (d, J = 17.7 Hz, 2H), 1.51 (d, J = 11.3 Hz, 1H), 1.41 (d, J = 10.3 Hz, 1H), 1.25 (s, 2H), 1.09 (d, J = 11.8 Hz, 3H), 0.98 (s, 2H), 0.77 (d, J = 22.2 Hz, 3H). | 606 | 88% |
| 4-49 | [indole linked to naphthalene-1-sulfonamide] | ¹H NMR (400 MHz, DMSO) δ 14.69 (s, 1H), 11.58 (s, 1H), 1029 (s, 1H), 8.91 (s, 1H), 8.40 (s, 1H), 8.05 (dd, J = 15.6, 8.6 Hz, 2H), 7.97 (s, 2H), 7.83 (d, J = 8.2 Hz, 1H), 7.72-7.56 (m, 2H), 7.18 (d, J = 8.0 Hz, 1H), 7.04 (t, J = 8.0 Hz, 1H), 6.98 (d, J = 7.5 Hz, 1H), 6.81 (s, 1H), 4.35 (s, 1H), 2.54 (s, 3H), 1.23 (s, 2H), 1.04 (s, 2H). | 582 | 100% |

TABLE 4-continued

| Compound No. | R³ = | NMR | MS (MH⁺) | HPLC |
|---|---|---|---|---|
| 4-50 | | ¹H NMR (400 MHz, DMSO) δ 14.72 (s, 1H), 11.68 (s, 1H), 10.26 (s, 1H), 8.92 (s, 1H), 8.00 (s, 1H), 7.74 (s, 1H), 7.29 (s, 1H), 7.19 (s, 1H), 7.03 (s, 1H), 8.93 (s, 2H), 4.43 (s, 1H), 2.79 (s, 3H), 2.31 (s, 6H), 2.10 (s, 3H), 1.24 (s, 2H), 1.07 (s, 2H). | 538 | 90% |
| 4-51 | | ¹H NMR (400 MHz, DMSO) δ 14.73 (s, 1H), 11.62 (s, 1H), 10.08 (s, 1H), 8.93 (s, 1H), 8.00 (d, J = 7.6 Hz, 1H) 7.76 (d, J = 8.6 Hz, 2H), 7.18 (d, J = 7.7 Hz, 2H), 7.02 (d, J = 18.7 Hz, 2H), 4.44 (s, 1H), 3.63 (s, 3H), 2.76 (s, 3H), 1.24 (s, 2H), 1.08 (s, 2H). | 536 | 99% |
| 4-52 | | ¹H NMR (400 MHz, DMSO) δ 14.72 (s, 1H), 11.68 (s, 1H), 9.29 (s, 1H), 8.93 (s, 1H), 8.81 (s, 1H), 8.31 (s, 1H), 8.03 (d, J = 8.9 Hz, 1H), 7.15 (s, 2H), 7.02 (dd, J = 24.0, 8.3 Hz, 2H), 6.94 (s, 1H), 4.44 (s, 1H), 3.91 (s, 3H), 2.80 (s, 3H), 1.25 (d, J = 15.5 Hz, 2H), 1.08 (s, 2H). | 575 | 96% |

TABLE 4-continued
| Compound No. | R³ = | NMR | MS (MH⁺) | HPLC |
|---|---|---|---|---|
| 4-53 |  | ¹H NMR (400 MHz, DMSO) δ 14.71 (s, 1H), 11.72 (s, 1H), 10.04 (s, 1H), 8.94 (s, 1H), 8.02 (d, J = 10.3 Hz, 1H), 7.71 (s, 1H), 7.24 (s, 1H), 7.15 (d, J = 7.0 Hz, 1H), 7.04 (s, 1H), 4.44 (s, 1H), 3.98 (s, 2H), 3.76 (s, 2H), 3.43 (s, 2H), 3.07 (d, J = 24.3 Hz, 4H), 2.78 (s, 3H), 2.69 (d, J = 10.9 Hz, 1H), 1.26 (s, 2H), 1.08 (s, 2H). | 533 | 99% |
| 4-54 |  | ¹H NMR (400 MHz, DMSO) δ 14.71 (s, 1H), 11.72 (s, 1H), 10.03 (s, 1H), 8.94 (s, 1H), 8.02 (d, J = 8.9 Hz, 1H), 7.70 (s, 1H), 7.24 (s, 1H), 7.14 (s, 1H), 7.03 (s, 1H), 5.33 (s, 1H), 4.43 (s, 1H), 4.03 (s, 2H), 3.03 (s, 4H), 2.78 (s, 3H), 2.00 (d, J = 7.6 Hz, 2H), 1.24 (s, 9H), 1.08 (s, 2H), 0.85 (s, 2H). | 632 | 96% |
| 4-55 |  | ¹H NMR (400 MHz, DMSO) δ 14.71 (s, 1H), 11.72 (s, 1H), 10.04 (s, 1H), 9.57 (s, 1H), 8.94 (s, 1H), 8.02 (d, J = 8.9 Hz, 1H), 7.71 (d, J = 7.8 Hz, 1H), 7.26 (d, J = 7.6 Hz, 1H), 7.15 (d, J = 9.1 Hz, 1H), 7.03 (d, J = 9.6 Hz, 1H), 4.44 (s, 1H), 2.99 (s, 1H), 2.82 (s, 3H), 2.78 (s, 2H), 2.54 (s, 2H), 1.26 (s, 2H), 1.08 (s, 2H). | 491 | 91% |

TABLE 4-continued

| Compound No. | R³ = | NMR | MS (MH⁺) | HPLC |
|---|---|---|---|---|
| 4-56 | (2-indolyl with 4-NH-C(SMe)=N-CN substituent) | ¹H NMR (400 MHz, DMSO) δ 14.71 (s, 1H), 11.87 (s, 1H), 10.45 (s, 1H), 8.93 (s, 1H), 8.02 (d, J = 8.8 Hz, 1H) 7.47 (d, J = 7.2 Hz, 1H) 7.23 (s, 1H), 7.07 (d, J = 7.9 Hz, 1H), 6.68 (s, 1H), 4.42 (s, 1H), 2.78 (s, 3H), 2.68 (s, 3H), 1.26 (s, 2H), 1.08 (s, 2H). | 490 | 96% |
| 4-57 | (2-indolyl with 4-CH₂NMe₂ substituent) | ¹H NMR (400 MHz, DMSO) δ 14.78 (s, 1H), 11.75 (s, 1H), 9.64 (s, 1H), 8.92 (s, 1H), 7.99 (d, J = 8.7 Hz, 1H), 7.83 (s, 1H), 7.70 (s, 1H), 7.63 (d, J = 7.8 Hz, 1H), 7.18 (d, J = 8.6 Hz, 1H), 4.48 (s, 2H), 4.40 (s, 1H), 2.72 (d, J = 27.2 Hz, 7H), 2.62 (s, 3H), 1.25 (s, 2H), 1.08 (s, 2H). | M—(Me)₂N 389 | 100% |
| 4-58 | (N-(2-dimethylaminoethyl)-indol-5-yl) | ¹H NMR (400 MHz, DMSO) δ 14.79 (s, 1H), 9.84 (s, 1H), 8.92 (s, 1H), 7.97 (d, J = 8.2 Hz, 1H), 7.77 (d, J = 8.7 Hz, 1H), 7.62 (s, 1H), 7.56 (s, 1H), 7.20 (d, J = 8.0 Hz, 1H), 6.63 (s, 1H), 4.64 (s, 2H), 4.39 (s, 1H), 3.57 (s, 2H), 2.88 (s, 6H), 2.65 (s, 3H), 1.24 (s, 2H), 1.08 (s, 2H). | 448 | 100% |

TABLE 4-continued

![quinoline core structure with R3 substituent, F, Me, cyclopropyl-N, and carboxylic acid]

| Compound No. | R³ = | NMR | MS (MH⁺) | HPLC |
|---|---|---|---|---|
| 4-59 | ![2-yl-4-hydroxyindole] | ¹H NMR (400 MHz, DMSO) δ 14.76 (s, 1H), 11.62 (s, 1H), 9.68 (s, 1H), 8.92 (s, 1H), 7.99 (s, 1H), 6.95 (s, 2H), 6.77 (s, 1H), 6.46 (s, 1H), 4.43 (s, 1H), 2.80 (s, 3H), 1.27 (s, 2H), 1.07 (s, 4H). | 393 | 99% |
| 4-60 | ![2-yl-5,6-dimethoxyindole] | ¹H NMR (400 MHz, DMSO) δ 14.77 (s, 1H), 11.29 (s, 1H), 8.91 (s, 1H), 7.97 (d, J = 9.0 Hz, 1H), 7.13 (s, 1H), 6.97 (s, 1H), 6.61 (s, 1H), 4.42 (s, 1H), 3.80 (d, J = 13.7 Hz, 7H), 2.78 (s, 3H), 1.26 (s, 2H), 1.06 (s, 2H). | 437 | 99% |
| 4-61 | ![2-yl-6-hydroxyindole] | ¹H NMR (400 MHz, DMSO) δ 14.74 (s, 1H), 11.29 (s, 1H), 8.91 (s, 1H), 8.81 (s, 1H), 7.98 (d, J = 9.1 Hz, 1H), 7.27 (d, J = 8.8 Hz, 1H), 6.93 (s, 1H), 6.71 (d, J = 8.4 Hz, 1H), 6.53 (s, 1H), 4.41 (s, 2H), 2.77 (s, 3H), 1.25 (s, 2H), 1.06 (s, 2H). | 393 | 98% |
| 4-62 | ![2-yl-7-hydroxyindole] | ¹H NMR (400 MHz, DMSO) δ 14.75 (s, 1H), 11.50 (s, 1H), 9.79 (s, 1H), 8.91 (s, 1H), 7.97 (d, J = 8.7 Hz, 1H), 7.07 (d, J = 6.7 Hz, 1H), 6.86 (s, 1H), 6.60 (s, 2H), 4.41 (s, 1H), 2.76 (s, 3H), 1.23 (s, 2H), 1.08 (s, 2H). | 393 | 100% |
| 4-63 | ![2-yl-4-formylindole] | ¹H NMR (400 MHz, DMSO) δ 12.18 (s, 1H), 10.24 (s, 1H), 8.93 (s, 1H), 8.04 (d, J = 8.8 Hz, 1H), 7.87 (d, J = 8.8 Hz, 2H), 7.78 (d, J = 7.0 Hz, 1H), 7.46 (d, J = 7.3 Hz, 2H), 7.35 (s, 1H), 4.43 (s, 1H), 2.77 (s, 3H), 1.27 (s, 2H), 1.09 (s, 2H). | 405 | 85% |

TABLE 4-continued

| Compound No. | R³ = | NMR | MS (MH⁺) | HPLC |
|---|---|---|---|---|
| 4-64 | [structure with NO₂, CN, indole] | ¹H NMR (400 MHz, DMSO) δ 14.55 (s, 1H), 13.88 (s, 1H), 8.94 (s, 1H), 8.10 (d, J = 8.4 Hz, 1H), 8.01 (dd, J = 14.5, 7.6 Hz, 2H), 7.62 (s, 1H), 4.44 (s, 1H), 2.71 (s, 3H), 1.24 (s, 2H), 1.08 (s, 2H). | 447 | 89% |
| 4-65 | [structure with 2,4-difluorophenyl quinolone and indole] | ¹H NMR (400 MHz, DMSO) δ 14.44 (s, 1H), 11.53 (s, 1H), 8.84 (s, 1H), 8.16 (d, J = 9.1 Hz, 1H), 7.95 (d, J = 7.2 Hz, 1H), 7.69 (d, J = 9.7 Hz, 1H), 7.58 (t, J = 10.6 Hz, 1H), 7.42 (d, J = 7.4 Hz, 2H), 7.16 (t, J = 7.5 Hz, 1H), 7.04 (t, J = 7.4 Hz, 1H), 6.62 (s, 1H), 5.77 (s, 1H), 1.77 (d, J = 17.9 Hz, 3H). | 449 | 94.06% |
| 4-66 | [structure with cyclopropyl quinolone and indole] | ¹H NMR (400 MHz, DMSO) δ 14.79 (s, 1H), 11.42 (s, 1H), 8.70 (s, 1H), 8.04 (d, J = 8.2 Hz, 1H), 7.57 (d, J = 8.2 Hz, 1H), 7.42 (d, J = 8.0 Hz, 1H), 7.25 (s, 1H), 6.96 (d, J = 8.1 Hz, 1H), 6.86 (d, J = 7.7 Hz, 1H), 6.61 (s, 1H), 4.23 (s, 1H), 2.70 (s, 3H), 1.06 (s, 2H), 0.81 (s, 2H). | 359 | 91.2% |

TABLE 4-continued

| Compound No. | R³ = | NMR | MS (MH⁺) | HPLC |
|---|---|---|---|---|
| 4-67 | 4-azaindol-4-yl | ¹H NMR (400 MHz, DMSO) δ 11.76 (s, 1H), 8.71 (s, 1H), 8.16 (d, J = 4.8 Hz, 1H), 7.81 (d, J = 8.8 Hz, 1H), 7.36 (s, 1H), 5.94 (dd, J = 3.4, 1.8 Hz, 1H), 5.10 (s, 1H), 4.22-4.08 (m, 1H), 2.33 (s, 3H), 1.09-0.88 (m, 4H). | 378 | 97% |
| 4-68 | 7-azaindol-3-yl | ¹H NMR (400 MHz, DMSO) δ 12.33 (s, 1H), 8.92 (s, 1H), 8.35 (d, J = 4.4 Hz, 1H), 7.99 (d, J = 8.8 Hz, 1H), 7.87 (s, 1H), 7.77 (d, J = 7.8 Hz, 1H), 7.21 (dd, J = 7.7, 4.0 Hz, 1H), 4.47-4.34 (m, 2H), 2.69 (s, 3H), 1.28 (d, J = 6.6 Hz, 2H), 1.10 (s, 2H). | 378 | 98% |
| 4-69 | 1-methyl-7-azaindol-2-yl | ¹H NMR (400 MHz, DMSO) δ 8.94 (s, 1H), 8.39 (t, J = 3.1 Hz, 1H), 8.08 (t, J = 9.0 Hz, 2H), 7.22 (dd, J = 8.1, 4.1 Hz, 1H), 6.74 (d, J = 2.9 Hz, 1H), 4.48-4.36 (m, 1H), 2.67 (s, 3H), 1.26 (d, J = 7.0 Hz, 4H), 1.09 (s, 4H). | 392 | 98% |
| 4-70 | 1-methyl-6-azaindol-2-yl | ¹H NMR (400 MHz, DMSO) δ 8.94 (s, 1H), 8.39 (t, J = 3.1 Hz, 1H), 8.07 (t, J = 9.0 Hz, 1H), 7.21 (dt, J = 7.7, 3.7 Hz, 1H), 6.74 (d, J = 2.9 Hz, 1H), 4.50-4.32 (m, 1H), 2.67 (s, 3H), 1.33-1.19 (d, J = 7.0 Hz, 2H), 1.09 (s, 2H). | 392 | 96% |

TABLE 4-continued

[Structure: quinolone carboxylic acid with cyclopropyl N-substituent, 6-F, 8-Me, and R³ substituent]

| Compound No. | R³ = | NMR | MS (MH⁺) | HPLC |
|---|---|---|---|---|
| 4-71 | 5-(1H-pyrrolo[2,3-b]pyridinyl) | ¹H NMR (400 MHz, DMSO) δ 14.73 (s, 1H), 11.96 (s, 1H), 8.92(s, 1H), 8.24 (s, 1H), 8.06 (s, 1H), 8.00 (d, J = 8.7 Hz, 1H), 7.61 (t, J = 2.8 Hz, 1H), 6.57 (s, 1H), 4.59-4.15 (dm, 1H), 2.64 (s, 3H), 1.26 (d, J = 6.8 Hz, 2H), 1.09 (m, 2H). | 378 | 98% |
| 4-72 | 2-methyl-1H-pyrrolo[2,3-b]pyridine N-oxide | ¹H NMR (400 MHz, DMSO) δ 14.67 (s, 1H), 13.15 (s, 1H), 8.93 (s, 1H), 8.27 (d, J = 6.1 Hz, 1H), 8.01 (d, J = 8.8 Hz, 1H), 7.78 (d, J = 7.9 Hz, 1H), 7.19 (t, J = 7.1 Hz, 1H), 6.88 (s, 1H), 4.49-4.33 (m, 1H), 2.77 (s, 3H), 1.39-1.21 (d, J = 7.0 Hz, 2H), 1.15-1.01 (m, 2H). | 394 | 98% |
| 4-73 | 5-cyano-2-methyl-1H-pyrrolo[2,3-b]pyridine | ¹H NMR (400 MHz, DMSO) δ 14.63 (s, 1H), 12.94 (s, 1H), 8.93 (s, 1H), 8.72 (s, 1H), 8.65 (s, 1H), 8.04 (d, J = 8.7 Hz, 1H), 6.93 (s, 1H), 4.53-4.29 (m, 1H), 2.77 (s, 3H), 1.32-1.19 (m, 3H), 1.17-0.95 (m, 2H). | 403 | 92% |
| 4-74 | 4-cyano-2-methyl-1H-pyrrolo[2,3-b]pyridine | ¹H NMR (400 MHz, DMSO) δ 13.00 (s, 1H), 13.00 (s, 1H), 8.94 (s, 1H), 8.53 (s, 7H), 8.04 (d, J = 8 Hz, 1H), 7.69 (dd, J = 4.4, 2.4 Hz, 1H), 7.01 (s, 6H), 4.58-4.31 (m, 1H), 2.78 (s, 3H), 1.27 (d, J = 6.6 Hz, 15H), 1.18-1.01 (m, 16H). | 403 | 92% |
| 4-75 | 3-nitro-2-methyl-1H-pyrrolo[2,3-b]pyridine | ¹H NMR (400 MHz, DMSO) δ 14.57(s, 1H), 13.95 (s, 1H), 8.94 (s, 1H), 8.58 (s, 2H), 8.09 (d, J = 8.7 Hz, 1H), 7.60-7.51 (m, 1H), 4.53-4.33 (m, 1H), 2.73 (s, 3H), 1.35-1.17 (m, 2H), 1.15-1.01 (m, 2H). | 423 | 86% |

TABLE 4-continued

| Compound No. | R³ = | NMR | MS (MH⁺) | HPLC |
|---|---|---|---|---|
| 4-76 | [3-substituted 7-azaindole N-oxide] | ¹H NMR (400 MHz, DMSO) δ 13.25 (s, 1H), 8.99 (s, 1H), 8.36 (d, J = 5.9 Hz, 1H), 8.07 (d, J = 8.7 Hz, 1H), 7.95 (s, 1H), 8.02 (d, J = 8.0 Hz, 1H), 7.52 (d, J = 5.9 Hz, 1H), 7.28 (t, J = 6.8 Hz, 1H), 2.76 (s, 3H), 1.34 (d, J = 6.8 Hz, 2H), 1.26-1.06 (m, 2H). | 394 | 98% |
| 4-77 | [2-substituted 7-azaindole] | ¹H NMR (400 MHz, DMSO) δ 12.56 (s, 1H), 8.93 (s, 1H), 8.38 (t, J = 3.6 Hz, 1H), 8.20 (d, J = 7.4 Hz, 1H), 8.02 (d, J = 9.1 Hz, 1H), 7.26 (dd, J = 8.0, 4.1 Hz, 1H), 6.83 (s, 1H), 4.57-4.33 (m, 1H), 2.78 (s, 3H), 1.35-1.19 (d, J = 6.9 Hz, 2H), 1.15-1.01 (s, 2H). | 378 | 98% |
| 4-78 | [2-substituted 4-hydroxy-7-azaindole with pyrimidine] | ¹H NMR (400 MHz, DMSO) δ 14.65 (s, 1H), 12.47 (s, 1H), 11.98 (s, 1H), 8.91 (s, 1H), 7.95 (m, 2H), 6.76 (s, 1H), 4.51-4.36 (m, 1H), 2.78 (s, 3H), 1.26 (d, J = 6.9 Hz, 2H), 1.17-1.01 (m, 2H). | 395 | 95% |
| 4-79 | [2-substituted pyrrolopyrimidine] | ¹H NMR (400 MHz, DMSO) δ 14.57 (s, 1H), 13.19 (d, J = 8.5 Hz, 1H), 9.29 (d, J = 2.9 Hz, 1H), 9.02 (d, J = 2.4 Hz, 1H), 8.94 (s, 1H), 8.05 (d, J = 8.8 Hz, 1H), 7.06 (s, 1H), 4.49-4.35 (m, 1H), 2.77 (s, 3H), 1.26 (d, J = 7.2 Hz, 2H), 1.13-0.99 (s, 2H). | 379 | 98% |
| 4-80 | [2-substituted 6-azaindole] | ¹H NMR (400 MHz, DMSO) δ 15.167 (s, 1H), 14.59 (s, 1H), 13.80 (s, 1H), 9.32 (s, 1H), 8.96 (d, J = 2.3 Hz, 1H), 8.40 (d, J = 6.1 Hz, 1H), 8.25 (d, J = 6.0 Hz, 1H), 8.10 (d, J = 8.4 Hz, 1H), 7.27 (s, 1H), 4.51-4.39 (m, 1H), 2.76 (m, 3H), 1.29-1.17 (d, J = 7.0 Hz, 2H), 1.17-0.97 (m, 2H). | 378 | 85% |

TABLE 4-continued

[Structure: quinolone core with R³, F, Me, cyclopropyl, CO₂H]

| Compound No. | R³ = | NMR | MS (MH⁺) | HPLC |
|---|---|---|---|---|
| 4-81 | [7-azaindole, 2-position attachment] | ¹H NMR (400 MHz, DMSO) δ 14.56 (s, 1H), 13.05 (s, 1H), 8.95 (s, 1H), 8.68 (s, 1H), 8.08 (d, J = 9.1 Hz, 1H), 7.62 (s, 1H), 7.12 (s, 1H), 4.51-4.36 (m, 1H), 2.76 (s, 3H), 1.33-1.19 (d, J = 7.1 Hz, 2H), 1.13-1.05 (s, 2H). | 378 | 85% |
| 4-82 | [6-azaindole, 2-position attachment] | ¹H NMR (400 MHz, DMSO) δ 14.88 (s, 1H), 14.57 (s, 1H), 13.46 (s, 1H), 9.41 (s, 1H), 8.96 (s, 1H), 8.52 (d, J = 6.5 Hz, 1H), 8.21-7.93 (m, 2H), 7.38 (s, 1H), 4.53-4.29 (m, 1H), 2.77 (s, 3H), 1.35-1.17 (d, J = 6.7 Hz, 2H), 1.19-1.03 (s, 2H). | 378 | 98% |
| 4-83 | [indole with 4-CO₂H, 2-position attachment] | | 421 | 90% |
| 4-84 | [indole with 5-CO₂H, 2-position attachment] | | 421 | 98% |
| 4-85 | [indole with 4-NHC(O)CH₂CH₂Cl, 2-position attachment] | | 482 | 93% |

TABLE 4-continued

[Structure: quinolone core with OH, =O, F, Me, R³ substituents, N-cyclopropyl]

| Compound No. | R³ = | NMR | MS (MH⁺) | HPLC |
|---|---|---|---|---|
| 4-86 | 5-methyl-benzofuran-2-yl | ¹H NMR (400 MHz, DMSO) δ 14.60 (s, 1H), 10.06 (s, 1H), 8.81 (s, 1H), 7.88 (d, J = 8.5 Hz, 1H), 7.21 (s, 1H), 7.05 (d, J = 8.1 Hz, 1H), 6.80 (d, J = 8.1 Hz, 1H), 4.36 (m, 1H), 3.08 (s, 2H), 1.06 (m, 4H). | 392 | 95% |
| 4-87 | benzofuran-2-yl | ¹H NMR (400 MHz, DMSO) δ 14.57 (s, 1H), 8.91 (s, 1H), 8.03 (d, J = 9.3 Hz, 1H), 7.80 (d, J = 7.7 Hz, 1H), 7.73 (d, J = 8.3 Hz, 1H), 7.56-7.22 (m, 3H), 4.57-4.32 (m, 1H), 2.84 (s, 3H), 1.27 (m, 2H), 1.06 (m, 2H). | 378 | 98% |
| 4-88 | 4-CO₂H-benzofuran-2-yl | ¹H NMR (400 MHz, DMSO) δ 14.50 (s, 1H), 13.22 (s, 1H), 8.84 (s, 1H), 8.10-7.80 (m, 2H), 7.74-7.58 (s, 1H), 7.49 (s, 1H), 4.38 (m, 1H), 2.78 (s, 3H), 1.30-1.12 (m, 2H), 1.00 (m, 2H). | 422 | 98% |
| 4-89 | 5-F-benzofuran-2-yl | ¹H NMR (400 MHz, DMSO) δ 14.56 (s, 1H), 8.93 (s, 1H), 8.02 (d, J = 9.2 Hz, 1H), 7.76 (dd, J = 8.8, 3.5 Hz, 1H), 7.61 (d, J = 8.6 Hz, 1H), 7.41 (s, 1H), 7.28 (t, J = 9.3 Hz, 1H), 4.43 (m, 1H), 2.82 (s, 3H), 1.26 (d, J = 6.4 Hz, 3H), 1.05 (s, 2H). | 396 | 98% |
| 4-90 | 6-F-benzofuran-2-yl | ¹H NMR (400 MHz, DMSO) δ 8.88 (s, 1H), 7.95 (d, J = 8.9 Hz, 1H), 7.76 (s, 1H), 7.61 (d, J = 8.9 Hz, 1H), 7.36 (s, 1H), 7.20 (t, J = 9.0 Hz, 1H), 4.35 (m, 1H), 2.76 (s, 3H), 1.30-1.09 (m, 3H), 0.96 (s, 2H). | 396 | 98% |
| 4-91 | benzothiophen-2-yl | ¹H NMR (400 MHz, DMSO) δ 14.57 (s, 1H), 8.86 (s, 1H), 7.96 (m, 3H), 7.59 (s, 1H), 7.41 (d, J = 5.1 Hz, 2H), 4.35 (m, 1H), 2.72 (s, 3H), 1.17 (m, 2H), 1.00 (m, 2H). | 394 | 96% |

TABLE 4-continued

| Compound No. | R³ = | NMR | MS (MH⁺) | HPLC |
|---|---|---|---|---|
| 4-92 | benzo[b]thiophen-3-yl | ¹H NMR (400 MHz, DMSO) δ 14.65 (s, 1H), 8.86 (s, 1H), 8.08 (d, J = 7.6 Hz, 1H), 7.97 (m, 2H), 7.36 (m, 3H), 4.32 (m, 1H), 2.57 (s, 3H), 1.03 (m, 4H). | 394 | 98% |
| 4-93 | 4-nitrobenzofuran-2-yl | ¹H NMR (400 MHz, DMSO) δ 14.51 (s, 1H), 8.92 (ss, 1H), 8.32 (d, J = 8.1 Hz, 1H), 8.28 (d, J = 8.0 Hz, 1H), 8.05 (t, J = 13.1 Hz, 1H), 7.90 (s, 1H), 7.70 (t, J = 8.2 Hz, 1H), 4.45 (m, 1H), 2.86 (s, 3H), 1.26 (t, J = 11.6 Hz, 2H), 1.10 (d, J = 21.6 Hz, 2H). | 423 | 98% |
| 4-94 | benzofuran-3-yl | ¹H NMR (400 MHz, DMSO) δ 14.46 (s, 1H), 8.69 (s, 1H), 8.14 (s, 1H), 7.75 (d, J = 9.2 Hz, 1H), 7.52 (dd, J = 8.8, 3.5 Hz, 1H), 7.20-7.11 (m, 3H), 4.43 (s, 1H), 2.64 (s, 3H), 1.26 (d, J = 6.4 Hz, 3H), 1.05 (s, 2H). | 378 | 98% |
| 4-95 | 7-fluorobenzofuran-2-yl | ¹H NMR (400 MHz, DMSO) δ 14.55 (s, 1H), 8.94 (s, 1H), 8.05 (d, J = 9.3 Hz, 1H), 7.64 (d, J = 2.9 Hz, 1H), 7.54 (s, 1H), 7.36 (d, J = 6.6 Hz, 2H), 4.44 (m, 1H), 2.85 (s, 3H), 1.34-1.19 (m, 2H), 1.06 (s, 2H). | 396 | 96% |
| 4-96 | 5-cyano-2-methylbenzofuran-2-yl | ¹H NMR (400 MHz, DMSO) δ 8.91 (s, 1H), 8.38 (s, 1H), 8.04 (d, J = 9.2 Hz, 1H), 7.96 (d, J = 8.4 Hz, 1H), 7.88 (d, J = 8.5 Hz, 1H), 7.55 (s, 1H), 4.44 (m, 1H), 2.83 (s, 3H), 1.35-1.18 (m, 2H), 1.06 (m, 2H). | 403 | 93% |

TABLE 4-continued

| Compound No. | R³ = | NMR | MS (MH⁺) | HPLC |
|---|---|---|---|---|
| 4-97 | F₃CO— [2-methylbenzofuran-5-yl] | ¹H NMR (400 MHz, DMSO) δ 14.56 (s, 1H), 8.94 (s, 1H), 8.04 (d, J = 9.1 Hz, 1H), 7.95-7.77 (m, 2H), 7.53-7.33 (m, 2H), 2.83 (m, 1H), 4.45 (m, 2H), 2.83 (m, 1H), 1.27 (d, J = 6.3 Hz, 2H), 1.05 (s, 2H). | 462 | 98% |
| 4-98 | NH₂— [2-methylbenzofuran-4-yl] | ¹H NMR (400 MHz, DMSO) δ 14.61 (s, 1H), 8.86 (s, 1H), 7.95 (d, J = 9.0 Hz, 1H), 7.43 (s, 1H), 7.03 (t, J = 8.1 Hz, 1H), 6.77 (d, J = 7.4 Hz, 1H), 6.39 (d, J = 7.1 Hz, 1H), 4.38 (m, 1H), 2.77 (s, 3H), 1.19 (m, 2H), 0.98 (m, 1H). | 393 | 96% |

TABLE 5

| Compound No. | R³ | R² | R¹ | NMR | MS (MH⁺) | HPLC |
|---|---|---|---|---|---|---|
| 5-1 | 7-tBu-benzoxazinone (3-oxo-3,4-dihydro-2H-benzo[b][1,4]oxazin-6-yl) | Me | Cyclopropyl | ¹H NMR (400 MHz, DMSO) δ 14.72 (s, 1H), 10.91 (s, 1H), 8.89 (s, 1H), 7.94 (d, J = 8.60 Hz, 1H), 7.13-6.90 (m, 3H), 4.67 (s, 2H), 4.38 (s, 1H), 2.62 (s, 3H), 1.23 (d, J = 5.80 Hz, 2H), 1.04 (s, 2H). | 409 | 97% |
| 5-2 | 7-tBu-benzothiazinone | Me | Cyclopropyl | ¹H NMR (400 MHz, DMSO) δ 14.71 (s, 1H), 10.78 (s, 1H), 8.90 (s, 1H), 7.95 (d, J = 8.72 Hz, 1H), 7.41 (s, 1H), 7.22 (d, J = 8.03 Hz, 1H), 7.13 (d, J = 8.17 Hz, 1H), 4.38 (s, 1H), 3.57 (s, 2H), 2.62 (s, 3H), 1.24 (d, J = 6.14 Hz, 2H), 1.05 (s, 2H). | 425 | 98% |
| 5-3 | 7-tBu-5-NO₂-benzoxazinone | Me | Cyclopropyl | ¹H NMR (400 MHz, DMSO) δ 14.70 (s, 1H), 10.64 (s, 1H), 8.98 (s, 1H), 8.05 (d, J = 8.72 Hz, 1H), 7.90 (s, 1H), 7.62 (s, 1H), 4.92 (s, 1H), 4.46 (s, 2H), 2.71 (s, 3H), 1.30 (s, 3H), 1.15 (s, 2H). | 454 | 97% |
| 5-4 | 7-tBu-5-CN-benzoxazinone | Me | Cyclopropyl | ¹H NMR (400 MHz, DMSO) δ 14.66 (s, 1H), 11.39 (s, 1H), 8.90 (s, 1H), 7.96 (d, J = 8.72 Hz, 1H), 7.57 (s, 1H), 7.43 (s, 2H), 4.39 (s, 1H), 2.62 (s, 3H), 1.23 (d, J = 5.26 Hz, 2H), 1.06 (s, 2H). | 434 | 98% |

TABLE 5-continued

| Compound No. | R³ = | R² = | R¹ = | NMR | MS (MH⁺) | HPLC |
|---|---|---|---|---|---|---|
| 5-5 | 6-tert-butyl-3-oxo-3,4-dihydro-2H-benzo[b][1,4]oxazine | OMe | Cyclopropyl | ¹H NMR (400 MHz, DMSO) δ 14.72 (s, 1H), 10.94 (s, 1H), 8.80 (s, 1H), 7.90 (s, 1H), 7.11 (d, J = 26.18 Hz, 2H), 4.67 (s, 2H), 1.15 (s, 4H). | 425 | 98% |
| 5-6 | 6-tert-butyl-3-oxo-3,4-dihydro-2H-benzo[b][1,4]oxazine | Me | Cyclopropyl | ¹H NMR (400 MHz, DMSO) δ 14.75 (s, 1H), 10.87 (s, 1H), 8.90 (s, 1H), 7.96 (d, J = 8.58 Hz, 1H), 7.14 (d, J = 8.35 Hz, 1H), 6.97 (d, J = 8.15 Hz, 1H), 6.89 (s, 1H), 4.69 (s, 2H), 4.39 (s, 1H), 2.62 (s, 3H), 1.23 (s, 2H), 1.04 (s, 2H). | 409 | 98% |
| 5-9 | 6-tert-butyl-3,4-dihydroquinolin-2(1H)-one | Me | Cyclopropyl | ¹H NMR (400 MHz, DMSO) δ 14.74 (s, 1H), 10.28 (s, 1H), 8.90 (s, 1H), 7.94 (d, J = 8.20 Hz, 1H), 7.23 (s, 1H), 7.17 (s, 1H), 7.03 (s, 1H), 4.38 (s, 2H), 2.97 (s, 2H), 2.63 (s, 2H), 1.23 (s, 2H), 1.04 (s, 2H). | 407 | 85% |
| 5-10 | 6-tert-butylquinazoline-2,4(1H,3H)-dione | Me | Cyclopropyl | ¹H NMR (400 MHz, DMSO) δ 14.71 (s, 1H), 11.47 (s, 1H), 11.30 (s, 1H), 8.91 (s, 1H), 7.98 (d, J = 8.50 Hz, 1H), 7.89 (s, 1H), 7.70 (d, J = 8.10 Hz, 1H), 7.35 (d, J = 8.11 Hz, 1H), 4.40 (s, 1H), 3.49 (d, J = 87.04 Hz, 2H), 2.62 (s, 3H), 1.23 (s, 2H), 1.08 (s, 3H). | 422 | 95% |

TABLE 5-continued

| Compound No. | R³ = | R² = | R¹ = | NMR | MS (MH⁺) | HPLC |
|---|---|---|---|---|---|---|
| 5-11 | pyrido-pyrimidinedione (as drawn) | Me | Cyclopropyl | ¹H NMR (400 MHz, DMSO) δ 14.67 (s, 1H), 11.96 (s, 1H), 11.63 (s, 1H), 8.92 (s, 1H), 8.69 (s, 1H), 8.34 (s, 1H), 8.00 (d, J = 8.65 Hz, 1H), 4.41 (s, 1H), 2.61 (d, J = 29.62 Hz, 3H), 1.24 (d, J = 5.11 Hz, 2H), 1.09 (s, 2H). | 423 | 99% |
| 5-12 | quinoxalinedione (as drawn) | Me | Cyclopropyl | ¹H NMR (400 MHz, DMSO) δ 14.73 (s, 1H), 12.44-11.74 (m, 2H), 8.91 (s, 1H), 7.98 (d, J = 8.01 Hz, 1H), 7.53-7.03 (m, 3H), 4.39 (s, 1H), 2.61 (s, 3H), 1.20 (d, J = 26.27 Hz, 3H), 1.05 (s, 2H). | 422 | 96% |
| 5-13 | 3,4-dihydro-2H-benzo[b][1,4]oxazine (as drawn) | Me | Cyclopropyl | ¹H NMR (400 MHz, DMSO) δ 14.83 (s, 1H), 8.88 (s, 1H), 7.90 (s, 2H), 6.70 (s, 3H), 4.27 (d, J = 77.51 Hz, 4H), 2.60 (d, J = 25.07 Hz, 3H), 1.23 (s, 2H), 1.02 (s, 2H). | 395 | 98% |
| 5-14 | 3,4-dihydro-2H-benzo[b][1,4]oxazine (as drawn) | OMe | Cyclopropyl | ¹H NMR (400 MHz, DMSO) δ 14.78 (s, 1H), 8.76 (s, 1H), 7.83 (d, J = 9.18 Hz, 1H), 6.92-6.81 (m, 2H), 6.70 (d, J = 7.26 Hz, 1H), 6.19 (d, J = 22.26 Hz, 1H), 4.16 (s, 4H), 3.39 (s, 3H), 2.50 (s, 7H). | 411 | 96% |

TABLE 5-continued

| Compound No. | R³ = | R² = | R¹ = | NMR | MS (MH⁺) | HPLC |
|---|---|---|---|---|---|---|
| 5-15 | (6-substituted 3,4-dihydro-2H-benzo[1,4]oxazine) | 8-N | Cyclopropyl | ¹H NMR (400 MHz, DMSO) δ 14.55 (s, 1H), 8.61 (s, 1H), 8.19 (d, J = 11.38 Hz, 1H), 7.55 (d, J = 8.31 Hz, 1H), 7.47 (s, 1H), 6.68 (s, 1H), 6.54 (d, J = 8.26 Hz, 1H), 4.00 (s, 2H), 3.73 (s, 1H), 1.15-0.91 (m, 5H). | 382 | 94% |
| 5-16 | (6-substituted 1,2,3,4-tetrahydroquinoline) | Me | Cyclopropyl | ¹H NMR (400 MHz, DMSO) δ 14.90 (s, 1H), 8.94 (s, 1H), 7.94 (d, J = 9.06 Hz, 1H), 6.95 (d, J = 8.81 Hz, 2H), 6.63 (d, J = 7.73 Hz, 1H), 6.14 (s, 1H), 4.43 (s, 1H), 3.31 (s, 2H), 2.79 (s, 2H), 2.70 (s, 3H), 1.90 (s, 2H), 1.30 (s, 2H), 1.08 (s, 2H). | 393 | 94% |
| 5-17 | (7-substituted 5-nitro-3,4-dihydro-2H-benzo[1,4]oxazine) | Me | Cyclopropyl | ¹H NMR (400 MHz, DMSO) δ 14.71 (s, 1H), 8.89 (s, 1H), 8.60 (s, 1H), 7.94 (d, J = 8.81 Hz, 1H), 7.67 (s, 1H), 7.10 (s, 1H), 4.38 (s, 1H), 4.27 (s, 2H), 3.63 (s, 2H), 2.66 (s, 3H), 1.24 (d, J = 5.67 Hz, 2H), 1.07 (s, 2H). | 440 | 97% |
| 5-18 | (7-substituted 5-amino-3,4-dihydro-2H-benzo[1,4]oxazine) | Me | Cyclopropyl | ¹H NMR (400 MHz, DMSO) δ 10.19 (s, 1H), 8.89 (s, 1H), 7.91 (d, J = 8.74 Hz, 1H), 6.33 (s, 1H), 6.24 (s, 1H), 4.57 (s, 2H), 4.38 (s, 2H), 2.64 (s, 3H), 1.23 (d, J = 5.42 Hz, 3H), 1.03 (s, 2H). | 424 | 97% |

TABLE 5-continued

| Compound No. | R³ = | R² = | R¹ = | NMR | MS (MH⁺) | HPLC |
|---|---|---|---|---|---|---|
| 5-19 | [3,4-dihydro-2H-benzo[b][1,4]oxazin-5-yl(methyl)amino structure] | Me | Cyclopropyl | ¹H NMR (400 MHz, DMSO) δ 8.88 (s, 1H), 7.91 (s, 1H), 6.29 (s, 1H), 6.18 (s, 1H), 4.37 (s, 2H), 4.18 (s, 3H), 3.10 (s, 2H), 2.65 (d, J = 16.81 Hz, 6H), 1.23 (s, 3H), 1.03 (s, 2H). | 424 | 97% |
| 5-20 | [pyrido-oxazine structure] | Me | Cyclopropyl | ¹H NMR (400 MHz, DMSO) δ 8.97 (s, 1H), 8.01 (d, J = 9.26 Hz, 1H), 7.85-7.65 (m, 2H), 7.64-7.40 (m, 1H), 7.36 (s, 1H), 4.46 (s, 1H), 4.32 (s, 3H), 3.63 (s, 3H), 2.74 (s, 3H), 1.30 (d, J = 5.75 Hz, 2H), 1.11 (s, 2H). | 396 | 98% |
| 5-21 | [benzoxazine-CN structure] | Me | Cyclopropyl | ¹H NMR (400 MHz, DMSO) δ 14.72 (s, 1H), 8.85 (d, J = 23.76 Hz, 1H), 7.87 (t, J = 19.93 Hz, 1H), 7.17 (s, 1H), 6.99 (d, J = 9.29 Hz, 2H), 4.37 (s, 1H), 4.20 (s, 2H), 3.59 (s, 1H), 3.44 (s, 2H), 2.63 (s, 3H), 1.24 (s, 2H), 1.07 (d, J = 23.80 Hz, 2H). | 420 | 95% |
| 5-22 | [benzoxazine-CN structure] | Me | Cyclopropyl | ¹H NMR (400 MHz, DMSO) δ 14.67 (s, 1H), 8.78 (s, 1H), 7.87 (d, J = 9.24 Hz, 1H), 7.26 (d, J = 10.63 Hz, 1H), 7.11 (s, 1H), 7.04 (s, 1H), 4.20 (s, 3H), 2.00 (dd, J = 7.56, 15.22 Hz, 1H), 1.21 (d, J = 14.05 Hz, 4H). | 436 | 98% |

TABLE 5-continued

| Compound No. | R³ = | R² = | R¹ = | NMR | MS (MH⁺) | HPLC |
|---|---|---|---|---|---|---|
| 5-24 | (pyridine-fused morpholine group) | OMe | Cyclopropyl | ¹H NMR (400 MHz, DMSO) δ 8.77 (s, 1H), 7.87 (d, J = 9.25 Hz, 1H), 7.75 (s, 1H), 7.20 (s, 1H), 7.14 (s, 1H), 4.17 (s, 3H), 3.47 (s, 3H), 1.32-1.05 (m, 8H). | 412 | 96% |
| 5-25 | (1,2,3,4-tetrahydroquinoxaline group) | Me | Cyclopropyl | ¹H NMR (400 MHz, DMSO) δ 14.82 (s, 1H), 10.92 (s, 1H), 10.86 (s, 1H), 8.96 (s, 1H), 7.98 (t, J = 12.31 Hz, 1H), 7.15 (d, J = 7.60 Hz, 1H), 7.00 (d, J = 8.89 Hz, 2H), 4.44 (s, 1H), 2.67 (s, 3H), 1.28 (s, 2H), 1.12 (s, 2H). | 394 | 98% |
| 5-26 | (1,2,3,4-tetrahydroquinoxaline group) | OMe | Cyclopropyl | ¹H NMR (400 MHz, DMSO) δ 14.63 (s, 1H), 10.94 (s, 1H), 10.87 (s, 1H), 8.86 (s, 1H), 7.97 (d, J = 8.82 Hz, 1H), 7.17 (d, J = 7.41 Hz, 3H), 4.29 (s, 1H), 1.23 (s, 4H). | 410 | 98% |
| 5-27 | (3,4-dihydro-2H-benzo[b][1,4]thiazine group) | Me | Cyclopropyl | ¹H NMR (400 MHz, DMSO) δ 8.95 (s, 1H), 7.96 (d, J = 8.75 Hz, 1H), 6.96 (d, J = 10.17 Hz, 1H), 6.92 (d, J = 8.04 Hz, 1H), 6.72 (d, J = 7.83 Hz, 1H), 4.44 (s, 1H), 3.63 (s, 2H), 3.09 (s, 2H), 2.70 (s, 3H), 1.30 (d, J = 5.29 Hz, 2H), 1.10 (s, 2H). | 411 | 98% |

TABLE 5-continued

| Compound No. | R³ = | R² = | R¹ = | NMR | MS (MH⁺) | HPLC |
|---|---|---|---|---|---|---|
| 5-28 | (structure: benzothiazine S,S-dioxide with NH) | Me | Cyclopropyl | ¹H NMR (400 MHz, DMSO) δ 14.74 (s, 1H), 8.89 (s, 1H), 7.94 (d, J = 8.48 Hz, 1H), 7.53 (s, 1H), 7.44 (s, 1H), 7.33 (d, J = 8.57 Hz, 1H), 6.94 (d, J = 8.45 Hz, 1H), 4.39 (s, 1H), 3.80 (s, 2H), 3.48 (s, 2H), 2.64 (s, 3H), 1.23 (s, 2H), 1.06 (s, 2H). | 443 | 98% |
| 5-29 | (structure: benzoxazinone with NH) | Me | Cyclopropyl | ¹H NMR (400 MHz, DMSO) δ 14.67 (s, 1H), 10.84 (s, 1H), 8.83 (s, 1H), 7.86 (d, J = 8.65 Hz, 1H), 6.52 (s, 2H), 4.38 (s, 2H), 4.31 (s, 1H), 3.89 (s, 2H), 2.54 (s, 3H), 1.16 (s, 2H), 1.00 (s, 2H). | 436 | 98% |
| 5-30 | (structure: benzoxazinone with NH) | OMe | Cyclopropyl | ¹H NMR (400 MHz, DMSO) δ 14.71 (s, 1H), 10.91 (s, 1H), 8.79 (s, 1H), 7.88 (d, J = 9.15 Hz, 1H), 6.75 (d, J = 14.51 Hz, 2H), 4.45 (t, J = 4.51 Hz, 2H), 4.27-4.16 (m, 1H), 3.96 (t, J = 4.53 Hz, 2H), 1.17 (d, J = 7.20 Hz, 4H). | 452 | 99% |
| 5-31 | (structure: dihydrobenzoxazine with CH₂OH) | Me | Cyclopropyl | ¹H NMR (400 MHz, DMSO) δ 8.94 (s, 1H), 7.95 (d, J = 8.62 Hz, 1H), 6.79 (dd, J = 7.23, 14.68 Hz, 3H), 4.43 (s, 1H), 4.23 (d, J = 10.57 Hz, 1H), 4.06 (d, J = 10.42 Hz, 1H), 3.60-3.41 (m, 3H), 2.70 (s, 3H), 1.30 (d, J = 5.98 Hz, 2H), 1.09 (s, 2H). | 425 | 99% |

TABLE 5-continued

| Compound No. | R³ = | R² = | R¹ = | NMR | MS (MH⁺) | HPLC |
|---|---|---|---|---|---|---|
| 5-32 | (7-membered benzoxazepine) | Me | Cyclopropyl | ¹H NMR (400 MHz, DMSO) δ 8.95 (s, 1H), 7.98 (d, J = 8.04 Hz, 1H), 7.09 (s, 1H), 6.96 (s, 2H), 4.44 (s, 1H), 4.15 (s, 2H), 3.29 (s, 3H), 2.69 (s, 3H), 2.02 (s, 2H), 1.30 (s, 2H), 1.10 (s, 2H). | 409 | 99% |
| 5-33 | (methyl-benzoxazine) | Me | Cyclopropyl | ¹H NMR (400 MHz, DMSO) δ 8.76 (s, 1H), 7.77 (d, J = 8.81 Hz, 1H), 6.59 (s, 3H), 4.25 (s, 1H), 4.04 (s, 2H), 3.27 (d, J = 11.94 Hz, 1H), 2.96-2.79 (m, 1H), 2.52 (s, 3H), 1.18 (t, J = 8.54 Hz, 3H), 1.12 (d, J = 5.48 Hz, 2H), 0.91 (s, 2H). | 409 | 98% |
| 5-34 | (methyl-benzoxazine) | Me | Cyclopropyl | ¹H NMR (400 MHz, DMSO) δ 8.71 (s, 1H), 7.72 (d, J = 8.62 Hz, 1H), 6.54 (s, 3H), 4.20 (s, 2H), 4.03 (d, J = 10.38 Hz, 2H), 3.52 (t, J = 8.97 Hz, 1H), 3.31 (s, 1H), 2.46 (s, 3H), 1.07 (d, J = 5.70 Hz, 2H), 0.96 (d, J = 4.88 Hz, 3H), 0.86 (s, 2H). | 409 | 98% |
| 5-35 | (piperidine-fused benzodiazepinone) | Me | Cyclopropyl | ¹H NMR (400 MHz, DMSO) δ 10.57 (s, 1H), 8.89 (s, 1H), 7.93 (d, J = 8.73 Hz, 1H), 7.48 (d, J = 52.24 Hz, 1H), 6.96 (d, J = 7.83 Hz, 1H), 6.80 (s, 1H), 6.74 (d, J = 7.83 Hz, 1H), 4.38 (s, 1H), 3.76 (d, J = 12.76 Hz, 1H), 2.63 (s, 3H), 2.07 (s, 1H), 1.85 (s, 1H), 1.66 (s, 1H), 1.58-1.37 (m, 3H), 1.23 (d, J = 6.52 Hz, 2H), 1.06 (s, 2H). | 462 | 98% |

TABLE 5-continued

| Compound No. | R³ = | R² = | R¹ = | NMR | MS (MH⁺) | HPLC |
|---|---|---|---|---|---|---|
| 5-36 | [benzoxazinone, t-Bu] | Cl | Cyclopropyl | ¹H NMR (400 MHz, DMSO) δ 10.02 (s, 1H), 10.70 (s, 1H), 8.92 (s, 1H), 8.69 (d, J = 8.48 Hz, 1H), 7.82 (s, 1H), 7.04 (d, J = 22.18 Hz, 1H), 6.64 (d, J = 10.90 Hz, 2H), 4.52-4.28 (m, 3H), 4.01-3.82 (m, 2H), 1.20 (t, J = 10.03 Hz, 2H), 1.12 (d, J = 3.28 Hz, 2H). | 456 | 97% |
| 5-37 | [benzoxazine, t-Bu] | 8-Me | fluorocyclopropyl | ¹H NMR (400 MHz, DMSO) δ 8.85 (d, J = 3.12 Hz, 1H), 7.90 (d, J = 8.88 Hz, 1H), 6.71 (d, J = 5.48 Hz, 3H), 5.23 (d, J = 3.10 Hz, 1H), 5.07 (d, J = 2.78 Hz, 1H), 4.42-4.27 (m, 1H), 4.22-4.12 (m, 2H), 2.55 (s, 3H), 1.74 (ddd, J = 8.97, 14.93, 17.91 Hz, 1H), 1.62-1.45 (m, 1H). | 413 | 98% |
| 5-38 | [benzoxazinone, t-Bu] | 8-Me | fluorocyclopropyl | ¹H NMR (400 MHz, DMSO) δ 14.44 (d, J = 137.56 Hz, 2H), 10.82 (d, J = 88.59 Hz, 1H), 8.85 (t, J = 9.38 Hz, 1H), 7.93 (t, J = 10.51 Hz, 1H), 6.56 (t, J = 40.40 Hz, 2H), 4.44 (d, J = 4.54 Hz, 3H), 4.39-4.29 (m, 1H), 4.04-3.90 (m, 3H), 2.54 (s, 3H), 1.64 (m, 2H). | 454 | 98% |
| 5-39 | [pyridooxazine, t-Bu] | Cl | Cyclopropyl | ¹H NMR (400 MHz, DMSO) δ 8.92 (s, 1H), 8.10 (d, J = 8.56 Hz, 1H), 7.69 (s, 1H), 7.18 (s, 1H), 4.41 (s, 2H), 4.23-4.19 (m, 3H) 3.51 (s, 2H), 1.22 (d, J = 6.34 Hz, 2H), 1.11 (s, 2H). | 416 | 98% |

TABLE 5-continued

| Compound No. | R³ = | R² = | R¹ | NMR | MS (MH⁺) | HPLC |
|---|---|---|---|---|---|---|
| 5-40 | (benzoxazine-imidazoline with methyl) | Me | Cyclopropyl | ¹H NMR (400 MHz, DMSO) δ 14.67 (s, 1H), 8.91 (s, 1H), 7.97 (d, J = 8.68 Hz, 1H), 7.35 (s, 1H), 6.99 (s, 1H), 4.68 (d, J = 4.53 Hz, 2H), 4.58 (d, J = 4.64 Hz, 2H), 4.40 (dd, J = 3.32, 6.77 Hz, 1H), 2.61 (s, 3H), 1.24 (d, J = 6.14 Hz, 2H), 1.10 (s, 2H). | 434 | 98% |
| 5-41 | (benzoxazinone) | 8-OMe | fluorocyclopropyl | ¹H NMR (400 MHz, DMSO) δ 14.59 (s, 1H), 10.91 (s, 1H), 8.82 (s, 1H), 7.89 (d, J = 9.04 Hz, 1H), 6.74 (d, J = 14.28 Hz, 2H), 5.08 (d, J = 64.31 Hz, 1H), 4.45 (s, 2H), 4.19 (s, 1H), 3.96 (s, 2H), 1.80 (d, J = 26.47 Hz, 1H), 1.65 (dd, J = 7.14, 16.55 Hz, 1H). | 470 | 98% |
| 5-42 | (benzoxazine NH) | 8-OMe | fluorocyclopropyl | ¹H NMR (400 MHz, DMSO) δ 8.80 (s, 1H), 7.86 (d, J = 8.14 Hz, 1H), 6.87 (d, J = 9.34 Hz, 1H), 6.84 (s, 1H), 6.70 (d, J = 8.14 Hz, 1H), 5.18-4.96 (m, 1H), 4.17 (s, 3H), 3.36 (s, 2H), 1.84-1.58 (m, 2H). | 429 | 98% |
| 5-43 | (benzoxazine NH with F) | Me | Cyclopropyl | ¹H NMR (400 MHz, DMSO) δ 14.75-14.70 (s, 1H), 8.80-8.76 (s, 1H), 7.89-7.83 (d, J = 9.4 Hz, 1H), 6.92-6.86 (d, J = 11.4 Hz, 1H), 6.77-6.73 (s, 1H), 6.16-6.10 (s, 1H), 4.27-4.15 (s, 3H), 3.47-3.41 (s, 3H), 3.40-3.34 (q, J = 3.6 Hz, 2H), 1.20-1.09 (dd, J = 14.4, 5.5 Hz, 4H). | 429 | 90% |

TABLE 5-continued

| Compound No. | R³ = | R² = | R¹ = | NMR | MS (MH⁺) | HPLC |
|---|---|---|---|---|---|---|
| 5-44 | 5-chloro-2,3-dihydro-1,4-benzoxazin-7-yl | Me | Cyclopropyl | ¹H NMR (400 MHz, DMSO) δ 14.77-14.65 (s, 1H), 8.80-8.76 (s, 1H), 7.89-7.83 (d, J = 9.3 Hz, 1H), 7.09-7.03 (t, J = 1.6 Hz, 1H), 6.90-6.84 (t, J = 1.6 Hz, 1H), 6.19-6.10 (s, 1H), 4.26-4.15 (m, 3H), 3.48-3.39 (s, 5H), 1.20-1.09 (ddd, J = 10.6, 5.5, 3.0 Hz, 4H). | 445 | 100% |
| 5-45 | 5-methyl-2,3-dihydro-1,4-benzoxazin-7-yl | Me | Cyclopropyl | ¹H NMR (400 MHz, DMSO) δ 8.80-8.74 (s, 1H), 7.88-7.80 (d, J = 9.3 Hz, 1H), 6.81-6.71 (dd, J = 17.1, 2.1 Hz, 2H), 4.28-4.18 (tt, J = 7.2, 4.3 Hz, 1H), 4.18-4.12 (t, J = 4.2 Hz, 2H), 3.44-3.35 (m, 5H), 2.16-2.10 (s, 3H), 1.20-1.08 (m, 4H). | 425 | 100% |
| 5-46 | 5-amino-2,3-dihydro-1,4-benzoxazin-7-yl | Me | Cyclopropyl | ¹H NMR (400 MHz, DMSO) δ 8.79-8.75 (s, 1H), 7.87-781 (d, J = 9.3 Hz, 1H), 6.55-8.49 (s, 1H), 6.43-6.39 (s, 1H), 4.27-4.18 (s, 1H), 4.16-4.10 (t, J = 4.3 Hz, 2H), 3.33-3.5 (s, 2H), 2.57-2.52 (s, 3H), 1.20-1.09 (m, 4H). | 426 | 96% |
| 5-47 | 5-nitro-2,3-dihydro-1,4-benzoxazin-7-yl | Me | Cyclopropyl | ¹H NMR (400 MHz, DMSO) δ 14.83-14.56 (s, 1H), 8.81-8.77 (s, 1H), 8.66-8.59 (m, 1H), 7.95-7.89 (d, J = 9.3 Hz, 1H), 7.89-7.84 (t, J = 1.7 Hz, 1H), 7.24-7.19 (s, 1H), 4.30-4.18 (m, 3H), 3.67-3.60 (q, J = 3.8 Hz, 2H), 3.52-3.44 (s, 3H), 1.20-1.12 (td, J = 6.5, 5.8, 2.7 Hz, 4H). | 456 | 100% |

TABLE 5-continued

| Compound No. | R³ = | R² = | R¹ = | NMR | MS (MH⁺) | HPLC |
|---|---|---|---|---|---|---|
| 5-48 | (imidazo-fused dihydrobenzoxazine) | Me | Cyclopropyl | ¹H NMR (400 MHz, DMSO) δ 15.22-14.17 (m, 1H), 8.97-8.90 (s, 1H), 8.84-8.80 (s, 1H), 7.97-7.90 (d, J = 9.0 Hz, 1H), 7.51-7.47 (s, 1H), 7.07-7.02 (s, 1H), 4.69-4.57 (s, 4H), 4.28-4.18 (p, J = 5.7 Hz, 1H), 3.42-3.35 (s, 3H), 1.21-1.12 (d, J = 5.6 Hz, 4H). | 436 | 100% |
| 5-49 | (triazolo-fused dihydrobenzoxazine) | Me | Cyclopropyl | ¹H NMR (400 MHz, DMSO) δ 14.70-14.66 (s, 1H), 8.84-8.80 (s, 1H), 7.97-7.92 (d, J = 9.0 Hz, 1H), 7.78-7.74 (s, 1H), 7.08-7.04 (s, 1H), 5.00-4.94 (t, J = 4.9 Hz, 2H), 4.82-4.74 (t, J = 4.8 Hz, 2H), 4.27-4.18 (p, J = 5.7 Hz, 1H), 3.43-3.38 (s, 3H), 1.21-1.13 (d, J = 5.6 Hz, 4H). | 437 | 85% |
| 5-50 | (fluoro-dihydroquinolinone) | OMe | Cyclopropyl | ¹H NMR (400 MHz, DMSO) δ 14.72 (s, 1H), 8.94 (s, 1H), 7.87 (d, J = 9.4 Hz, 1H), 6.89 (d, J = 11.4 Hz, 1H), 6.75 (s, 1H), 6.13 (s, 1H), 4.21 (m, 3H), 3.40 (s, 3H), 1.31-0.94 (m, 4H). | 429 | 90% |
| 5-51 | (chloro-dihydrobenzoxazine) | Me | Cyclopropyl | ¹H NMR (400 MHz, DMSO) δ 14.72 (s, 1H), 8.88 (s, 1H), 7.91 (d, J = 8.8 Hz, 1H), 6.91 (s, 1H), 6.72 (s, 1H), 6.07 (s, 1H), 4.48-4.30 (m, 1H), 4.20 (m, 2H), 3.43 (m, 2H), 2.70-2.56 (m, 3H), 1.24 (d, J = 4.0 Hz, 2H), 1.04 (s, 2H). | 429 | 98% |

TABLE 5-continued

| Compound No. | R³ = | R² = | R¹ = | NMR | MS (MH⁺) | HPLC |
|---|---|---|---|---|---|---|
| 5-52 | [7-substituted 2,3-dihydro-[1,4]oxazino-imidazole] | Me | Cyclopropyl | ¹H NMR (400 MHz, DMSO) δ 14.5 (b, 1H), 8.91 (s, 1H), 8.86 (s, 1H), 7.97 (d, J = 8.8 Hz, 1H), 7.34 (s, 1H), 6.90 (s, 1H), 4.63 (s, 4H), 4.39 (mz, 1H), 2.61 (s, 3H), 1.24 (d, J = 4.6 Hz, 2H), 1.09 (s, 2H). | 420 | 98% |
| 5-53 | [7-substituted 5-iodo-3,4-dihydro-2H-benzo[1,4]oxazine] | Me | Cyclopropyl | ¹H NMR (400 MHz, DMSO) δ 14.73 (s, 1H), 8.88 (s, 1H), 7.90 (d, J = 8.8 Hz, 1H), 7.22 (s, 1H), 6.76 (s, 1H), 4.44-4.28 (m, 1H), 4.15 (s, 2H), 3.43 (m, 2H), 2.65 (s, 3H), 1.24 (s, 2H), 1.04 (s, 2H). | 521 | 97% |
| 5-54 | [7-substituted 5-fluoro-3,4-dihydro-2H-benzo[1,4]oxazine] | Me | Cyclopropyl | ¹H NMR (400 MHz, DMSO) δ 14.73 (s, 1H), 8.89 (s, 1H), 7.91 (d, J = 7.8 Hz, 1H), 6.75 (d, J = 11.3 Hz, 1H), 6.59 (s, 1H), 4.37 (m, 1H), 4.22 (s, 2H), 3.39 (s, 2H), 2.65 (s, 3H), 1.22 (m, 2H), 1.00 (m, 2H). | 413 | 97% |
| 5-55 | [7-substituted 3,4-dihydro-2H-benzo[1,4]oxazine] | Cl | Cyclopropyl | ¹H NMR (400 MHz, DMSO) δ 8.90 (s, 1H), 8.05 (d, J = 3.6 Hz, 1H), 6.91-6.49 (m, 3H), 4.46-4.36 (m, 1H), 4.16 (m, 2H), 3.49 (m, 2H), 2.67 (s, 3H), 1.19 (t, J = 15.1 Hz, 2H), 1.09 (s, 2H). | 415 | 98% |

TABLE 5-continued
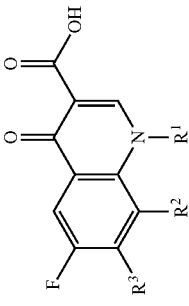
| Compound No. | R³ = R² = R¹ = | NMR | MS (MH⁺) | HPLC |
|---|---|---|---|---|
| 5-56 |  | ¹H NMR (400 MHz, DMSO) δ 8.77 (s, 1H), 8.15 (d, J = 7.00 Hz, 1H), 7.24-7.02 (m, 2H), 6.78 (d, J = 3.23 Hz, 1H), 4.28-4.13 (m, 2H), 4.05-3.86 (m, 1H), 3.49-3.34 (m, 2H), 2.90 (d, J = 2.66 Hz, 3H), 1.44-1.32 (m, 2H), 1.28-1.17 (m, 2H). | 395 | 98% |
| 5-57 |  | ¹H NMR (400 MHz, DMSO) δ 15.13 (s, 1H), 8.84 (s, 1H), 8.16 (d, J = 8.2 Hz, 1H), 7.71 (s, 1H), 7.20-7.06 (m, 2H), 6.73 (t, J = 16.6 Hz, 1H), 4.30 (m, 1H), 4.22-4.17 (m, 2H), 3.68 (s, 2H), 3.44 (s, 3H), 1.43-0.95 (m, 4H). | 393 | 98% |

TABLE 6

| Compound No. | R³ = | R² = | NMR | MS (MH⁺) | HPLC |
|---|---|---|---|---|---|
| 6-1 | MeO-phenyl (3-position) | Me | ¹H NMR (400 MHz, MeOD) δ 7.92 (s, 1H), 7.35 (m, 2H), 6.96 (s, 1H), 6.80 (m, 2H), 4.30-4.19 (m, 1H), 3.75 (s, 3H), 2.59 (s, 3H), 0.96 (m, 2H), 0.79 (m, 2H). | 368 | 98% |
| 6-2 | 2-MeO-phenyl | Me | ¹H NMR (400 MHz, DMSO) δ 14.75 (s, 1H), 8.89 (s, 1H), 7.92 (d, J = 8.6 Hz, 1H), 7.50 (t, J = 7.7 Hz, 1H), 7.24 (dd, J = 15.3, 7.9 Hz, 2H), 7.14 (d, J = 7.4 Hz, 1H), 4.38 (m, 1H), 3.76 (s, 3H), 2.55 (s, 3H), 1.41-1.15 (m, 2H), 1.12-0.96 (m, 2H). | 482 | 90% |
| 6-3 | 4-BnO-phenyl | Me | ¹H NMR (400 MHz, DMSO) δ 14.80 (s, 1H), 8.95 (s, 1H), 8.00 (d, J = 8.8 Hz, 1H), 7.57 (d, J = 7.2 Hz, 2H), 7.49 (t, J = 7.3 Hz, 2H), 7.45-7.36 (m, 3H), 7.26 (d, J = 8.6 Hz, 2H), 5.25 (s, 2H), 4.54-4.32 (m, 1H), 2.67 (s, 3H), 1.30 (d, J = 6.2 Hz, 2H), 1.11 (s, 2H). | 444 | 99% |
| 6-4 | 4-MeO-phenyl | Me | ¹H NMR (400 MHz, DMSO) δ 14.76 (s, 1H), 8.90 (s, 1H), 7.94 (d, J = 8.5 Hz, 1H), 7.35 (d, J = 8.0 Hz, 2H), 7.12 (d, J = 8.2 Hz, 2H), 4.38 (s, 1H), 3.84 (s, 3H), 2.61 (s, 3H), 1.23 (d, J = 6.2 Hz, 2H), 1.05 (s, 2H). | 368 | 96% |
| 6-5 | 4-i-PrO-phenyl | Me | ¹H NMR (400 MHz, DMSO) δ 14.63 (s, 1H), 8.88 (s, 1H), 7.92 (d, J = 8.9 Hz, 1H), 7.31 (d, J = 8.4 Hz, 2H), 7.08 (d, J = 8.7 Hz, 2H), 4.71 (dt, J = 12.0, 6.0 Hz, 1H), 4.38 (m, 1H), 2.58 (d, J = 6.0 Hz, 3H), 1.32 (d, J = 6.0 Hz, 6H), 1.23 (q, J = 6.9 Hz, 2H), 1.02 (s, 2H). | 396 | 99% |
| 6-6 | 4-F₃CO-phenyl | Me | ¹H NMR (400 MHz, DMSO) δ 14.68 (s, 1H), 8.91 (s, 1H), 7.98 (d, J = 8.8 Hz, 1H), 7.58 (s, 4H), 4.52-4.24 (m, 1H), 2.60 (s, 3H), 1.23 (q, J = 7.0 Hz, 2H), 1.15-1.01 (m, 2H). | 422 | 99% |
| 6-7 | 3-F₃CO-phenyl | Me | ¹H NMR (400 MHz, DMSO) δ 14.66 (s, 1H), 8.91 (s, 1H), 7.99 (d, J = 8.8 Hz, 1H), 7.72 (t, J = 7.9 Hz, 1H), 7.54 (d, J = 8.3 Hz, 1H), 7.52-7.44 (m, 2H), 4.52-4.20 (m, 1H), 2.60 (s, 3H), 1.23 (d, J = 6.8 Hz, 2H), 1.08 (s, 2H). | 422 | 99% |
| 6-8 | 2-OCF₃-phenyl | Me | ¹H NMR (400 MHz, DMSO) δ 14.48 (s, 1H), 8.76 (s, 1H), 7.86 (d, J = 8.7 Hz, 1H), 7.60-7.52 (m, 1H), 7.45 (ddd, J = 10.9, 9.8, 4.6 Hz, 3H), 4.25 (dt, J = 10.7, 3.6 Hz, 1H), 2.43 (s, 3H), 1.06 (dq, J = 9.4, 7.1 Hz, 2H), 0.99-0.71 (m, 3H). | 422 | 99% |

TABLE 6-continued

| Compound No. | R³ = | R² = | NMR | MS (MH⁺) | HPLC |
|---|---|---|---|---|---|
| 6-9 | 3,4,5-trimethoxyphenyl | Me | ¹H NMR (400 MHz, DMSO) δ 14.64 (s, 1H), 8.83 (s, 1H), 7.87 (d, J = 8.7 Hz, 1H), 6.61 (s, 2H), 4.33 (m, 1H), 3.74 (s, 6H), 3.68 (s, 3H), 2.57 (s, 3H), 1.18 (d, J = 6.4 Hz, 2H), 1.01 (s, 2H). | 428 | 95% |
| 6-10 | 2,4-dimethoxyphenyl | Me | ¹H NMR (400 MHz, DMSO) δ 14.80 (s, 1H), 8.88 (s, 1H), 7.90 (d, J = 8.6 Hz, 1H), 7.17 (d, J = 8.3 Hz, 1H), 6.76 (d, J = 2.2 Hz, 1H), 6.70 (dd, J = 8.4, 2.3 Hz, 1H), 4.47-4.28 (m, 1H), 3.85 (s, 3H), 3.75 (s, 3H), 2.55 (s, 3H), 1.21 (dd, J = 6.7, 4.5 Hz, 2H), 1.02 (dd, J = 10.3, 4.5 Hz, 2H). | 398 | 96% |
| 6-11 | 3-fluoro-4-methoxyphenyl | Me | ¹H NMR (400 MHz, DMSO) δ 14.70 (s, 1H), 8.80 (s, 1H), 7.86 (d, J = 8.1 Hz, 1H), 7.32 (m, 2H), 7.16 (d, J = 7.2 Hz, 1H), 4.25 (s, 1H), 3.92 (s, 3H), 2.57 (s, 3H), 1.41-1.10 (m, 2H), 0.89 (m, 2H). | 386 | 96% |
| 6-12 | 3,4-dimethoxyphenyl | Me | ¹H NMR (400 MHz, DMSO) δ 14.74 (s, 1H), 8.90 (s, 1H), 7.93 (d, J = 8.8 Hz, 1H), 7.13 (d, J = 8.3 Hz, 1H), 6.97 (s, 1H), 6.93 (dd, J = 8.2, 1.7 Hz, 1H), 4.39 (tt, J = 7.1, 3.8 Hz, 1H), 3.84 (s, 3H), 3.79 (s, 3H), 2.63 (s, 3H), 1.24 (d, J = 6.8 Hz, 2H), 1.07 (s, 2H). | 398 | 99% |
| 6-13 | 3-chloro-4-methoxyphenyl | Me | ¹H NMR (400 MHz, DMSO) δ 14.70 (s, 1H), 8.90 (s, 1H), 7.94 (d, J = 8.7 Hz, 1H), 7.54 (s, 1H), 7.35 (dd, J = 18.3, 8.3 Hz, 2H), 4.39 (m, 1H), 3.95 (s, 3H), 2.62 (s, 3H), 1.23 (d, J = 5.8 Hz, 2H), 1.06 (s, 2H). | 402 | 99% |
| 6-14 | 4-methoxy-3-(trifluoromethyl)phenyl | Me | ¹H NMR (400 MHz, DMSO) δ 14.69 (s, 1H), 8.91 (s, 1H), 7.97 (d, J = 8.6 Hz, 1H), 7.72 (d, J = 8.6 Hz, 1H), 7.67 (s, 1H), 7.47 (d, J = 8.6 Hz, 1H), 4.40 (m, 1H), 3.99 (s, 3H), 2.61 (s, 3H), 1.24 (d, J = 5.6 Hz, 2H), 1.08 (s, 2H). | 436 | 99% |
| 6-15 | 4-methoxy-3-methylphenyl | Me | ¹H NMR (400 MHz, DMSO) δ 14.76 (s, 1H), 8.89 (s, 1H), 7.93 (d, J = 8.5 Hz, 1H), 7.20 (d, J = 12.7 Hz, 2H), 7.11 (d, J = 8.0 Hz, 1H), 4.38 (m, 1H), 3.87 (s, 3H), 2.64 (s, 3H), 2.23 (s, 3H), 1.23 (m, 2H), 1.07 (m, 2H). | 382 | 99% |
| 6-16 | 3-amino-4-methoxyphenyl | Me | ¹H NMR (400 MHz, DMSO) δ 14.78 (s, 1H), 8.88 (s, 1H), 7.91 (d, J = 8.6 Hz, 1H), 6.95 (d, J = 7.4 Hz, 1H), 6.62 (s, 1H), 6.52 (d, J = 6.8 Hz, 1H), 4.94 (s, 2H), 4.39 (s, 1H), 3.84 (s, 3H), 2.63 (s, 3H), 1.23 (s, 2H), 1.03 (s, 2H). | 383 | 95% |

TABLE 6-continued

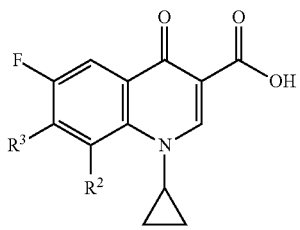

| Compound No. | R³ = | R² = | NMR | MS (MH⁺) | HPLC |
|---|---|---|---|---|---|
| 6-17 | morpholinoacetamide-MeO-phenyl | Me | $^1$H NMR (400 MHz, DMSO) δ 14.66 (s, 1H), 10.16 (s, 1H), 8.91 (s, 1H), 7.96 (d, J = 8.9 Hz, 2H), 7.26 (dd, J = 28.6, 8.1 Hz, 2H), 4.39 (m, 1H), 4.24 (m, 2H), 3.86 (m, 4H), 3.33 (m, 4H), 2.63 (s, 3H), 1.22 (d, J = 6.1 Hz, 2H), 1.05 (s, 2H). | 510 | 90% |
| 6-18 | MeO₂SHN-MeO-phenyl | Me | $^1$H NMR (400 MHz, DMSO) δ 14.73 (s, 1H), 9.12 (s, 1H), 8.90 (s, 1H), 7.95 (d, J = 9.0 Hz, 1H), 7.29 (s, 1H), 7.26 (s, 2H), 4.39 (m, 1H), 3.92 (s, 3H), 3.01 (s, 3H), 2.62 (s, 3H), 1.35-1.15 (m, 2H), 1.06 (m, 2H). | 461 | 98% |
| 6-19 | H₂N-urea-MeO-phenyl | Me | $^1$H NMR (400 MHz, DMSO) δ 14.76 (s, 1H), 8.89 (s, 1H), 8.14 (d, J = 14.8 Hz, 2H), 7.94 (d, J = 8.9 Hz, 1H), 7.14 (d, J = 8.3 Hz, 1H), 6.90 (d, J = 7.9 Hz, 1H), 6.28 (s, 2H), 4.39 (s, 1H), 3.93 (s, 3H), 2.65 (s, 3H), 1.19 (m, 2H), 1.04 (m, 2H). | 426 | 98% |
| 6-20 | t-BuO-benzoate-MeO-phenyl | Me | $^1$H NMR (400 MHz, DMSO) δ 14.73 (s, 1H), 8.91 (s, 1H), 7.97 (d, J = 8.7 Hz, 1H), 7.56 (d, J = 6.9 Hz, 2H), 7.31 (d, J = 8.5 Hz, 1H), 4.39 (m, 1H), 3.91 (s, 3H), 2.62 (s, 3H), 1.52 (s, 9H), 1.24 (m, 2H), 1.07 (m, 2H). | 468 | 98% |
| 6-21 | HO-benzoate-MeO-phenyl | Me | $^1$H NMR (400 MHz, DMSO) δ 14.80 (s, 1H), 12.93 (s, 1H), 8.97 (s, 1H), 8.02 (d, J = 8.8 Hz, 1H), 7.70 (s, 1H), 7.62 (d, J = 8.8 Hz, 1H), 7.38 (d, J = 0.8 Hz, 1H), 4.39 (m, 1H), 3.67 (s, 3H), 2.62 (s, 3H), 1.52 (s, 9H), 1.30 (m, 2H), 1.13 (m, 2H). | 412 | 98% |
| 6-22 | H₂N-ethylamide-MeO-phenyl | Me | $^1$H NMR (400 MHz, DMSO) δ 14.72 (s, 1H), 8.92 (s, 1H), 8.52 (s, 1H), 7.97 (d, J = 8.3 Hz, 1H), 7.81 (s, 3H), 7.57 (d, J = 7.9 Hz, 1H), 7.36 (d, J = 8.4 Hz, 1H), 4.39 (s, 1H), 3.96 (d, J = 24.7 Hz, 3H), 3.54 (s, 2H), 2.99 (s, 2H), 2.69-2.54 (m, 3H), 1.23 (d, J = 5.3 Hz, 2H), 1.07 (s, 2H). | 454 | 95% |
| 6-24 | Me₂N-ethylamide-MeO-phenyl | Me | $^1$H NMR (400 MHz, DMSO) δ 14.72 (s, 1H), 9.40 (s, 1H), 8.92 (s, 1H), 8.60 (s, 1H), 7.99 (s, 1H), 7.81 (s, 1H), 7.57 (s, 1H), 7.38 (s, 1H), 4.40 (s, 1H), 4.00 (s, 3H), 3.66 (s, 2H), 3.28 (s, 2H), 2.85 (s, 6H), 2.61 (s, 3H), 1.24 (s, 2H), 1.07 (s, 2H). | 482 | 99% |
| 6-25 | BocHN-ethylamide-MeO-phenyl | Me | $^1$H NMR (400 MHz, DMSO) δ 14.73 (s, 1H), 8.91 (s, 1H), 8.37 (s, 1H), 7.96 (d, J = 8.3 Hz, 1H), 7.75 (s, 1H), 7.53 (d, J = 8.2 Hz, 1H), 7.33 (d, J = 8.4 Hz, 1H), 6.95 (s, 1H), 4.40 (s, 1H), 3.98 (s, 3H), 3.33 (d, J = 5.1 Hz, 2H), 3.13 (d, J = 5.4 Hz, 2H), 2.61 (s, 3H), 1.36 (s, 9H), 1.24 (d, J = 4.4 Hz, 2H), 1.07 (s, 2H). | 554 | 95% |

TABLE 6-continued

| Compound No. | R³ = | R² = | NMR | MS (MH⁺) | HPLC |
|---|---|---|---|---|---|
| 6-26 | (2-methoxy-5-yl benzaldehyde) | Me | ¹H NMR (400 MHz, DMSO) δ 14.72 (s, 1H), 10.43 (s, 1H), 8.91 (s, 1H), 7.97 (d, J = 8.7 Hz, 1H), 7.74 (d, J = 8.8 Hz, 1H), 7.70 (s, 1H), 7.45 (d, J = 8.6 Hz, 1H), 4.39 (m, 1H), 4.02 (s, 3H), 2.61 (s, 3H), 1.23 (m, 2H), 1.07 (m, 2H). | 396 | 98% |
| 6-27 | (2-methoxy-5-yl, oxazol-5-yl) | Me | ¹H NMR (400 MHz, DMSO) δ 14.65 (s, 1H), 8.91 (s, 1H), 8.47 (s, 1H), 7.97 (d, J = 8.7 Hz, 1H), 7.71 (s, 1H), 7.66 (s, 1H), 7.44 (d, J = 8.7 Hz, 1H), 7.38 (d, J = 8.6 Hz, 1H), 4.40 (m, 1H), 4.05 (s, 3H), 2.65 (s, 3H), 1.25 (d, J = 6.7 Hz, 2H), 1.08 (s, 2H). | 435 | 90% |
| 6-28 | (2-methoxy-5-yl, CH₂CN) | Me | ¹H NMR (400 MHz, DMSO) δ 14.71 (s, 1H), 8.90 (s, 1H), 7.96 (d, J = 8.4 Hz, 1H), 7.40 (d, J = 11.8 Hz, 2H), 7.26 (d, J = 8.0 Hz, 1H), 4.39 (s, 1H), 3.94 (s, 5H), 2.62 (s, 3H), 1.23 (s, 2H), 1.06 (s, 2H). | 407 | 95% |
| 6-29 | (2-methoxy-5-yl, CH₂NH₂) | Me | ¹H NMR (400 MHz, DMSO) δ 14.68 (s, 1H), 10.43 (s, 1H), 8.91 (s, 1H), 7.97 (d, J = 8.8 Hz, 1H), 7.86-7.62 (m, 2H), 7.44 (d, J = 8.5 Hz, 1H), 4.39 (s, 1H), 4.02 (s, 2H), 2.64 (s, 3H), 1.23 (s, 2H), 1.07 (s, 2H). | 396 | 95% |
| 6-30 | (2-methoxy-5-yl, benzimidazol-2-yl) | Me | ¹H NMR (400 MHz, DMSO) δ 14.66 (s, 2H), 8.93 (s, 1H), 8.33 (s, 1H), 8.02 (d, J = 8.6 Hz, 1H), 7.80 (s, 2H), 7.71 (d, J = 8.5 Hz, 1H), 7.56 (d, J = 8.4 Hz, 1H), 7.46 (s, 2H), 4.42 (s, 1H), 4.17 (s, 3H), 2.66 (s, 3H), 1.35-1.15 (m, 2H), 1.09 (s, 2H). | 484 | 85% |
| 6-31 | (2-methoxy-5-yl, CH=NOH) | Me | ¹H NMR (400 MHz, DMSO) δ 14.74 (s, 1H), 11.37 (s, 1H), 8.90 (s, 1H), 8.35 (s, 1H), 7.96 (d, J = 8.1 Hz, 1H), 7.64 (s, 1H), 7.43 (d, J = 8.1 Hz, 1H), 7.27 (d, J = 8.5 Hz, 1H), 4.39 (s, 1H), 3.92 (s, 3H), 2.63 (s, 3H), 1.23 (d, J = 5.2 Hz, 2H), 1.06 (s, 2H). | 411 | 95% |
| 6-32 | (2-methoxy-5-yl, CONH₂) | Me | ¹H NMR (400 MHz, DMSO) δ 14.75 (s, 1H), 8.91 (s, 1H), 7.97 (d, J = 8.7 Hz, 1H), 7.78 (s, 2H), 7.70 (s, 1H), 7.54 (d, J = 8.2 Hz, 1H), 7.33 (d, J = 8.4 Hz, 1H), 4.40 (s, 1H), 3.98 (s, 3H), 2.61 (s, 3H), 1.23 (s, 2H), 1.07 (s, 2H). | 411 | 94% |
| 6-33 | (2-methoxy-5-yl, CH₂-(4-methylpiperazin-1-yl)) | Me | ¹H NMR (400 MHz, DMSO) δ 14.73 (s, 1H), 8.92 (s, 1H), 7.96 (d, J = 8.6 Hz, 1H), 7.37 (s, 2H), 7.23 (d, J = 7.3 Hz, 1H), 4.39 (m, 1H), 3.89 (s, 3H), 3.74 (m, 4H), 3.07 (s, 4H), 2.76 (s, 3H), 2.62 (s, 3H), 1.24 (s, 2H), 1.06 (s, 2H). | 480 | 96% |

TABLE 6-continued

| Compound No. | R³ = | R² = | NMR | MS (MH⁺) | HPLC |
|---|---|---|---|---|---|
| 6-34 | (N-methylaminomethyl, MeO-phenyl) | Me | ¹H NMR (400 MHz, DMSO) δ 14.73 (s, 1H), 8.92 (s, 1H), 8.87 (s, 1H), 7.97 (d, J = 8.1 Hz, 1H), 7.48 (s, 2H), 7.29 (d, J = 8.7 Hz, 1H), 4.40 (m, 1H), 4.18 (s, 2H), 3.94 (s, 3H), 2.63 (s, 3H), 2.55 (s, 3H), 1.24 (s, 2H), 1.05 (s, 2H). | 411 | 86% |
| 6-35 | (NC, MeO-phenyl) | Me | ¹H NMR (400 MHz, DMSO) δ 14.69 (s, 1H), 8.91 (s, 1H), 7.97 (d, J = 8.6 Hz, 1H), 7.91 (s, 1H), 7.75 (d, J = 8.1 Hz, 1H), 7.44 (d, J = 8.1 Hz, 1H), 4.39 (s, 1H), 4.02 (s, 3H), 2.61 (s, 3H), 1.23 (s, 2H), 1.07 (s, 2H). | 393 | 95% |
| 6-36 | (HOCH₂, MeO-phenyl) | Me | ¹H NMR (400 MHz, DMSO) δ 14.78 (s, 1H), 8.90 (s, 1H), 7.95 (d, J = 8.7 Hz, 1H), 7.37 (s, 1H), 7.26 (d, J = 8.0 Hz, 1H), 7.13 (d, J = 8.3 Hz, 1H), 5.18 (s, 1H), 4.57 (s, 2H), 4.39 (s, 1H), 3.87 (s, 3H), 2.62 (s, 3H), 1.23 (s, 2H), 1.05 (s, 2H). | 398 | 95% |
| 6-37 | (Me₂N-CH₂CH₂-O-N=CH, MeO-phenyl) | Me | ¹H NMR (400 MHz, DMSO) δ 14.71 (s, 1H), 9.63 (s, 1H), 8.92 (s, 1H), 8.51 (s, 1H), 7.98 (d, J = 8.5 Hz, 1H), 7.67 (s, 1H), 7.52 (d, J = 8.3 Hz, 1H), 7.32 (d, J = 8.5 Hz, 1H), 4.43 (m, 3H), 3.94 (s, 3H), 3.43 (s, 2H), 2.80 (d, J = 24.7 Hz, 6H), 2.62 (s, 3H), 1.23 (s, 2H), 1.07 (s, 2H). | 482 | 95% |
| 6-38 | (benzo[1,3]dioxole) | Me | ¹H NMR (400 MHz, DMSO) δ 14.74 (s, 1H), 8.90 (s, 1H), 7.93 (d, J = 9.2 Hz, 1H), 7.10 (d, J = 8.0 Hz, 1H), 7.02 (s, 1H), 6.86 (d, J = 8.0 Hz, 1H), 6.13 (s, 2H), 4.38 (m, 1H), 2.62 (s, 3H), 1.23 (m, 2H), 1.05 (m, 2H). | 382 | 98% |
| 6-39 | (benzo[1,3]dioxole-CHO) | Me | ¹H NMR (400 MHz, DMSO) δ 14.67 (s, 1H), 10.11 (s, 1H), 8.91 (s, 1H), 7.97 (d, J = 8.7 Hz, 1H), 7.33 (d, J = 1.6 Hz, 1H), 7.29 (d, J = 1.6 Hz, 1H), 6.45-6.21 (s, 2H), 4.41-4.30 (m, 1H), 2.74-2.56 (s, 3H), 1.33-1.17 (d, J = 6.6 Hz, 2H), 1.12-0.96 (t, J = 3.1 Hz, 2H). | 410 | 98% |
| 6-40 | (benzo[1,3]dioxole-CH=N-OH) | Me | ¹H NMR (400 MHz, DMSO) δ 14.69 (s, 1H), 11.53 (s, 1H), 8.90 (s, 1H), 8.16 (s, 1H), 7.95 (d, J = 8.7 Hz, 1H), 7.08 (d, J = 1.7 Hz, 1H), 7.02 (d, J = 1.7 Hz, 1H), 6.21 (s, 2H), 4.48-4.16 (m, 1H), 2.64 (s, 3H), 1.35-1.21 (d, J = 6.8 Hz, 2H), 1.12-1.01 (m, 2H). | 425 | 98% |

TABLE 6-continued

| Compound No. | R³ = | R² = | NMR | MS (MH⁺) | HPLC |
|---|---|---|---|---|---|
| 6-41 | benzodioxole with CN | Me | ¹H NMR (400 MHz, DMSO) δ 14.64 (s, 1H), 8.90 (s, 1H), 7.96 (d, J = 8.8 Hz, 1H), 7.36 (d, J = 1.6 Hz, 1H), 7.4 (d, J = 1.6 Hz, 1H), 6.36 (s, 2H), 4.52-4.26 (m, 1H), 2.63 (s, 3H), 1.35-1.15 (d, J = 6.6 Hz, 2H), 1.10-0.99 (m, 2H). | 407 | 98% |
| 6-42 | benzodioxole with ethynyl | Me | ¹H NMR (400 MHz, DMSO) δ 14.68 (s, 1H), 8.89 (s, 1H), 794 (d, J = 8.7 Hz, 1H), 7.06 (d, J = 1.5 Hz, 1H), 6.95 (d, J = 1.5 Hz, 1H), 6.22 (s, 2H), 4.57-4.46 (s, 1H), 4.42-4.30 (m, 1H), 2.63 (s, 3H), 1.33-1.15 (d, J = 6.2 Hz, 2H), 1.12-0.90 (m, 1H). | 406 | 95% |
| 6-43 | benzodioxole with CH₂OH | OMe | ¹H NMR (400 MHz, DMSO) δ 14.70 (s, 1H), 8.80 (s, 1H), 7.90 (d, J = 9.1 Hz, 1H), 7.06 (s, 1H), 7.01 (s, 1H), 6.13 (s, 2H), 5.31 (t, J = 5.6 Hz, 1H), 4.54 (d, J = 5.6 Hz, 2H), 4.34-4.12 (mz, 1H), 3.44 (s, 3H), 1.33-0.99 (m, 4H). | 428 | 97% |
| 6-44 | benzodioxole with vinyl | Me | ¹H NMR (400 MHz, DMSO) δ 14.69 (s, 1H), 8.89 (s, 1H), 7.93 (d, J = 8.7 Hz, 1H), 6.97 (s, 1H), 6.93 (s, 1H), 6.73 (dd, J = 17.7, 11.3 Hz, 1H), 6.20 (s, 2H), 6.00 (d, J = 17.6 Hz, 1H), 5.49 (d, J = 11.5 Hz, 1H), 4.53-4.25 (m, 1H), 2.75-2.57 (s, 3H), 1.32-1.17 (d, J = 6.7 Hz, 2H), 1.11-0.89 (m, 2H). | 408 | 95% |
| 6-45 | benzodioxole with ethynyl | OMe | ¹H NMR (400 MHz, DMSO) δ 14.66 (s, 1H), 8.80 (s, 1H), 7.90 (d, J = 9.1 Hz, 1H), 7.17 (s, 1H), 7.09 (s, 1H), 6.23 (s, 2H), 4.49 (s, 1H), 4.34-4.14 (m, 1H), 3.47-3.42 (s, 3H), 1.31-0.96 (m, 4H). | 422 | 98% |
| 6-46 | benzodioxole with CN | OMe | ¹H NMR (400 MHz, DMSO) δ 14.62 (s, 1H), 8.81 (s, 1H), 7.93 (d, J = 9.1 Hz, 1H), 7.45 (s, 1H), 7.44 (s, 1H), 6.36 (s, 2H), 4.39-4.04 (m, 1H), 3.46 (s, 3H), 1.26-1.06 (m, 4H). | 423 | 98% |

TABLE 6-continued

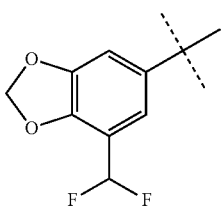

| Compound No. | R³ = | R² = | NMR | MS (MH⁺) | HPLC |
|---|---|---|---|---|---|
| 6-47 | 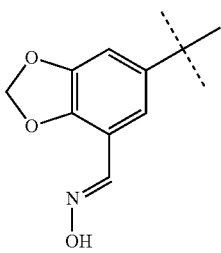 | OMe | ¹H NMR (400 MHz, DMSO) δ 14.65 (s, 1H), 8.80 (s, 1H), 7.92 (d, J = 9.1 Hz, 1H), 7.30 (s, 1H), 7.19 (s, 1H), 7.17 (t, J = 56 Hz, 1H), 6.27 (s, 2H), 4.33-4.17 (m, 1H), 3.45 (s, 3H), 1.29-0.97 (m, 4H). | 448 | 92% |
| 6-48 | 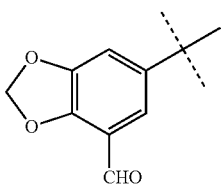 | OMe | ¹H NMR (400 MHz, DMSO) δ 14.67 (s, 1H), 8.80 (s, 1H), 7.93 (d, J = 9.1 Hz, 1H), 7.77 (s, 1H), 7.42 (t, J = 1.4 Hz, 1H), 7.28 (t, J = 1.3 Hz, 1H), 7.25 (s, 1H), 6.27 (s, 2H), 4.33-4.13 (m, 1H), 3.449 (s, 3H), 1.37-0.87 (m, 4H). | 441 | 98% |
| 6-49 | 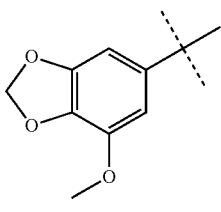 | OMe | ¹H NMR (400 MHz, DMSO) δ 14.66 (s, 1H), 10.12 (d, J = 1.2 Hz, 1H), 8.81 (s, 1H), 7.93 (d, J = 9.5 Hz, 1H), 7.44 (s, 1H), 7.42 (s, 1H), 6.35 (s, 2H), 4.33-4.17 (m, 1H), 3.46 (s, 3H), 1.32-0.97 (m, 4H). | 426 | 98% |
| 6-50 | 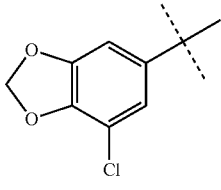 | OMe | ¹H NMR (400 MHz, DMSO) δ 14.68 (s, 1H), 8.80 (s, 1H), 7.89 (d, J = 9.1 Hz, 1H), 6.83-6.80 (t, J = 1.3 Hz, 1H), 6.80-6.76 (t, J = 1.2 Hz, 1H), 6.11 (s, 2H), 4.34-4.12 (m, 1H), 3.86 (s, 3H), 3.31 (s, 3H), 1.26-1.02 (m, 4H). | 428 | 98% |
| 6-51 | 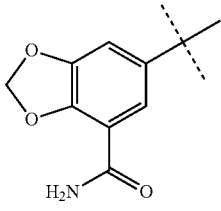 | OMe | ¹H NMR (400 MHz, DMSO) δ 14.70-14.61 (s, 1H), 8.84-8.78 (s, 1H), 7.96-7.88 (d, J = 9.0 Hz, 1H), 7.14 (s, 1H), 7.13 (s, 1H), 6.33-6.22 (s, 2H), 4.26-4.18 (m, 1H), 3.47 (s, 3H), 1.20-1.11 (m, 4H). | 432 | 95% |
| 6-52 | | OMe | ¹H NMR (400 MHz, DMSO) δ 14.67 (s, 1H), 8.80 (s, 1H), 7.92 (d, J = 9.1 Hz, 1H), 7.77 (s, 1H), 7.42 (s, 1H), 7.28 (s, 1H), 7.25 (s, 1H), 6.27 (s, 2H), 4.22 (m, 1H), 3.44 (s, 3H), 1.17 (m, 4H). | 441 | 85% |

TABLE 6-continued

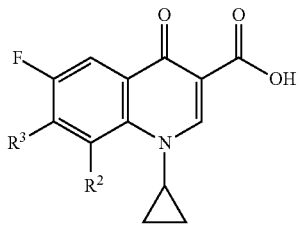

| Compound No. | R³ = | R² = | NMR | MS (MH⁺) | HPLC |
|---|---|---|---|---|---|
| 6-53 | (3,4-methylenedioxy-6-cyanophenyl) | OMe, N-(2-fluorocyclopropyl) | $^1$H NMR (400 MHz, DMSO) δ 14.49 (s, 1H), 8.83 (s, 1H), 7.94 (d, J = 8.0 Hz, 1H), 7.42 (s, 1H), 6.36 (s, 2H), 5.10 (m, 1H), 4.18 (m, 1H), 3.47 (s, 3H), 1.82-1.63 (m, 4H). | 441 | 98% |
| 6-54 | (3,4-methylenedioxy-6-hydroxyiminomethylphenyl) | OMe, N-(2-fluorocyclopropyl) | $^1$H NMR (400 MHz, DMSO) δ 14.50 (s, 1H), 11.55 (s, 1H), 8.83 (s, 1H), 8.16 (s, 1H), 7.92 (d, J = 8.0 Hz, 1H), 7.27 (s, 1H), 7.10 (s, 1H), 6.22 (s, 1H), 5.10 (m, 1H), 4.18 (m, 1H), 3.47 (s, 3H), 1.82-1.63 (m, 4H). | 459 | 95% |
| 6-55 | (4-methoxyphenyl) | Me, N-(2,4-difluorophenyl) | $^1$H NMR (400 MHz, DMSO) δ 14.47 (s, 1H), 8.82 (s, 1H), 8.10 (d, J = 8.7 Hz, 1H), 8.00-7.87 (m, 1H), 7.66 (t, J = 9.4 Hz, 1H), 7.37 (t, J = 8.3 Hz, 1H), 7.21 (d, J = 8.0 Hz, 2H), 7.06 (d, J = 8.1 Hz, 2H), 3.81 (s, 3H). | 440 | 99% |
| 6-56 | (4-methoxyphenyl) | fused oxazine with methyl | $^1$H NMR (400 MHz, DMSO) δ 15.44-15.10 (s, 1H), 9.12-8.99 (t, J = 1.7 Hz, 1H), 8.03-7.92 (dt, J = 8.4, 1.8 Hz, 1H), 7.67-7.56 (dd, J = 8.6, 2.5 Hz, 3H), 7.16-6.98 (m, 2H), 5.03-4.89 (d, J = 7.3 Hz, 1H), 4.60-4.47 (d, J = 11.4 Hz, 1H), 4.44-4.33 (d, J = 11.5 Hz, 1H), 3.86-3.75 (t, J = 1.7 Hz, 3H), 1.53-1.42 (d, J = 6.3 Hz, 3H). | 352 | 99% |

TABLE 7

| Compound No. | R16 = | R2 = | NMR | MS (MH+) | HPLC |
|---|---|---|---|---|---|
| 7-1 | H | Me | 1H NMR (400 MHz, DMSO) δ 14.74 (s, 1H), 8.90 (s, 1H), 7.95 (d, J = 9.3 Hz, 1H), 7.80 (s, 2H), 7.27 (s, 1H), 4.39 (s, 1H), 2.68 (s, 3H), 1.23 (s, 3H), 1.03 (s, 2H). | 344 | 100% |
| 7-2 | EtHN-CH2-C(CH3)2- | Me | 1H NMR (400 MHz, DMSO) δ 14.69 (s, 1H), 9.37 (s, 2H), 8.91 (s, 1H), 7.96 (d, J = 8.9 Hz, 1H), 7.87 (s, 1H), 7.51 (s, 1H), 4.43 (s, 3H), 3.00 (d, J = 6.2 Hz, 2H), 2.71 (s, 3H), 1.24 (d, J = 6.4 Hz, 5H), 1.03 (s, 2H). | 401 | 95% |
| 7-3 | HON=C(CN)-C(CH3)2- | Me | 1H NMR (400 MHz, DMSO) δ 14.70 (s, 1H), 13.87 (s, 1H), 8.91 (s, 1H), 7.98 (d, J = 8.1 Hz, 2H), 7.60 (s, 1H), 4.41 (s, 1H), 2.70 (s, 3H), 1.23 (s, 2H), 1.06 (s, 2H). | 412 | 100% |
| 7-4 | CH2CN | Me | 1H NMR (400 MHz, DMSO) δ 14.75 (s, 1H), 8.90 (s, 1H), 7.95 (d, J = 8.8 Hz, 1H), 7.76 (s, 1H), 7.22 (s, 1H), 5.76 (s, 2H), 4.40 (m, 1H), 2.69 (s, 3H), 1.23 (m, 2H), 1.04 (s, 2H). | 383 | 97% |
| 7-5 | CHO | Me | 1H NMR (400 MHz, DMSO) δ 14.67 (s, 1H), 10.03 (s, 1H), 8.92 (s, 1H), 8.39 (s, 1H), 8.23 (s, 1H), 7.99 (d, J = 9.1 Hz, 1H), 4.42 (s, 1H), 2.71 (s, 3H), 1.24 (d, J = 6.4 Hz, 2H), 1.05 (s, 2H). | 372 | 98% |
| 7-6 | HON=CH-C(CH3)2- | Me | 1H NMR (400 MHz, DMSO) δ 14.70 (s, 1H), 11.34 (d, J = 16.3 Hz, 1H), 8.90 (s, 1H), 8.40 (s, 1H), 7.96 (d, J = 8.6 Hz, 1H), 7.78 (s, 1H), 7.42 (d, J = 14.9 Hz, 1H), 4.40 (s, 1H), 2.71 (s, 3H), 1.24 (d, J = 5.8 Hz, 2H), 1.04 (s, 2H). | 387 | 96% |
| 7-7 | HON=C(OH)-C(CH3)2- | Me | 1H NMR (400 MHz, DMSO) δ 13.57-13.17 (m, 1H), 11.49 (s, 1H), 9.30 (s, 1H), 8.77 (s, 1H), 8.09 (s, 1H), 7.90 (d, J = 9.3 Hz, 1H), 7.83 (s, 1H), 4.33 (s, 1H), 2.66 (s, 3H), 1.22 (d, J = 7.5 Hz, 2H), 0.97 (s, 2H). | 403 | 100% |
| 7-8 | CONH2 | Me | 1H NMR (400 MHz, DMSO) δ 14.70 (s, 1H), 8.91 (s, 1H), 8.12 (s, 1H), 7.98 (m, 2H), 7.89 (s, 1H), 7.57 (s, 1H), 4.41 (s, 1H), 2.71 (s, 3H), 1.25 (d, J = 5.7 Hz, 2H), 1.03 (s, 2H). | 387 | 100% |
| 7-9 | CO2H | Me | 1H NMR (400 MHz, DMSO) δ 14.69 (s, 1H), 13.34 (s, 1H), 8.91 (s, 1H), 8.12 (s, 1H), 7.96 (d, J = 8.7 Hz, 1H), 7.86 (s, 1H), 4.40 (s, 1H), 2.69 (s, 3H), 1.24 (d, J = 6.2 Hz, 2H), 1.05 (s, 2H). | 388 | 100% |
| 7-10 | HOOC-CH=CH-C(CH3)2- | Me | 1H NMR (400 MHz, DMSO) δ 14.68 (s, 1H), 12.49 (s, 1H), 8.87 (s, 1H), 7.96 (d, J = 11.9 Hz, 2H), 7.81 (d, J = 15.8 Hz, 1H), 7.69 (s, 1H), 6.30 (d, J = 15.7 Hz, 1H), 4.40 (s, 1H), 2.71 (s, 3H), 1.24 (d, J = 6.4 Hz, 2H), 1.04 (s, 2H). | 414 | 95% |
| 7-11 | tetrazol-5-yl-C(CH3)2- | Me | 1H NMR (400 MHz, DMSO) δ 14.69 (s, 1H), 8.92 (s, 1H), 8.13 (s, 1H), 8.00 (d, J = 8.7 Hz, 1H), 7.91 (s, 1H), 4.42 (s, 1H), 2.74 (s, 3H), 1.24 (s, 2H), 1.06 (s, 2H). | 412 | 100% |
| 7-12 | 3-(ethoxycarbonyl)-1H-pyrrol-2-yl-C(CH3)2- | Me | 1H NMR (400 MHz, DMSO) δ 14.75 (s, 1H), 11.75 (s, 1H), 8.90 (s, 1H), 7.97 (s, 1H), 7.58 (s, 1H), 7.46 (s, 1H), 7.26 (s, 1H), 7.13 (s, 1H), 7.00 (s, 2H), 4.41 (s, 1H), 4.17 (d, J = 6.9 Hz, 2H), 2.75 (s, 3H), 1.99 (s, 2H), 1.23 (s, 3H), 1.04 (s, 2H), 0.85 (s, 2H). | 481 | 100% |

TABLE 7-continued

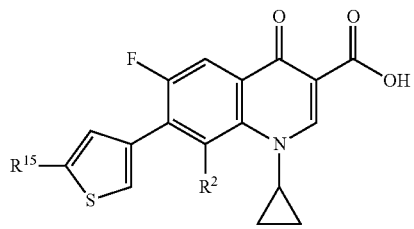

| Compound No. | R16 = | R2 = | NMR | MS (MH+) | HPLC |
|---|---|---|---|---|---|
| 7-13 | oxazole | Me | $^1$H NMR (400 MHz, DMSO) δ 14.70 (s, 1H), 8.91 (s, 1H), 8.49 (s, 1H), 7.97 (d, J = 8.7 Hz, 1H), 7.91 (s, 1H), 7.64 (s, 2H), 4.41 (s, 1H), 2.73 (s, 3H), 1.25 (d, J = 6.5 Hz, 2H), 1.05 (s, 2H). | 411 | 95% |
| 7-14 | benzimidazole | Me | $^1$H NMR (400 MHz, DMSO) δ 14.90-14.46 (m, 1H), 8.93 (s, 1H), 8.05 (s, 1H), 8.02 (d, J = 8.4 Hz, 2H), 7.63 (s, 2H), 7.28 (s, 2H), 4.44 (s, 1H), 2.78 (s, 3H), 1.27 (d, J = 6.4 Hz, 2H), 1.07 (s, 2H). | 460 | 100% |
| 7-15 | phenyl-triazole | Me | $^1$H NMR (400 MHz, DMSO) δ 8.92 (s, 1H), 8.07 (d, J = 6.7 Hz, 2H), 7.99 (d, J = 8.8 Hz, 1H), 7.91 (s, 1H), 7.79 (s, 1H), 7.54 (s, 3H), 4.42 (s, 1H), 2.76 (s, 3H), 1.26 (d, J = 6.0 Hz, 3H), 1.07 (m, 2H). | 478 | 95% |
| 7-16 | methyl-triazole | Me | $^1$H NMR (400 MHz, DMSO) δ 14.68 (b, 1H), 13.75 (s, 1H), 8.90 (s, 1H), 7.96 (d, J = 8.9 Hz, 1H), 7.77 (s, 1H), 7.61 (s, 1H), 4.47-4.32 (m, 1H), 2.73 (s, 3H), 2.41 (s, 3H), 1.25 (t, J = 6.3 Hz, 2H), 1.07 (s, 2H). | 425 | 98% |
| 7-17 | CN | OMe | $^1$H NMR (400 MHz, DMSO) δ 14.63 (s, 1H), 8.80 (s, 1H), 8.42 (s, 1H), 7.28 (s, 1H), 7.96 (d, J = 9.2 Hz, 1H), 4.47-4.32 (m, 1H), 3.47 (s, 3H), 1.23-1.15 (m, 4H). | 385 | 98% |
| 7-18 | methyl-triazole | OMe | $^1$H NMR (400 MHz, DMSO) δ 8.57 (s, 1H), 7.72 (s, 2H), 7.58 (s, 1H), 7.43 (d, J = 9.7 Hz, 1H), 4.13 (m, 1H), 3.27 (s, 3H), 2.20 (s, 3H), 1.05-0.81 (m, 4H). | 441 | 98% |
| 7-19 | methyl-triazole | Cl | $^1$H NMR (400 MHz, DMSO) δ 8.93 (s, 1H), 8.13 (d, J = 8.0 Hz, 1H), 7.86 (s, 1H), 7.67 (s, 1H), 4.13 (m, 1H), 2.40 (s, 3H), 1.24-1.12 (m, 4H). | 445 | 85% |

TABLE 8-1

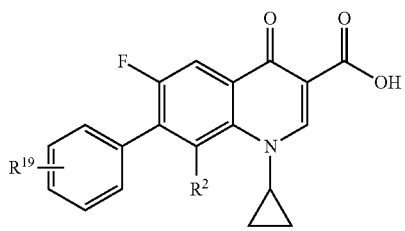

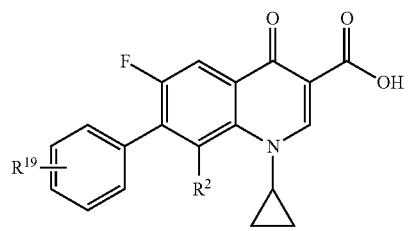

| Compound No. | R19 = | R2 = | MS (MH+) | Compound No. | R19 = | R2 = | MS (MH+) |
|---|---|---|---|---|---|---|---|
| 8-1 | H | Me | 352.36 | 8-6 | 3-Me | Me | 351.37 |
| 8-2 | 3-NH2 | Me | 337.34 | 8-7 | 4-Me | Me | 351.37 |
| 8-3 | 4-F | Me | 355.33 | 8-8 | 2,3-Dimethyl | Me | 365.4 |
| 8-4 | 4-CO2H | Me | 381.35 | 8-9 | 2-Cl | Me | 371.79 |
| 8-5 | 2-NH2 | Me | 352.36 | 8-10 | 4-Cl | Me | 371.79 |

TABLE 8-1-continued

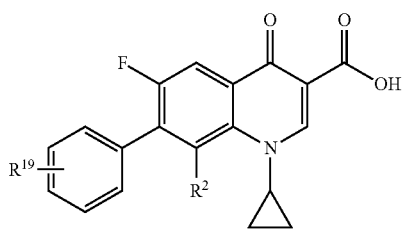

| Compound No. | R19 = | R2 = | MS (MH+) |
| --- | --- | --- | --- |
| 8-11 | 3-CO2H | Me | 381.35 |
| 8-12 | 3-CF3 | Me | 405.34 |
| 8-13 | 3,4-Dichloro | Me | 406.23 |
| 8-14 | 3-F | Me | 355.33 |
| 8-15 | 4-tBu | Me | 393.45 |
| 8-16 | 4-MeO | Cyclopropyl | 393.41 |
| 8-17 | 4-Ph | Me | 413.44 |
| 8-18 | 4-NO2 | Me | 382.34 |
| 8-19 | 3,4-Dichloro | MeO | 404.24 |
| 8-20 | 4-MeO | Me | 365.38 |
| 8-21 | 3,4-Dimethyl | Me | 365.4 |
| 8-22 | 4-CF3 | Me | 405.34 |
| 8-24 | 3-CONH2 | Me | 380.37 |
| 8-25 | 4-NH2 | Me | 352.36 |
| 8-26 | 4-OH | Me | 353.34 |
| 8-27 | 4-OMe | F | 353.34 |
| 8-28 | 4-OMe | NO2 | 398.34 |
| 8-29 | 4-OMe | Cl | 387.79 |
| 8-30 | 4-OMe | NH2 | 368.36 |
| 8-31 | 4-OMe | Br | 432.24 |
| 8-32 | 4-OMe | H | 353.34 |
| 8-33 | 4-OMe | CN | 378.35 |
| 8-34 | 4-OMe | CH2F | 385.36 |
| 8-35 | 4-OMe | MeO | 383.37 |
| 8-36 | 4-OMe | CH2Br | 446.27 |
| 8-37 | 4-OMe | CH2OH | 383.37 |
| 8-38 | 4-OMe | CHF2 | 403.35 |
| 8-39 | 4-Amino-3-hydroxy | Me | 368.36 |
| 8-40 | 4-OMe | CHO | 381.35 |
| 8-41 | 4-OMe | C≡CH | 377.37 |
| 8-42 | 4-OMe | Et | 381.4 |
| 8-43 | 4-OMe | CH=CH2 | 379.38 |
| 8-44 | 3,4-Diamino | Me | 367.37 |
| 8-45 | 4-Amino-3-nitro | Me | 397.36 |
| 8-46 | 4-Methylamino-3-nitro | Me | 411.38 |
| 8-47 | 3-Dimethylamino | Me | 380.41 |
| 8-48 | 2,4-Dinitro-3-dimethylamino | Me | 470.41 |
| 8-49 | 4-Nitro-3-dimethylamino | Me | 425.41 |
| 8-50 | 2-Nitro-3-dimethylamino | Me | 425.41 |
| 8-51 | 4-Dimethylamino-3-nitro | Me | 425.41 |
| 8-52 | 4-Ethylamino-3-nitro | Me | 425.41 |
| 8-53 | 4-Dimethylamino | Me | 380.41 |
| 8-54 | 3-Formyl-4-nitro | Me | 410.35 |
| 8-55 | 4-Amino-3-nitro | Me | 413.36 |
| 8-56 | 3-Fluoro-4-nitro | Me | 400.33 |

TABLE 8-2

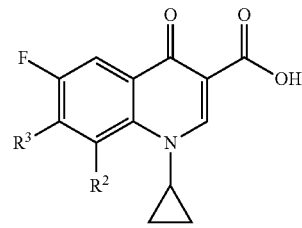

| Compound No. | R3 = | R2 = | MS (MH+) |
| --- | --- | --- | --- |
| 8-57 | ![](cyclopropylmethyl-HN-tBu-nitrophenyl) | Me | 451.45 |
| 8-58 | | Me | 465.47 |
| 8-59 | ![](H2N-piperidinyl-tBu-nitrophenyl) | Me | 480.49 |
| 8-60 | ![](SMe/NC-HN-tBu-nitrophenyl) | Me | 495.48 |
| 8-61 | ![](Me2N-piperidinyl-tBu-nitrophenyl) | Me | 508.54 |
| 8-62 | | Me | 452.44 |
| 8-63 | | Me | 466.46 |

TABLE 8-2-continued
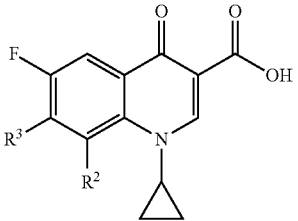
| Compound No. | R³ = | R² = | MS (MH⁺) |
|---|---|---|---|
| 8-64 | 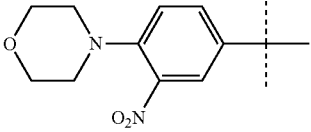 | Me | 467.45 |
| 8-65 | 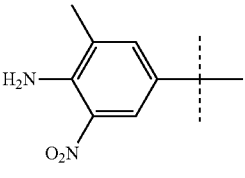 | Me | 411.38 |
| 8-66 | 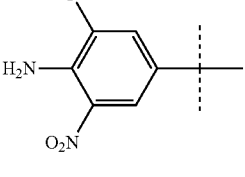 | Me | 415.35 |
| 8-67 | 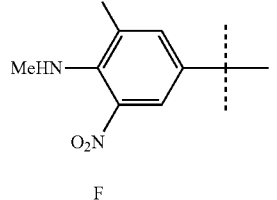 | Me | 425.41 |
| 8-68 | 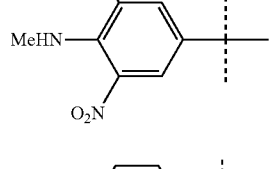 | Me | 429.37 |
| 8-69 | 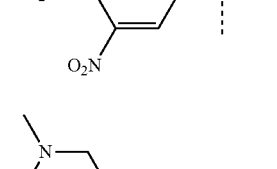 | Me | 426.35 |
| 8-70 | 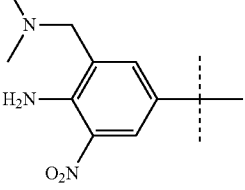 | Me | 454.45 |
| 8-71 | 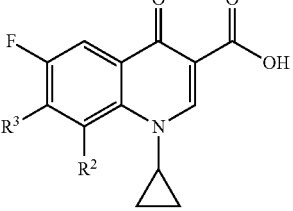 | Me | 449.39 |
| 8-72 | 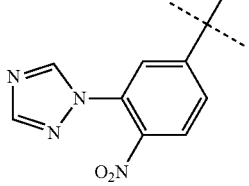 | Me | 454.45 |
| 8-73 | 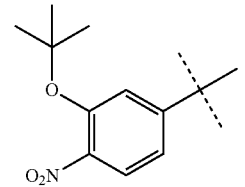 | Me | 463.42 |
| 8-74 | 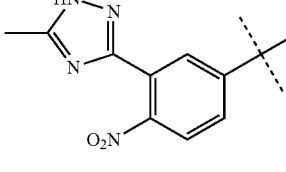 | Me | 447.46 |
| 8-75 | 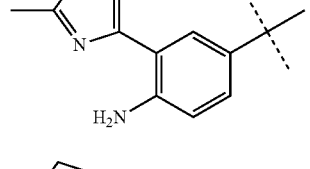 | Me | 406.45 |
| 8-76 | 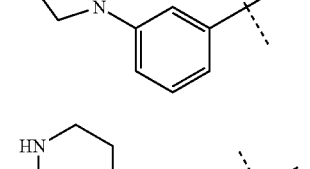 | Me | 421.46 |
| 8-77 | 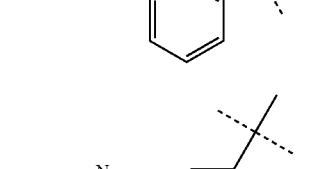 | Me | 418.42 |

TABLE 9

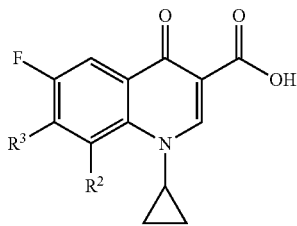

| Compound No. | R³ = | R² = | MS (MH⁺) |
|---|---|---|---|
| 9-1 | 3-bromo-isoxazol-5-yl | Me | 407.19 |
| 9-2 | 3-phenyl-isoxazol-5-yl | Me | 404.39 |
| 9-3 | 3-(furan-2-yl)-isoxazol-5-yl | Me | 394.35 |
| 9-4 | 3-(pyrrolidin-2-yl)-isoxazol-5-yl | Me | 397.4 |
| 9-5 | 3-(1H-pyrrol-2-yl)-isoxazol-5-yl | Me | 392.38 |
| 9-6 | 1H-pyrrol-3-yl | Me | 362.32 |
| 9-7 | 1H-pyrazol-5-yl | Me | 326.32 |
| 9-8 | 4-oxo-4,5,6,7-tetrahydro-1H-indol-2-yl | Me | 394.4 |
| 9-9 | 4,5,6,7-tetrahydro-1H-indol-2-yl | Me | 380.41 |

TABLE 9-continued

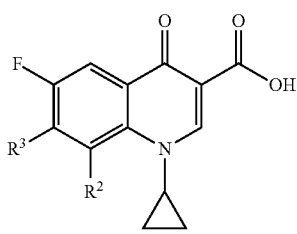

| Compound No. | R³ = | R² = | MS (MH⁺) |
|---|---|---|---|
| 9-10 | 4-amino-4,5,6,7-tetrahydro-1H-indol-2-yl | Me | 395.43 |
| 9-11 | 5-(aminomethyl)-1H-pyrrol-2-yl | Me | 355.36 |
| 9-12 | 6-oxo-6,7-dihydro-1H-pyrrolo[2,3-b]pyridin-2-yl | Me | 393.37 |
| 9-13 | furan-2-yl | Me | 327.31 |
| 9-14 | 5-bromo-furan-2-yl | Me | 406.2 |
| 9-15 | 5-(thiophen-2-yl)-furan-2-yl | Me | 409.43 |
| 9-16 | 5-nitro-furan-2-yl | Me | 372.3 |
| 9-17 | 2,5-dihydro-1H-pyrrol-3-yl | Me | 328.34 |
| 9-18 | 1-(pyrrolidin-3-yl)-2,5-dihydro-1H-pyrrol-3-yl | Me | 397.44 |

TABLE 9-continued

| Compound No. | R³ = | R² = | MS (MH⁺) |
|---|---|---|---|
| 9-19 | 4-pyridyl N-oxide | Me | 354.33 |
| 9-20 | 3-pyridyl N-oxide | Me | 354.33 |
| 9-21 | 3-trifluoromethyl-2-pyridone-5-yl | Me | 422.33 |
| 9-22 | 1,2,3,6-tetrahydropyridin-4-yl | Me | 342.36 |
| 9-24 | 1-(pyrrolidin-3-yl)-1,2,3,6-tetrahydropyridin-4-yl | Me | 411.47 |

Experimental Example 1

In Vitro Antibacterial Activity

All compounds were dissolved in dimethyl sulfoxide (DMSO, Merck, purity >99.9%) to achieve final 1 mg/ml desired concentrations.

MICs (minimum inhibitory concentrations) were determined by the broth microdilution technique with 96-well microdilution plates. The antimicrobials were tested using the following MIC ranges: 0.008 to 8 µg/ml. The plates were filled with 100 µl of reinforced clostridial medium (Oxoid; Unipath Ltd., Basingstoke, United Kingdom) per well containing the final antibiotic concentrations. The plates were thawed and preincubated for 3 hours in an anaerobic chamber (Thermal, USA) containing an atmosphere of 80% $N_2$, 15% $CO_2$, and 5% $H_2$. The bacterial inocula were prepared by suspending growth from 48 hours cultures in reinforced clostridial medium. The final inoculum was approximately $1.0 \times 10^{5-6}$ CFU/well. The plates were incubated for 48 hours at 37° C. in the anaerobic chamber. The MIC was defined as the lowest antibiotic concentration that inhibited visible growth. Ciprofloxacin, vancomycin and metronidazole were used as a positive control. The results are shown in Table 10.

TABLE 10

| | MIC of example compounds against C. difficile (µg/mL) | | | |
|---|---|---|---|---|
| Compound No. | C. difficile ATCC43255 | C. difficile ATCC700057 | C. difficile ATCC70092 | C. difficile IQCC23903 |
| 2-18 | 0.016-0.063 | 0.016-0.063 | ≤0.008-0.063 | 0.032-0.063 |
| 2-46 | 0.032-0.125 | 0.032-0.25 | 0.063-0.25 | 0.125-0.25 |
| 5-14 | 0.125-0.25 | 0.125-0.5 | 0.125-0.25 | 0.125-0.5 |
| 2-49 | 0.063-0.25 | 0.063-0.25 | 0.063-0.5 | 0.063-0.25 |
| 3-11 | ≤0.008-0.032 | 0.016-0.032 | ≤0.008-0.032 | ≤0.008-0.063 |
| 2-31 | ≤0.008-0.032 | 0.016-0.032 | 0.016-0.032 | 0.016-0.063 |
| 1-2 | 0.032-0.125 | 0.032-0.125 | 0.032-0.125 | 0.063-0.25 |
| 3-21 | 0.016-0.032 | 0.016-0.063 | 0.016-0.063 | 0.032-0.063 |
| 2-38 | 0.016-0.032 | 0.016-0.032 | 0.032-0.063 | 0.016-0.032 |
| 3-30 | 0.032-0.063 | 0.063-0.125 | 0.063-0.125 | 0.063-0.25 |

Experimental Example 2

In Vivo Antibacterial Efficacy

Figure 2:
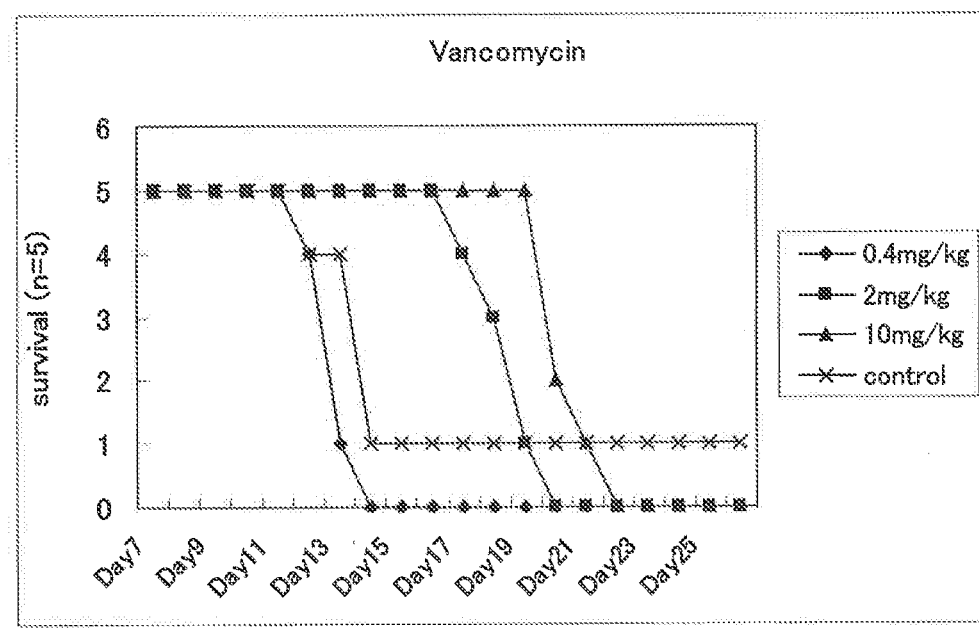
FIG. 2 is a graph showing the results of the animals administered with vancomycin in Experimental Example 2.

In vivo efficacy was evaluated in a hamster intestinal infection treatment model. Male Golden Syrian hamsters were purchased from Charles River Laboratories (Kingston, N.Y., USA) and were about 6 weeks of age, with weights ranging from 80 to 100 g at the start of the study. The animals were housed individually in filtered polycarbonate shoe-box style cages equipped with water bottles, and Harlan Teklab Global Diet 2016 was available ad libitum via food hoppers. The hamsters were pre-treated with clindamycin (1 mg/kg, p.o.) and vancomycin (50 mg/kg, p.o.), formulated in arabic gum, at Day 0. At Day 7, each hamster was inoculated via oral gavage with 0.5 mL of a suspension of *C. difficile* ATCC 43255 ($10^5$ CFU/body, p.o.). To prepare this inoculum, *C. difficile* was grown in GAM agar (Japan) for 5 days at 37° C., and the bacteria were harvested by centrifugation, rinsed twice with arabic gum, resuspended in arabic gum and the exact bacteria density was determined using the dilution plate count method. Oral dosing of compounds, pulverized and formulated in arabic gum was commenced the following day (Day 8). Treatments were administered once a day for 5 consecutive days at specified doses (10, 2, and 0.4 mg/kg), with five hamsters per group. Controls were included an uninfected group and an infected but untreated group, and vancomycin was used as positive control. The hamsters were observed daily to record clinical signs (duration, time of onset, time of recovery or death), and animals in a lethargic, clearly moribund state were euthanized. A necropsy was performed on animals that were either found dead or were euthanized at the end of the study (37 days). The results are shown in FIG. 1 and FIG. 2.

Preparation Example 1

An injection preparation is prepared from the following components.

| Components | Amount |
|---|---|
| Compound 1-2 | 200 mg |
| Glucose | 250 mg |
| Distilled water for injection | q.s. |
| Total | 5 ml |

Compound 1-2 and glucose are dissolved in distilled water for injection, and the solution is added to a 5 ml ampoule, which is purged with nitrogen gas and then subjected to sterilization at 121° C. for 15 minutes to give an injection preparation.

Preparation Example 2

Film coated tablets are prepared from the following components.

| Components | Amount |
|---|---|
| Compound 2-18 | 100 g |
| Avicel(registered trademark) | 40 g |
| Corn starch | 30 g |
| Magnesium stearate | 2 g |
| TC-5(registered trademark) | 10 g |
| Polyethylene glycol 6000 | 3 g |
| Castor oil | 40 g |
| Ethanol | 40 g |

Compound 2-18, Avicel (registered trademark of microcrystalline cellulose, manufactured by Asahi Kasei Corporation, Japan), corn starch and magnesium stearate are mixed and kneaded, and the mixture is tabletted using a conventional ponder (R 10 mm) for sugar coating (manufactured by Kikusui Seisakusho Ltd., Japan). The tablets thus obtained are coated with a film coating agent consisting of TC-5 (registered trademark of hydroxypropyl methylcellulose, manufactured by Shin-Etsu Chemical Co., Ltd., Japan), polyethylene glycol 6000, castor oil and ethanol to give film coated tablets.

Preparation Example 3

An ointment is prepared from the following components.

| Components | Amount |
|---|---|
| Compound 3-11 | 2 g |
| Purified lanolin | 5 g |
| Bleached beeswax | 5 g |
| White petrolatum | 88 g |
| Total | 100 g |

Bleached beeswax is made liquid by heating, and thereto are added compound 3-11, purified lanolin and white petrolatum, and the mixture is heated until it becomes liquid. The mixture is stirred until it is solidified to give an ointment.

The invention claimed is:

1. A compound represented by the formula (I)

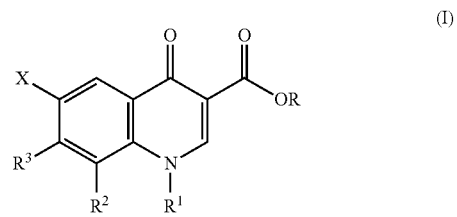

wherein

X is a fluorine atom;

R is a hydrogen atom or alkyl;

$R^1$ is (1) cyclopropyl optionally substituted by 1 to 3 halogen atoms or (2) phenyl optionally substituted by 1 to 3 halogen atoms;

$R^2$ is alkyl optionally substituted by 1 or 2 substituents selected from the group consisting of a halogen atom and hydroxyl; alkoxy; haloalkoxy; a chlorine atom; cyano; cyclopropyl; nitro; amino; formyl; alkenyl or alkynyl; or $R^1$ and $R^2$ are bonded to form a 5- or 6-membered ring optionally substituted by alkyl;

R³ is
(1) a fused heterocyclic group of the formula

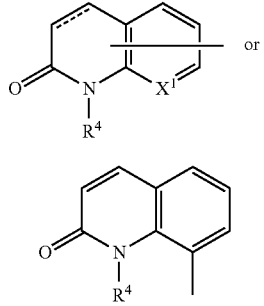

wherein
----- represents a single bond or a double bond,
X¹ is C(R⁵) or N,
R⁴ is a hydrogen atom or alkyl, and
R⁵ is (a) a hydrogen atom,
  (b) a halogen atom,
  (c) cyano,
  (d) nitro,
  (e) hydroxy,
  (f) alkyl optionally substituted by 1 to 3 halogen atoms,
  (g) alkenyl or alkynyl,
  (h) aryl, or
  (i) alkoxy optionally substituted by 1 to 3 halogen atoms,
when X¹ is C(R⁵), R⁴ and R⁵ are optionally bonded to form a 5- or 6-membered ring optionally substituted by oxo, said fused heterocyclic group is optionally substituted by 1 or 2 substituents selected from the group consisting of a halogen atom, cyano, nitro, hydroxy and alkyl,
(2) a group of the formula

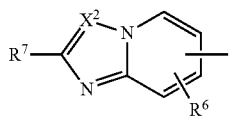

wherein
X² is C(R⁸) or N, and
R⁶, R⁷ and R⁸ are each independently,
  (a) a hydrogen atom,
  (b) a halogen atom,
  (c) cyano,
  (d) nitro,
  (e) amino,
  (f) alkyl optionally substituted by 1 to 3 substituents selected from the group consisting of a halogen atom, alkoxy and amino,
  (g) alkenyl,
  (h) alkynyl,
  (i) aryl,
  (j) formyl or CH=N—OH,
  (k) carboxy,
  (l) carbamoyl,
  (m) a 5- to 10-membered aromatic heterocyclic group optionally substituted by alkyl, or
  (n) alkenyloxy, (3) a group of the formula

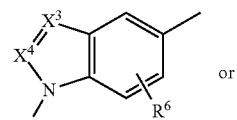

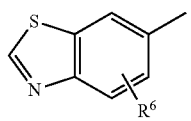

wherein
X³ and X⁴ are N, or
X³ is N and X⁴ is CR", wherein R" is hydrogen atom, amino, hydroxy, alkyl optionally substituted by 1 to 3 substituents selected from the group consisting of alkoxy and dimethylamino or mercapto, or
X³ is CH and X⁴ is N,
R' is a hydrogen atom or alkyl optionally substituted by 1 to 3 substituents selected from the group consisting of substituted hydroxyl and amino, and
R⁶ is as defined above,
(4) a group of the formula

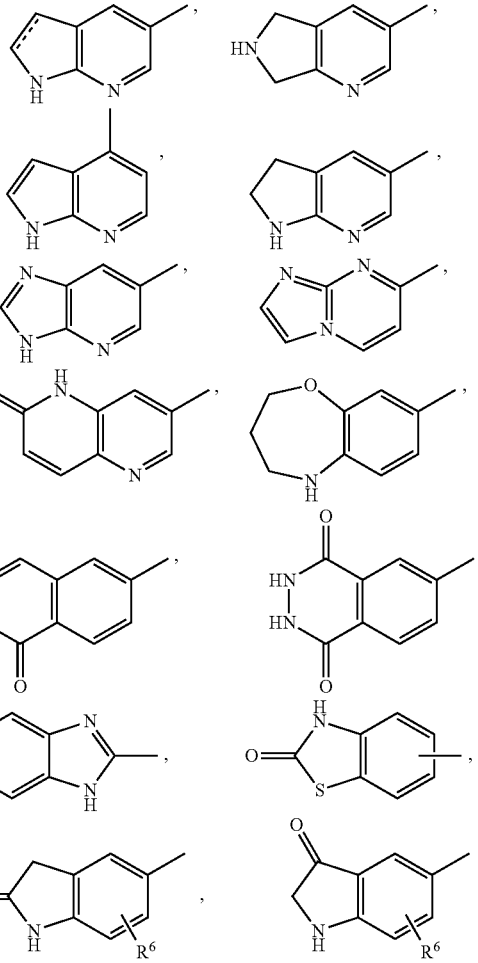

-continued

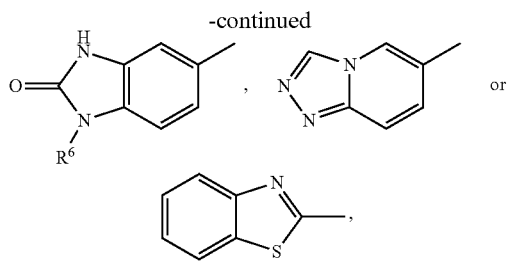

wherein
----- represents a single bond or a double bond and R⁶ is as defined above,
(5) 3-pyridyl optionally substituted by 1 or 2 substituents selected from the group consisting of
  (a) a halogen atom,
  (b) cyano,
  (c) nitro,
  (d) hydroxy,
  (e) amino,
  (f) alkyl optionally substituted by 1 to 3 substituents selected from the group consisting of a halogen atom, alkylamino, dialkylamino and hydroxy,
  (g) alkenyl, alkynyl
  (h) aryl,
  (i) cycloalkyl,
  (j) alkoxy,
  (k) alkylamino,
  (l) dialkylamino,
  (m) phenylamino optionally substituted by 1 to 3 halogen atoms,
  (n) a cyclic amino group optionally substituted by alkoxycarbonyl,
  (o) formyl,
  (p) carbamoyl optionally substituted by alkyl optionally substituted by hydroxy, and
  (q) a 5- to 10-membered aromatic heterocyclic group optionally substituted by alkyl,
(6) 4-pyridyl optionally substituted by a halogen atom,
(7) 5-pyrimidinyl optionally substituted by 1 or 2 substituents selected from the group consisting of amino, alkylamino, dialkylamino and carboxy,
(8) 2-indolyl, 3-indolyl, 5-indolyl, 6-indolyl, benzofuranyl, benzothiophenyl, benzoxazolyl or benzothiazolyl, each optionally substituted by 1 or 2 substituents selected from the group consisting of
  (a) a halogen atom,
  (b) cyano,
  (c) nitro,
  (d) hydroxy,
  (e) alkyl optionally substituted by 1 to 3 substituents selected from the group consisting of amino, alkoxycarbonylamino, alkylamino and dialkylamino,
  (f) alkoxy,
  (g) formyl,
  (h) carboxy, and
  (j) amino optionally substituted by 1 or 2 substituents selected from the group consisting of
    (i) alkoxycarbonyl,
    (ii) alkylcarbonyl optionally substituted by a substituent selected from the group consisting of
      (A) cycloalkyloxy optionally substituted by 1 to 3 alkyl,
      (B) alkylamino,
      (C) dialkylamino,
      (D) a cyclic amino group optionally substituted by alkoxycarbonyl, and
      (E) a halogen atom,
    (iii) phenylcarbonyl optionally substituted by 1 to 3 substituents selected from the group consisting of alkyl and alkoxy,
    (iv) cycloalkylcarbonyl,
    (v) a 5- to 10-membered aromatic heterocyclylcarbonyl group optionally substituted by alkyl optionally substituted by 1 to 3 halogen atoms,
    (vi) benzylcarbonyl optionally substituted by 1 to 3 substituents selected from the group consisting of a halogen atom and alkoxy,
    (vii) arylsulfonyl optionally substituted by alkoxy,
    (viii) cycloalkylalkylsulfonyl optionally substituted by 1 to 3 substituents selected from the group consisting of alkyl and oxo,
    (ix) a 5- to 10-membered aromatic heterocyclylsulfonyl group optionally substituted by 1 to 3 alkyl, and
    (x) —C(=N—CN)—SR⁹ wherein R⁹ is alkyl,
(9) a group of the formula

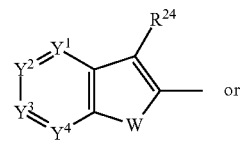 (F)

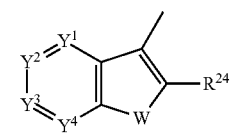 (G)

wherein
one of Y¹, Y², Y³ and Y⁴ is N or N⁺(—O⁻), and the remaining three are each C(R²⁵), C(R²⁶) and C(R²⁷),
W is O, S, NH or N(R²³)
R²³ is a hydrogen atom or alkyl, and
R²⁴, R²⁵, R²⁶ and R²⁷ are each independently,
  (a) a hydrogen atom,
  (b) cyano, or
  (c) nitro,
(10) a group of the formula

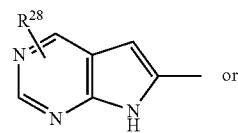 (H)

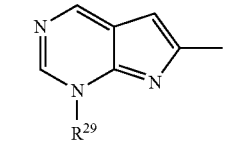 (J)

wherein
R²⁸ is a hydrogen atom or hydroxy, and
R²⁹ is a hydrogen atom or alkyl,

(11) a group of the formula

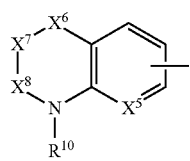
(K)

wherein $X^5$ is $C(R^{11})$ or N, $X^6$ is $CH_2$, $C(=O)$, O, S, $SO_2$ or $N(R^{12})$, $X^7$ is $CH(R^{13})$, $C(=O)$ or $N(R^{14})$, $X^8$ is $CH(R^{15})$ or $C(=O)$, $R^{10}$, $R^{12}$ and $R^{14}$ are each independently,
- (a) a hydrogen atom or
- (b) alkyl, and $R^{11}$, $R^{13}$ and $R^{15}$ are independently,
- (a) a hydrogen atom,
- (b) a halogen atom,
- (c) cyano,
- (d) nitro,
- (e) amino,
- (f) alkylamino,
- (g) dialkylamino,
- (h) alkyl optionally substituted by hydroxy, or
- (i) alkenyl, when $X^5$ is $C(R^{11})$, $R^{10}$ and $R^{11}$ are optionally bonded to form a 5- or 6-membered ring optionally substituted by alkyl or oxo, and when $X^6$ is $N(R^{12})$ and $X^7$ is $CH(R^{13})$, $R^{12}$ and $R^{13}$ are optionally bonded to form a 5- or 6-membered ring,

(12) a group of the formula

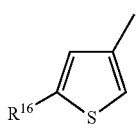
(L)

wherein $R^{16}$ is
- (a) a hydrogen atom,
- (b) alkyl optionally substituted by 1 to 3 substituents selected from the group consisting of cyano, alkylamino and dialkylamino,
- (c) alkenyl optionally substituted by carboxy,
- (d) formyl,
- (e) carboxy,
- (f) carbamoyl,
- (g) —$C(R^{17})$=N—OH wherein $R^{17}$ is a hydrogen atom, cyano or hydroxy,
- (h) a 5- to 10-membered aromatic heterocyclic group optionally substituted by alkyl, alkoxycarbonyl, carboxy or phenyl, or cyano,

(13) a group of the formula

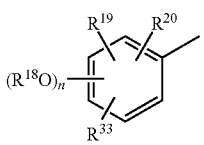
(M)

wherein $R^{18}$ is a hydrogen atom or alkyl optionally substituted by 1 to 3 substituents selected from the group consisting of a halogen atom and phenyl, n is 0 or 1, $R^{19}$, $R^{20}$ and $R^{33}$ are each independently,
- (a) a hydrogen atom,
- (b) a halogen atom,
- (c) cyano,
- (d) alkyl optionally substituted by 1 to 3 substituents selected from the group consisting of
  - (i) a halogen atom
  - (ii) cyano,
  - (iii) hydroxy,
  - (iv) amino,
  - (v) alkylamino,
  - (vi) dialkylamino, and
  - (vii) a cyclic amino group optionally substituted by alkyl,
- (e) alkoxy,
- (f) amino optionally substituted by 1 or 2 substituents selected from the group consisting of
  - (i) alkylcarbonyl optionally substituted by a cyclic amino group,
  - (ii) alkylsulfonyl,
  - (iii) carbamoyl,
  - (iv) alkyl, cycloalkyl or cycloalkylalkyl, and
  - (v) 5- to 10-membered saturated heterocyclic group,
- (g) carboxy,
- (h) alkoxycarbonyl,
- (i) carbamoyl optionally substituted by alkyl optionally substituted by amino, alkylamino, dialkylamino or alkoxycarbonylamino,
- (j) formyl,
- (k) a 5- to 10-membered aromatic heterocyclic group optionally substituted by alkyl,
- (l) —CH=N—$OR^{21}$ wherein $R^{21}$ is a hydrogen atom or alkyl optionally substituted by alkylamino or dialkylamino,
- (m) nitro,
- (n) a 5- to 10-membered saturated heterocyclic group optionally substituted by amino,
- (o) phenyl, or
- (p) —NHC(SMe)=CHCN,

(14) a group of the formula

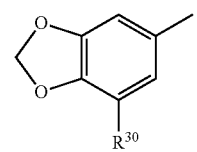
(N)

wherein $R^{30}$ is (a) a hydrogen atom,
- (b) a halogen atom,
- (c) cyano, (d) alkyl optionally substituted by 1 to 3 substituents selected from the group consisting of a halogen atom and hydroxy,
(e) alkenyl,
(f) alkynyl,
(g) alkoxy,
(h) formyl,
(i) —CH=N—OH, or
(j) carbamoyl,
(15) naphthyl or isochromenyl,
(16) quinolyl or isoquinolyl, or their oxide derivatives,
(17) a group of the formula

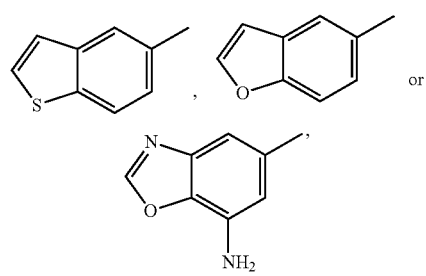

(18) a group of the formula

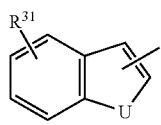

wherein
U is O or S, and
$R^{31}$ is (a) a hydrogen atom,
(b) a halogen atom,
(c) alkyl optionally substituted by 1 to 3 halogen atoms,
(d) carboxy,
(e) nitro,
(f) cyano, or
(g) amino,
(19) a group of the formula

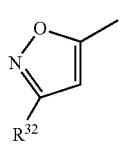

wherein
$R^{32}$ is (a) a halogen atom,
(b) phenyl, or
(c) a group of the formula

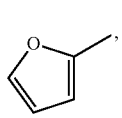 , 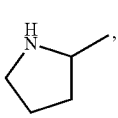 or

(20) a group of the formula

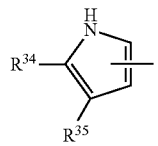

wherein
$R^{34}$ and $R^{35}$ are each independently,
(a) a hydrogen atom, or
(b) aminoalkyl,
or
$R^{34}$ and $R^{35}$ are bonded to form a 6-membered ring optionally substituted by amino or oxo,
(21) a group of the formula

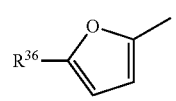

wherein $R^{36}$ is
(a) a hydrogen atom,
(b) a halogen atom,
(c) nitro, or
(d) thienyl, or
(22) a group of the formula

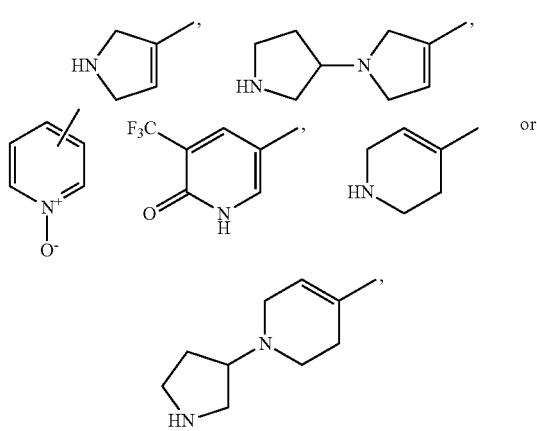

or a salt thereof,
providing that, when $R^1$ and $R^2$ are bonded to form a 6-membered ring substituted by alkyl, $R^3$ is not 4-pyridyl, quinolyl or isoquinolyl.

2. The compound of claim 1, wherein $R^3$ is a fused heterocyclic group of the formula (A)

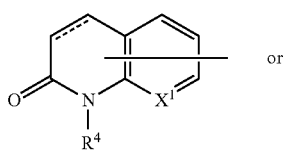 or

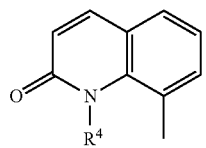

wherein ------, $X^1$ and $R^4$ are as defined in claim 1, and said fused heterocyclic group is optionally substituted by 1 or 2 substituents selected from the group consisting of a halogen atom, cyano, nitro, hydroxy and alkyl, or a salt thereof.

3. The compound of claim 1, wherein $R^3$ is a group of the formula

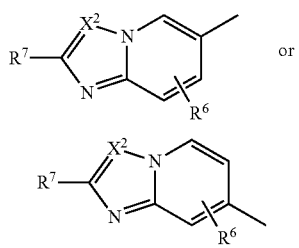

wherein $X^2$, $R^6$ and $R^7$ are as defined in claim 1, or a salt thereof.

4. The compound of claim 1, wherein $R^3$ is a group of the formula

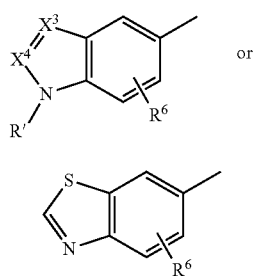

wherein $X^3$, $X^4$, $R^6$ and R' are as defined in claim 1, or a salt thereof.

5. The compound of claim 1, wherein $R^3$ is a group of the formula

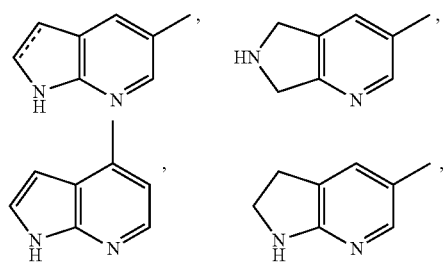

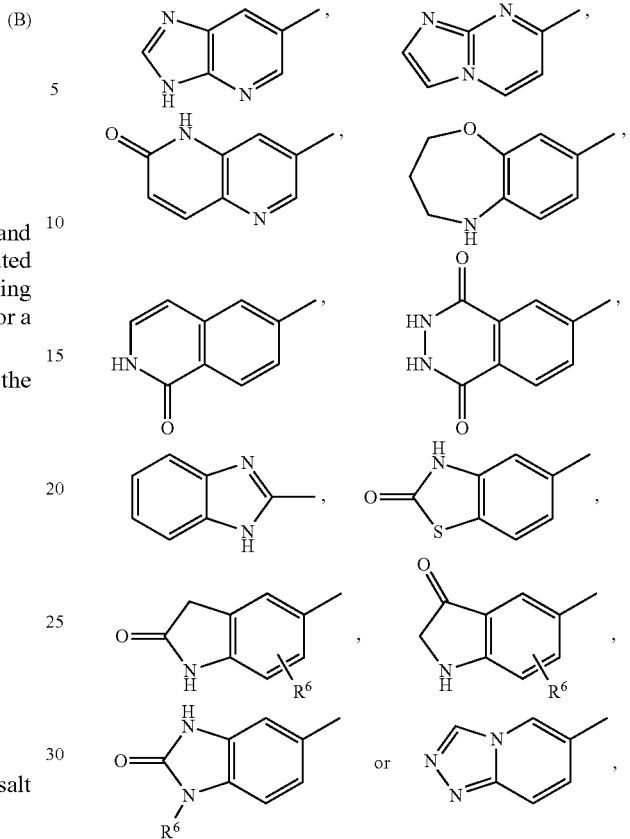

wherein ------ and $R^6$ are as defined in claim 1, or a salt thereof.

6. The compound of claim 1, wherein $R^3$ is a group of the formula

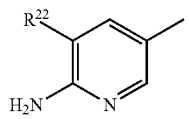

wherein $R^{22}$ is
 (a) a halogen atom,
 (b) cyano,
 (c) nitro,
 (d) alkyl optionally substituted by 1 to 3 substituents selected from the group consisting of a halogen atom, alkylamino, dialkylamino and hydroxy,
 (e) alkenyl, alkynyl,
 (f) aryl,
 (g) cycloalkyl,
 (h) alkoxy,
 (i) formyl, or
 (j) carbamoyl optionally substituted by alkyl optionally substituted by hydroxyl, or a salt thereof.

7. The compound of claim 1, wherein $R^3$ is 5-pyrimidinyl substituted by 1 or 2 substituents selected from the group consisting of amino, alkylamino, dialkylamino and carboxy, or a salt thereof.

8. The compound of claim 1, wherein $R^3$ is 2-indolyl optionally substituted by 1 or 2 substituents selected from the group consisting of (a) a halogen atom,
(b) cyano,
(c) nitro,
(d) hydroxy,
(e) alkyl optionally substituted by 1 to 3 substituents selected from the group consisting of amino, alkoxycarbonylamino, alkylamino and dialkylamino,
(f) alkoxy,
(g) formyl,
(h) carboxy, or
(j) amino optionally substituted by 1 or 2 substituents selected from the group consisting of
  (i) alkoxycarbonyl,
  (ii) alkylcarbonyl optionally substituted by a substituent selected from the group consisting of
    (A) cycloalkyloxy optionally substituted by 1 to 3 alkyl,
    (B) alkylamino,
    (C) dialkylamino,
    (D) a cyclic amino group optionally substituted by alkoxycarbonyl, and
    (E) a halogen atom,
  (iii) phenylcarbonyl optionally substituted by 1 to 3 substituents selected from the group consisting of alkyl and alkoxy,
  (iv) cycloalkylcarbonyl,
  (v) a 5- to 10-membered aromatic heterocyclylcarbonyl group optionally substituted by alkyl optionally substituted by 1 to 3 halogen atoms,
  (vi) benzylcarbonyl optionally substituted by 1 to 3 substituents selected from the group consisting of a halogen atom and alkoxy,
  (vii) arylsulfonyl optionally substituted by alkoxy,
  (viii) cycloalkylalkylsulfonyl optionally substituted by 1 to 3 substituents selected from the group consisting of alkyl and oxo,
  (ix) a 5- to 10-membered aromatic heterocyclylsulfonyl group optionally substituted by 1 to 3 alkyl, and
  (x) —C(=N—CN)—SR$^9$ wherein R$^9$ is alkyl,
or a salt thereof.

9. The compound of claim 1, wherein R$^3$ is a group formula of the

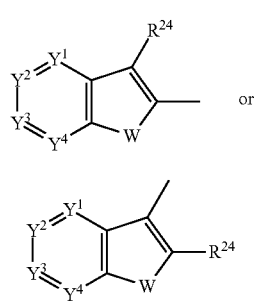

wherein Y$^1$, Y$^2$, Y$^3$, Y$^4$, W and R$^{24}$ are as defined in claim 1, or a salt thereof.

10. The compound of claim 1, wherein R$^3$ is a group of the formula

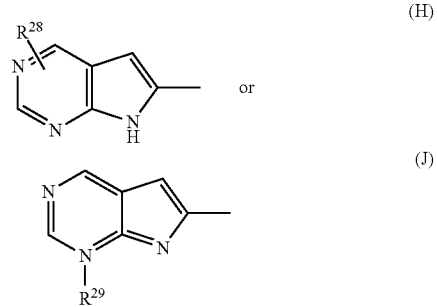

wherein R$^{28}$ and R$^{29}$ are as defined in claim 1, or a salt thereof.

11. The compound of claim 1, wherein R$^3$ is a group of the formula

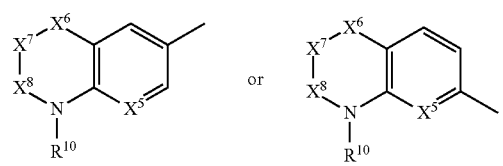

wherein X$^5$, X$^6$, X$^7$, X$^8$ and R$^{10}$ are as defined in claim 1, or a salt thereof.

12. The compound of claim 1, wherein R$^3$ is a group of the formula

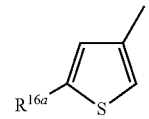

wherein R$^{16a}$ is
(a) alkyl optionally substituted by 1 to 3 substituents selected from the group consisting of cyano, alkylamino and dialkylamino,
(b) alkenyl optionally substituted by carboxy,
(c) formyl,
(d) carboxy,
(e) carbamoyl,
(f) —C(R$^{17}$)=N—OH wherein R$^{17}$ is a hydrogen atom, cyano or hydroxy,
(g) a 5- to 10-membered aromatic heterocyclic group optionally substituted by alkyl, alkoxycarbonyl, carboxy or phenyl, or
(h) cyano,
or a salt thereof.

13. The compound of claim 1, wherein R$^3$ is a group of the formula

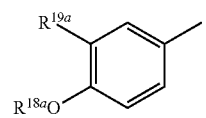

wherein
R$^{18a}$ is alkyl, and
R$^{19a}$ is (a) a halogen atom, (b) cyano,
(c) alkyl optionally substituted by 1 to 3 substituents selected from the group consisting of
  (i) a halogen atom,
  (ii) cyano,
  (iii) hydroxy,
  (iv) amino,
  (v) alkylamino,
  (vi) dialkylamino, and
  (vii) a cyclic amino group optionally substituted by alkyl,
(d) alkoxy,
(e) amino optionally substituted by 1 or 2 substituents selected from the group consisting of
  (i) alkylcarbonyl optionally substituted by a cyclic amino group,
  (ii) alkylsulfonyl,
  (iii) carbamoyl, and
  (iv) alkyl or cycloalkyl,
(f) carboxy,
(g) alkoxycarbonyl,
(h) carbamoyl optionally substituted by alkyl optionally substituted by amino, alkylamino, dialkylamino or alkoxycarbonylamino,
(i) formyl,
(j) a 5- to 10-membered aromatic heterocyclic group optionally substituted by alkyl,
(k) —CH=N—OR$^{21}$ wherein R$^{21}$ is a hydrogen atom or alkyl optionally substituted by alkylamino or dialkylamino, or
(l) nitro,
or a salt thereof.

14. The compound of claim 1, wherein R$^3$ is a group of the formula

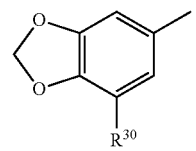

(N)

wherein R$^{30}$ is as defined in claim 1, or a salt thereof.

15. The compound of claim 1, wherein R$^3$ is naphthyl or isochromenyl, or a salt thereof.

16. The compound of claim 1, wherein R$^3$ is quinolyl or isoquinolyl, or their oxide derivatives, or a salt thereof.

17. The compound of claim 1, wherein R is a hydrogen atom, or a salt thereof.

18. The compound of claim 1, wherein R$^1$ is cyclopropyl, 2-fluorocyclopropyl or 2,4-difluorophenyl, or a salt thereof.

19. The compound of claim 1, wherein R$^2$ is methyl, methoxy or a chlorine atom, or a salt thereof.

20. A pharmaceutical composition comprising a compound of claim 1 or a salt thereof and a pharmaceutically acceptable carrier.

21. An antimicrobial agent comprising a compound of claim 1 or a salt thereof.

22. A method for treating a bacterial infection which comprises administering an effective amount of a compound of claim 1 or a salt thereof to a human or an animal.

* * * * *

UNITED STATES PATENT AND TRADEMARK OFFICE
CERTIFICATE OF CORRECTION

PATENT NO. : 9,067,887 B2  
APPLICATION NO. : 14/193656  
DATED : June 30, 2015  
INVENTOR(S) : Mamuti Abudusaimi et al.

It is certified that error appears in the above-identified patent and that said Letters Patent is hereby corrected as shown below:

On the Title Page, after Item (63), "Related U.S. Application Data", and before Item (51), "Int. Cl.", insert the following missing data:

-- (30) Foreign Application Priority Data
Aug. 31, 2011 (CN)........................................ PCT/CN2011/001477
Aug. 6, 2012 (CN)........................................ PCT/CN/2012/001044 --

Signed and Sealed this
Seventeenth Day of November, 2015

Michelle K. Lee
*Director of the United States Patent and Trademark Office*

UNITED STATES PATENT AND TRADEMARK OFFICE
CERTIFICATE OF CORRECTION

PATENT NO. : 9,067,887 B2
APPLICATION NO. : 14/193656
DATED : June 30, 2015
INVENTOR(S) : Mamuti Abudusaimi et al.

It is certified that error appears in the above-identified patent and that said Letters Patent is hereby corrected as shown below:

In the Claims
Claim 1, col. 245, line 49,
"$R^8$, $R^7$ and $R^8$" should read -- $R^6$, $R^7$ and $R^8$ --.

Claim 1, col. 246, line 35,

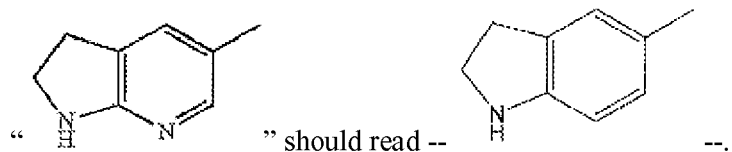 should read -- --.

Claim 1, col. 246, line 40,

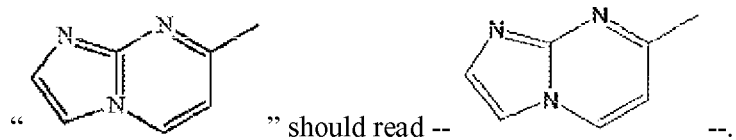 should read -- --.

Claim 1, col. 249, lines 65-67,
"(h) a 5- to 10-membered aromatic heterocyclic group optionally substituted by alkyl, alkoxycarbonyl, carboxy or phenyl, or cyano," should read
-- (h) a 5- to 10-membered aromatic heterocyclic group optionally substituted by alkyl, alkoxycarbonyl, carboxy or phenyl, or
    (i) cyano, --.

Claim 5, col. 253, line 65,

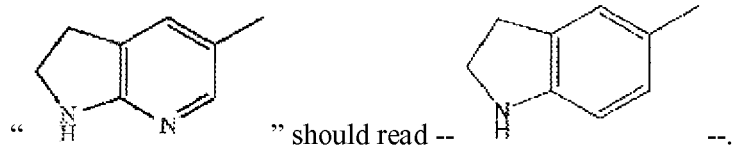 should read -- --.

Signed and Sealed this
Seventeenth Day of May, 2016

Michelle K. Lee
*Director of the United States Patent and Trademark Office*

CERTIFICATE OF CORRECTION (continued)
U.S. Pat. No. 9,067,887 B2

Claim 5, col. 254, line 1,

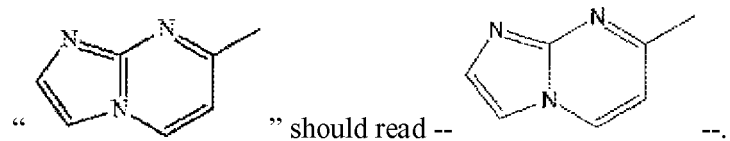

" should read --    --.

Claim 10, col. 256, line 10,

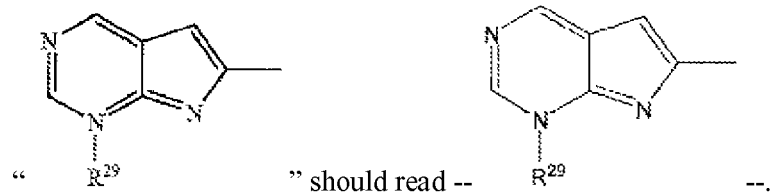

" should read --    --.